United States Patent
Gibbons et al.

(10) Patent No.: US 11,891,613 B2
(45) Date of Patent: Feb. 6, 2024

(54) BACTERIAL STRAINS WITH TOXIN COMPLEX FOR INSECT CONTROL

(71) Applicant: **PIONEER HI-BRED INTERNATIONA

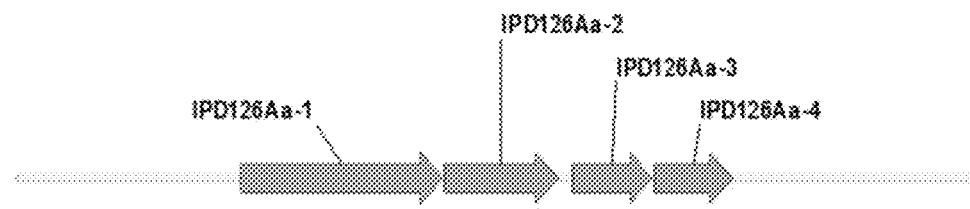
PMC3671E9-1 IPD126 island rc-short
35775 bp
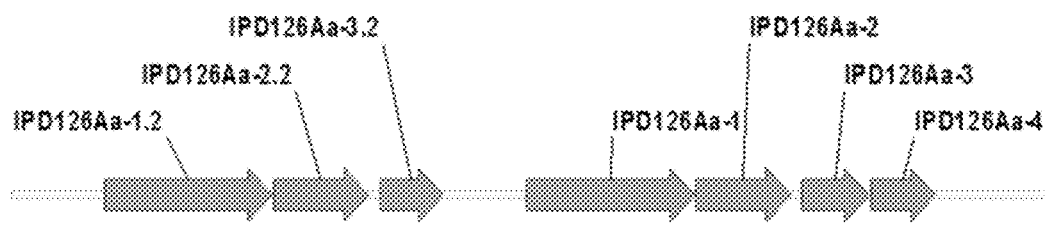
PCM3671E3-1 IPD126 island s
46405 bp
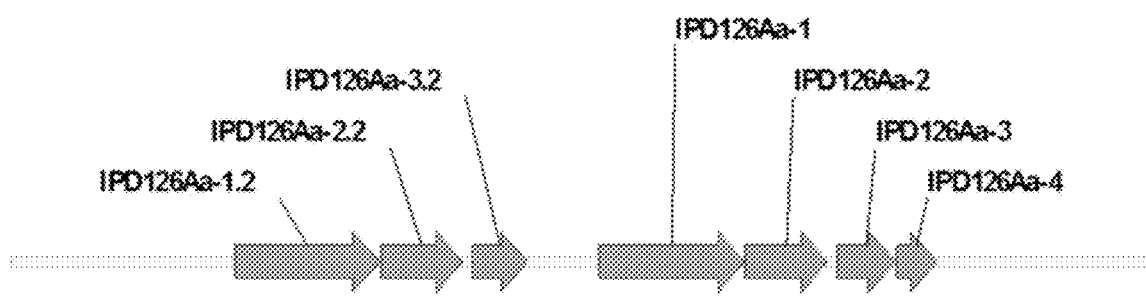
PMCJ4082D4-1 IPD126 island s
59091 bp

_US 11,891,613 B2_

BACTERIAL STRAINS WITH TOXIN COMPLEX FOR INSECT CONTROL

FIELD

Biological strains, compositions, and methods of using the strains and compositions for reducing overall insect damage. Also provided are novel genes that encode pesticidal proteins. These pesticidal proteins and the nucleic acid sequences that encode them are useful in preparing pesticidal formulations and in the production of transgenic pest-resistant plants.

REFERENCE TO SEQUENCE LISTING SUBMITTED ELECTRONICALLY

The official copy of the sequence listing is submitted electronically via EFS-Web as an ASCII formatted sequence listing with a file named 8472_SeqList.txt created on Oct. 8, 2020 and having a size of 344 kilobytes and is filed concurrently with the specification. The sequence listing contained in this ASCII formatted document is part of the specification and is herein incorporated by reference in its entirety.

BACKGROUND

Certain species of microorganisms of the genus *Bacillus* are known to possess pesticidal activity against a range of insect pests including Lepidoptera, Diptera, Coleoptera, Hemiptera and others. *Bacillus thuringiensis* (Bt) and *Bacillus popilliae* are among the most successful biocontrol agents discovered to date. Insect pathogenicity has also been attributed to strains of *B. larvae, B. lentimorbus, B. sphaericus* and *B. cereus*. Microbial insecticides, particularly those obtained from *Bacillus* strains, have played an important role in agriculture as alternatives to chemical pest control.

Crop plants have been developed with enhanced insect resistance by genetically engineering crop plants to produce pesticidal proteins from *Bacillus*. For example, corn and cotton plants have been genetically engineered to produce pesticidal proteins isolated from strains of Bt. These genetically modified crops are now widely used in agriculture and have provided the farmer with an environmentally friendly alternative to traditional insect-control methods. While they have proven to be very successful commercially, these genetically modified, insect-resistant crop plants provide resistance to only a narrow range of the economically important insect pests. In some cases, insects can develop resistance to different insecticidal compounds, which raises the need to identify alternative biological control agents for pest control.

There has been a long felt need for environmentally friendly compositions and methods for controlling or eradicating insect pests of agricultural significance, i.e., methods that are selective, environmentally inert, non-persistent, and biodegradable, and that fit well into insect pest management schemes.

SUMMARY

Some embodiments relate to a composition comprising a *Pantoea agglomerans*, wherein the *Pantoea agglomerans* has insecticidal activity. In some embodiments, the methods and compositions relate to a insecticidal bacterial strain comprising IPD126 gene or gene cluster. In some embodiments, the IPD126 gene comprises an amino acid sequence having at least 90% sequence identity to any one of SEQ ID NOs: 19-36. In some embodiments, the methods and compositions relate to bacterial strains comprising a 16S RNA sequence having at least 95% identity to any one of SEQ ID NOs: 37-39.

In one embodiment, the disclosure relates to a composition comprising a *Pantoea agglomerans* strain PMC3671E3-1 (NRRL Deposit No. B-67697), wherein the *Pantoea agglomerans* strain PMC3671E3-1 has insecticidal activity.

In one embodiment, the disclosure relates to a composition comprising a *Pantoea agglomerans* strain PMC3671E9-1 (NRRL Deposit No. B-67698), wherein the *Pantoea agglomerans* strain PMC3671E9-1 has insecticidal activity.

In one embodiment, the disclosure relates to a composition comprising a *Pantoea agglomerans* strain PMCJ4082D4-1 (NRRL Deposit No. B-67699), wherein the *Pantoea agglomerans* strain PMCJ4082D4-1 has insecticidal activity.

In yet another embodiment, the disclosure relates methods and compositions comprising a bacterial strain disclosed herein, or a progeny, mutant, or variant thereof, a fermentate produced from a strain disclosed herein progeny, mutant, or variant thereof in an effective amount to achieve an effect of inhibit growth of a plant pathogen, pest or insect. In another embodiment, the composition further comprises a biocontrol agent selected from the group consisting of bacteria, fungi, yeast, protozoans, viruses, entomopathogenic nematodes, botanical extracts, proteins, secondary metabolites, and inoculants.

In another embodiment, the compositions and methods disclosed herein further comprise one or more agrochemically active compounds selected from the group consisting of an insecticide, a fungicide, a bactericide, and a nematicide. In still another embodiment, the composition further comprises a compound selected from the group consisting of a safener, a lipo-chitooligosaccharide, an isoflavone, and a ryanodine receptor modulator.

In another embodiment, the compositions and methods comprise at least one at least one seed, plant, or plant part. In one embodiment, the seed, plant, or plant part is genetically modified.

In one embodiment, the compositions and methods inhibit the growth of one or more plant pathogens, pests, or insects including but not limited to bacteria, a fungus, a virus, protozoa, nematode, or an arthropod. In one embodiment, the compositions and methods inhibit the growth of an insect, including but not limited to a Coleopteran, Hemipteran, or Lepidopteran insect. In still another embodiment, the composition inhibits the growth of *Diabrotica virgifera virgifera, Ostrinia nubilalis, Spodoptera frugiperda, Pseudoplusia includens, Anticarsia gemmatalis, Plutella xylostella*, and/or *Aphis fabae*.

In another embodiment, the compositions and methods comprise an effective amount to provide pesticidal activity to bacteria, plants, plant cells, tissues and seeds. In another embodiment, the composition is an effective amount to provide pesticidal activity to Coleopteran or Lepidopteran insects. In still another embodiment, the composition is an effective amount to provide pesticidal activity to *Diabrotica virgifera virgifera, Ostrinia nubilalis, Spodoptera frugiperda, Pseudoplusia includens, Anticarsia gemmatalis, Plutella xylostella*, and/or *Aphis fabae*.

In another embodiment, the compositions and methods comprise in an effective amount to improve plant performance including but not limited to increased root formation, increased root mass, increased root function, increased shoot height, increased shoot function, increased flower bud presence, increased flower bud formation, increased seed germination, increased yield, increased total plant wet weight, and increased total plant dry weight.

In another embodiment, the disclosure relates to a method comprising applying a composition comprising a bacterial strain disclosed herein, or a progeny, mutant, or variant thereof, a fermentate produced from a strain disclosed herein, or a progeny, mutant, or variant thereof, a plant, plant part or soil in an effective amount to achieve an effect selected from the group consisting of: inhibit a plant pathogen, pest, or insect or to prevent damage to a plant by a pathogen, pest, or insect; improve plant performance; improve plant yield; improve plant vigor; increase phosphate availability; increase production of a plant hormone; increase root formation; increase shoot height in a plant, increase leaf length of a plant; increase flower bud formation of a plant; increase total plant fresh weight; increase total plant dry weight; and increase seed germination.

In another embodiment, the method further comprises applying a biocontrol agent, wherein the biocontrol agent is selected from the group consisting of bacteria, fungi, yeast, protozoans, viruses, entomopathogenic nematodes, botanical extracts, proteins, secondary metabolites, and inoculants.

In yet another embodiment, the method further comprises applying an agrochemically active compound selected from the group consisting of an insecticide, a fungicide, a bactericide, and a nematicide.

In still another embodiment, the method further comprises applying a compound selected from the group consisting of a safener, a lipo-chitooligosaccharide, an isoflavone, and a ryanodine receptor modulator.

In another embodiment, the method comprises applying the composition in an effective amount to inhibit growth of a plant pathogen, including but not limited to bacteria, a fungus, a nematode, an insect, a virus, and protozoa.

In one aspect compositions and methods for conferring pesticidal activity to bacteria, plants, plant cells, tissues and seeds are provided. Compositions include nucleic acid molecules encoding sequences for pesticidal and insecticidal polypeptides, vectors comprising those nucleic acid molecules, and host cells comprising the vectors. Compositions also include the pesticidal polypeptide sequences and antibodies to those polypeptides. Compositions also comprise transformed bacteria, plants, plant cells, tissues and seeds.

In another aspect methods are provided for producing the polypeptides and for using those polypeptides for controlling or killing a Hemipteran, Coleopteran, Lepidopteran, or nematode pests. The transgenic plants of the embodiments express one or more of the pesticidal sequences disclosed herein. In various embodiments, the transgenic plant further comprises one or more additional genes for insect resistance, for example, one or more additional genes for controlling Hemipteran, Coleopteran, Lepidopteran, or nematode pests. It will be understood by one of skill in the art that the transgenic plant may comprise any gene imparting an agronomic trait of interest.

In another aspect methods for detecting the nucleic acids and polypeptides of the embodiments in a sample are also included. A kit for detecting the presence of an IPD126 polypeptide or detecting the presence of a polynucleotide encoding an IPD126 polypeptide in a sample is provided. The kit may be provided along with all reagents and control samples necessary for carrying out a method for detecting the intended agent, as well as instructions for use.

In another aspect, the compositions and methods of the embodiments are useful for the production of organisms with enhanced pest resistance or tolerance. These organisms and compositions comprising the organisms are desirable for agricultural purposes. The compositions of the embodiments are also useful for generating altered or improved proteins that have pesticidal activity or for detecting the presence of IPD126 polypeptides.

DESCRIPTION OF FIGURES

FIG. 1 shows IPD126 gene clusters in insecticidal strains of *Pantoea agglomerans*.

DESCRIPTION OF THE SEQUENCES

The disclosure can be more fully understood from the following detailed description and the accompanying drawings and Sequence Listing that form a part of this application.

The sequence descriptions summarize the Sequence Listing attached hereto, which is hereby incorporated by reference. The Sequence Listing contains one letter codes for nucleotide sequence characters and the single and three letter codes for amino acids as defined in the IUPAC-IUB standards described in *Nucleic Acids Research* 13:3021-3030 (1985) and in the *Biochemical Journal* 219(2):345-373 (1984).

TABLE 1

| Sequence Listing Description | |
|---|---|
| Strain_Gene | SEQ ID NO: |
| PMC3671E9-1_IPD126Aa-1 DNA | 1 |
| PMC3671E9-1_IPD126Aa-2 DNA | 2 |
| PMC3671E9-1_IPD126Aa-3 DNA | 3 |
| PMC3671E9-1_IPD126Aa-4 DNA | 4 |
| PCM3671E3-1_IPD126Aa-1 DNA | 5 |
| PCM3671E3-1_IPD126Aa-2 DNA | 6 |
| PCM3671E3-1_IPD126Aa-3 DNA | 7 |
| PCM3671E3-1_IPD126Aa-4 DNA | 8 |
| PCM3671E3-1_IPD126Aa-1.2 DNA | 9 |
| PCM3671E3-1_IPD126Aa-2.2 DNA | 10 |
| PCM3671E3-1_IPD126Aa-3.2 DNA | 11 |
| PMCJ4082D4-1_IPD126Aa-1 DNA | 12 |
| PMCJ4082D4-1_IPD126Aa-2 DNA | 13 |
| PMCJ4082D4-1_IPD126Aa-3 DNA | 14 |
| PMCJ4082D4-1_IPD126Aa-4 DNA | 15 |
| PMCJ4082D4-1_IPD126Aa-1.2 DNA | 16 |
| PMCJ4082D4-1_IPD126Aa-2.2 DNA | 17 |
| PMCJ4082D4-1_IPD126Aa-3.2 DNA | 18 |
| PMC3671E9-1_IPD126Aa-1 protein | 19 |
| PMC3671E9-1_IPD126Aa-2 Protein | 20 |
| PMC3671E9-1_IPD126Aa-3 Protein | 21 |
| PMC3671E9-1_IPD126Aa-4 Protein | 22 |
| PCM3671E3-1_IPD126Aa-1 protein | 23 |
| PCM3671E3-1_IPD126Aa-2 protein | 24 |
| PCM3671E3-1_IPD126Aa-3 Protein | 25 |
| PCM3671E3-1_IPD126Aa-4 Protein | 26 |
| PCM3671E3-1_IPD126Aa-1.2 protein | 27 |
| PCM3671E3-1_IPD126Aa-2.2 Protein | 28 |
| PCM3671E3-1_IPD126Aa-3.2 Protein | 29 |
| PMCJ4082D4-1_IPD126Aa-1 Protein | 30 |
| PMCJ4082D4-1_IPD126Aa-2 protein | 31 |
| PMCJ4082D4-1_IPD126Aa-3 protein | 32 |
| PMCJ4082D4-1_IPD126Aa-4 protein | 33 |
| PMCJ4082D4-1_IPD126Aa-1.2 protein | 34 |
| PMCJ4082D4-1_IPD126Aa-2.2 protein | 35 |
| PMCJ4082D4-1_IPD126Aa-3.2 protein | 36 |
| PMC3671E3-1-16S | 37 |
| PMC3671E9-1-16S | 38 |
| PMCJ4082D4-1-16S | 39 |

DETAILED DESCRIPTION

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof, and so forth. All technical and scientific terms used herein have the same meaning as commonly understood to one of ordinary skill in the art to which this disclosure belongs unless clearly indicated otherwise.

As used herein, "administer" refers to the action of introducing a strain and/or a composition to an environment for pathogen, pest, or insect inhibition or to improve plant performance.

As used herein, the term "agrochemically active compounds" refers to any substance that is or may be customarily used for treating plants including, but not limited to, fungicides, bactericides, insecticides, acaricides, nematicides, molluscicides, safeners, plant growth regulators, and plant nutrients, as well as, microorganisms.

As used herein, a composition may be a liquid, a heterogeneous mixture, a homogeneous mixture, a powder, a solution, a dispersion or any combination thereof.

As used herein, "effective amount" refers to a quantity of a bacterial strain disclosed herein, or a progeny, mutant, or variant thereof, a fermentate produced from a strain disclosed herein progeny, mutant, or variant thereof sufficient to inhibit growth of a pathogenic microorganism or to impede the rate of growth of the pathogenic microorganism. In another embodiment, the term "effective amount" refers to a quantity of a bacterial strain disclosed herein, or a progeny, mutant, or variant thereof, a fermentate produced from a strain disclosed herein progeny, mutant, or variant thereof sufficient to improve plant performance. In another embodiment, the term "effective amount" refers to a quantity of a bacterial strain disclosed herein, or a progeny, mutant, or variant thereof, a fermentate produced from a strain disclosed herein progeny, mutant, or variant thereof, sufficient to control, kill, inhibit, and reduce the number, emergence, or growth of a pathogen, pest, or insect. In another embodiment, the term "effective amount" refers to a quantity of a bacterial strain disclosed herein, or a progeny, mutant, or variant thereof, a fermentate produced from a strain disclosed herein progeny, mutant, or variant thereof sufficient to prevent damage from a pathogen, pest, or insect. One skilled in the art will recognized that an effective amount of a bacterial strain disclosed herein, or a progeny, mutant, or variant thereof, a fermentate produced from a strain disclosed herein progeny, mutant, or variant thereof may not reduce the numbers of pathogens, pests or insects, but is effective in decreasing damage to plants and/or plant parts as a result of a pathogen, pest or insect. For example, a pesticidally effective amount may reduce pathogen, pest or insect emergence, or damage to seeds, roots, shoots, or foliage of plants that are treated compared to those that are untreated.

As used herein, "fermentate broth," "fermentate," or "fermented broth" refers to a media. used to grow or ferment a bacterial strain disclosed herein. The bacterial strain may be removed from a media by filtration, sterilization, or other means. The leftover broth contains metabolites produced by a bacterial strain disclosed herein, which is collectively referred to as a "fermentate broth," "fermentate," or "fermented broth."

As used herein, the term "inhibit" refers to destroy, prevent, reduce, resist, control, decrease, slow or otherwise interfere with the growth or survival of a pathogen, pest, or insect when compared to the growth or survival of the pathogen, pest, or insect in an untreated control. Any of the terms of inhibit, destroy, prevent, control, decrease, slow, interfere, resist, or reduce may be used interchangeably. In one embodiment, to "inhibit" is to destroy, prevent, control, reduce, resist, decrease, slow or otherwise interfere with the growth, emergence, or survival of a pathogen, pest, or insect by at least about 3% to at least about 100%, or any value in between for example at least about 10%, 15%, 20%, 25%, 30%, 35%, 40%, 45%, 50%, 55%, 60%, 65%, 70%, 75%, 80%, 85%, 90%, 95%, 99%, or 100% when compared to the growth or survival of the pathogen, pest, or insect in an untreated control. The amount of inhibition can be measured as described herein or by other methods known in the art. As used herein, "protects a plant from a pathogen, pest, or insect pest" is intended to mean the limiting or eliminating of the pathogen, pest, or insect related damage to a plant and/or plant part by, for example, inhibiting the ability of the pathogen, pest, or insect to grow, emerge, feed, and/or reproduce or by killing the pathogen, pest, or insect. As used herein, pesticidal and/or insecticidal activity refers to an activity of compound, composition, and or method that protects a plant and/or plant part from a pathogen, pest, or insect.

In some embodiments, inhibition a pathogen, pest, or insect lasts for or provides protection for greater than a day, two days, three days, four days, five days, six days, a week, two weeks, three weeks, a month or more after of a bacterial strain disclosed herein, or a progeny, mutant, or variant thereof, a fermentate produced from a strain disclosed herein progeny, mutant, or variant thereof disclosed herein is applied to subject material. In another embodiment, inhibition a pathogen, pest or insect lasts from one to seven days, from seven to 14 days, from 14 to 21 days, or from 21 to 30 days or more. In another embodiment, the inhibition of the growth of a pathogen, pest, or insect lasts for or provides protection for greater than the time from application to adult emergence of the pathogen, pest, or insect.

As used herein, the term "genetically modified" is intended to mean any species containing a genetic trait, loci, or sequence that was not found in the species or strain prior to manipulation. A genetically modified plant may be transgenic, cis-genic, genome edited, or bred to contain a new genetic trait, loci, or sequence. A genetically modified plant or bacteria may be prepared by means known to those skilled in the art, such as transformation by bombardment, by a gene editing technique such as Cas/CRISPR or TALENS, or by breeding techniques. As used herein, a "trait" is a new or modified locus or sequence of a genetically modified plant or bacteria, including but not limited to a transgenic plant or bacteria. In some embodiments, a bacterial strain disclosed herein, or a progeny, mutant, or variant thereof, may be edited. In some embodiments any bacterial strain may be modified or edited to comprise an IPD126 gene. In some embodiments, the methods and compositions relate to an insecticidal bacterial strain comprising an IPD126 gene As used herein, the term "environment of a plant or plant part" is intended to mean the area surrounding the plant or plant part, including but not limited to the soil, the air, or in-furrow. The environment of a plant or plant part may be in proximity, touching, adjacent to, or in the same field as the plant or plant part. The compositions described herein may be applied to the environment of the plant or plant part as a seed treatment, as a foliar application, as a granular application, as a soil application, or as an encapsulated application. As used herein, "in-furrow" is intended to mean within or near the area where a seed is planted. The compositions disclosed herein may be applied in-furrow concurrently or simultaneously with a seed. In another embodiment, the compositions disclosed herein may be applied sequentially, either before or after a seed is planted.

As used herein, the term "different mode of action" is used to refer to a pesticidal composition inhibiting a pathogen, pest, or insect through a pathway or receptor that is different from another pesticidal composition. As used herein, the term "different mode of action" includes the pesticidal effects of one or more pesticidal compositions to different binding sites (i.e., different toxin receptors and/or different sites on the same toxin receptor) in the gut membranes of insects or through the RNA interference pathway to different target genes.

As used herein, the term "pathogen, pest, or insect" includes but is not limited to pathogenic fungi, bacteria, mites, ticks, pathogenic microorganisms, and nematodes, as well as insect from the orders Coleoptera, Lepidoptera, Mallophaga, Homoptera, Hemiptera, Orthoptera, Thysanoptera, Dermaptera, Isoptera, Anoplura, Siphonatpera, Trichoptera, and others, including but not limited to *Diabrotica virgifera virgifera, Diabrotica undecimpunctata howardi*, and *Diabrotica barberi*.

Larvae of the order Lepidoptera include, but are not limited to, armyworms, cutworms, loopers and heliothines in the family Noctuidae Spodoptera frugiperda JE Smith (fall armyworm); *S. exigua* Hübner (beet armyworm); *S. litura* Fabricius (tobacco cutworm, cluster caterpillar); *Mamestra configurata* Walker (bertha armyworm); *M. brassicae* Linnaeus (cabbage moth); *Agrotis ipsilon* Hufnagel (black cutworm); *A. orthogonia* Morrison (western cutworm); *A. subterranea* Fabricius (granulate cutworm); *Alabama argillacea* Hübner (cotton leaf worm); *Trichoplusia ni* Hübner (cabbage looper); *Pseudoplusia includens* Walker (soybean looper); *Anticarsia gemmatalis* Hübner (velvetbean caterpillar); *Hypena scabra* Fabricius (green cloverworm); *Heliothis virescens* Fabricius (tobacco budworm); *Pseudaletia unipuncta* Haworth (armyworm); *Athetis mindara* Barnes and Mcdunnough (rough skinned cutworm); *Euxoa messoria* Harris (darksided cutworm); *Earias insulana* Boisduval (spiny bollworm); *E. vittella* Fabricius (spotted bollworm); *Helicoverpa armigera* Hübner (American bollworm); *H. zea* Boddie (corn earworm or cotton bollworm); *Melanchra picta* Harris (zebra caterpillar); *Egira (Xylomyges) curialis* Grote (citrus cutworm); borers, casebearers, webworms, coneworms, and skeletonizers from the family Pyralidae *Ostrinia nubilalis* Hübner (European corn borer); *Amyelois transitella* Walker (naval orangeworm); *Anagasta kuehniella* Zeller (Mediterranean flour moth); *Cadra cautella* Walker (almond moth); *Chilo suppressalis* Walker (rice stem borer); *C. partellus*, (sorghum borer); *Corcyra cephalonica* Stainton (rice moth); *Crambus caliginosellus* Clemens (corn root webworm); *C. teterrellus* Zincken (bluegrass webworm); *Cnaphalocrocis medinalis* Guenée (rice leaf roller); *Desmia funeralis* Hübner (grape leaffolder); *Diaphania hyalinata* Linnaeus (melon worm); *D. nitidalis* Stoll (pickleworm); *Diatraea grandiosella* Dyar (southwestern corn borer), *D. saccharalis* Fabricius (surgarcane borer); *Eoreuma loftini* Dyar (Mexican rice borer); *Ephestia elutella* Hübner (tobacco (cacao) moth); *Galleria mellonella* Linnaeus (greater wax moth); *Herpetogramma licarsisalis* Walker (sod webworm); *Homoeosoma electellum* Hulst (sunflower moth); *Elasmopalpus lignosellus* Zeller (lesser cornstalk borer); *Achroia grisella* Fabricius (lesser wax moth); *Loxostege sticticalis* Linnaeus (beet webworm); *Orthaga thyrisalis* Walker (tea tree web moth); *Maruca testulalis* Geyer (bean pod borer); *Plodia interpunctella* Hübner (Indian meal moth); *Scirpophaga incertulas* Walker (yellow stem borer); *Udea rubigalis* Guenée (celery leaftier); and leafrollers, budworms, seed worms and fruit worms in the family Tortricidae *Acleris gloverana* Walsingham (Western blackheaded budworm); *A. variana* Fernald (Eastern blackheaded budworm); *Archips argyrospila* Walker (fruit tree leaf roller); *A. rosana* Linnaeus (European leaf roller); and other *Archips* species, *Adoxophyes orana* Fischer von Rösslerstamm (summer fruit tortrix moth); *Cochylis hospes* Walsingham (banded sunflower moth); *Cydia latiferreana* Walsingham (filbertworm); *C. pomonella* Linnaeus (coding moth); *Platynota flavedana* Clemens (variegated leafroller); *P. stultana* Walsingham (omnivorous leafroller); *Lobesia botrana* Denis & Schiffermüller (European grape vine moth); *Spilonota ocellana* Denis & Schiffermüller (eyespotted bud moth); *Endopiza viteana* Clemens (grape berry moth); *Eupoecilia ambiguella* Hübner (vine moth); *Bonagota salubricola* Meyrick (Brazilian apple leafroller); *Grapholita molesta* Busck (oriental fruit moth); *Suleima helianthana* Riley (sunflower bud moth); *Argyrotaenia* spp.; *Choristoneura* spp.

Selected other agronomic pests in the order Lepidoptera include, but are not limited to, *Alsophila pometaria* Harris (fall cankerworm); *Anarsia lineatella* Zeller (peach twig borer); *Anisota senatoria* J. E. Smith (orange striped oakworm); *Antheraea pernyi* Guérin-Méneville (Chinese Oak Tussah Moth); *Bombyx mori* Linnaeus (Silkworm); *Bucculatrix thurberiella* Busck (cotton leaf perforator); *Colias eurytheme* Boisduval (alfalfa caterpillar); *Datana integerrima* Grote & Robinson (walnut caterpillar); *Dendrolimus sibiricus* Tschetwerikov (Siberian silk moth), *Ennomos subsignaria* Hübner (elm spanworm); *Erannis tiliaria* Harris (linden looper); *Euproctis chrysorrhoea* Linnaeus (browntail moth); *Harrisina americana* Guérin-Méneville (grapeleaf skeletonizer); *Hemileuca oliviae* Cockrell (range caterpillar); *Hyphantria cunea* Drury (fall webworm); *Keiferia lycopersicella* Walsingham (tomato pinworm); *Lambdina fiscellaria fiscellaria* Hulst (Eastern hemlock looper); *L. fiscellaria lugrubrosa* Hulst (Western hemlock looper); *Leucoma salicis* Linnaeus (satin moth); *Lymantria dispar* Linnaeus (gypsy moth); *Manduca quinquemaculata* Haworth (five spotted hawk moth, tomato hornworm); *M. sexta* Haworth (tomato hornworm, tobacco hornworm); *Operophtera brumata* Linnaeus (winter moth); *Paleacrita vernata* Peck (spring cankerworm); *Papilio cresphontes* Cramer (giant swallowtail orange dog); *Phryganidia californica* Packard (California oakworm); *Phyllocnistis citrella* Stainton (citrus leafminer); *Phyllonorycter blancardella* Fabricius (spotted tentiform leafminer); *Pieris brassicae* Linnaeus (large white butterfly); *P. rapae* Linnaeus (small white butterfly); *P. napi* Linnaeus (green veined white butterfly); *Platyptilia carduidactyla* Riley (artichoke plume moth); *Plutella xylostella* Linnaeus (diamondback moth); *Pectinophora gossypiella* Saunders (pink bollworm); *Pontia protodice* Boisduval and Leconte (Southern cabbageworm); *Sabulodes aegrotata* Guenée (omnivorous looper); *Schizura concinna* J. E. Smith (red humped caterpillar); *Sitotroga cerealella* Olivier (Angoumois grain moth); *Thaumetopoea pityocampa* Schiffermuller (pine processionary caterpillar); *Tineola bisselliella* Hummel (webbing clothesmoth); *Tuta absoluta* Meyrick (tomato leafminer); *Yponomeuta padella* Linnaeus (ermine moth); *Heliothis subflexa* Guenée; *Malacosoma* spp. and *Orgyia* spp.

Of interest are larvae and adults of the order Coleoptera including weevils from the families Anthribidae, Bruchidae and Curculionidae (including, but not limited to: *Anthono-*

*mus grandis* Boheman (boll weevil); *Lissorhoptrus oryzophilus* Kuschel (rice water weevil); *Sitophilus granarius* Linnaeus (granary weevil); *S. oryzae* Linnaeus (rice weevil); *Hypera punctata* Fabricius (clover leaf weevil); *Cylindrocopturus adspersus* LeConte (sunflower stem weevil); *Smicronyx fulvus* LeConte (red sunflower seed weevil); *S. sordidus* LeConte (gray sunflower seed weevil); *Sphenophorus maidis* Chittenden (maize billbug)); flea beetles, cucumber beetles, rootworms, leaf beetles, potato beetles and leafminers in the family Chrysomelidae (including, but not limited to: *Leptinotarsa decemlineata* Say (Colorado potato beetle); *Diabrotica virgifera virgifera* LeConte (western corn rootworm); *D. barberi* Smith and Lawrence (northern corn rootworm); *D. undecimpunctata howardi* Barber (southern corn rootworm); *Chaetocnema pulicaria* Melsheimer (corn flea beetle); *Phyllotreta cruciferae* Goeze (Crucifer flea beetle); *Phyllotreta striolata* (stripped flea beetle); *Colaspis brunnea* Fabricius (grape *colaspis*); *Oulema melanopus* Linnaeus (cereal leaf beetle); *Zygogramma exclamationis* Fabricius (sunflower beetle)); beetles from the family Coccinellidae (including, but not limited to: *Epilachna varivestis* Mulsant (Mexican bean beetle)); chafers and other beetles from the family Scarabaeidae (including, but not limited to: *Popillia japonica* Newman (Japanese beetle); *Cyclocephala borealis* Arrow (northern masked chafer, white grub); *C. immaculata* Olivier (southern masked chafer, white grub); *Rhizotrogus majalis* Razoumowsky (European chafer); *Phyllophaga crinita* Burmeister (white grub); *Ligyrus gibbosus* De Geer (carrot beetle)); carpet beetles from the family Dermestidae; wireworms from the family Elateridae, *Eleodes* spp., *Melanotus* spp.; *Conoderus* spp.; *Limonius* spp.; *Agriotes* spp.; *Ctenicera* spp.; *Aeolus* spp.; bark beetles from the family Scolytidae and beetles from the family Tenebrionidae.

Adults and immatures of the order Diptera are of interest, including leafminers *Agromyza parvicornis* Loew (corn blotch leafminer); midges (including, but not limited to: *Contarinia sorghicola* Coquillett (sorghum midge); *Mayetiola destructor* Say (Hessian fly); *Sitodiplosis mosellana* Géhin (wheat midge); *Neolasioptera murtfeldtiana* Felt, (sunflower seed midge)); fruit flies (Tephritidae), *Oscinella frit* Linnaeus (fruit flies); maggots (including, but not limited to: *Delia platura* Meigen (seedcorn maggot); *D. coarctata* Fallen (wheat bulb fly) and other *Delia* spp., *Meromyza americana* Fitch (wheat stem maggot); *Musca domestica* Linnaeus (house flies); *Fannia canicularis* Linnaeus, *F. femoralis* Stein (lesser house flies); *Stomoxys calcitrans* Linnaeus (stable flies)); face flies, horn flies, blow flies, *Chrysomya* spp.; *Phormia* spp. and other muscoid fly pests, horse flies *Tabanus* spp.; bot flies *Gastrophilus* spp.; *Oestrus* spp.; cattle grubs *Hypoderma* spp.; deer flies *Chrysops* spp.; *Melophagus ovinus* Linnaeus (keds) and other *Brachycera*, mosquitoes *Aedes* spp.; *Anopheles* spp.; *Culex* spp.; black flies *Prosimulium* spp.; *Simulium* spp.; biting midges, sand flies, sciarids, and other *Nematocera*.

Included as insects of interest are adults and nymphs of the orders Hemiptera and Homoptera such as, but not limited to, adelgids from the family Adelgidae, plant bugs from the family Miridae, cicadas from the family Cicadidae, leafhoppers, *Empoasca* spp.; from the family Cicadellidae, planthoppers from the families Cixiidae, Flatidae, Fulgoroidea, Issidae and Delphacidae, treehoppers from the family Membracidae, psyllids from the family Psyllidae, whiteflies from the family Aleyrodidae, aphids from the family Aphididae, phylloxera from the family Phylloxeridae, mealybugs from the family Pseudococcidae, scales from the families Asterolecanidae, Coccidae, Dactylopiidae, Diaspididae, Eriococcidae Ortheziidae, Phoenicococcidae and Margarodidae, lace bugs from the family Tingidae, stink bugs from the family Pentatomidae, cinch bugs, *Blissus* spp.; and other seed bugs from the family Lygaeidae, spittlebugs from the family Cercopidae squash bugs from the family Coreidae and red bugs and cotton stainers from the family Pyrrhocoridae.

Agronomically important members from the order Homoptera further include, but are not limited to: *Acyrthisiphon pisum* Harris (pea aphid); *Aphis craccivora* Koch (cowpea aphid); *A. fabae* Scopoli (black bean aphid); *A. gossypii* Glover (cotton aphid, melon aphid); *A. maidiradicis* Forbes (corn root aphid); *A. pomi* De Geer (apple aphid); *A. spiraecola* Patch (spirea aphid); *Aulacorthum solani* Kaltenbach (foxglove aphid); *Chaetosiphon fragaefolii* Cockerell (strawberry aphid); *Diuraphis noxia* Kurdjumov/Mordvilko (Russian wheat aphid); *Dysaphis plantaginea* Paaserini (rosy apple aphid); *Eriosoma lanigerum* Hausmann (woolly apple aphid); *Brevicoryne brassicae* Linnaeus (cabbage aphid); *Hyalopterus pruni* Geoffroy (mealy plum aphid); *Lipaphis erysimi* Kaltenbach (turnip aphid); *Metopolophium dirrhodum* Walker (cereal aphid); *Macrosiphum euphorbiae* Thomas (potato aphid); *Myzus persicae* Sulzer (peach-potato aphid, green peach aphid); *Nasonovia ribisnigri* Mosley (lettuce aphid); *Pemphigus* spp. (root aphids and gall aphids); *Rhopalosiphum maidis* Fitch (corn leaf aphid); *R. padi* Linnaeus (bird cherry-oat aphid); *Schizaphis graminum* Rondani (greenbug); *Sipha flava* Forbes (yellow sugarcane aphid); *Sitobion avenae* Fabricius (English grain aphid); *Therioaphis maculata* Buckton (spotted alfalfa aphid); *Toxoptera aurantii* Boyer de Fonscolombe (black citrus aphid) and *T. citricida* Kirkaldy (brown citrus aphid); *Melanaphis sacchari* (sugarcane aphid); *Adelges* spp. (adelgids); *Phylloxera devastatrix* Pergande (pecan *phylloxera*); *Bemisia tabaci* Gennadius (tobacco whitefly, sweetpotato whitefly); *B. argentifolii* Bellows & Perring (silverleaf whitefly); *Dialeurodes citri* Ashmead (citrus whitefly); *Trialeurodes abutiloneus* (bandedwinged whitefly) and *T. vaporariorum* Westwood (greenhouse whitefly); *Empoasca fabae* Harris (potato leafhopper); *Laodelphax striatellus* Fallen (smaller brown planthopper); *Macrolestes quadrilineatus* Forbes (aster leafhopper); *Nephotettix cinticeps* Uhler (green leafhopper); *N. nigropictus* Stal (rice leafhopper); *Nilaparvata lugens* Stal (brown planthopper); *Peregrinus maidis* Ashmead (corn planthopper); *Sogatella furcifera* Horvath (white-backed planthopper); *Sogatodes orizicola* Muir (rice delphacid); *Typhlocyba pomaria* McAtee (white apple leafhopper); *Erythroneoura* spp. (grape leafhoppers); *Magicicada septendecim* Linnaeus (periodical cicada); *Icerya purchasi* Maskell (cottony cushion scale); *Quadraspidiotus perniciosus* Comstock (San Jose scale); *Planococcus citri* Risso (citrus mealybug); *Pseudococcus* spp. (other mealybug complex); *Cacopsylla pyricola* Foerster (pear psylla); *Trioza diospyri* Ashmead (persimmon psylla).

Agronomically important species of interest from the order Hemiptera include, but are not limited to: *Acrosternum hilare* Say (green stink bug); *Anasa tristis* De Geer (squash bug); *Blissus leucopterus leucopterus* Say (chinch bug); *Corythuca gossypii* Fabricius (cotton lace bug); *Cyrtopeltis modesta* Distant (tomato bug); *Dysdercus suturellus* Herrich-Schiffer (cotton stainer); *Euschistus servus* Say (brown stink bug); *E. variolarius* Palisot de Beauvois (one-spotted stink bug); *Graptostethus* spp. (complex of seed bugs); *Leptoglossus corculus* Say (leaf-footed pine seed bug); *Lygus lineolaris* Palisot de Beauvois (tarnished plant bug); *L. Hesperus* Knight (Western tarnished plant bug); *L. pratensis* Linnaeus (common meadow bug); *L. rugulipennis*

Poppius (European tarnished plant bug); *Lygocoris pabulinus* Linnaeus (common green capsid); *Nezara viridula* Linnaeus (southern green stink bug); *Oebalus pugnax* Fabricius (rice stink bug); *Oncopeltus fasciatus* Dallas (large milkweed bug); *Pseudatomoscelis seriatus* Reuter (cotton fleahopper).

Furthermore, embodiments may be effective against Hemiptera such, *Calocoris norvegicus* Gmelin (strawberry bug); *Orthops campestris* Linnaeus; *Plesiocoris rugicollis* Fallen (apple capsid); *Cyrtopeltis modestus* Distant (tomato bug); *Cyrtopeltis notatus* Distant (suckfly); *Spanagonicus albofasciatus* Reuter (whitemarked fleahopper); *Diaphnocoris chlorionis* Say (honeylocust plant bug); *Labopidicola allii* Knight (onion plant bug); *Pseudatomoscelis seriatus* Reuter (cotton fleahopper); *Adelphocoris rapidus* Say (rapid plant bug); *Poecilocapsus lineatus* Fabricius (four-lined plant bug); *Nysius ericae* Schilling (false chinch bug); *Nysius raphanus* Howard (false chinch bug); *Nezara viridula* Linnaeus (Southern green stink bug); *Eurygaster* spp.; *Coreidae* spp.; *Pyrrhocoridae* spp.; *Tinidae* spp.; *Blostomatidae* spp.; *Reduviidae* spp. and *Cimicidae* spp.

Also included are adults and larvae of the order Acari (mites) such as *Aceria tosichella* Keifer (wheat curl mite); *Petrobia latens* Müller (brown wheat mite); spider mites and red mites in the family Tetranychidae, *Panonychus ulmi* Koch (European red mite); *Tetranychus urticae* Koch (two spotted spider mite); (*T. mcdanieli* McGregor (McDaniel mite); *T. cinnabarinus* Boisduval (carmine spider mite); *T. turkestani* Ugarov & Nikolski (strawberry spider mite); flat mites in the family Tenuipalpidae, *Brevipalpus lewisi* McGregor (citrus flat mite); rust and bud mites in the family Eriophyidae and other foliar feeding mites and mites important in human and animal health, i.e., dust mites in the family Epidermoptidae, follicle mites in the family Demodicidae, grain mites in the family Glycyphagidae, ticks in the order Ixodidae. *Ixodes scapularis* Say (deer tick); *I. holocyclus* Neumann (Australian paralysis tick); *Dermacentor variabilis* Say (American dog tick); *Amblyomma americanum* Linnaeus (lone star tick) and scab and itch mites in the families Psoroptidae, Pyemotidae and Sarcoptidae.

Insect pests of the order Thysanura are of interest, such as *Lepisma saccharina* Linnaeus (silverfish); *Thermobia domestica* Packard (firebrat).

Additional arthropod pests covered include: spiders in the order Araneae such as *Loxosceles reclusa* Gertsch and Mulaik (brown recluse spider) and the *Latrodectus mactans* Fabricius (black widow spider) and centipedes in the order Scutigeromorpha such as *Scutigera coleoptrata* Linnaeus (house centipede).

Insect pest of interest include the superfamily of stink bugs and other related insects including but not limited to species belonging to the family Pentatomidae (*Nezara viridula, Halyomorpha halys, Piezodorus guildini, Euschistus servus, Acrosternum hilare, Euschistus heros, Euschistus tristigmus, Acrosternum hilare, Dichelops furcatus, Dichelops melacanthus*, and *Bagrada hilaris* (Bagrada Bug)), the family Plataspidae (*Megacopta cribraria*—Bean plataspid) and the family Cydnidae (*Scaptocoris castanea*—Root stink bug) and Lepidoptera species including but not limited to: diamond-back moth, e.g., *Helicoverpa zea* Boddie; soybean looper, e.g., *Pseudoplusia includens* Walker and velvet bean caterpillar e.g., *Anticarsia gemmatalis* Hübner.

Methods for measuring pesticidal activity are well known in the art. See, for example, Czapla and Lang, (1990) *J. Econ. Entomol.* 83:2480-2485; Andrews, et al., (1988) *Biochem. J.* 252:199-206; Marrone, et al., (1985) *J. of Economic Entomology* 78:290-293 and U.S. Pat. No. 5,743,477. Generally, the pesticide is mixed and used in feeding assays. See, for example Marrone, et al., (1985) *J. of Economic Entomology* 78:290-293. Such assays can include contacting plants with one or more pests and determining the plant's ability to survive and/or cause the death of the pests.

"Percent (%) sequence identity" with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments, an IPD126 polypeptide comprises an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOs: 19-36. In some embodiments, a nucleic acid sequence encoding an IPD126 polynucleotide sequence having at least about 80%, 81%, 82%, 83%, 84%, 85%, 86%, 87%, 88%, 89%, 90%, 91%, 92%, 93%, 94%, 95%, 96%, 97%, 98%, 99% or greater identity across the entire length of the amino acid sequence of any one of SEQ ID NOs: 1-18.

As used herein, the term "plant" refers to all plants, plant parts, seed, and plant populations, such as desirable and undesirable wild plants, cultivars, transgenic plants, and plant varieties (whether or not protectable by plant variety or plant breeder's rights). Cultivars and plant varieties can be plants obtained by conventional propagation and breeding methods that can be assisted or supplemented by one or more biotechnological methods such as by use of double haploids, protoplast fusion, random and directed mutagenesis, molecular or genetic markers or by bioengineering and genetic engineering methods.

The embodiments disclosed herein may generally be used for any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

As used herein, the term "plant parts" refers to all above ground and below ground parts and organs of plants such as shoot, leaf, blossom and root, whereby for example leaves, needles, stems, branches, blossoms, fruiting bodies, fruits and seeds, as well as roots, tubers, corms and rhizomes are included. Crops and vegetative and generative propagating material, for example, cuttings, corms, rhizomes, tubers, runners and seeds are also plant parts.

As used herein, the term "viable" refers to a microbial cell, propagule, or spore that is metabolically active or able to differentiate. Thus, propagules, such as spores, are "viable" when they are dormant and capable of germinating.

The embodiments disclosed herein relate to a *Pantoea agglomerans* strain PMC3671E3-1 (NRRL Deposit No. B-67697), a *Pantoea agglomerans* strain PMC3671E9-1 (NRRL Deposit No. B-67698), or a *Pantoea agglomerans* strain PMCJ4082D4-1 (NRRL Deposit No. B-67699); and/or a fermentate produced from a growth medium comprising a *Pantoea agglomerans* strain PMC3671E3-1 (NRRL Deposit No. B-67697), a *Pantoea agglomerans* strain PMC3671E9-1 (NRRL Deposit No. B-67698), or a *Pantoea agglomerans* strain PMCJ4082D4-1 (NRRL Deposit No. B-67699. In one embodiment the bacterial strain disclosed herein, or a progeny, mutant, or variant thereof; and/or a fermentate produced from a strain disclosed herein progeny, mutant, or variant thereof; compositions and methods find use in inhibiting, controlling, or killing a pathogen, pest, or insect, including, but is not limited to, fungi, pathogenic fungi, bacteria, mites, ticks, pathogenic microorganisms, and nematodes, as well as insects from the orders Coleoptera, Diptera, Hymenoptera, Lepidoptera, Mallophaga, Homoptera, Hemiptera Orthroptera, Thysanoptera, Dermaptera, Isoptera, Anoplura, Siphonaptera, Trichoptera, etc., particularly Coleoptera, including but not limited to *Diabrotica virgifera virgifera, Diabrotica undecimpunctata howardi*, and *Diabrotica barberi*, and for producing compositions with pesticidal activity.

The *Pantoea agglomerans* strain PMC3671E3-1 (NRRL Deposit No. B-67697), *Pantoea agglomerans* strain PMC3671E9-1 (NRRL Deposit No. B-67698), and *Pantoea agglomerans* strain PMCJ4082D4-1 (NRRL Deposit No. B-67699) were deposited on Nov. 9, 2018 at the Agricultural Research Service Culture Collection (NRRL), 1815 North University Street, Peoria, Ill., 61604. The deposits were made under the provisions of the Budapest Treaty on the International Recognition of the Deposit of Microorganisms for the Purposes of Patent Procedure. Further, these deposits will be maintained under the terms of the Budapest Treaty on the International Recognition of the Deposit of Microorganisms for the Purposes of Patent Procedure. Access to these deposits will be available during the pendency of the application to the Commissioner of Patents and Trademarks and persons determined by the Commissioner to be entitled thereto upon request. Upon allowance of any claims in the application, the Applicant will make available to the public, pursuant to 37 C.F.R. § 1.808, sample(s) of the deposits. The deposits will be maintained in the NRRL depository, which is a public depository, for a period of 30 years, or 5 years after the most recent request, or for the enforceable life of the patent, whichever is longer, and will be replaced if it becomes nonviable during that period. Additionally, Applicant has satisfied all the requirements of 37 C.F.R. §§ 1.801-1.809, including providing an indication of the viability of the sample upon deposit.

Some embodiments relate to compositions comprising or consisting of or consisting essentially of a bacterial strain disclosed herein, or a progeny, mutant, or variant thereof, a fermentate produced from a strain disclosed herein progeny, mutant, or variant thereof. In one embodiment, the compositions are biologically pure cultures of the strain disclosed herein.

Some embodiments relate to a composition comprising a bacterial strain disclosed herein, or a progeny, mutant, or variant thereof, a fermentate produced from a strain disclosed herein progeny, mutant, or variant thereof disclosed herein and one or more compounds or agents selected from the group consisting of: agrochemically active compounds, biocontrol agents, lipo-chitooligosaccharide compounds (LCOs), isoflavones, quinazolines, insecticidal compounds, azolopyrimidinylamines, polymeric compounds, ionic compound, substituted thiophenes, substituted dithiines, fluopyramm, enaminocarbonyl compounds, strigolactone compound, and dithiino-tetracarboximide compounds.

A further embodiment relates to the use of a first composition comprising a bacterial strain disclosed herein, or a progeny, mutant, or variant thereof, a fermentate produced from a strain disclosed herein progeny, mutant, or variant thereof disclosed herein and a second composition comprising one or more compounds or agents selected from the group consisting of: agrochemically active compounds, biocontrol agents, lipo-chitooligosaccharide compounds (LCOs), isoflavones, quinazolines, insecticidal compound, azolopyrimidinylamine, polymeric compounds, ionic compound, substituted thiophenes, substituted dithiines, fluopyramm, enaminocarbonyl compounds, strigolactone compound, and dithiino-tetracarboximide compounds.

In one embodiment, the disclosure relates to a composition comprising a bacterial strain disclosed herein, or a progeny, mutant, or variant thereof, a fermentate produced from a strain disclosed herein progeny, mutant, or variant thereof disclosed herein and one or more biocontrol agents. As used herein, the term "biocontrol agent" ("BCA") includes bacteria, fungi or yeasts, protozoans, viruses, entomopathogenic nematodes, and botanical extracts, or products produced by microorganisms including proteins or secondary metabolite, and inoculants that have one or both of the following characteristics: (1) inhibits or reduces plant infestation and/or growth of pathogens, pests, or insects, including but not limited to pathogenic fungi, bacteria, and nematodes, as well as arthropod pests such as insects, arachnids, chilopods, diplopods, or that inhibits plant infestation and/or growth of a combination of plant pathogens, pests, or insects; (2) improves plant performance; (3) improves plant yield; (4) improves plant vigor; and (5) improves plant health.

In one embodiment, the disclosure relates to a composition comprising a bacterial strain disclosed herein, or a progeny, mutant, or variant thereof, a fermentate produced from a strain disclosed herein progeny, mutant, or variant thereof disclosed herein and one or more agrochemically active compounds. Agrochemically active compounds are substances that are or may be used for treating a seed, a plant, plant part, or the environment of the seed or plant or plant part including but not limited to fungicides, bactericides, insecticides, acaricides, nematicides, molluscicides, safeners, plant growth regulators, plant nutrients, chemical entities with a known mechanism of action, additional microorganisms, and biocontrol agents.

In another embodiment, the disclosure relates to a first composition comprising a bacterial strain disclosed herein, or a progeny, mutant, or variant thereof, a fermentate produced from a strain disclosed herein progeny, mutant, or variant thereof and a second composition comprising one or more agrochemically active compounds, wherein the first and second composition may inhibit plant pathogens, pests, or insects and/or improve plant performance.

In one embodiment, the first and second compositions can be applied at the same time to a seed, a plant, plant part, or the environment of the plant. In another embodiment, the first composition can be applied to the seed followed by application of the second composition to the seed. In yet another embodiment, the second composition can be applied to the seed followed by, application of the first composition to the seed.

In another embodiment, the first composition can be applied to the plant or plant part followed by application of the second composition to the plant or plant part. In yet another embodiment, the second composition can be applied to the plant or plant part followed by application of the first composition to the plant or plant part.

In another embodiment, the first composition can be applied to the seed and the second composition applied to the plant or plant part. In yet another embodiment, the second composition can be applied to the seed and the first composition applied to the plant or plant part.

In another embodiment, the first composition may be planted on or near the seed in a field. In yet another embodiment, the second composition can be applied to the seed and the first composition applied to the plant or plant part.

In one embodiment, the disclosure relates to the use of a bacterial strain disclosed herein, or a progeny, mutant, or variant thereof, a fermentate produced from a strain disclosed herein, progeny, mutant, or variant thereof, disclosed herein with a composition comprising an insecticidal protein from *Pseudomonas* sp. such as PSEEN3174 (Monalysin; (2011) *PLoS Pathogens* 7:1-13); from *Pseudomonas protegens* strain CHA0 and Pf-5 (previously *fluorescens*) (Pechy-Tarr, (2008) *Environmental Microbiology* 10:2368-2386; GenBank Accession No. EU400157); from *Pseudomonas Taiwanensis* (Liu, et al., (2010) *J. Agric. Food Chem.*, 58:12343-12349) and from *Pseudomonas pseudoalcligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010) *The Open Toxicology Journal*, 3:101-118 and Morgan, et al., (2001) *Applied and Envir. Micro.* 67:2062-2069); U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514; and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry51 and Cry55 classes of δ-endotoxin genes and the *B. thuringiensis* cytolytic Cyt1 and Cyt2 genes. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/ which can be accessed on the world-wide web using the "www" prefix). The insecticidal activity of Cry proteins is well known to one skilled in the art (for review, see, van Frannkenhuyzen, (2009) *J. Invert. Path.* 101:1-16).

In one embodiment the composition comprises a silencing element of one or more polynucleotides of interest resulting in suppression of one or more target pathogen, pest, or insect polypeptides. By "silencing element" is it intended to mean a polynucleotide which when contacted by or ingested by a pest, is capable of reducing or eliminating the level or expression of a target polynucleotide or the polypeptide encoded thereby. The silencing element employed can reduce or eliminate the expression level of the target sequence by influencing the level of the target RNA transcript or, alternatively, by influencing translation and thereby affecting the level of the encoded polypeptide. Silencing elements may include, but are not limited to, a sense suppression element, an antisense suppression element, a double stranded RNA, a siRNA, an amiRNA, a miRNA, or a hairpin suppression element.

Nucleic acid molecules including silencing elements for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. US Patent Application publication 2014/0275208 describes polynucleotide silencing elements targeting RyanR and PAT3. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubulin Homologous Sequence.

Some embodiments comprise an additional component, which may be a carrier, an adjuvant, a solubilizing agent, a suspending agent, a diluent, an oxygen scavenger, an antioxidant, a food material, an anti-contaminant agent, or combinations thereof.

In another embodiment, the additional component(s) may be required for the application to which the strain or composition is to be utilized. For example, if the strain or composition is to be utilized on, or in, an agricultural product, the additional component(s) may be an agriculturally acceptable carrier, excipient, or diluent. Likewise, if the strain or composition is to be utilized on, or in, a foodstuff the additional component(s) may be an edible carrier, excipient or diluent.

In one aspect, the one or more additional component(s) is a carrier, excipient, or diluent. "Carriers" or "vehicles" mean materials suitable for compound administration and include any such material known in the art such as, for example, any liquid, gel, solvent, liquid diluent, solubilizer, or the like, which is non-toxic and does not interact with any components of the composition in a deleterious manner.

Examples of nutritionally acceptable carriers include, for example, water, salt solutions, alcohol, silicone, waxes, petroleum jelly, vegetable oils, polyethylene glycols, propylene glycol, liposomes, sugars, gelatin, lactose, amylose, magnesium stearate, talc, surfactants, silicic acid, viscous paraffin, perfume oil, fatty acid monoglycerides and diglycerides, petroethral fatty acid esters, hydroxymethyl-cellulose, polyvinylpyrrolidone, and the like.

Examples of excipients include but are not limited to: microcrystalline cellulose and other celluloses, lactose, sodium citrate, calcium carbonate, dibasic calcium phosphate, glycine, starch, milk sugar, and high molecular weight polyethylene glycols.

Examples of diluents include but are not limited to: water, ethanol, propylene glycol and glycerin, and combinations thereof.

The other components may be used simultaneously (e.g. when they are in admixture together or even when they are delivered by different routes) or sequentially (e.g. they may be delivered by different routes).

The composition or its diluent may also contain chelating agents such as EDTA, citric acid, tartaric acid, etc. Moreover, the composition or its diluent may contain active agents selected from fatty acids esters, such as mono- and diglycerides, non-ionic surfactants, such as polysorbates, phospholipids, etc. Emulsifiers may enhance the stability of the composition, especially after dilution.

The bacterial strain disclosed herein, or a progeny, mutant, or variant thereof, a fermentate produced from a strain disclosed herein progeny, mutant, or variant thereof may be used in any suitable form—whether when alone or when present in a composition. The compositions may be formulated in any suitable way to ensure that the composition comprises an active compound(s) of interest.

The bacterial strain disclosed herein, or a progeny, mutant, or variant thereof, a fermentate produced from a strain disclosed herein progeny, mutant, or variant thereof compositions thereof may be in the form of a dry powder that can be sprinkled on or mixed in with a product. The compositions in the form of a dry powder may include an additive such as microcrystalline cellulose, gum tragacanth, gelatin, starch, lactose, alginic acid, Primogel, or corn starch (which can be used as a disintegrating agent).

In yet another embodiment, a bacterial strain disclosed herein, or a progeny, mutant, or variant thereof, a fermentate produced from a strain disclosed herein progeny, mutant, or variant thereof compositions disclosed herein can be a spray-dried fermentate re-suspended in $H_2O$ to a percentage selected from the following: 0.05-1, 1-3, 3-5, 5-7, 7-10, 10-15, 15-20, and greater than 20%. In another embodiment, one or more than one clarification step(s) can be performed prior to spray-drying.

In one embodiment, the compositions disclosed herein can comprise concentrated, dried propagules, from the strain disclosed herein. In one embodiment, compositions can be in the range of $1 \times 10^3$ to $1 \times 10^{13}$ CFU/g.

In one embodiment, the compositions disclosed herein can be applied in wet or partially or completely desiccated form or in slurry, gel, or other form.

In at least some embodiments, the compositions disclosed herein can be freeze-dried or lypholized. In at least some embodiments, the compositions can be mixed with a carrier. The carrier includes but is not limited to whey, maltodextrin, sucrose, dextrose, limestone (calcium carbonate), rice hulls, yeast culture, dried starch, clay, and sodium silico aluminate. The compositions can also be used with or without preservatives and in concentrated, un-concentrated, or diluted form. In one embodiment, the compositions can be in the form of a pellet or a biologically pure pellet.

The compositions described herein can be added to one or more carrier. Where used, the carrier(s) and the compositions can be added to a ribbon or paddle mixer and mixed for about 15 minutes, although the timing can be increased or decreased. The components are blended such that a uniform mixture of the culture and carrier(s) is produced. The final product is preferably a dry, flowable powder.

In one embodiment, the compositions may be formulated as a liquid, a dry powder, or a granule. The dry powder or granules may be prepared by means known to those skilled in the art, such as, in top-spray fluid bed coater, in a bottom spray Wurster, or by drum granulation (e.g. high sheer granulation), extrusion, pan coating or in a micro-ingredients mixer.

In another embodiment, the compositions disclosed herein may be provided as a spray-dried or freeze-dried powder.

In yet another embodiment, the compositions are in a liquid formulation. Such liquid consumption may contain one or more of the following: a buffer, salt, sorbitol, and/or glycerol.

In one embodiment, the compositions disclosed herein may be formulated with at least one physiologically acceptable carrier selected from at least one of maltodextrin, calcined (illite) clay, limestone (calcium carbonate), cyclodextrin, wheat or a wheat component, sucrose, starch, $Na_2SO_4$, Talc, PVA, sorbitol, benzoate, sorbiate, glycerol, sucrose, propylene glycol, 1,3-propane diol, glucose, parabens, sodium chloride, citrate, acetate, phosphate, calcium, metabisulfite, formate and mixtures thereof.

In one embodiment, the compositions disclosed herein may be formulated by encapsulation technology to improve stability and as a way to protect the compositions from seed applications. In one embodiment the encapsulation technology may comprise a bead polymer for timed release of the compositions over time. In one embodiment, the encapsulated compositions may be applied in a separate application of beads in-furrow to the seeds. In another embodiment, the encapsulated compositions may be co-applied along with seeds simultaneously.

The coating agent usable for the sustained release microparticles of an encapsulation embodiment may be a substance which is useful for coating the microgranular form with the substance to be supported thereon. Any coating agent which can form a coating difficultly permeable for the supported substance may be used in general, without any particular limitation. For example, higher saturated fatty acid, wax, thermoplastic resin, thermosetting resin and the like may be used.

Examples of useful higher saturated fatty acid include stearic acid, zinc stearate, stearic acid amide and ethylenebis-stearic acid amide; those of wax include synthetic waxes such as polyethylene wax, carbon wax, Hoechst wax, and fatty acid ester; natural waxes such as carnauba wax, bees wax and Japan wax; and petroleum waxes such as paraffin wax and petrolatum. Examples of thermoplastic resin include polyolefins such as polyethylene, polypropylene, polybutene and polystyrene; vinyl polymers such as polyvinyl acetate, polyvinyl chloride, polyvinylidene chloride, polyacrylic acid, polymethacrylic acid, polyacrylate and polymethacrylate; diene polymers such as butadiene polymer, isoprene polymer, chloroprene polymer, butadiene-styrene copolymer, ethylene-propylene-diene copolymer, styrene-isoprene copolymer, MMA-butadiene copolymer and acrylonitrile-butadiene copolymer; polyolefin copolymers such as ethylene-propylene copolymer, butene-ethylene copolymer, butene-propylene copolymer, ethylene-vinyl acetate copolymer, ethylene-acrylic acid copolymer, styreneacrylic acid copolymer, ethylene-methacrylic acid copolymer, ethylene-methacrylic ester copolymer, ethylene-carbon monoxide copolymer, ethylene-vinyl acetate-carbon monoxide copolymer, ethylene-vinyl acetate-vinyl chloride copolymer and ethylene-vinyl acetate-acrylic copolymer; and vinyl chloride copolymers such as vinyl chloride-vinyl acetate copolymer and vinylidene chloride-vinyl chloride copolymer. Examples of thermosetting resin include polyurethane resin, epoxy resin, alkyd resin, unsaturated polyester resin, phenolic resin, urea-melamine resin, urea resin and silicone resin. Of those, thermoplastic acrylic ester resin, butadienestyrene copolymer resin, thermosetting polyurethane resin and epoxy resin are preferred, and among the preferred resins, particularly thermosetting polyurethane resin is preferred. These coating agents can be used either singly or in combination of two or more kinds.

In one embodiment, the compositions may include a seed, a part of a seed, a plant, or a plant part.

All plants, plant parts, seeds or soil may be treated in accordance with the compositions and methods disclosed herein. The compositions disclosed herein may include a plant, a plant part, a seed, a seed part, or soil. The compositions and methods disclosed herein may be applied to the seed, the plant or plant parts, the fruit, or the soil in which the plants grow.

Some embodiments relate to a method for reducing plant pathogen, pest, or insect damage to a plant or plant part comprising: (a) treating a seed with a composition disclosed herein prior to planting. In another embodiment, the method further comprises: (b) treating a plant part obtained from the seed with a composition disclosed herein. The composition used in step (a) may be the same or different than the composition used in step (b).

Some embodiments relate to a method for reducing plant pathogen, pest, or insect damage to a plant or plant part comprising: (a) treating the soil surrounding a seed or plant a bacterial strain disclosed herein, or a progeny, mutant, or variant thereof, a fermentate produced from a strain disclosed herein progeny, mutant, or variant thereof. In another embodiment, the method further comprises: (b) treating a plant part with a bacterial strain disclosed herein, or a progeny, mutant, or variant thereof, a fermentate produced from a strain disclosed herein progeny, mutant, or variant thereof disclosed herein. The bacterial strain disclosed herein, or a progeny, mutant, or variant thereof, a fermentate produced from a strain disclosed herein progeny, mutant, or variant thereof used in step (a) may be the same or different than a bacterial strain disclosed herein, or a progeny, mutant, or variant thereof, a fermentate produced from a strain disclosed herein progeny, mutant, or variant thereof used in step (b).

Some embodiments relate to a method for reducing plant pathogen, pest, or insect damage to a plant or plant part comprising: (a) treating a seed prior to planting with a bacterial strain disclosed herein, or a progeny, mutant, or variant thereof, a fermentate produced from a strain disclosed herein progeny, mutant, or variant thereof disclosed herein. In another embodiment, the method further comprises: (b) treating the soil surrounding the seed or plant with a bacterial strain disclosed herein, or a progeny, mutant, or variant thereof, a fermentate produced from a strain disclosed herein progeny, mutant, or variant thereof disclosed herein. In still another embodiment, the method further comprises: (c) treating a plant part of a plant produced from the seed with a bacterial strain disclosed herein, or a progeny, mutant, or variant thereof, a fermentate produced from a strain disclosed herein progeny, mutant, or variant thereof disclosed herein. The bacterial strain disclosed herein, or a progeny, mutant, or variant thereof, a fermentate produced from a strain disclosed herein progeny, mutant, or variant thereof used in step (a) may be the same or different than the bacterial strain disclosed herein, or a progeny, mutant, or variant thereof, a fermentate produced from a strain disclosed herein progeny, mutant, or variant thereof used in step (b). The bacterial strain disclosed herein, or a progeny, mutant, or variant thereof, a fermentate produced from a strain disclosed herein progeny, mutant, or variant thereof used in step (a) may be the same or different than the bacterial strain disclosed herein, or a progeny, mutant, or variant thereof, a fermentate produced from a strain disclosed herein progeny, mutant, or variant thereof, used in step (c). The bacterial strain disclosed herein, or a progeny, mutant, or variant thereof, a fermentate produced from a strain disclosed herein progeny, mutant, or variant thereof used in step (b) may be the same or different than the bacterial strain disclosed herein, or a progeny, mutant, or variant thereof, a fermentate produced from a strain disclosed herein progeny, mutant, or variant thereof used in step (c).

In one embodiment, wild plant species and plant cultivars, or those obtained by conventional biological breeding, such as crossing or protoplast fusion, and parts thereof, can be treated with a bacterial strain disclosed herein, or a progeny, mutant, or variant thereof, a fermentate produced from a strain disclosed herein progeny, mutant, or variant thereof disclosed herein. In another embodiment, transgenic plants and plant cultivars obtained by genetic engineering, and plant parts thereof, are treated with a bacterial strain disclosed herein, or a progeny, mutant, or variant thereof, a fermentate produced from a strain disclosed herein progeny, mutant, or variant thereof disclosed herein.

In another embodiment, plants or plant cultivars (obtained by plant biotechnology methods such as genetic engineering or editing) that may be treated according to the strains, compositions and methods disclosed herein are herbicide-tolerant plants, i.e. plants made tolerant to one or more given herbicides. Such plants can be obtained either by genetic modification, or by selection of plants containing a mutation imparting such herbicide tolerance. Herbicide-resistant plants are for example glyphosate-tolerant plants, i.e. plants made tolerant to the herbicide glyphosate or salts thereof. Plants can be made tolerant to glyphosate through different means. For example, glyphosate-tolerant plants can be obtained by transforming the plant with a gene encoding the enzyme 5-enolpyruvylshilcimate-3-phosphate synthase (EPSPS).

Plants or plant cultivars (obtained by plant biotechnology methods such as genetic engineering or editing) that may also be treated are insect-resistant genetically modified plants, i.e. plants made resistant to attack by certain target insects. Such plants can be obtained by genetic transformation, or by selection of plants containing a mutation imparting such insect resistance.

In another embodiment, plants or plant cultivars (obtained by plant biotechnology methods such as genetic engineering) that may be treated according to the disclosure are tolerant to abiotic stresses. Such plants can be obtained by genetic transformation, or by selection of plants containing a mutation imparting such stress resistance.

In another embodiment, plants or plant cultivars (obtained by plant biotechnology methods such as genetic engineering or editing) that may be treated according to the disclosure are conventionally bred, by mutagenesis, or genetically engineered to contain a combination or stack of valuable traits, including but not limited to, herbicide tolerance, insect resistance, and abiotic stress tolerance.

The embodiments disclosed herein also apply to plant varieties which will be developed, or marketed, in the future and which have these genetic traits or traits to be developed in the future.

As used herein, applying a bacterial strain disclosed herein, or a progeny, mutant, or variant thereof, a fermentate produced from a strain disclosed herein progeny, mutant, or variant thereof to a seed, a plant, or plant part includes contacting the seed, plant, or plant part directly and/or indirectly with the bacterial strain disclosed herein, or a progeny, mutant, or variant thereof, a fermentate produced from a strain disclosed herein progeny, mutant, or variant thereof. In one embodiment, a bacterial strain disclosed herein, or a progeny, mutant, or variant thereof, a fermentate produced from a strain disclosed herein progeny, mutant, or variant thereof may be directly applied as a spray, a rinse, or a powder, or any combination thereof.

As used herein, a spray refers to a mist of liquid particles that contain a bacterial strain disclosed herein, or a progeny, mutant, or variant thereof, a fermentate produced from a strain disclosed herein progeny, mutant, or variant thereof of the present disclosure. In one embodiment, a spray may be applied to a plant or plant part while a plant or plant part is being grown. In another aspect, a spray may be applied to a plant or plant part while a plant or plant part is being fertilized. In another aspect, a spray may be applied to a plant or plant part while a plant or plant part is being harvested. In another aspect, a spray may be applied to a plant or plant part after a plant or plant part has been harvested. In another aspect, a spray may be applied to a plant or plant part while a plant or plant part is being processed. In another aspect, a spray may be applied to a plant or plant part while a plant or plant part is being packaged. In another aspect, a spray may be applied to a plant or plant part while a plant or plant part is being stored.

In another embodiment, a bacterial strain disclosed herein, or a progeny, mutant, or variant thereof, a fermentate produced from a strain disclosed herein progeny, mutant, or variant thereof disclosed herein may be applied directly to a plant or plant part as a rinse. As used herein, a rinse is a liquid containing a bacterial strain disclosed herein, or a progeny, mutant, or variant thereof, a fermentate produced from a strain disclosed herein progeny, mutant, or variant thereof disclosed herein. Such a rinse may be poured over a plant or plant part. A plant or plant part may also be immersed or submerged in the rinse, then removed and allowed to dry.

In another embodiment, a bacterial strain disclosed herein, or a progeny, mutant, or variant thereof, a fermentate produced from a strain disclosed herein progeny, mutant, or variant thereof may be applied to a plant or plant part and may cover 50% of the surface area of a plant material. In another embodiment, a bacterial strain disclosed herein, or a progeny, mutant, or variant thereof, a fermentate produced from a strain disclosed herein progeny, mutant, or variant thereof may be applied to a plant or plant part and may cover a percentage of the surface area of a plant material selected from the group consisting of: from 50% to about 95%, from 60% to about 95%, from 70% to about 95%, from 80% to about 95%, and from 90% to about 95%.

In another aspect, a bacterial strain disclosed herein, or a progeny, mutant, or variant thereof, a fermentate produced from a strain disclosed herein progeny, mutant, or variant thereof may cover from about 20% to about 30%, from about 30% to about 40%, from about 40% to about 50%, from about 50% to about 60%, from about 60% to about 70%, from about 70% to about 80%, from about 80% to about 90%, from about 90% to about 95%, from about 95% to about 98%, from about 98% to about 99% or 100% of the surface area of a plant or plant part.

In another aspect, a bacterial strain disclosed herein, or a progeny, mutant, or variant thereof, a fermentate produced from a strain disclosed herein progeny, mutant, or variant thereof disclosed herein may be applied directly to a plant or plant part as a powder. As used herein, a powder is a dry or nearly dry bulk solid composed of a large number of very fine particles that may flow freely when shaken or tilted. A dry or nearly dry powder composition disclosed herein preferably contains a low percentage of water, such as, for example, in various aspects, less than 5%, less than 2.5%, or less than 1% by weight.

In another aspect, a composition can be applied indirectly to the plant or plant part. For example, a plant or plant part having a bacterial strain disclosed herein, or a progeny, mutant, or variant thereof, a fermentate produced from a strain disclosed herein progeny, mutant, or variant thereof already applied may be touching a second plant or plant part so that a bacterial strain disclosed herein, or a progeny, mutant, or variant thereof, a fermentate produced from a strain disclosed herein progeny, mutant, or variant thereof rubs off on a second plant or plant part. In a further aspect, a bacterial strain disclosed herein, or a progeny, mutant, or variant thereof, a fermentate produced from a strain disclosed herein progeny, mutant, or variant thereof may be applied using an applicator. In various aspects, an applicator may include, but is not limited to, a syringe, a sponge, a paper towel, or a cloth, or any combination thereof.

A contacting step may occur while a plant material is being grown, while a plant or plant part is being fertilized, while a plant or plant part is being harvested, after a plant or plant part has been harvested, while a plant or plant part is being processed, while a plant or plant part is being packaged, or while a plant or plant part is being stored in warehouse or on the shelf of a store.

In another embodiment, a bacterial strain disclosed herein, or a progeny, mutant, or variant thereof, a fermentate produced from a strain disclosed herein progeny, mutant, or variant thereof disclosed herein may be a colloidal dispersion. A colloidal dispersion is a type of chemical mixture where one substance is dispersed evenly throughout another. Particles of the dispersed substance are only suspended in the mixture, unlike a solution, where they are completely dissolved within. This occurs because the particles in a colloidal dispersion are larger than in a solution—small enough to be dispersed evenly and maintain a homogenous appearance, but large enough to scatter light and not dissolve. Colloidal dispersions are an intermediate between homogeneous and heterogeneous mixtures and are sometimes classified as either "homogeneous" or "heterogeneous" based upon their appearance.

In one embodiment, the bacterial strain disclosed herein, or a progeny, mutant, or variant thereof, a fermentate produced from a strain disclosed herein progeny, mutant, or variant thereof compositions and methods disclosed herein are suitable for use with a seed. In another embodiment, the bacterial strain disclosed herein, or a progeny, mutant, or variant thereof, a fermentate produced from a strain disclosed herein progeny, mutant, or variant thereof compositions and methods disclosed herein are suitable for use with a seed of one or more of any of the plants recited previously.

In still another embodiment, the bacterial strain disclosed herein, or a progeny, mutant, or variant thereof, a fermentate produced from a strain disclosed herein progeny, mutant, or variant thereof compositions and methods disclosed herein can be used to treat transgenic or genetically, modified or edited seed. A transgenic seed refers to the seed of plants containing at least one heterologous gene that allows the expression of a polypeptide or protein not naturally found in the plant. The heterologous gene in transgenic seed can originate, for example, from microorganisms of the species *Bacillus, Rhizobium, Pseudomonas, Serratia, Trichoderma, Clavibacter, Glomus* or *Gliocladium*.

In one embodiment, the seed is treated in a state in which it is sufficiently stable so that the treatment does not cause any damage. In general, treatment of the seed may take place at any point in time between harvesting and sowing. In one embodiment, the seed used is separated from the plant and freed from cobs, shells, stalks, coats, hairs or the flesh of the fruits. Thus, it is possible to use, for example, seed which has been harvested, cleaned and dried. Alternatively, it is also possible to use seed which, after drying, has been treated, for example, with water and then dried again.

In one embodiment, seed is treated with a bacterial strain disclosed herein, or a progeny, mutant, or variant thereof, a fermentate produced from a strain disclosed herein progeny, mutant, or variant thereof compositions and methods disclosed herein in such a way that the germination of the seed is not adversely affected, or that the resulting plant is not damaged.

In one embodiment, a bacterial strain disclosed herein, or a progeny, mutant, or variant thereof, a fermentate produced from a strain disclosed herein progeny, mutant, or variant thereof compositions disclosed herein may be applied directly to the seed. For example, the bacterial strain disclosed herein, or a progeny, mutant, or variant thereof, fermentate produced from a strain disclosed herein progeny, mutant, or variant thereof compositions disclosed herein may be applied without additional components and without having been diluted.

In another embodiment, a bacterial strain disclosed herein, or a progeny, mutant, or variant thereof, a fermentate produced from a strain disclosed herein progeny, mutant, or variant thereof disclosed herein may be applied to the seed in the form of a suitable formulation. Suitable formulations and methods for the treatment of seed are known to the person skilled in the art and are described, for example, in the following documents: U.S. Pat. Nos. 4,272,417 A, 4,245, 432 A, 4,808,430 A, 5,876,739 A, US 2003/0176428 A1, WO 2002/080675 A1, WO 2002/028186 A2.

A bacterial strain disclosed herein, or a progeny, mutant, or variant thereof, a fermentate produced from a strain disclosed herein progeny, mutant, or variant thereof disclosed herein can be converted into customary seed dressing formulations, such as solutions, emulsions, suspensions, powders, foams, slurries or other coating materials for seed, and also ULV formulations. These formulations are prepared in a known manner by mixing A bacterial strain disclosed herein, or a progeny, mutant, or variant thereof, a fermentate produced from a strain disclosed herein progeny, mutant, or variant thereof disclosed herein with customary additives, such as, for example, customary extenders and also solvents or diluents, colorants, wetting agents, dispersants, emulsifiers, defoamers, preservatives, secondary thickeners, adhesives, gibberellins and water as well.

In another embodiment, suitable colorants that may be present in the seed dressing formulations include all colorants customary for such purposes. Use may be made both of pigments, of sparing solubility in water, and of dyes, which are soluble in water. Examples that may be mentioned include the colorants known under the designations Rhodamine B, C.I. Pigment Red 112, and C.I. Solvent Red 1.

In another embodiment, suitable wetting agents that may be present in the seed dressing formulations include all substances that promote wetting and are customary in the formulation of active agrochemical substances. With preference it is possible to use alkylnaphthalene-sulphonates, such as diisopropyl- or diisobutylnaphthalene-sulphonates.

In still another embodiment, suitable dispersants and/or emulsifiers that may be present in the seed dressing formulations include all nonionic, anionic, and cationic dispersants that are customary in the formulation of active agrochemical substances. In one embodiment, nonionic or anionic dispersants or mixtures of nonionic or anionic dispersants can be used. In one embodiment, nonionic dispersants include but are not limited to ethylene oxide-propylene oxide block polymers, alkylphenol polyglycol ethers, and tristyrylphenol polyglycol ethers, and their phosphated or sulphated derivatives.

In still another embodiment, defoamers that may be present in the seed dressing formulations to be used include all foam-inhibiting compounds that are customary in the formulation of agrochemically active compounds including but not limited to silicone defoamers, magnesium stearate, silicone emulsions, long-chain alcohols, fatty acids and their salts and also organofluorine compounds and mixtures thereof.

In still another embodiment, secondary thickeners that may be present in the seed dressing formulations include all compounds which can be used for such purposes in agrochemical compositions, including but not limited to cellulose derivatives, acrylic acid derivatives, polysaccharides, such as xanthan gum or Veegum, modified clays, phyllosilicates, such as attapulgite and bentonite, and also finely divided silicic acids.

Suitable adhesives that may be present in the seed dressing formulations may include all customary binders which can be used in seed dressings. Polyvinylpyrrolidone, polyvinyl acetate, polyvinyl alcohol and tylose may be mentioned as being preferred.

In yet another embodiment, seed dressing formulations may be used directly or after dilution with water beforehand to treat seed of any of a very wide variety of types. The seed dressing formulations or their dilute preparations may also be used to dress seed of transgenic plants. In this context, synergistic effects may also arise in interaction with the substances formed by expression.

Suitable mixing equipment for treating seed with the seed dressing formulations or the preparations prepared from them by adding water includes all mixing equipment that can commonly be used for dressing. The specific procedure adopted when dressing comprises introducing the seed into a mixer, adding the particular desired amount of seed dressing formulation, either as it is or following dilution with water beforehand, and carrying out mixing until the formulation is uniformly distributed on the seed. Optionally, a drying operation follows.

In various embodiments, a bacterial strain disclosed herein, or a progeny, mutant, or variant thereof, a fermentate produced from a strain disclosed herein progeny, mutant, or variant thereof, can be added to the plant, plant part, and/or seed at a rate of about $1\times10^2$ to $1\times10^{13}$ colony forming units (cfu) per seed, including about $1\times10^3$ cfu/seed, or about $1\times10^4$ cfu/seed, $1\times10^5$ cfu/seed, or about $1\times10^6$ cfu/seed, or about $1\times10^7$ cfu/seed, or about $1\times10^8$ cfu/seed, or about $1\times10^9$ cfu/seed, or about $1\times10^{10}$ cfu/seed, or about $1\times10^{11}$ cfu/seed, or about $1\times10^{12}$ cfu/seed, or about $1\times10^{13}$ cfu/seed including about $1\times10^3$ to $1\times10^8$ cfu/seed about $1\times10^3$ to $1\times10^7$ cfu/seed, about $1\times10^3$ to $1\times10^5$ cfu/seed, about $1\times10^3$ to $1\times10^6$ cfu/seed, about $1\times10^3$ to $1\times10^4$ cfu/seed, about $1\times10^3$ to $1\times10^9$ cfu/seed, about $1\times10^3$ to $1\times10^{10}$ cfu/seed, about $1\times10^3$ to $1\times10^{11}$ cfu/seed, about $1\times10^3$ to $1\times10^{12}$ cfu/seed, about $1\times10^3$ to $1\times10^{13}$ cfu/seed, about $1\times10^4$ to $1\times10^8$ cfu/seed about $1\times10^4$ to $1\times10^7$ cfu/seed, about $1\times10^4$ to $1\times10^5$ cfu/seed, about $1\times10^4$ to $1\times10^6$ cfu/seed, about $1\times10^4$ to $1\times10^9$ cfu/seed, about $1\times10^4$ to $1\times10^{10}$ cfu/seed, about $1\times10^{11}$ to $1\times10^9$ cfu/seed, about $1\times10^4$ to $1\times10^{12}$ cfu/seed about $1\times10^4$ to $1\times10^{13}$ cfu/seed, about $1\times10^5$ to $1\times10^7$ cfu/per seed, about $1\times10^5$ to $1\times10^6$ cfu/per seed, about $1\times10^5$ to $1\times10^8$ cfu/per seed, about $1\times10^5$ to $1\times10^9$ cfu/per seed, about $1\times10^5$ to $1\times10^{10}$ cfu/per seed, about $1\times10^5$ to $1\times10^{11}$ cfu/per seed, about $1\times10^5$ to $1\times10^{12}$ cfu/per seed, about $1\times10^5$ to $1\times10^{13}$ cfu/per seed, about $1\times10^6$ to $1\times10^8$ cfu/per seed, about $1\times10^6$ to $1\times10^7$ cfu/per seed, about $1\times10^6$ to $1\times10^9$ cfu/per seed, about $1\times10^6$ to $1\times10^{10}$ cfu/per seed, about $1\times10^6$ to $1\times10^{11}$ cfu/per seed, about $1\times10^6$ to $1\times10^{12}$ cfu/per seed, about $1\times10^6$ to $1\times10^{13}$ cfu/per seed, about $1\times10^7$ to $1\times10^8$ cfu/per seed, about $1\times10^7$ to $1\times10^9$ cfu/per seed, about $1\times10^7$ to $1\times10^{10}$ cfu/per seed, about $1\times10^7$ to $1\times10^{11}$ cfu/per seed, about $1\times10^7$ to $1\times10^{12}$ cfu/per seed, about $1\times10^7$ to $1\times10^{13}$ cfu/per seed, about $1\times10^8$ to $1\times10^9$ cfu/per seed, about $1\times10^8$ to $1\times10^{10}$ cfu/per seed, about $1\times10^8$ to $1\times10^{11}$ cfu/per seed, about $1\times10^8$ to $1\times10^{12}$ cfu/per seed, about $1\times10^8$ to $1\times10^{13}$ cfu/per seed, about $1\times10^9$ to $1\times10^{10}$ cfu/per seed, about $1\times10^9$ to $1\times10^{11}$ cfu/per seed, about $1\times10^9$ to $1\times10^{12}$ cfu/per seed, about $1\times10^9$ to $1\times10^{13}$ cfu/per seed, about $1\times10^{10}$ to $1\times10^{11}$ cfu/per seed, about $1\times10^{10}$ to $1\times10^{12}$ cfu/per seed, about $1\times10^{10}$ to $1\times10^{13}$ cfu/per seed, about $1\times10^{111}$ to $1\times10^{12}$ cfu/per seed, about $1\times10^{11}$ to $1\times10^{13}$ cfu/per seed, and about $1\times10^{12}$ to $1\times10^{13}$ cfu/per seed. As used herein, the tem "colony forming unit" or "cfu" is a unit capable of growing and producing a colony of a microbial strain in favorable conditions.

In one embodiment, a bacterial strain disclosed herein, or a progeny, mutant, or variant thereof, a fermentate produced from a strain disclosed herein progeny, mutant, or variant thereof, may be formulated as a liquid seed treatment. A seed treatment may comprise at least one a bacterial strain disclosed herein, or a progeny, mutant, or variant thereof, a fermentate produced from a strain disclosed herein progeny, mutant, or variant thereof. The seeds are substantially uniformly coated with one or more layers of a bacterial strain disclosed herein, or a progeny, mutant, or variant thereof, a fermentate produced from a strain disclosed herein progeny, mutant, or variant thereof, using conventional methods of mixing, spraying or a combination thereof. Application is done using equipment that accurately, safely, and efficiently applies seed treatment products to seeds. Such equipment uses various types of coating technology such as rotary coaters, drum coaters, fluidized bed techniques, spouted beds, rotary mists or a combination thereof.

In one embodiment, the application is done via either a spinning "atomizer" disk or a spray nozzle that evenly distributes the seed treatment onto the seed as it moves through the spray pattern. In yet another embodiment, the seed is then mixed or tumbled for an additional period of time to achieve additional treatment distribution and drying. The seeds may be primed or unprimed before coating with a composition disclosed herein to increase the uniformity of germination and emergence. In an alternative embodiment, a dry powder composition can be metered onto the moving seed.

In still another embodiment, the seeds may be coated via a continuous or batch coating process. In a continuous coating process, continuous flow equipment simultaneously meters both the seed flow and the seed treatment products. A slide gate, cone and orifice, seed wheel, or weight device (belt or diverter) regulates seed flow. Once the seed flow rate through treating equipment is determined, the flow rate of the seed treatment is calibrated to the seed flow rate in order to deliver the desired dose to the seed as it flows through the seed treating equipment. Additionally, a computer system may monitor the seed input to the coating machine, thereby maintaining a constant flow of the appropriate amount of seed.

In a batch coating process, batch treating equipment weighs out a prescribed amount of seed and places the seed into a closed treating chamber or bowl where the corresponding of seed treatment is then applied. The seed and seed treatment are then mixed to achieve a substantially uniform coating on each seed. This batch is then dumped out of the treating chamber in preparation for the treatment of the next batch. With computer control systems, this batch process is automated enabling it to continuously repeat the batch treating process.

A variety of additives can be added to the seed treatments. Binders can be added and include those composed preferably of an adhesive polymer that can be natural or synthetic without phytotoxic effect on the seed to be coated. A variety of colorants may be employed, including organic chromophores classified as nitroso, nitro, azo, including monoazo, bisazo, and polyazo, diphenylmethane, triarylmethane, xanthene, methane, acridine, thiazole, thiazine, indamine, indophenol, azine, oxazine, anthraquinone, and phthalocyanine. Other additives that can be added include trace nutrients such as salts of iron, manganese, boron, copper, cobalt, molybdenum, and zinc. A polymer or other dust control agent can be applied to retain the treatment on the seed surface.

Other conventional seed treatment additives include, but are not limited to, coating agents, wetting agents, buffering agents, and polysaccharides. At least one agriculturally acceptable carrier can be added to the seed treatment formulation such as water, solids or dry powders. The dry powders can be derived from a variety of materials such as wood barks, calcium carbonate, gypsum, vermiculite, talc, humus, activated charcoal, and various phosphorous compounds.

In one embodiment, the seed coating can comprise of at least one filler, which is an organic or inorganic, natural or synthetic component with which a bacterial strain disclosed herein, or a progeny, mutant, or variant thereof, a fermentate produced from a strain disclosed herein progeny, mutant, or variant thereof described herein is combined to facilitate its application onto the seed. In one embodiment, the filler is an inert solid such as clays, natural or synthetic silicates, silica, resins, waxes, solid fertilizers (for example ammonium salts), natural soil minerals, such as kaolins, clays, talc, lime, quartz, attapulgite, montmorillonite, bentonite, or diatomaceous earths, or synthetic minerals, such as silica, alumina, or silicates, in particular aluminum or magnesium silicates.

In one embodiment, a bacterial strain disclosed herein, or a progeny, mutant, or variant thereof, a fermentate produced from a strain disclosed herein progeny, mutant, or variant thereof disclosed herein may be formulated by encapsulation technology to improve fungal spore stability and as a way to protect the fungal spores from seed applied fungicides. In one embodiment the encapsulation technology may comprise a bead polymer for timed release of fungal spores over time. In one embodiment, the encapsulation technology may comprise a zeolite material. In one embodiment, an encapsulated bacterial strain disclosed herein, or a progeny, mutant, or variant thereof, fermentate produced from a strain disclosed herein progeny, mutant, or variant thereof may be applied in a separate application of beads in-furrow to the seeds. In another embodiment, the encapsulated bacterial strain disclosed herein, or a progeny, mutant, or variant thereof, fermentate produced from a strain disclosed herein progeny, mutant, or variant thereof may be co-applied along with seeds simultaneously.

Insect resistance management (IRM) is the term used to describe practices aimed at reducing the potential for insect pests to become resistant to an insect management tactic. IRM maintenance of Bt (*Bacillus thuringiensis*) derived pesticidal proteins, other pesticidal proteins, a chemical, a biological agent, or other biologicals, is of great importance because of the threat insect resistance poses to the future use of pesticidal plant-incorporated protectants and insecticidal trait technology as a whole. Specific IRM strategies, such as the refuge strategy, mitigate insect resistance to specific insecticidal proteins produced in corn, soybean, cotton, and other crops. However, such strategies result in portions of crops being left susceptible to one or more pests in order to ensure that non-resistant insects develop and become available to mate with any resistant pests produced in protected crops. Accordingly, from a farmer/producer's perspective, it is highly desirable to have as small a refuge as possible and yet still manage insect resistance, in order that the greatest yield be obtained while still maintaining the efficacy of the pest control method used, whether Bt, a different pesticidal protein, chemical, biological agent or other biologicals, some other method, or combinations thereof.

Another strategy to reduce the need for refuge is the pyramiding of traits with different modes of action against a target insect pest. For example, Bt toxins that have different modes of action pyramided in one transgenic plant are able to have reduced refuge requirements due to reduced resistance risk. Different modes of action in a pyramid combination also extend the durability of each trait, as resistance is slower to develop to each trait.

Currently, the size, placement, and management of the refuge are often considered critical to the success of refuge strategies to mitigate insect resistance to the Bt/pesticidal trait produced in corn, cotton, soybean, and other crops. Because of the decrease in yield in refuge planting areas, some farmers choose to eschew the refuge requirements, and others do not follow the size and/or placement requirements. These issues result in either no refuge or a less effective refuge, and a corresponding risk of the increase in the development of resistance pests.

Accordingly, there remains a need for methods for managing pest resistance in a plot of pest resistant crop plants. It would be useful to provide an improved method for the protection of plants, especially corn or other crop plants, from feeding damage by pests. It would be particularly useful if such a method would reduce the required application rate of conventional chemical pesticides, and also if it would limit the number of separate field operations that were required for crop planting and cultivation. In addition, it would be useful to have a method of deploying a biocontrol agent that increases the durability of an insecticidal trait or increases the efficacy of many resistance management strategies.

One embodiment relates to a method of reducing or preventing the resistance of pests to a plant pesticidal composition comprising providing a plant protection composition, such as a Bt pesticidal protein, a transgenic pesticidal protein, other pesticidal proteins, chemical pesticides, or pesticidal biological entomopathogens, to a plant and/or plant part or a planted area or insecticidal trait and providing a bacterial strain disclosed herein, or a progeny, mutant, or variant thereof, a fermentate produced from a strain disclosed herein progeny, mutant, or variant thereof described herein to the plant and/or plant part or planted area. Another embodiment relates to a method of reducing or preventing the resistance to a plant insecticidal trait comprising providing or contacting a plant with a bacterial strain disclosed herein, or a progeny, mutant, or variant thereof, a fermentate produced from a strain disclosed herein progeny, mutant, or variant thereof described herein.

A further embodiment relates to a method of increasing the durability of plant pest compositions comprising providing a plant protection composition to a plant or planted area, and providing a bacterial strain disclosed herein, or a progeny, mutant, or variant thereof, a fermentate produced from a strain disclosed herein progeny, mutant, or variant thereof described herein to the plant or planted area, wherein the bacterial strain disclosed herein, or a progeny, mutant, or variant thereof, fermentate produced from a strain disclosed herein progeny, mutant, or variant thereof described herein have a different mode of action than the plant protection composition.

In a still further embodiment, the refuge required may be reduced or eliminated by the presence of a bacterial strain disclosed herein, or a progeny, mutant, or variant thereof, a fermentate produced from a strain disclosed herein progeny, mutant, or variant thereof described herein applied to the non-refuge plants. In another embodiment, the refuge may include a bacterial strain disclosed herein, or a progeny, mutant, or variant thereof, a fermentate produced from a strain disclosed herein progeny, mutant, or variant thereof described herein as a spray, bait, or as a different mode of action.

In one embodiment, a composition comprises a bacterial strain disclosed herein, or a progeny, mutant, or variant thereof, a fermentate produced from a strain disclosed herein progeny, mutant, or variant thereof disclosed herein and a non-Bt insecticidal trait increases resistance to a pathogen, pest, or insect. In another embodiment, the non-Bt insecticidal trait comprises a plant-derived insecticidal protein, a bacterial/archeal-derived insecticidal protein not from a Bt (such as a *Pseudomonas* insecticidal protein), an animal-derived insecticidal protein, or a silencing element. In another embodiment, a composition comprising a bacterial strain disclosed herein, or a progeny, mutant, or variant thereof, a fermentate produced from a strain disclosed herein progeny, mutant, or variant thereof disclosed herein and a non-Bt insecticidal trait increases durability of the non-Bt insecticidal trait. In another embodiment, the non-Bt insecticidal trait comprises a PIP-72 polypeptide of PCT Serial Number PCT/US14/55128. In another embodiment, the non-Bt insecticidal trait comprises a polynucleotide silencing elements targeting RyanR (DvSSJ) (US Patent Application publication 2014/0275208). In another embodiment, the non-Bt insecticidal trait comprises a polynucleotide silencing elements targeting RyanR (DvSSJ) (US Patent Application publication 2014/0275208, herein incorporated by reference in its entirety) and a PIP-72 polypeptide of PCT Serial Number PCT/US14/55128, herein incorporated by reference in its entirety.

In another embodiment, a composition comprising a bacterial strain disclosed herein, or a progeny, mutant, or variant thereof, a fermentate produced from a strain disclosed herein progeny, mutant, or variant thereof disclosed herein and a fungal entomopathogen disclosed in U.S. Pat. No. 9,993,006, herein incorporated by reference in its entirety.

In some embodiments, a composition comprises a bacterial strain disclosed herein, or a progeny, mutant, or variant thereof, a fermentate produced from a strain disclosed herein progeny, mutant, or variant thereof disclosed herein and a Bt insecticidal trait that increases resistance to a pathogen, pest, or insect. A Bt insecticidal trait may have activity to Coleopteran, Lepidopteran, or Hemipteran plant pests. The compositions disclosed herein may provide to a plant or plant part additive or synergistic resistance to a pathogen, pest, or insect plant in combination with a Bt insecticidal trait. In one embodiment, a composition comprises a bacterial strain disclosed herein, or a progeny, mutant, or variant thereof, a fermentate produced from a strain disclosed herein progeny, mutant, or variant thereof disclosed herein and a Bt insecticidal trait, wherein the Bt insecticidal trait comprises a Cry3B toxin disclosed in U.S. Pat. Nos. 8,101,826, 6,551,962, 6,586,365, 6,593,273, and PCT Publication WO 2000/011185, a mCry3B toxin disclosed in U.S. Pat. Nos. 8,269,069, and 8,513,492, a mCry3A toxin disclosed in U.S. Pat. Nos. 8,269,069, 7,276,583 and 8,759,620, or a Cry34/35 toxin disclosed in U.S. Pat. Nos. 7,309,785, 7,524,810, 7,985,893, 7,939,651 and 6,548,291, and transgenic events containing these Bt insecticidal toxins and other Coleopteran active Bt insecticidal traits for example, event MON863 disclosed in U.S. Pat. No. 7,705,216, event MIR604 disclosed in U.S. Pat. No. 8,884,102, event 5307 disclosed in U.S. Pat. No. 9,133,474, event DAS-59122 disclosed in U.S. Pat. No. 7,875,429, event DP-4114 disclosed in U.S. Pat. No. 8,575,434, event MON87411 disclosed in US Published Patent Application Number 2013/0340111, and event MON88017 disclosed in U.S. Pat. No. 8,686,230 all of which are incorporated herein by reference. All publications, patents and patent applications mentioned in the specification indicate the level of those skilled in the art to which this disclosure pertains. All publications, patents and patent applications are incorporated by reference to the same extent as if each individual publication, patent or patent application was specifically and individually indicated to be incorporated by reference.

IPD126 Proteins and Variants and Fragments Thereof

IPD126 polypeptides are encompassed by the disclosure as set forth in SEQ ID NOs: 19-36. "IPD126 polypeptide," and "IPD126 protein" as used herein interchangeably refers to a polypeptide(s) having insecticidal activity including but not limited to insecticidal activity against one or more insect pests of the Lepidoptera, Hemiptera, and/or Coleoptera orders. A variety of IPD126 polypeptides are contemplated.

"Sufficiently identical" is used herein to refer to an amino acid sequence that has at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity. In one embodiment the IPD126 polypeptide has at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity compared to any one of SEQ ID NOs: 19-36. The term "about" when used herein in context with percent sequence identity means +/−1.0%.

A "recombinant protein" is used herein to refer to a protein that is no longer in its natural environment, for example in vitro or in a recombinant bacterial or plant host cell.

"Fragments" or "biologically active portions" include polypeptide fragments comprising amino acid sequences sufficiently identical to an IPD126 polypeptide and that exhibit insecticidal activity. "Fragments" or "biologically active portions" of IPD126 polypeptides includes fragments comprising amino acid sequences sufficiently identical to the amino acid sequence set forth in any one of SEQ ID NOs: 19-36 wherein the IPD126 polypeptide has insecticidal activity. Such biologically active portions can be prepared by recombinant techniques and evaluated for insecticidal activity.

"Variants" as used herein refers to proteins or polypeptides having an amino acid sequence that is at least about 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, 99% or greater identical to the parental amino acid sequence.

In some embodiments an IPD126 polypeptide comprises an amino acid sequence having at least about 40%, 45%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity to the full length or a fragment of the amino acid sequence of any one of SEQ ID NOs: 19-36, wherein the IPD126 polypeptide has insecticidal activity.

In some embodiments an IPD126 polypeptide comprises an amino acid sequence of any one or more of SEQ ID NOS: 19-36 having 1, 2, 3, 4, 5, 6, 7, 8, 9, 10 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95 or more amino acid substitutions compared to the amino acid at the corresponding position of any one or more of the respective SEQ ID NOS: 19-36.

Methods for such manipulations are generally known in the art. For example, amino acid sequence variants of an IPD126 polypeptide can be prepared by mutations in the DNA. This may also be accomplished by one of several forms of mutagenesis, such as for example site-specific double strand break technology, and/or in directed evolution. In some aspects, the changes encoded in the amino acid sequence will not substantially affect the function of the protein. Such variants will possess a desired pesticidal activity. However, it is understood that the ability of an IPD126 polypeptide to confer pesticidal activity or other polypeptide physical property may be improved or altered by the use of such techniques upon the compositions of this disclosure.

Conservative amino acid substitutions may be made at one or more predicted nonessential amino acid residues. A "nonessential" amino acid residue is a residue that can be altered from the wild-type sequence of an IPD126 polypeptide without altering the biological activity. A "conservative amino acid substitution" is one in which the amino acid residue is replaced with an amino acid residue having a similar side chain. Families of amino acid residues having similar side chains have been defined in the art. These families include: amino acids with basic side chains (e.g., lysine, arginine, histidine); acidic side chains (e.g., aspartic acid, glutamic acid); polar, negatively charged residues and their amides (e.g., aspartic acid, asparagine, glutamic, acid, glutamine; uncharged polar side chains (e.g., glycine, asparagine, glutamine, serine, threonine, tyrosine, cysteine); small aliphatic, nonpolar or slightly polar residues (e.g., Alanine, serine, threonine, proline, glycine); nonpolar side chains (e.g., alanine, valine, leucine, isoleucine, proline, phenylalanine, methionine, tryptophan); large aliphatic, nonpolar residues (e.g., methionine, leucine, isoleucine, valine, cystine); beta-branched side chains (e.g., threonine, valine, isoleucine); aromatic side chains (e.g., tyrosine, phenylalanine, tryptophan, histidine); large aromatic side chains (e.g., tyrosine, phenylalanine, tryptophan).

Amino acid substitutions may be made in nonconserved regions that retain function. In general, such substitutions would not be made for conserved amino acid residues or for amino acid residues residing within a conserved motif, where such residues are essential for protein activity. Examples of residues that are conserved and that may be essential for protein activity include, for example, residues that are identical between all proteins contained in an alignment of similar or related toxins to the sequences of the embodiments (e.g., residues that are identical in an alignment of homologous proteins). Examples of residues that are conserved but that may allow conservative amino acid substitutions and still retain activity include, for example, residues that have only conservative substitutions between all proteins contained in an alignment of similar or related toxins to the sequences of the embodiments (e.g., residues that have only conservative substitutions between all proteins contained in the alignment homologous proteins). However, one of skill in the art would understand that functional variants may have minor conserved or nonconserved alterations in the conserved residues.

Variant nucleotide and amino acid sequences of the disclosure also encompass sequences derived from mutagenic and recombinogenic procedures such as DNA shuffling. With such a procedure, one or more different IPD126 polypeptide coding regions can be used to create a new IPD126 polypeptide possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between a pesticidal gene and other known pesticidal genes to obtain a new gene coding for a protein with an improved property of interest, such as an increased insecticidal activity. Strategies for such DNA shuffling are known in the art. See, for example, Stemmer, (1994) *Proc. Natl. Acad. Sci. USA* 91:10747-10751; Stemmer, (1994) *Nature* 370:389-391; and U.S. Pat. Nos. 5,605,793 and 5,837,458.

In some embodiments, chimeric polypeptides are provided comprising regions of at least two different IPD126 polypeptides selected from any one or more of SEQ ID NOS: 19-36.

Nucleic Acid Molecules, and Variants and Fragments Thereof

Isolated or recombinant nucleic acid molecules comprising nucleic acid sequences encoding IPD126 polypeptides or biologically active portions thereof, as well as nucleic acid molecules sufficient for use as hybridization probes to identify nucleic acid molecules encoding proteins with regions of sequence homology are provided. As used herein, the term "nucleic acid molecule" refers to DNA molecules (e.g., recombinant DNA, cDNA, genomic DNA, plastid DNA, mitochondrial DNA) and RNA molecules (e.g., mRNA) and analogs of the DNA or RNA generated using nucleotide analogs. The nucleic acid molecule can be single-stranded or double-stranded, but preferably is double-stranded DNA.

An "isolated" nucleic acid molecule (or DNA) is used herein to refer to a nucleic acid sequence (or DNA) that is no longer in its natural environment, for example in vitro. A "recombinant" nucleic acid molecule (or DNA) is used herein to refer to a nucleic acid sequence (or DNA) that is in a recombinant bacterial or plant host cell. In some embodiments, an "isolated" or "recombinant" nucleic acid is free of sequences (preferably protein encoding sequences) that naturally flank the nucleic acid (i.e., sequences located at the 5' and 3' ends of the nucleic acid) in the genomic DNA of the organism from which the nucleic acid is derived. For purposes of the disclosure, "isolated" or "recombinant" when used to refer to nucleic acid molecules excludes isolated chromosomes. For example, in various embodiments, the recombinant nucleic acid molecules encoding IPD126 polypeptides can contain less than about 5 kb, 4 kb, 3 kb, 2 kb, 1 kb, 0.5 kb or 0.1 kb of nucleic acid sequences that naturally flank the nucleic acid molecule in genomic DNA of the cell from which the nucleic acid is derived.

In some embodiments an isolated nucleic acid molecule encoding IPD126 polypeptides has one or more change in the nucleic acid sequence compared to the native or genomic nucleic acid sequence. In some embodiments the change in the native or genomic nucleic acid sequence includes but is not limited to: changes in the nucleic acid sequence due to the degeneracy of the genetic code; changes in the nucleic acid sequence due to the amino acid substitution, insertion, deletion and/or addition compared to the native or genomic sequence; removal of one or more intron; deletion of one or more upstream or downstream regulatory regions; and deletion of the 5' and/or 3' untranslated region associated with the genomic nucleic acid sequence. In some embodiments the nucleic acid molecule encoding an IPD126 polypeptide is a non-genomic sequence.

A variety of polynucleotides that encode IPD126 polypeptides or related proteins are contemplated. Such polynucleotides are useful for production of IPD126 polypeptides in host cells when operably linked to a suitable promoter, transcription termination and/or polyadenylation sequences. Such polynucleotides are also useful as probes for isolating homologous or substantially homologous polynucleotides that encode IPD126 polypeptides or related proteins.

The polynucleotides of any one or more of SEQ ID NOS: 1-18, can be used to express IPD126 polypeptides in recombinant bacterial hosts that include but are not limited to *Agrobacterium, Bacillus, Escherichia, Salmonella, Lysinibacillus, Acetobacter, Pseudomonas* and *Rhizobium* bacterial host cells. The polynucleotides are also useful as probes for isolating homologous or substantially homologous polynucleotides encoding IPD126 polypeptides or related proteins. Such probes can be used to identify homologous or substantially homologous polynucleotides, or portions thereof, derived from *Bacillus thurengiensis.*

Polynucleotides encoding IPD126 polypeptides can also be synthesized de novo from an IPD126 polypeptide sequence. The sequence of the polynucleotide gene can be deduced from an IPD126 polypeptide sequence through use of the genetic code. Computer programs such as "Back-Translate" (GCG™ Package, Acclerys, Inc. San Diego, Calif) can be used to convert a peptide sequence to the corresponding nucleotide sequence encoding the peptide. Examples of IPD126 polypeptide sequences that can be used to obtain corresponding nucleotide encoding sequences include, but are not limited to the IPD126 polypeptides of SEQ ID NOS: 19-36. Furthermore, synthetic IPD126 polynucleotide sequences of the disclosure can be designed so that they will be expressed in plants.

In some embodiments the nucleic acid molecule encoding a IPD126 polypeptide is a polynucleotide having the sequence set forth in any one of SEQ ID NOS: 1-18, and variants, fragments and complements thereof. "Complement" is used herein to refer to a nucleic acid sequence that is sufficiently complementary to a given nucleic acid sequence such that it can hybridize to the given nucleic acid sequence to thereby form a stable duplex. "Polynucleotide sequence variants" is used herein to refer to a nucleic acid sequence that except for the degeneracy of the genetic code encodes the same polypeptide.

In some embodiments the nucleic acid molecule encoding the IPD126 polypeptide is a non-genomic nucleic acid sequence. As used herein a "non-genomic nucleic acid sequence" or "non-genomic nucleic acid molecule" or "non-genomic polynucleotide" refers to a nucleic acid molecule that has one or more change in the nucleic acid sequence compared to a native or genomic nucleic acid sequence. In some embodiments the change to a native or genomic nucleic acid molecule includes but is not limited to: changes in the nucleic acid sequence due to the degeneracy of the genetic code; optimization of the nucleic acid sequence for expression in plants; changes in the nucleic acid sequence to introduce at least one amino acid substitution, insertion, deletion and/or addition compared to the native or genomic sequence; removal of one or more intron associated with the genomic nucleic acid sequence; insertion of one or more heterologous introns; deletion of one or more upstream or downstream regulatory regions associated with the genomic nucleic acid sequence; insertion of one or more heterologous upstream or downstream regulatory regions; deletion of the 5' and/or 3' untranslated region associated with the genomic nucleic acid sequence; insertion of a heterologous 5' and/or 3' untranslated region; and modification of a polyadenylation site. In some embodiments the non-genomic nucleic acid molecule is a synthetic nucleic acid sequence.

In some embodiments the nucleic acid molecule encoding a IPD126 polypeptide disclosed herein is a non-genomic polynucleotide having a nucleotide sequence having at least 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or greater sequence identity, to the nucleic acid sequence of any one of SEQ ID NOS: 1-18, wherein the IPD126 polypeptide has insecticidal activity.

In some embodiments the nucleic acid molecule encodes an IPD126 polypeptide variant comprising one or more amino acid substitutions to the amino acid sequence of any one of SEQ ID NOS: 19-36.

Nucleic acid molecules that are fragments of these nucleic acid sequences encoding IPD126 polypeptides are also encompassed by the embodiments. "nucleotide fragment" as used herein refers to a portion of the nucleic acid sequence encoding an IPD126 polypeptide. A nucleotide fragment of a nucleic acid sequence may encode a biologically active portion of an IPD126 polypeptide or it may be a fragment that can be used as a hybridization probe or PCR primer using methods disclosed below. Nucleic acid molecules that are fragments of a nucleic acid sequence encoding an IPD126 polypeptide comprise at least about 150, 180, 210, 240, 270, 300, 330, 360, 400, 450, or 500 contiguous nucleotides or up to the number of nucleotides present in a full-length nucleic acid sequence encoding an IPD126 polypeptide disclosed herein, depending upon the intended use. "Contiguous nucleotides" is used herein to refer to nucleotide residues that are immediately adjacent to one another. Fragments of the nucleic acid sequences of the embodiments will encode protein fragments that retain the biological activity of the IPD126 polypeptide and, hence, retain insecticidal activity. "Retains insecticidal activity" is used herein to refer to a polypeptide having at least about 10%, at least about 30%, at least about 50%, at least about 70%, 80%, 90%, 95% or higher of the insecticidal activity of any one of the full-length IPD126 polypeptides set forth in SEQ ID NOS: 19-36. In some embodiments, the insecticidal activity is against a Lepidopteran species. In one embodiment, the insecticidal activity is against a Coleopteran species. In some embodiments, the insecticidal activity is against one or more insect pests of the corn rootworm complex: western corn rootworm, *Diabrotica virgifera*; northern corn rootworm, *D. barberi*: Southern corn rootworm or spotted cucumber beetle; *Diabrotica undecimpunctata howardi, Diabrotica speciosa*, and the Mexican corn rootworm, *D. virgifera zeae*. In one embodiment, the insecticidal activity is against a *Diabrotica* species.

In some embodiments the IPD126 polypeptide is encoded by a nucleic acid sequence sufficiently homologous to any one of the nucleic acid sequences of SEQ ID NOS: 1-18.

“Percent (%) sequence identity” with respect to a reference sequence (subject) is determined as the percentage of amino acid residues or nucleotides in a candidate sequence (query) that are identical with the respective amino acid residues or nucleotides in the reference sequence, after aligning the sequences and introducing gaps, if necessary, to achieve the maximum percent sequence identity, and not considering any amino acid conservative substitutions as part of the sequence identity. Alignment for purposes of determining percent sequence identity can be achieved in various ways that are within the skill in the art, for instance, using publicly available computer software such as BLAST, BLAST-2. Those skilled in the art can determine appropriate parameters for aligning sequences, including any algorithms needed to achieve maximal alignment over the full length of the sequences being compared. The percent identity between the two sequences is a function of the number of identical positions shared by the sequences (e.g., percent identity of query sequence=number of identical positions between query and subject sequences/total number of positions of query sequence×100).

In some embodiments an IPD126 polynucleotide encodes an IPD126 polypeptide comprising an amino acid sequence having at least about 80%, 81%, 82%, 83%, 84%, 85%, 86%, 87%, 88%, 89%, 90%, 91%, 92%, 93%, 94%, 95%, 96%, 97%, 98%, 99% or greater sequence identity across the entire length of the amino acid sequence of any one of SEQ ID NOS: 19-36.

In some embodiments polynucleotides are provided encoding chimeric polypeptides comprising regions of at least two different IPD126 polypeptides of the disclosure.

The embodiments also encompass nucleic acid molecules encoding IPD126 polypeptide variants. “Variants” of the IPD126 polypeptide encoding nucleic acid sequences include those sequences that encode the IPD126 polypeptides disclosed herein but that differ conservatively because of the degeneracy of the genetic code as well as those that are sufficiently identical as discussed above. Naturally occurring allelic variants can be identified with the use of well-known molecular biology techniques, such as polymerase chain reaction (PCR) and hybridization techniques as outlined below. Variant nucleic acid sequences also include synthetically derived nucleic acid sequences that have been generated, for example, by using site-directed mutagenesis but which still encode the IPD126 polypeptides disclosed as discussed below.

The present disclosure provides isolated or recombinant polynucleotides that encode any of the IPD126 polypeptides disclosed herein. Those having ordinary skill in the art will readily appreciate that due to the degeneracy of the genetic code, a multitude of nucleotide sequences encoding IPD126 polypeptides of the present disclosure exist.

The skilled artisan will further appreciate that changes can be introduced by mutation of the nucleic acid sequences thereby leading to changes in the amino acid sequence of the encoded IPD126 polypeptides, without altering the biological activity of the proteins. Thus, variant nucleic acid molecules can be created by introducing one or more nucleotide substitutions, additions and/or deletions into the corresponding nucleic acid sequence disclosed herein, such that one or more amino acid substitutions, additions or deletions are introduced into the encoded protein. Mutations can be introduced by standard techniques, such as site-directed mutagenesis and PCR-mediated mutagenesis. Such variant nucleic acid sequences are also encompassed by the present disclosure.

The polynucleotides of the disclosure and fragments thereof are optionally used as substrates for a variety of recombination and recursive recombination reactions, in addition to standard cloning methods as set forth in, e.g., Ausubel, Berger and Sambrook, i.e., to produce additional pesticidal polypeptide homologues and fragments thereof with desired properties. A variety of such reactions are known. Methods for producing a variant of any nucleic acid listed herein comprising recursively recombining such polynucleotide with a second (or more) polynucleotide, thus forming a library of variant polynucleotides are also embodiments of the disclosure, as are the libraries produced, the cells comprising the libraries and any recombinant polynucleotide produced by such methods. Additionally, such methods optionally comprise selecting a variant polynucleotide from such libraries based on pesticidal activity, as is wherein such recursive recombination is done in vitro or in vivo.

The nucleotide sequences of the embodiments can also be used to isolate corresponding sequences from a bacterial source. In this manner, methods such as PCR, hybridization, and the like can be used to identify such sequences based on their sequence homology to the sequences set forth herein. Sequences that are selected based on their sequence identity to the entire sequences set forth herein or to fragments thereof are encompassed by the embodiments. Such sequences include sequences that are orthologs of the disclosed sequences. The term “orthologs” refers to genes derived from a common ancestral gene and which are found in different species as a result of speciation. Genes found in different species are considered orthologs when their nucleotide sequences and/or their encoded protein sequences share substantial identity as defined elsewhere herein. Functions of orthologs are often highly conserved among species.

To identify potential IPD126 polypeptides from bacterium collections, the bacterial cell lysates can be screened with antibodies generated against IPD126 using Western blotting and/or ELISA methods. This type of assay can be performed in a high throughput fashion. Positive samples can be further analyzed by various techniques such as antibody based protein purification and identification. Methods of generating antibodies are well known in the art as discussed infra.

In hybridization methods, all or part of the pesticidal nucleic acid sequence can be used to screen cDNA or genomic libraries. Methods for construction of such cDNA and genomic libraries are generally known in the art and are disclosed in Sambrook and Russell, (2001), supra. The so-called hybridization probes may be genomic DNA fragments, cDNA fragments, RNA fragments or other oligonucleotides and may be labeled with a detectable group such as 32P or any other detectable marker, such as other radio-isotopes, a fluorescent compound, an enzyme or an enzyme co-factor. Probes for hybridization can be made by labeling synthetic oligonucleotides based on the IPD126 polypeptide-encoding nucleic acid sequences disclosed herein. Degenerate primers designed on the basis of conserved nucleotides or amino acid residues in the nucleic acid sequence or encoded amino acid sequence can additionally be used. The probe typically comprises a region of nucleic acid sequence that hybridizes under stringent conditions to at least about 12, at least about 25, at least about 50, 75, 100, 125, 150, 175 or 200 consecutive nucleotides of nucleic acid sequences encoding IPD126 polypeptides of the disclosure or a fragment or variant thereof. Methods for the preparation of probes for hybridization and stringency conditions are generally known in the art and are disclosed in Sambrook and Russell, (2001), supra, herein incorporated by reference.

Antibodies

Antibodies to an IPD126 polypeptide of the embodiments or to variants or fragments thereof are also encompassed. The antibodies of the disclosure include polyclonal and monoclonal antibodies as well as fragments thereof which retain their ability to bind to an IPD126 polypeptide. An antibody, monoclonal antibody or fragment thereof is said to be capable of binding a molecule if it is capable of specifically reacting with the molecule to thereby bind the molecule to the antibody, monoclonal antibody or fragment thereof. The term “antibody” (Ab) or “monoclonal antibody” (Mab) is meant to include intact molecules as well as fragments or binding regions or domains thereof (such as, for example, Fab and F(ab).sub.2 fragments) which are capable of binding hapten. Such fragments are typically produced by proteolytic cleavage, such as papain or pepsin. Alternatively, hapten-binding fragments can be produced through the application of recombinant DNA technology or through synthetic chemistry. Methods for the preparation of the antibodies of the present disclosure are generally known in the art. For example, see, Antibodies, A Laboratory Manual, Ed Harlow and David Lane (eds.) Cold Spring Harbor Laboratory, N.Y. (1988), as well as the references cited therein. Standard reference works setting forth the general principles of immunology include: Klein, J. Immunology: The Science of Cell-Noncell Discrimination, John Wiley & Sons, N.Y. (1982); Dennett, et al., Monoclonal Antibodies, Hybridoma: A New Dimension in Biological Analyses, Plenum Press, N.Y. (1980) and Campbell, “Monoclonal Antibody Technology,” In Laboratory Techniques in Biochemistry and Molecular Biology, Vol. 13, Burdon, et al., (eds.), Elsevier, Amsterdam (1984). See also, U.S. Pat. Nos. 4,196,265; 4,609,893; 4,713,325; 4,714,681; 4,716,111; 4,716,117 and 4,720,459. Antibodies against IPD126 polypeptides or antigen-binding portions thereof can be produced by a variety of techniques, including conventional monoclonal antibody methodology, for example the standard somatic cell hybridization technique of Kohler and Milstein, (1975) *Nature* 256:495. Other techniques for producing monoclonal antibody can also be employed such as viral or oncogenic transformation of B lymphocytes. An animal system for preparing hybridomas is a murine system. Immunization protocols and techniques for isolation of immunized splenocytes for fusion are known in the art. Fusion partners (e.g., murine myeloma cells) and fusion procedures are also known. The antibody and monoclonal antibodies of the disclosure can be prepared by utilizing an IPD126 polypeptide as antigens.

A kit for detecting the presence of an IPD126 polypeptide or detecting the presence of a nucleotide sequence encoding an IPD126 polypeptide in a sample is provided. In one embodiment, the kit provides antibody-based reagents for detecting the presence of an IPD126 polypeptide in a tissue sample. In another embodiment, the kit provides labeled nucleic acid probes useful for detecting the presence of one or more polynucleotides encoding an IPD126 polypeptide. The kit is provided along with appropriate reagents and controls for carrying out a detection method, as well as instructions for use of the kit.

Receptor Identification and Isolation

Receptors to the IPD126 polypeptides of the embodiments or to variants or fragments thereof are also encompassed. Methods for identifying receptors are known in the art (see, Hofmann, et. al., (1988) *Eur. J. Biochem.* 173:85-91; Gill, et al., (1995) *J. Biol. Chem.* 27277-27282) and can be employed to identify and isolate the receptor that recognizes the IPD126 polypeptide using the brush-border membrane vesicles from susceptible insects. In addition to the radioactive labeling method listed in the cited literatures, an IPD126 polypeptide can be labeled with fluorescent dye and other common labels such as streptavidin. Brush-border membrane vesicles (BBMV) of susceptible insects such as soybean looper and stink bugs can be prepared according to the protocols listed in the references of Hofmann and Gill above and separated on SDS-PAGE gel and blotted on suitable membrane. Labeled IPD126 polypeptide can be incubated with blotted membrane of BBMV and labeled IPD126 polypeptide can be identified with the labeled reporters. Identification of protein band(s) that interact with the IPD126 polypeptide can be detected by N-terminal amino acid gas phase sequencing or mass spectrometry based protein identification method (Patterson, (1998) 10.22, 1-24, Current Protocol in Molecular Biology published by John Wiley & Son Inc). Once the protein is identified, the corresponding gene can be cloned from genomic DNA or cDNA library of the susceptible insects and binding affinity can be measured directly with the IPD126 polypeptide. Receptor function for insecticidal activity by the IPD126 polypeptide can be verified by RNAi type of gene knock out method (Rajagopal, et al., (2002) *J. Biol. Chem.* 277:46849-46851).

Nucleotide Constructs, Expression Cassettes and Vectors

The use of the term “nucleotide constructs” herein is not intended to limit the embodiments to nucleotide constructs comprising DNA. Those of ordinary skill in the art will recognize that nucleotide constructs, particularly polynucleotides and oligonucleotides composed of ribonucleotides and combinations of ribonucleotides and deoxyribonucleotides, may also be employed in the methods disclosed herein. The nucleotide constructs, nucleic acids, and nucleotide sequences of the embodiments additionally encompass all complementary forms of such constructs, molecules, and sequences. Further, the nucleotide constructs, nucleotide molecules, and nucleotide sequences of the embodiments encompass all nucleotide constructs, molecules, and sequences which can be employed in the methods of the embodiments for transforming plants including, but not limited to, those comprised of deoxyribonucleotides, ribonucleotides, and combinations thereof. Such deoxyribonucleotides and ribonucleotides include both naturally occurring molecules and synthetic analogues. The nucleotide constructs, nucleic acids, and nucleotide sequences of the embodiments also encompass all forms of nucleotide constructs including, but not limited to, single-stranded forms, double-stranded forms, hairpins, stem-and-loop structures and the like.

A further embodiment relates to a transformed organism such as an organism selected from plant and insect cells, bacteria, yeast, baculovirus, protozoa, nematodes and algae. The transformed organism comprises a DNA molecule of the embodiments, an expression cassette comprising the DNA molecule or a vector comprising the expression cassette, which may be stably incorporated into the genome of the transformed organism.

The sequences of the embodiments are provided in DNA constructs for expression in the organism of interest. The construct will include 5' and 3' regulatory sequences operably linked to a sequence of the embodiments. The term "operably linked" as used herein refers to a functional linkage between a promoter and a second sequence, wherein the promoter sequence initiates and mediates transcription of the DNA sequence corresponding to the second sequence. Generally, operably linked means that the nucleic acid sequences being linked are contiguous and where necessary to join two protein coding regions in the same reading frame. The construct may additionally contain at least one additional gene to be cotransformed into the organism. Alternatively, the additional gene(s) can be provided on multiple DNA constructs.

Such a DNA construct is provided with a plurality of restriction sites for insertion of the IPD126 polypeptide gene sequence of the disclosure to be under the transcriptional regulation of the regulatory regions. The DNA construct may additionally contain selectable marker genes.

The DNA construct will generally include in the 5' to 3' direction of transcription: a transcriptional and translational initiation region (i.e., a promoter), a DNA sequence of the embodiments, and a transcriptional and translational termination region (i.e., termination region) functional in the organism serving as a host. The transcriptional initiation region (i.e., the promoter) may be native, analogous, foreign or heterologous to the host organism and/or to the sequence of the embodiments. Additionally, the promoter may be the natural sequence or alternatively a synthetic sequence. The term "foreign" as used herein indicates that the promoter is not found in the native organism into which the promoter is introduced. Where the promoter or any other nucleotide or amino acid sequence is "foreign" or "heterologous" to the sequence of the embodiments, it is intended that the nucleotide or amino acid sequence is not the native or naturally occurring promoter or nucleotide sequence for the operably linked sequence of the embodiments. As used herein, a chimeric gene comprises a coding sequence operably linked to a transcription initiation region that is heterologous to the coding sequence. Where the promoter is a native or natural sequence, the expression of the operably linked sequence is altered from the wild-type expression, which results in an alteration in phenotype.

In some embodiments the DNA construct comprises a polynucleotide encoding an IPD126 polypeptide of the embodiments. In some embodiments the DNA construct comprises a polynucleotide encoding a fusion protein comprising an IPD126 polypeptide of the embodiments.

In some embodiments the DNA construct may also include a transcriptional enhancer sequence. As used herein, the term an "enhancer" refers to a DNA sequence which can stimulate promoter activity, and may be an innate element of the promoter or a heterologous element inserted to enhance the level or tissue-specificity of a promoter. Various enhancers are known in the art including for example, introns with gene expression enhancing properties in plants (US Patent Application Publication Number 2009/0144863, the ubiquitin intron (i.e., the maize ubiquitin intron 1 (see, for example, NCBI sequence S94464)), the omega enhancer or the omega prime enhancer (Gallie, et al., (1989) *Molecular Biology of RNA* ed. Cech (Liss, New York) 237-256 and Gallie, et al., (1987) *Gene* 60:217-25), the CaMV 35S enhancer (see, e.g., Benfey, et al., (1990) *EMBO J.* 9:1685-96) and the enhancers of U.S. Pat. No. 7,803,992 may also be used. The above list of transcriptional enhancers is not meant to be limiting. Any appropriate transcriptional enhancer can be used in the embodiments.

The termination region may be native with the transcriptional initiation region, may be native with the operably linked DNA sequence of interest, may be native with the plant host or may be derived from another source (i.e., foreign or heterologous to the promoter, the sequence of interest, the plant host or any combination thereof).

Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acid Res.* 15:9627-9639.

Where appropriate, a nucleic acid may be optimized for increased expression in the host organism. Thus, where the host organism is a plant, the synthetic nucleic acids can be synthesized using plant-preferred codons for improved expression. See, for example, Campbell and Gowri, (1990) *Plant Physiol.* 92:1-11 for a discussion of host-preferred usage. For example, although nucleic acid sequences of the embodiments may be expressed in both monocotyledonous and dicotyledonous plant species, sequences can be modified to account for the specific preferences and GC content preferences of monocotyledons or dicotyledons as these preferences have been shown to differ (Murray et al. (1989) *Nucleic Acids Res.* 17:477-498). Thus, the maize-preferred for a particular amino acid may be derived from known gene sequences from maize. Maize usage for 28 genes from maize plants is listed in Table 4 of Murray, et al., supra. Methods are available in the art for synthesizing plant-preferred genes. See, for example, Murray, et al., (1989) *Nucleic Acids Res.* 17:477-498, and Liu H et al. *Mol Bio Rep* 37:677-684, 2010, herein incorporated by reference. A *Zea maize* usage table can be also found at kazusa.or.jp//cgi-bin/show.cgi?species=4577, which can be accessed using the www prefix. A *Glycine max* usage table can be found at kazusa.or.jp//cgi-bin/show.cgi?species=3847&aa=1&style=N, which can be accessed using the www prefix.

In some embodiments the recombinant nucleic acid molecule encoding an IPD126 polypeptide has maize optimized codons.

Additional sequence modifications are known to enhance gene expression in a cellular host. These include elimination of sequences encoding spurious polyadenylation signals, exon-intron splice site signals, transposon-like repeats, and other well-characterized sequences that may be deleterious to gene expression. The GC content of the sequence may be adjusted to levels average for a given cellular host, as calculated by reference to known genes expressed in the host cell. The term "host cell" as used herein refers to a cell which contains a vector and supports the replication and/or expression of the expression vector is intended. Host cells may be prokaryotic cells such as *E. coli* or eukaryotic cells such as yeast, insect, amphibian or mammalian cells or monocotyledonous or dicotyledonous plant cells. An example of a monocotyledonous host cell is a maize host cell. When possible, the sequence is modified to avoid predicted hairpin secondary mRNA structures.

In preparing the expression cassette, the various DNA fragments may be manipulated so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the embodiments. The promoters can be selected based on the desired outcome. The nucleic acids can be combined with constitutive, tissue-preferred, inducible or other promoters for expression in the host organism. Suitable constitutive promoters for use in a plant host cell include, for example, the core promoter of the Rsyn7 promoter and other constitutive promoters disclosed in WO 1999/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026) and the like. Other constitutive promoters include, for example, those discussed in U.S. Pat. Nos. 5,608,149; 5,608,144; 5,604,121; 5,569,597; 5,466,785; 5,399,680; 5,268,463; 5,608,142 and 6,177,611.

Generally, the expression cassette will comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones and 2,4-dichlorophenoxyacetate (2,4-D). Additional examples of suitable selectable marker genes include, but are not limited to, genes encoding resistance to chloramphenicol (Herrera Estrella, et al., (1983) *EMBO J.* 2:987-992); methotrexate (Herrera Estrella, et al., (1983) *Nature* 303:209-213 and Meijer, et al., (1991) *Plant Mol. Biol.* 16:807-820); streptomycin (Jones, et al., (1987) *Mol. Gen. Genet.* 210:86-91); spectinomycin (Bretagne-Sagnard, et al., (1996) *Transgenic Res.* 5:131-137); bleomycin (Hille, et al., (1990) *Plant Mol. Biol.* 7:171-176); sulfonamide (Guerineau, et al., (1990) *Plant Mol. Biol.* 15:127-136); bromoxynil (Stalker, et al., (1988) *Science* 242:419-423); glyphosate (Shaw, et al., (1986) *Science* 233:478-481 and U.S. patent application Ser. Nos. 10/004,357 and 10/427,692); phosphinothricin (DeBlock, et al., (1987) *EMBO J.* 6:2513-2518). See generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon*, pp. 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad Sci. USA* 86:5400-5404; Fuerst, et al., (1989) *Proc. Natl. Acad. Sci. USA* 86:2549-2553; Deuschle, et al., (1990) *Science* 248: 480-483; Gossen, (1993) Ph.D. Thesis, University of Heidelberg; Reines, et al., (1993) *Proc. Natl. Acad Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimicrob. Agents Chemother.* 35:1591-1595; Kleinschnidt, et al., (1988) *Biochemistry* 27:1094-1104; Bonin, (1993) Ph.D. Thesis, University of Heidelberg; Gossen, et al., (1992) *Proc. Natl. Acad Sci. USA* 89:5547-5551; Oliva, et al., (1992) *Antimicrob. Agents Chemother.* 36:913-919; Hlavka, et al., (1985) *Handbook of Experimental Pharmacology*, Vol. 78 (Springer-Verlag, Berlin) and Gill, et al., (1988) *Nature* 334:721-724.

The above list of selectable marker genes is not meant to be limiting. Any selectable marker gene can be used in the embodiments.

Plant Transformation

The methods of the embodiments involve introducing a polypeptide or polynucleotide into a plant. "Introducing" as used herein means presenting to the plant the polynucleotide or polypeptide in such a manner that the sequence gains access to the interior of a cell of the plant. The methods of the embodiments do not depend on a particular method for introducing a polynucleotide or polypeptide into a plant, only that the polynucleotide(s) or polypeptide(s) gains access to the interior of at least one cell of the plant. Methods for introducing polynucleotide(s) or polypeptide(s) into plants are known in the art including, but not limited to, stable transformation methods, transient transformation methods, and virus-mediated methods.

"Stable transformation" as used herein means that the nucleotide construct introduced into a plant integrates into the genome of the plant and is capable of being inherited by the progeny thereof "Transient transformation" as used herein means that a polynucleotide is introduced into the plant and does not integrate into the genome of the plant or a polypeptide is introduced into a plant. "Plant" as used herein refers to whole plants, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells and pollen).

Transformation protocols as well as protocols for introducing nucleotide sequences into plants may vary depending on the type of plant or plant cell, i.e., monocot or dicot, targeted for transformation. Suitable methods of introducing nucleotide sequences into plant cells and subsequent insertion into the plant genome include microinjection (Crossway, et al., (1986) *Biotechniques* 4:320-334), electroporation (Riggs, et al., (1986) *Proc. Natl. Acad. Sci. USA* 83:5602-5606), *Agrobacterium*-mediated transformation (U.S. Pat. Nos. 5,563,055 and 5,981,840), direct gene transfer (Paszkowski, et al., (1984) *EMBO J.* 3:2717-2722) and ballistic particle acceleration (see, for example, U.S. Pat. Nos. 4,945,050; 5,879,918; 5,886,244 and 5,932,782; Tomes, et al., (1995) in *Plant Cell, Tissue, and Organ Culture: Fundamental Methods*, ed. Gamborg and Phillips, (Springer-Verlag, Berlin) and McCabe, et al., (1988) *Biotechnology* 6:923-926) and Led transformation (WO 00/28058). For potato transformation see, Tu, et al., (1998) *Plant Molecular Biology* 37:829-838 and Chong, et al., (2000) *Transgenic Research* 9: 71-78. Additional transformation procedures can be found in Weissinger, et al., (1988) *Ann. Rev. Genet.* 22:421-477; Sanford, et al., (1987) *Par-* ticulate *Science and Technology* 5:27-37 (onion); Christou, et al., (1988) *Plant Physiol.* 87:671-674 (soybean); McCabe, et al., (1988) *Bio/Technology* 6:923-926 (soybean); Finer and McMullen, (1991) *In Vitro Cell Dev. Biol.* 27P:175-182 (soybean); Singh, et al., (1998) *Theor. Appl. Genet.* 96:319-324 (soybean); Datta, et al., (1990) *Biotechnology* 8:736-740 (rice); Klein, et al., (1988) *Proc. Natl. Acad. Sci. USA* 85:4305-4309 (maize); Klein, et al., (1988) *Biotechnology* 6:559-563 (maize); U.S. Pat. Nos. 5,240,855; 5,322,783 and 5,324,646; Klein, et al., (1988) *Plant Physiol.* 91:440-444 (maize); Fromm, et al., (1990) *Biotechnology* 8:833-839 (maize); Hooykaas-Van Slogteren, et al., (1984) *Nature (London)* 311:763-764; U.S. Pat. No. 5,736,369 (cereals); Bytebier, et al., (1987) *Proc. Natl. Acad. Sci. USA* 84:5345-5349 (Liliaceae); De Wet, et al., (1985) in *The Experimental Manipulation of Ovule Tissues*, ed. Chapman, et al., (Longman, New York), pp. 197-209 (pollen); Kaeppler, et al., (1990) *Plant Cell Reports* 9:415-418 and Kaeppler, et al., (1992) *Theor. Appl. Genet.* 84:560-566 (whisker-mediated transformation); D'Halluin, et al., (1992) *Plant Cell* 4:1495-1505 (electroporation); Li, et al., (1993) *Plant Cell Reports* 12:250-255 and Christou and Ford, (1995) *Annals of Botany* 75:407-413 (rice); Osjoda, et al., (1996) *Nature Biotechnology* 14:745-750 (maize via *Agrobacterium tumefaciens*).

In specific embodiments, the sequences of the embodiments can be provided to a plant using a variety of transient transformation methods. Such transient transformation methods include, but are not limited to, the introduction of the IPD126 polynucleotide or variants and fragments thereof directly into the plant or the introduction of the IPD126 polypeptide transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al, (1994) *Proc. Natl. Acad. Sci.* 91:2176-2180 and Hush, et al., (1994) *The Journal of Cell Science* 107:775-784. Alternatively, the IPD126 polynucleotide can be transiently transformed into the plant using techniques known in the art. Such techniques include viral vector system and the precipitation of the polynucleotide in a manner that precludes subsequent release of the DNA. Thus, transcription from the particle-bound DNA can occur, but the frequency with which it is released to become integrated into the genome is greatly reduced. Such methods include the use of particles coated with polyethylimine (PEI; Sigma #P3143).

Methods are known in the art for the targeted insertion of a polynucleotide at a specific location in the plant genome. In one embodiment, the insertion of the polynucleotide at a desired genomic location is achieved using a site-specific recombination system. See, for example, WO 1999/25821, WO 1999/25854, WO 1999/25840, WO 1999/25855 and WO 1999/25853. Briefly, the polynucleotide of the embodiments can be contained in transfer cassette flanked by two non-identical recombination sites. The transfer cassette is introduced into a plant have stably incorporated into its genome a target site which is flanked by two non-identical recombination sites that correspond to the sites of the transfer cassette. An appropriate recombinase is provided and the transfer cassette is integrated at the target site. The polynucleotide of interest is thereby integrated at a specific chromosomal position in the plant genome.

Plant transformation vectors may be comprised of one or more DNA vectors needed for achieving plant transformation. For example, it is a common practice in the art to utilize plant transformation vectors that are comprised of more than one contiguous DNA segment. These vectors are often referred to in the art as "binary vectors". Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the pesticidal gene are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux, (2000) *Trends in Plant Science* 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g., immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Following integration of heterologous foreign DNA into plant cells, one then applies a maximum threshold level of appropriate selection in the medium to kill the untransformed cells and separate and proliferate the putatively transformed cells that survive from this selection treatment by transferring regularly to a fresh medium. By continuous passage and challenge with appropriate selection, one identifies and proliferates the cells that are transformed with the plasmid vector. Molecular and biochemical methods can then be used to confirm the presence of the integrated heterologous gene of interest into the genome of the transgenic plant.

Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g., Hiei, et al., (1994) *The Plant Journal* 6:271-282; Ishida, et al, (1996) *Nature Biotechnology* 14:745-750). Explants are typically transferred to a fresh supply of the same medium and cultured routinely. A general description of the techniques and methods for generating transgenic plants are found in Ayres and Park, (1994) *Critical Reviews in Plant Science* 13:219-239 and Bommineni and Jauhar, (1997) *Maydica* 42:107-120. Since the transformed material contains many cells; both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting hybrid having constitutive or inducible expression of the desired phenotypic characteristic identified. Two or more generations may be grown to ensure that expression of the desired phenotypic characteristic is stably maintained and inherited and then seeds harvested to ensure that expression of the desired phenotypic characteristic has been achieved.

The embodiments further relate to plant-propagating material of a transformed plant of the embodiments including, but not limited to, seeds, tubers, corms, bulbs, leaves and cuttings of roots and shoots.

The embodiments may be used for transformation of any plant species, including, but not limited to, monocots and dicots. Examples of plants of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables ornamentals, and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.), and members of the genus *Cucumis* such as cucumber (*C. sativus*), cantaloupe (*C. cantalupensis*), and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*), and chrysanthemum. Conifers that may be employed in practicing the embodiments include, for example, pines such as loblolly pine (*Pinus taeda*), slash pine (*Pinus elliotii*), *ponderosa* pine (*Pinus ponderosa*), lodgepole pine (*Pinus contorta*), and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*); and cedars such as Western red cedar (*Thuja plicata*) and Alaska yellow-cedar (*Chamaecyparis nootkatensis*). Plants of the embodiments include crop plants (for example, corn, alfalfa, sunflower, *Brassica*, soybean, cotton, safflower, peanut, sorghum, wheat, millet, tobacco, etc.), such as corn and soybean plants.

Turf grasses include, but are not limited to: annual bluegrass (*Poa annua*); annual ryegrass (*Lolium multiflorum*); Canada bluegrass (*Poa compressa*); Chewing's fescue (*Festuca rubra*); colonial bentgrass (*Agrostis tenuis*); creeping bentgrass (*Agrostis palustris*); crested wheatgrass (*Agropyron desertorum*); fairway wheatgrass (*Agropyron cristatum*); hard fescue (*Festuca longifolia*); Kentucky bluegrass (*Poa pratensis*); orchardgrass (*Dactylis glomerata*); perennial ryegrass (*Lolium perenne*); red fescue (*Festuca rubra*); redtop (*Agrostis alba*); rough bluegrass (*Poa triviahs*); sheep fescue (*Festuca ovina*); smooth bromegrass (*Bromus inermis*); tall fescue (*Festuca arundinacea*); timothy (*Phleum pratense*); velvet bentgrass (*Agrostis canina*); weeping alkaligrass (*Puccinelia distans*); western wheatgrass (*Agropyron smithii*); Bermuda grass (*Cynodon* spp.); St. Augustine grass (*Stenotaphrum secundatum*); zoysia grass (*Zoysia* spp.); Bahia grass (*Paspalum notatum*); carpet grass (*Axonopus affinis*); centipede grass (*Eremochloa ophiuroides*); kikuyu grass (*Pennisetum clandesinum*); seashore paspalum (*Paspalum vaginatum*); blue gramma (*Bouteloua gracilis*); buffalo grass (*Buchloe dactyloids*); sideoats gramma (*Bouteloua curtipendula*).

Plants of interest include grain plants that provide seeds of interest, oil-seed plants, and leguminous plants. Seeds of interest include grain seeds, such as corn, wheat, barley, rice, sorghum, rye, millet, etc. Oil-seed plants include cotton, soybean, safflower, sunflower, *Brassica*, maize, alfalfa, palm, coconut, flax, castor, olive, etc. Leguminous plants include beans and peas. Beans include guar, locust bean, fenugreek, soybean, garden beans, cowpea, mung bean, lima bean, fava bean, lentils, chickpea, etc.

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell, (2001) Molecular Cloning: A Laboratory Manual. Cold Spring Harbor Laboratory Press, Cold Spring Harbor, NY). PCR is carried out using oligonucleotide primers specific to the gene of interest or *Agrobacterium* vector background, etc.

Plant transformation may be confirmed by Southern blot analysis of genomic DNA (Sambrook and Russell, (2001) supra). In Northern blot analysis, RNA is isolated from specific tissues of transformant, fractionated in a formaldehyde agarose gel, and blotted onto a nylon filter according to standard procedures that are routinely used in the art (Sambrook and Russell, (2001) supra). Expression of RNA encoded by the pesticidal gene is then tested by hybridizing the filter to a radioactive probe derived from a pesticidal gene, by methods known in the art (Sambrook and Russell, (2001) supra). Western blot, biochemical assays and the like may be carried out on the transgenic plants to confirm the presence of protein encoded by the pesticidal gene by standard procedures (Sambrook and Russell, 2001, supra) using antibodies that bind to one or more epitopes present on the IPD126 polypeptide.

Methods to Introduce Genome Editing Technologies into Plants

In some embodiments, the disclosed IPD126 polynucleotide compositions can be introduced into the genome of a plant using genome editing technologies, or previously introduced IPD126 polynucleotides in the genome of a plant may be edited using genome editing technologies. For example, the disclosed polynucleotides can be introduced into a desired location in the genome of a plant through the use of double-stranded break technologies such as TALENs, meganucleases, zinc finger nucleases, CRISPR-Cas, and the like. For example, the disclosed polynucleotides can be introduced into a desired location in a genome using a CRISPR-Cas system, for the purpose of site-specific insertion. The desired location in a plant genome can be any desired target site for insertion, such as a genomic region amenable for breeding or may be a target site located in a genomic window with an existing trait of interest. Existing traits of interest could be either an endogenous trait or a previously introduced trait.

In some embodiments, where the disclosed IPD126 polynucleotide has previously been introduced into a genome, genome editing technologies may be used to alter or modify the introduced polynucleotide sequence. Site specific modifications that can be introduced into the disclosed IPD126 polynucleotide compositions include those produced using any method for introducing site specific modification, including, but not limited to, through the use of gene repair oligonucleotides (e.g. US Publication 2013/0019349), or through the use of double-stranded break technologies such as TALENs, meganucleases, zinc finger nucleases, CRISPR-Cas, and the like. Such technologies can be used to modify the previously introduced polynucleotide through the insertion, deletion or substitution of nucleotides within the introduced polynucleotide. Alternatively, double-stranded break technologies can be used to add additional nucleotide sequences to the introduced polynucleotide. Additional sequences that may be added include, additional expression elements, such as enhancer and promoter sequences. In another embodiment, genome editing technologies may be used to position additional insecticidally-active proteins in proximity to the disclosed IPD126 polynucleotide compositions disclosed herein within the genome of a plant, in order to generate molecular stacks of insecticidally-active proteins.

An "altered target site," "altered target sequence," "modified target site," and "modified target sequence" are used interchangeably herein and refer to a target sequence as disclosed herein that comprises at least one alteration when compared to non-altered target sequence. Such "alterations" include, for example: (i) replacement of at least one nucleotide, (ii) a deletion of at least one nucleotide, (iii) an insertion of at least one nucleotide, or (iv) any combination of (i)-(iii).

Stacking of Traits in Transgenic Plant

Transgenic plants may comprise a stack of one or more insecticidal polynucleotides disclosed herein with one or more additional polynucleotides resulting in the production or suppression of multiple polypeptide sequences. Transgenic plants comprising stacks of polynucleotide sequences can be obtained by either or both of traditional breeding methods or through genetic engineering methods. These methods include, but are not limited to, breeding individual lines each comprising a polynucleotide of interest, transforming a transgenic plant comprising a gene disclosed herein with a subsequent gene and co-transformation of genes into a single plant cell. As used herein, the term "stacked" includes having the multiple traits present in the same plant (i.e., both traits are incorporated into the nuclear genome, one trait is incorporated into the nuclear genome and one trait is incorporated into the genome of a plastid or both traits are incorporated into the genome of a plastid). In one non-limiting example, "stacked traits" comprise a molecular stack where the sequences are physically adjacent to each other. A trait, as used herein, refers to the phenotype derived from a particular sequence or groups of sequences. Co-transformation of genes can be carried out using single transformation vectors comprising multiple genes or genes carried separately on multiple vectors. If the sequences are stacked by genetically transforming the plants, the polynucleotide sequences of interest can be combined at any time and in any order. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO 1999/25821, WO 1999/25854, WO 1999/25840, WO 1999/25855 and WO 1999/25853, all of which are herein incorporated by reference.

In some embodiments, one or more of the polynucleotides encoding the IPD126 polypeptide(s) disclosed herein, alone or stacked with one or more additional insect resistance traits can be stacked with one or more additional input traits (e.g., herbicide resistance, fungal resistance, virus resistance, stress tolerance, disease resistance, male sterility, stalk strength, and the like) or output traits (e.g., increased yield, modified starches, improved oil profile, balanced amino acids, high lysine or methionine, increased digestibility, improved fiber quality, drought resistance, and the like). Thus, the polynucleotide embodiments can be used to provide a complete agronomic package of improved crop quality with the ability to flexibly and cost effectively control any number of agronomic pests.

Transgenes useful for stacking include but are not limited to: transgenes that confer resistance to an herbicide; transgenes that confer or contribute to an altered grain characteristic; genes that control male-sterility; genes that create a site for site specific dna integration; genes that affect abiotic stress resistance; genes that confer increased yield genes that confer plant digestibility; and transgenes that confer resistance to insects or disease.

Examples of transgenes that confer resistance to insects include genes encoding a *Bacillus thuringiensis* protein, a derivative thereof or a synthetic polypeptide modeled thereon. See, for example, Geiser, et al., (1986) *Gene* 48:109, who disclose the cloning and nucleotide sequence of a Bt delta-endotoxin gene. Moreover, DNA molecules encoding delta-endotoxin genes can be purchased from American Type Culture Collection (Rockville, Md.), for example, under ATCC® Accession Numbers 40098, 67136, 31995 and 31998. Other non-limiting examples of *Bacillus thuringiensis* transgenes being genetically engineered are given in the following patents and patent applications: U.S.

Pat. Nos. 5,188,960; 5,689,052; 5,880,275; 5,986,177; 6,023,013, 6,060,594, 6,063,597, 6,077,824, 6,620,988, 6,642,030, 6,713,259, 6,893,826, 7,105,332; 7,179,965, 7,208,474; 7,227,056, 7,288,643, 7,323,556, 7,329,736, 7,449,552, 7,468,278, 7,510,878, 7,521,235, 7,544,862, 7,605,304, 7,696,412, 7,629,504, 7,705,216, 7,772,465, 7,790,846, 7,858,849 and WO 1991/14778; WO 1999/31248; WO 2001/12731; WO 1999/24581 and WO 1997/40162.

Genes encoding pesticidal proteins may also be stacked including but are not limited to: insecticidal proteins from *Pseudomonas* sp. such as PSEEN3174 (Monalysin, (2011) *PLoS Pathogens*, 7:1-13), from *Pseudomonas protegens* strain CHAO and Pf-5 (previously *fluorescens*) (Pechy-Tarr, (2008) *Environmental Microbiology* 10:2368-2386: GenBank Accession No. EU400157); from *Pseudomonas taiwanensis* (Liu, et al., (2010) *J. Agric. Food Chem.* 58:12343-12349) and from *Pseudomonas pseudoalcaligenes* (Zhang, et al., (2009) *Annals of Microbiology* 59:45-50 and Li, et al., (2007) *Plant Cell Tiss. Organ Cult.* 89:159-168); insecticidal proteins from *Photorhabdus* sp. and *Xenorhabdus* sp. (Hinchliffe, et al., (2010)*The Open Toxinology Journal* 3:101-118 and Morgan, et al., (2001) *Applied and Envir. Micro.* 67:2062-2069), U.S. Pat. Nos. 6,048,838, and 6,379,946; a PIP-1 polypeptide of U.S. Pat. No. 9,688,730; an AfIP-1A and/or AfIP-1B polypeptide of U.S. Pat. No. 9,475,847; a PIP-47 polypeptide of US Publication Number US20160186204; an IPD045 polypeptide, an IPD064 polypeptide, an IPD074 polypeptide, an IPD075 polypeptide, and an IPD077 polypeptide of PCT Publication Number WO 2016/114973; an IPD080 polypeptide of PCT Serial Number PCT/US17/56517; an IPD078 polypeptide, an IPD084 polypeptide, an IPD085 polypeptide, an IPD086 polypeptide, an IPD087 polypeptide, an IPD088 polypeptide, and an IPD089 polypeptide of Serial Number PCT/US17/54160; PIP-72 polypeptide of US Patent Publication Number US20160366891; a PtIP-50 polypeptide and a PtIP-65 polypeptide of US Publication Number US20170166921; an IPD098 polypeptide, an IPD059 polypeptide, an IPD108 polypeptide, an IPD109 polypeptide of U.S. Ser. No. 62/521,084; a PtIP-83 polypeptide of US Publication Number US20160347799; a PtIP-96 polypeptide of US Publication Number US20170233440; an IPD079 polypeptide of PCT Publication Number WO2017/23486; an IPD082 polypeptide of PCT Publication Number WO 2017/105987, an IPD090 polypeptide of Serial Number PCT/US17/30602, an IPD093 polypeptide of U.S. Ser. No. 62/434,020; an IPD103 polypeptide of Serial Number PCT/US17/39376; an IPD101 polypeptide of U.S. Ser. No. 62/438,179; an IPD121 polypeptide of US Serial Number U.S. 62/508,514, and δ-endotoxins including, but not limited to, the Cry1, Cry2, Cry3, Cry4, Cry5, Cry6, Cry7, Cry8, Cry9, Cry10, Cry11, Cry12, Cry13, Cry14, Cry15, Cry16, Cry17, Cry18, Cry19, Cry20, Cry21, Cry22, Cry23, Cry24, Cry25, Cry26, Cry27, Cry28, Cry29, Cry30, Cry31, Cry32, Cry33, Cry34, Cry35, Cry36, Cry37, Cry38, Cry39, Cry40, Cry41, Cry42, Cry43, Cry44, Cry45, Cry46, Cry47, Cry49, Cry50, Cry51, Cry52, Cry53, Cry54, Cry55, Cry56, Cry57, Cry58, Cry59, Cry60, Cry61, Cry62, Cry63, Cry64, Cry65, Cry66, Cry67, Cry68, Cry69, Cry70, Cry71, and Cry72 classes of δ-endotoxin genes and the *B. thuringiensis* cytolytic Cyt1 and Cyt2 genes.

Examples of δ-endotoxins also include but are not limited to Cry1A proteins of U.S. Pat. Nos. 5,880,275 and 7,858,849; a DIG-3 or DIG-11 toxin (N-terminal deletion of α-helix 1 and/or α-helix 2 variants of Cry proteins such as Cry1A) of U.S. Pat. Nos. 8,304,604 and 8,304,605, Cry1B of U.S. patent application Ser. No. 10/525,318; Cry1C of U.S. Pat. No. 6,033,874; Cry1F of U.S. Pat. Nos. 5,188,960, 6,218,188; Cry1A/F chimeras of U.S. Pat. Nos. 7,070,982; 6,962,705 and 6,713,063); a Cry2 protein such as Cry2Ab protein of U.S. Pat. No. 7,064,249); a Cry3A protein including but not limited to an engineered hybrid insecticidal protein (eHIP) created by fusing unique combinations of variable regions and conserved blocks of at least two different Cry proteins (US Patent Application Publication Number 2010/0017914); a Cry4 protein; a Cry5 protein; a Cry6 protein; Cry8 proteins of U.S. Pat. Nos. 7,329,736, 7,449,552, 7,803,943, 7,476,781, 7,105,332, 7,378,499 and 7,462,760; a Cry9 protein such as such as members of the Cry9A, Cry9B, Cry9C, Cry9D, Cry9E, and Cry9F families; a Cry15 protein of Naimov, et al., (2008) *Applied and Environmental Microbiology* 74:7145-7151; a Cry22, a Cry34Ab1 protein of U.S. Pat. Nos. 6,127,180, 6,624,145 and 6,340,593; a CryET33 and CryET34 protein of U.S. Pat. Nos. 6,248,535, 6,326,351, 6,399,330, 6,949,626, 7,385,107 and 7,504,229; a CryET33 and CryET34 homologs of US Patent Publication Number 2006/0191034, 2012/0278954, and PCT Publication Number WO 2012/139004; a Cry35Ab1 protein of U.S. Pat. Nos. 6,083,499, 6,548,291 and 6,340,593; a Cry46 protein, a Cry51 protein, a Cry binary toxin; a TIC901 or related toxin; TIC807 of US 2008/0295207; ET29, ET37, TIC809, TIC810, TIC812, TIC127, TIC128 of PCT US 2006/033867; AXMI-027, AXMI-036, and AXMI-038 of U.S. Pat. No. 8,236,757; AXMI-031, AXMI-039, AXMI-040, AXMI-049 of U.S. Pat. No. 7,923,602; AXMI-018, AXMI-020, and AXMI-021 of WO 2006/083891; AXMI-010 of WO 2005/038032; AXMI-003 of WO 2005/021585; AXMI-008 of US 2004/0250311; AXMI-006 of US 2004/0216186; AXMI-007 of US 2004/0210965; AXMI-009 of US 2004/0210964; AXMI-014 of US 2004/0197917; AXMI-004 of US 2004/0197916; AXMI-028 and AXMI-029 of WO 2006/119457; AXMI-007, AXMI-008, AXMI-0080rf2, AXMI-009, AXMI-014 and AXMI-004 of WO 2004/074462; AXMI-150 of U.S. Pat. No. 8,084,416; AXMI-205 of US20110023184; AXMI-011, AXMI-012, AXMI-013, AXMI-015, AXMI-019, AXMI-044, AXMI-037, AXMI-043, AXMI-033, AXMI-034, AXMI-022, AXMI-023, AXMI-041, AXMI-063, and AXMI-064 of US 2011/0263488; AXMI-R1 and related proteins of US 2010/0197592; AXMI221Z, AXMI222z, AXMI223z, AXMI224z and AXMI225z of WO 2011/103248; AXMI218, AXMI219, AXMI220, AXMI226, AXMI227, AXMI228, AXMI229, AXMI230, and AXMI231 of WO11/103247; AXMI-115, AXMI-113, AXMI-005, AXMI-163 and AXMI-184 of U.S. Pat. No. 8,334,431; AXMI-001, AXMI-002, AXMI-030, AXMI-035, and AXMI-045 of US 2010/0298211; AXMI-066 and AXMI-076 of US2009/0144852; AXMI128, AXMI130, AXMI131, AXMI133, AXMI140, AXMI141, AXMI142, AXMI143, AXMI144, AXMI146, AXMI148, AXMI149, AXMI152, AXMI153, AXMI154, AXMI155, AXMI156, AXMI157, AXMI158, AXMI162, AXMI165, AXMI166, AXMI167, AXMI168, AXMI169, AXMI170, AXMI171, AXMI172, AXMI173, AXMI174, AXMI175, AXMI176, AXMI177, AXMI178, AXMI179, AXMI180, AXMI181, AXMI182, AXMI185, AXMI186, AXMI187, AXMI188, AXMI189 of U.S. Pat. No. 8,318,900; AXMI079, AXMI080, AXMI081, AXMI082, AXMI091, AXMI092, AXMI096, AXMI097, AXMI098, AXMI099, AXMI100, AXMI101, AXMI102, AXMI103, AXMI104, AXMI107, AXMI108, AXMI109, AXMI110, AXMI111, AXMI112, AXMI114, AXMI116, AXMI117, AXMI118, AXMI119, AXMI120, AXMI121, AXMI122, AXMI123, AXMI124, AXMI1257, AXMI1268, AXMI127, AXMI129, AXMI164, AXMI151, AXMI161, AXMI183, AXMI132, AXMI138, AXMI137 of US 2010/0005543; and Cry proteins such as Cry1A and Cry3A having modified proteolytic sites of U.S. Pat. No. 8,319,019; and a Cry1Ac, Cry2Aa and Cry1Ca toxin protein from *Bacillus thuringiensis* strain VBTS 2528 of US Patent Application Publication Number 2011/0064710. Other Cry proteins are well known to one skilled in the art (see, Crickmore, et al., "*Bacillus thuringiensis* toxin nomenclature" (2011), at lifesci.sussex.ac.uk/home/Neil_Crickmore/Bt/which can be accessed on the world-wide web using the "www" prefix). The insecticidal activity of Cry proteins is well known to one skilled in the art (for review, see, van Frannkenhuyzen, (2009) *J. Invert. Path.* 101:1-16). The use of Cry proteins as transgenic plant traits is well known to one skilled in the art and Cry-transgenic plants including but not limited to Cry1Ac, Cry1Ac+Cry2Ab, Cry1Ab, Cry1A.105, Cry1F, Cry1Fa2, Cry1F+Cry1Ac, Cry2Ab, Cry3A, mCry3A, Cry3Bb1, Cry34Ab1, Cry35Ab1, Vip3A, mCry3A, Cry9c and CBI-Bt have received regulatory approval (see, Sanahuja, (2011) *Plant Biotech Journal* 9:283-300 and the CERA (2010) GM Crop Database Center for Environmental Risk Assessment (CERA), ILSI Research Foundation, Washington D.C. at cera-gmc.org/index.php?action=gm_crop_database which can be accessed on the world-wide web using the "www" prefix). More than one pesticidal proteins well known to one skilled in the art can also be expressed in plants such as Vip3Ab & Cry1Fa (US2012/0317682), Cry1BE & Cry1F (US2012/0311746), Cry1CA & Cry1AB (US2012/0311745), Cry1F & CryCa (US2012/0317681), Cry1DA & Cry1BE (US2012/0331590), Cry1DA & Cry1Fa (US2012/0331589), Cry1AB & Cry1BE (US2012/0324606), and Cry1Fa & Cry2Aa, Cry1I or Cry1E (US2012/0324605). Pesticidal proteins also include insecticidal lipases including lipid acyl hydrolases of U.S. Pat. No. 7,491,869, and cholesterol oxidases such as from *Streptomyces* (Purcell et al. (1993) *Biochem Biophys Res Commun* 15:1406-1413). Pesticidal proteins also include VIP (vegetative insecticidal proteins) toxins of U.S. Pat. Nos. 5,877,012, 6,107,279, 6,137,033, 7,244,820, 7,615,686, and 8,237,020, and the like. Other VIP proteins are well known to one skilled in the art (see, lifesci.sussex.ac.uk/home/Neil_Crickmore/Bt/vip.html which can be accessed on the world-wide web using the "www" prefix). Pesticidal proteins also include toxin complex (TC) proteins, obtainable from organisms such as *Xenorhabdus, Photorhabdus* and *Paenibacillus* (see, U.S. Pat. Nos. 7,491,698 and 8,084,418). Some TC proteins have "stand alone" insecticidal activity and other TC proteins enhance the activity of the stand-alone toxins produced by the same given organism. The toxicity of a "stand-alone" TC protein (from *Photorhabdus, Xenorhabdus* or *Paenibacillus*, for example) can be enhanced by one or more TC protein "potentiators" derived from a source organism of a different genus. There are three main types of TC proteins. As referred to herein, Class A proteins ("Protein A") are stand-alone toxins. Class B proteins ("Protein B") and Class C proteins ("Protein C") enhance the toxicity of Class A proteins. Examples of Class A proteins are TcbA, TcdA, XptA1 and XptA2. Examples of Class B proteins are TcaC, TcdB, XptB1Xb and XptC1Wi. Examples of Class C proteins are TccC, XptC1Xb and XptB1Wi. Pesticidal proteins also include spider, snake and scorpion venom proteins. Examples of spider venom peptides include but are not limited to lycotoxin-1 peptides and mutants thereof (U.S. Pat. No. 8,334,366).

Further transgenes that confer resistance to insects may down-regulation of expression of target genes in insect pest species by interfering ribonucleic acid (RNA) molecules through RNA interference. RNA interference refers to the process of sequence-specific post-transcriptional gene silencing in animals mediated by short interfering RNAs (siRNAs) (Fire, et al., (1998) *Nature* 391:806). RNAi transgenes may include but are not limited to expression of dsRNA, siRNA, miRNA, iRNA, antisense RNA, or sense RNA molecules that down-regulate expression of target genes in insect pests. PCT Publication WO 2007/074405 describes methods of inhibiting expression of target genes in invertebrate pests including Colorado potato beetle. PCT Publication WO 2005/110068 describes methods of inhibiting expression of target genes in invertebrate pests including in particular Western corn rootworm as a means to control insect infestation. Furthermore, PCT Publication WO 2009/091864 describes compositions and methods for the suppression of target genes from insect pest species including pests from the *Lygus* genus. RNAi transgenes are provided for targeting the vacuolar ATPase H subunit, useful for controlling a coleopteran pest population and infestation as described in US Patent Application Publication 2012/0198586. PCT Publication WO 2012/055982 describes ribonucleic acid (RNA or double stranded RNA) that inhibits or down regulates the expression of a target gene that encodes: an insect ribosomal protein such as the ribosomal protein L19, the ribosomal protein L40 or the ribosomal protein S27A; an insect proteasome subunit such as the Rpn6 protein, the Pros 25, the Rpn2 protein, the proteasome beta 1 subunit protein or the Pros beta 2 protein; an insect β-coatomer of the COPI vesicle, the γ-coatomer of the COPI vesicle, the β'-coatomer protein or the ζ-coatomer of the COPI vesicle; an insect Tetraspanine 2 A protein which is a putative transmembrane domain protein; an insect protein belonging to the actin family such as Actin 5C; an insect ubiquitin-5E protein; an insect Sec23 protein which is a GTPase activator involved in intracellular protein transport; an insect crinkled protein which is an unconventional myosin which is involved in motor activity; an insect crooked neck protein which is involved in the regulation of nuclear alternative mRNA splicing; an insect vacuolar H+-ATPase G-subunit protein and an insect Tbp-1 such as Tat-binding protein. PCT publication WO 2007/035650 describes ribonucleic acid (RNA or double stranded RNA) that inhibits or down regulates the expression of a target gene that encodes Snf7. US Patent Application publication 2011/0054007 describes polynucleotide silencing elements targeting RPS10. PCT publication WO 2016/205445 describes polynucleotide silencing elements that reduce fecundity, with target polynucleotides, including NCLB, MAEL, BOULE, and VgR. US Patent Application publication 2014/0275208 and US2015/0257389 describes polynucleotide silencing elements targeting RyanR and PAT3. PCT publications WO/2016/138106, WO 2016/060911, WO 2016/060912, WO 2016/060913, and WO 2016/060914 describe polynucleotide silencing elements targeting COPI coatomer subunit nucleic acid molecules that confer resistance to Coleopteran and Hemipteran pests. US Patent Application Publications 2012/029750, US 20120297501, and 2012/0322660 describe interfering ribonucleic acids (RNA or double stranded RNA) that functions upon uptake by an insect pest species to down-regulate expression of a target gene in said insect pest, wherein the RNA comprises at least one silencing element wherein the silencing element is a region of double-stranded RNA comprising annealed complementary strands, one strand of which comprises or consists of a sequence of nucleotides which is at least partially complementary to a target nucleotide sequence within the target gene. US Patent Application Publication 2012/0164205 describe potential targets for interfering double stranded ribonucleic acids for inhibiting invertebrate pests including: a Chd3 Homologous Sequence, a Beta-Tubulin Homologous Sequence, a 40 kDa V-ATPase Homologous Sequence, a EF1α Homologous Sequence, a 26S Proteosome Subunit p28 Homologous Sequence, a Juvenile Hormone Epoxide Hydrolase Homologous Sequence, a Swelling Dependent Chloride Channel Protein Homologous Sequence, a Glucose-6-Phosphate 1-Dehydrogenase Protein Homologous Sequence, an Act42A Protein Homologous Sequence, a ADP-Ribosylation Factor 1 Homologous Sequence, a Transcription Factor IIB Protein Homologous Sequence, a Chitinase Homologous Sequences, a Ubiquitin Conjugating Enzyme Homologous Sequence, a Glyceraldehyde-3-Phosphate Dehydrogenase Homologous Sequence, an Ubiquitin B Homologous Sequence, a Juvenile Hormone Esterase Homolog, and an Alpha Tubuliln Homologous Sequence.

Methods for Killing an Insect Pest and Controlling an Insect Population

In some embodiments methods are provided for killing an insect pest, comprising contacting the insect pest, either simultaneously or sequentially, with an insecticidally-effective amount of a recombinant IPD126 polypeptide of the disclosure. In some embodiments methods are provided for killing an insect pest, comprising contacting the insect pest with an insecticidally-effective amount of one or more of a recombinant pesticidal protein of SEQ ID NOS: 19-36, or a variant or insecticidally active fragment thereof.

In some embodiments methods are provided for controlling an insect pest population, comprising contacting the insect pest population, either simultaneously or sequentially, with an insecticidally-effective amount of one or more of a recombinant IPD126 polypeptide of the disclosure. In some embodiments, methods are provided for controlling an insect pest population, comprising contacting the insect pest population with an insecticidally-effective amount of one or more of a recombinant IPD126 polypeptide of SEQ ID NOS: 19-36, or a variant or insecticidally active fragment thereof. As used herein, "controlling a pest population" or "controls a pest" refers to any effect on a pest that results in limiting the damage that the pest causes. Controlling a pest includes, but is not limited to, killing the pest, inhibiting development of the pest, altering fertility or growth of the pest in such a manner that the pest provides less damage to the plant, decreasing the number of offspring produced, producing less fit pests, producing pests more susceptible to predator attack or deterring the pests from eating the plant.

In some embodiments methods are provided for controlling an insect pest population resistant to a pesticidal protein, comprising contacting the insect pest population, either simultaneously or sequentially, with an insecticidally-effective amount of one or more of a recombinant IPD126 polypeptide of the disclosure. In some embodiments, methods are provided for controlling an insect pest population resistant to a pesticidal protein, comprising contacting the insect pest population with an insecticidally-effective amount of one or more of a recombinant IPD126 polypeptide of SEQ ID NOS: 19-36, or a variant or insecticidally active fragment thereof.

In some embodiments methods are provided for protecting a plant from an insect pest, comprising expressing in the plant or cell thereof at least one recombinant polynucleotide encoding a IPD126 polypeptide of the disclosure. In some embodiments methods are provided for protecting a plant from an insect pest, comprising expressing in the plant or cell thereof a recombinant polynucleotide encoding one or more IPD126 polypeptides of SEQ ID NOS: 19-36, or variants or insecticidally active fragments thereof.

Insect Resistance Management (IRM) Strategies

Expression of B. thuringiensis δ-endotoxins in transgenic corn plants has proven to be an effective means of controlling agriculturally important insect pests (Perlak, et al., 1990; 1993). However, in certain instances insects have evolved that are resistant to B. thuringiensis δ-endotoxins expressed in transgenic plants. Such resistance, should it become widespread, would clearly limit the commercial value of germplasm containing genes encoding such B. thuringiensis δ-endotoxins.

One way of increasing the effectiveness of the transgenic insecticides against target pests and contemporaneously reducing the development of insecticide-resistant pests is to use non-transgenic (i.e., non-insecticidal protein) refuges (a section of non-insecticidal crops/corn) with transgenic crops producing a single insecticidal protein active against target pests. The United States Environmental Protection Agency (epa.gov/oppbppdl/biopesticides/pips/bt_corn_refuge_2006.htm, which can be accessed using the www prefix) publishes the requirements for use with transgenic crops producing a single Bt protein active against target pests. In addition, the National Corn Growers Association, on their website: (ncga.com/insect-resistance-management-fact-sheet-bt-corn, which can be accessed using the www prefix) also provides similar guidance regarding refuge requirements. Due to losses to insects within the refuge area, larger refuges may reduce overall yield.

Another way of increasing the effectiveness of the transgenic insecticides against target pests and contemporaneously reducing the development of insecticide-resistant pests would be to have a repository of insecticidal genes that are effective against groups of insect pests and which manifest their effects through different modes of action.

Expression in a plant of two or more insecticidal compositions toxic to the same insect species, each insecticide being expressed at efficacious levels would be another way to achieve control of the development of resistance. This is based on the principle that evolution of resistance against two separate modes of action is far more unlikely than only one. Roush, for example, outlines two-toxin strategies, also called "pyramiding" or "stacking," for management of insecticidal transgenic crops. (The Royal Society. Phil. Trans. R. Soc. Lond. B. (1998) 353:1777-1786). Stacking or pyramiding of two different proteins each effective against the target pests and with little or no cross-resistance can allow for use of a smaller refuge. The US Environmental Protection Agency requires significantly less (generally 5%) structured refuge of non-Bt corn be planted than for single trait products (generally 20%). There are various ways of providing the IRM effects of a refuge, including various geometric planting patterns in the fields and in-bag seed mixtures, as discussed further by Roush.

In some embodiments the IPD126 polypeptides of the disclosure are useful as an insect resistance management strategy in combination (i.e., pyramided) with other pesticidal proteins or other transgenes (i.e., an RNAi trait) including but not limited to Bt toxins, Xenorhabdus sp. or Photorhabdus sp. insecticidal proteins, other insecticidally active proteins, and the like.

Provided are methods of controlling Lepidoptera and/or Coleoptera insect infestation(s) in a transgenic plant that promote insect resistance management, comprising expressing in the plant at least two different insecticidal proteins having different modes of action.

In some embodiments the methods of controlling Lepidoptera and/or Coleoptera insect infestation in a transgenic plant and promoting insect resistance management comprises the presentation of at least one of the IPD126 polypeptide insecticidal proteins to insects in the order Lepidoptera and/or Coleoptera.

In some embodiments the methods of controlling Lepidoptera and/or Coleoptera insect infestation in a transgenic plant and promoting insect resistance management comprises the presentation of at least one of the IPD126 polypeptides of SEQ ID NOS: 19-36, or variants or insecticidally active fragments thereof, insecticidal to insects in the order Lepidoptera and/or Coleoptera.

Also provided are methods of reducing likelihood of emergence of Lepidoptera and/or Coleoptera insect resistance to transgenic plants expressing in the plants insecticidal proteins to control the insect species, comprising expression of at least one of the IPD126 polypeptides to the insect species in combination with a second insecticidal protein to the insect species having different modes of action.

The following examples are offered by way of illustration and not by way of limitation.

EXAMPLES

Example 1. Coleoptera Diet-Based Feeding Assays

Western corn rootworm (WCRW, *Diabrotica virgifera virgifera*) bioassays were conducted using the cell lysates 10 microliter samples mixed with molten low-melt diet (Southland Products Inc., Lake Village, Arkansas) in a 96 well format. WCRW neonates were placed into each well of a 96 well plate. The assay was run four days at 25° C. and then was scored for insect mortality and stunting of insect growth. The scores were noted as dead, severely stunted (little or no growth but alive), stunted (growth to second instar but not equivalent to controls) or no activity.

Example 2. Strain Isolation, Cultivation and Activity Bioassay

Plant samples were collected from multiple locations in Iowa. Plant samples were broken into smaller pieces and submerged in PBS buffer. After 15 min at low rpm shaking, 100 ul of the wash was then serial diluted out and plated on several different isolation agar media. Various bacterial strains were picked and cultured in liquid Trypticase soy medium (Tryptone 17 g/L, enzymatic digest of soy meal 3 g/L, Dextrose 2.5 g/L, Sodium Chloride 5 g/L, K2HPO4 2.5 g/L) overnight at 26° C. with shaking at 250 rpm. The total protein was extracted from cell mass and used for insect bioassay. Some strains, including *Pantoea agglomerans* strain PMC3671E3-1 (NRRL Deposit No. B-67697), *Pantoea agglomerans* strain PMC3671E9-1 (NRRL Deposit No. B-67698), and *Pantoea agglomerans* strain PMCJ4082D4-1 (NRRL Deposit No. B-67699) showed strong insecticidal activity against WCRW. The insecticidal activity was further confirmed with new cultures.

Example 3. Strain Sequencing and Species Identification

Genomic DNA from strain PMC3671E9-1, PMC3671E3-1, and PMCJ4082D4-1 was extracted with a Sigma Bacterial Genomic DNA Extraction Kit (Cat #NA2110-KT, Sigma-Aldrich, PO Box 14508, St. Louis, MO 63178) according to the manufactures' instructions. The DNA concentration was determined using a NanoDrop Spectrophotometer (Thermo Scientific, 3411 Silverside Road, Bancroft Building, Suite 100, Wilmington, DE 19810) and the genomic DNA was diluted to 50 ng/ul with sterile water. The genomes were sequenced with Illumina and PacBio sequencers. The sequences were assembled and annotated. The 16S rDNA (SEQ ID NO: 37, SEQ ID NO: 38, and SEQ ID NO: 39) was extracted from the genome sequence and blasted against NCBI database. The results indicated that PMC3671E9-1, PMC3671E3-1, and and PMCJ4082D4-1 are *Pantoea agglomerans* strains.

Example 4. Active Protein Identification and Confirmation

This insecticidal activity of these strains exhibited heat and proteinase sensitivity indicating proteinaceous nature. Insecticidal activity against WCRW was observed from both cell culture supernatant and clear cell lysate from *Pantoea agglomerans* strain PMC3671E9-1 grown in Terrific Broth and cultured for 2 days at 26° C. with shaking at 250 rpm. 80 ml of *Cell* supernatant of PMC3671E9-1 was subjected to Tangential Flow Filtration in a 100 kDa MWCO Polyethersulfone (PES) membrane from Spectrum Labs equilibrated in 20 mM Tris-HCl buffer, pH 8.0, 150 mM NaCl (buffer A). The cell supernatant was concentrated, and buffer exchanged into buffer A and a volume of 8 ml was recovered. This material was loaded onto a Superdex 200 26/600 pg column (size exclusion, GE Healthcare) equilibrated in buffer A. Fractions corresponding with insecticidal activity were pooled and buffer exchanged into 1M Ammonium Sulfate, 20 mM Tris-HCl, pH 8 (buffer B) and applied to a Source 15 Phenyl 4.6/100 column (hydrophobic interaction, GE Healthcare) equilibrated in buffer B. Protein was eluted with a linear gradient from 1 M to 0 M ammonium sulfate. Fractions were desalted and subjected for identification of insecticidal activity. SDS-PAGE analysis of fractions with WCRW activity showed a band corresponding with insecticidal activity after staining with SYPRO ruby gel stain (Invitrogen). Mass spectrometry was used to identify a four gene operon encoded by strain PMC3671E9-1. The proteins were designated as IPD126Aa-1, IPD126Aa-2, IPD126Aa-3 and IPD126Aa-4.

The PMC3671E9-1 DNA fragment containing IPD126Aa-1, IPD126Aa-2, IPD126-3 and IPD126Aa-4 were subcloned into *E. coli*. The total protein extract from the transformed *E. coli* cells showed strong activity against WCRW, confirming the insecticidal activity of these proteins.

Example 5. Identification of Homologous Sequences

Genome sequences analysis indicated homolog sequences in other strains. *Pantoea agglomerans* strain PMC3671E3-1 contains all four IPD126 genes and have second copy of the first three genes upstream. Another *Pantoea agglomerans* strain, PMCJ4082D4-1 (NRRL Deposit No. B-67699), is also active on WCRW and contains two operons, similar to PMC3671E3-1. These corresponding homolog sequences show 70 to 100% amino acid sequence identities to those in PMC3671E9-1.

Example 6. Live Culture Assay and Results

WCRW bioassays were conducting using live cultures of 20 ul samples and molten artificial diet in a 96 well format. A serial dilution of the overnight PMC3671E3-1 culture was tested on multiple insect targets. The culture and washed pellet showed killing activity against WCRW.

TABLE 1

WCRW Bioactivity

PMC3671E3-1 culture

| Dilution | SBL | ECB | FAW | VBC | CEW | WCRW |
|---|---|---|---|---|---|---|
| 1 x | 0 | 0 | 0 | 0 | 0 | 3 |
| 1/2 x | 0 | 0.5 | 0 | 0 | 0 | 3 |
| 1/4 x | 0 | 0 | 0 | 0.25 | 0 | 3 |
| 1/8 x | 0 | 0.5 | 0 | 0 | 0 | 3 |
| 1/16 x | 0 | 0 | 0 | 0 | 0 | 3 |
| 1/32 x | 0 | 0 | 0 | 0.75 | 0 | 2.5 |
| 1/64 x | 0 | 0 | 0 | 0 | 0 | 2 |
| 1/128 x | 0.75 | 0.8 | 0 | 0 | 0 | 0 |

TABLE 1-continued

WCRW Bioactivity

PMC3671E3-1 spent media

| | SBL | ECB | FAW | VBC | CEW | WCRW |
|---|---|---|---|---|---|---|
| 1 x | 0 | 0.75 | 0 | 0 | 0 | 1.5 |
| 1/2 x | 0 | 0.25 | 0 | 0 | 0 | 1.5 |
| 1/4 x | 0 | 0.25 | 0 | 0.75 | 0 | 1 |
| 1/8 x | 0.25 | 0 | 0 | 0 | 0 | 1 |
| 1/16 x | 0 | 0 | 0 | 0 | 0 | 0 |
| 1/32 x | 0 | 0.5 | 0 | 0 | 0 | 0 |
| 1/64 x | 0.25 | 0 | 0 | 0 | 0 | 0 |
| 1/128 x | 0 | 0 | 0 | 0.75 | 0 | 0 |

PMC3671E3-1 washed cell pellet

| | SBL | ECB | FAW | VBC | CEW | WCRW |
|---|---|---|---|---|---|---|
| 1 x | 0 | 0 | 0 | 0 | 0 | 3 |
| 1/2 x | 0 | 0.25 | 0 | 0 | 0 | 3 |
| 1/4 x | 0 | 0.25 | 0 | 0 | 0 | 3 |
| 1/8 x | 0 | 0 | 0 | 0 | 0 | 3 |
| 1/16 x | 0.25 | 0 | 0 | 0 | 0 | 3 |
| 1/32 x | 0 | 0.75 | 0 | 0 | 0 | 2.5 |
| 1/64 x | 0.25 | 0 | 0 | 0 | 0 | 1.83 |
| 1/128 x | 0 | 0 | 0 | 0 | 0 | 1 |

Scores: 3-killing; 2-severe stunting; 1-stunting; 1-no activity.

What is claimed is:

1. A recombinant polynucleotide encoding an IPD126 polypeptide comprising an amino acid sequence having greater than 95% sequence identity compared to the amino acid sequence of SEQ ID NO: 19 and further comprising a heterologous regulatory sequence.

2. The recombinant polynucleotide of claim 1, wherein the recombinant polynucleotide comprises the polynucleotide of SEQ ID NO: 1.

3. A DNA construct comprising the recombinant polynucleotide of claim 1.

4. A transgenic plant or plant cell comprising the DNA construct of claim 3.

5. A method of controlling Lepidoptera and/or Coleoptera insect infestation in a transgenic plant and providing insect resistance management, comprising expressing in the plant the polynucleotide of claim 1.

* * * * *

SEQUENCE LISTING

<160> NUMBER OF SEQ ID NOS: 39

<210> SEQ ID NO 1
<211> LENGTH: 7569
<212> TYPE: DNA
<213> ORGANISM: Pantoea agglomerans

<400> SEQUENCE: 1

```
atgtatctga ccgaagaaat acttgccaaa ctgaatgccg gaaacggcaa gctacaatct      60
actgtagagc aggaaattac gctgccagat attatggtgc gctcttttgc tcaggtaaaa     120
gaactggcag gagacaggtt aagttggggt gagaaaaact tcctttatca gcaggctcag     180
acacagctga aagaaaataa aatggcagaa tcccgcattc tcagccgtgc caacccgcaa     240
ctggcaaatg ctgtccggct gggcatccgc cagtcttcga tgctgggtag ctatgacgac     300
ctgttcccgc agcgcgccag ccgctttgtt aagccaggtg cggttgcctc aatgttttca     360
ccggctggct atctgaccga gctgtaccgc gaggccagag gattacacaa ggctgaatcg     420
caatataatc ttgataaccg ccgtccggat ctggcctcgc tgacgctatc ccagtcaaac     480
atggatgacg agttgtccac cctgtcgctc tccaatgaac tgctgctgaa gttaattcag     540
tcaaaggaaa gcctgactta tgaacaggtt atggaaaagc tggcgactta cagactgacc     600
ggcaccacgc cttacaatca accctatgaa gcaatccgtc aggctatttt gctgcaggac     660
ccggagttta acgcgttcag taataatccg gcagtggccg caaaaatcaa caccagcggg     720
ctattaggca ttacttccga tatcgccccg gagctgcatg cgatactgac tgaagagata     780
acagaagaaa acgcggaagc actggttaaa aagaacttcg gcgatgtcaa tatcaagcag     840
ttccaaaatc ttgcgtggct ggccaactgg tacggcttgt cctatgagaa gcttaataac     900
ctggtaggca tgatttggtc cagagatgat cttgaccccg ctattgagca ctataaaaat     960
tccagcctgg tcactttggt ggctgaagac ggtggatcgc ttaacgcggt gttgattaag    1020
cgtactaaag gccatgattc cgatgatatg cattatgcgg aattaattcc tgtgggagga    1080
```

```
gacaaatttc agtacaactt cagccttatt gatgctgaag ccagtagttc ttattatcaa    1140
ttcggtacaa aaggaaagta ctcccaagat ttagttcctg caatccataa gcctttgctg    1200
ggtaatactc cctatgctgt tacattcaca cttacacaag agcagctaag taacccagtt    1260
gaaatatccc tgacgcatgg tagtggcggt ggtgatcgcc ttacctcaac aattttcact    1320
gttacgactt ccccatttga tatcttcctg ctgaagctga ataaacttat acgcctctat    1380
aaagccaccg gtatctcccc ggccagcatc aggaccgtga ttgaaagcga taacactgac    1440
cttatcatca cagaaagcgt attaagccag ctattctgga ctaattacta tacacaaacg    1500
ttcgaaatgg aattttctgc cgcactggtg ctggcaggag cggacatcgg tcagatagca    1560
cacagtgaaa gccagccaag tgcgttcacc cgcctgttta acacgccgcc gctggataac    1620
cagcagtttt cggccagcga cgagtcactg gatctggagc cgggtaaggg agccgatgct    1680
ttccggatcg ctgtacttaa acgtgcattg caggtgaatg acgccggact gtataccctt    1740
tatggtctga gtttcaccga taaagataaa aacggtgagt tgattccgtt caccactaaa    1800
attgagaacc tttctgccct ctatcgcacc cgactgctgg ccgacatatt taatatttct    1860
gtcactgagc tgagcatgct gctgtcggtt tcaccttatg ccagtcagaa ggtggacagc    1920
ctcaaaggtc aggcactaca tcagtttgtt actaccctca gcgactatat gcaacggctg    1980
aaagcgatga actggagcgt cagcgatctc tacctgatgc tgaccaacag ctacagcacg    2040
gtactgtcgc cagaaattaa aagcctgatg actaccctga aaatggact cagcgagcag    2100 gattttaaca cacggatga aatcgctcag ctgaatgcga cggcaccttt aatcgccgca    2160
gcgatgcagc ttgactccac agaaaccgct gcagcactgc tggaatggct taatcaattg    2220
caaccagcag ggctgacagt ggcaggtttc ctgtctcttg tgaatcagac gacacccgaa    2280
gataaggatg ttgtaaaact ggtctctttc tgccaggtga tggggcagct tgcactgatc    2340
gtgcgcaagg cggctctggg ctccagcgaa atcatctttg cagttgcgca tccggctatc    2400
tttaacaaag atgcgaactc actggctcag gatattggca cgctctttga cctgacccag    2460
ctgcatgcat ttctgacaga atgtggtact tatgcctctg aaattcttac ctcactgaat    2520
gaagggaacc tcgacgttag cacagtggcg acggcgctga cgctggacaa aactacactg    2580
gcgcaggcac ttgctcaggt ttcagaatct aaggccttt ctaactggca cgaactgcgt    2640
gatgcacttc agtggacaga tgccgccagc atttttcaaca tcacaccagt ggctctgact    2700
gcgatggtga acctgaaatt cagtggtgac aacgcttcac cgtatcagga gtgggtaacg    2760
gtcagcaaag ctatgcaggc cgggctgaat cagacgcaaa gtgctcagct gcaagcttcg    2820
ctggatgaat ccctcggtgc agccgtcagc gcctatgtga ttaaaaacag ttcgccgtcc    2880
tgggttaccg atcgcgacaa actttacagc tggctgctga ttgataacca ggtgtcggcg    2940
caggtcaaaa ccacccgcat cgccgaagcg attgccagcg tgcagctgta tgtaaaccgg    3000
gcattaagcg gccttgagaa tggccaatca atcactgacg ctgttgataa tgccgttaaa    3060
tccggggtat ttttacccg cgactgggat acatacaaca aacgctacag cacctgggcc    3120
ggcgtctctg agttggttta ctatccggaa aactatgttg acccgaccct gcgccctggt    3180
cagaccggca tgatgatga gatgctgcag acgcttagcc agagccagct gacgtccgat    3240
tcggtggaag acgcgttcaa aacctacatg acccgctttg aagaaatcgc taacctggat    3300
attgtcagcg gctatcatga caacctcaat gaccagaagg gtgtaacata tctgatcggt    3360
cgctccgctg ctggcgacta ttactggcgt tcggcagata tcagtaagct ttctgacggt    3420
```

```
aagctcccag ctaacgcctg ggccgagtgg aaaaaaatta ccaccgcgct gacgcccgta    3480
aataacctgg tgcgcccggt aatatttcag tcacgattgt atgtgacctg ggtggaaagc    3540
cgcgaagtcg gcatatccgc cgacaaagag cacaacagtg aaaccaaaat tctggagtat    3600
gctctgaagt atgcacatat tctgcatgac ggtacctgga gcgcacccgt gtctgttaag    3660
cttgagaacg gaacgctgcc tcttgacagc gtggctattg atgttacagg catgtattgc    3720
gcaaaggata cacagcatga ccagctttat attttatttt ataagaaaaa ggaaacttac    3780
aatgacgtca atgacgttct gaaaggaata atactgcacg atgacgggac taccaccatt    3840
acttccggta atagcgtatc tggattggtt gtctataaac aactggatac tactaaggaa    3900
gtcaggctga atacgcctta cccgggagga aaaacatact actctattaa taatatgagg    3960
gaatcgagta aatggggaga tgataatatt tcaatgctgt caggatgtag cgtgaaagat    4020
tttgtcttta ccgaaggcga tgggaaactg aatgttgcgt tcaatgccac cgaacgcatt    4080
atataccgtg gtaatccgga tagtcagggc tatgtggccc tggtcaatat gattaaagct    4140
atcggaaata ttgagacac ctttaaaatt ccggttttga attcaaatgg agagggctta    4200
gacaaacctt ttcatgtat attcagacag cctgatgaaa agactgatgc gattgcttat    4260
ttctccgatg tccagggatt aaatatagat catttcgctt tcaacgatga aagtcagaaa    4320
atgctgggtc gtatcttaag gcctgaagag aaagattttt ataaattaga gtgtgtcaat    4380
actaatctcc atatatacaa agacagtagc aaaacaatca aaccggataa cttcgtgtat    4440
tttggcccag gcatggatct tatcgtagtt aaaggaatga tcgtggaaac ccttttttgga   4500 ttatttggag agcttaaaac cggaataaaa gataagagtg tgaaactatc cgtttctgcc    4560
ggagtcattg acaattcacc agccgctacg aagactaagt atacattcga cgaatcgctg    4620
tatgttattg aaggccaaac cgtttctatt caacttagtg aatttaaaga aaataatatt    4680
gaccttgaat tcactttctt tgcttctgga gacagtggga actcactagg caaaagtgtc    4740
atcagcgcaa cattgacccg aacgagtgaa aacactatac ccgttatttc tctgaataaa    4800
acctctgaca acgcgcagta tttgcagtat ggcattcatc gcataagggt gaatacgctg    4860
tttgcaaaac agctggttgc gcgcgcgaac gccggactgg acactgtact gtctatggca    4920
acccagcagc tgacggaacc taaaatgggc aaaggtgcgt acattgacct tgaacttaat    4980
gccagcagcg atggcagttc ggcggtattt gaagtattga tgtgtgacgt ttttaccaaa    5040
ggtgaccgca ttgctttgac cagcggcaca ctcagcccca cagcacgcac cagctgctca    5100
tttttcattc cccgactggg tgagtctact gaatctccat ggaatatgta ttttgcgta    5160 aaaactcaga atgatgagag taagcgggta gaagtaatgg gaggcgaggg gaaatggagt    5220
taccagtacg tcgatgaatc tggtactgcc attaagccgc cctataccga tccatatatt    5280
gcaagcgtat atgtacggaa cgatacaaca gagccgatgg acttcaacgg tgccaatgcg    5340
ctctatttct gggaaatgtt ctattacgta ccgatgatgg tatttaagcg cctgctaagc    5400
gaaagtaagt tcgctgaagc gacccagtgg atcaaatata tctggaatcc cgatggctat    5460
ctggtgaaca atcagcccgc gacctatagc tggaatgtgc gcccgctgga ggaggatacc    5520
tcctggcacg ctgacccgct agactcggtt aaccgggatg ctgtcgcgca ggccgatccg    5580
ctgcactaca aggttgctac ttttatggcg taccttgatc tgctgattgc ccgcggtgat    5640
gctgcctatc gccagctgga gcgcgatacc ctgaatgaag ccaaaatgtg gtacgtgcag    5700
gcgctgaaca tccttggcga tgaacccctac cagtcatcat ccagcggctg gagctcgcca    5760
gttctctcca gcgcagcagc tcagactaca gagaaaaacg ttcagcaggc gatgctggcg    5820
```

-continued

```
gtgcgtcagc agcctgacgc aggagaactg cgcaccgcca actcgctgac tgacctgttc    5880
ctgccccagc agaacgcgaa gctggctggt tactggcaga cgctggcgca gcgcctgtat    5940
aacctgcgcc acaacctgtc aattgacggc agcccattgt cactggccat ctatgccgcg    6000
ccagccgatc cggcagcgct gctcagcgcg gcggtcaaca gcgcgtccgg cggcagcgac    6060
ctgcctgctg ttgttatgcc gctgtaccgc ttcccggtca ttctggagag cgcccggggg    6120
atggcaggtc aactgatcca gttcggcagc acgctgctca gcattgctga acggcaggat    6180
gcggaagcgt tgtcggagct gatgcagact cagggtagtc aactgatttt gcagagcatc    6240
gcactgcaaa acagtacgat ttctgaaatt gatgcggata aaccgtgct ggaagcgagc     6300 ctaagcggtg cacgttcgcg cctcgaccgg tacaccacgc tgtatgacga ggatgtaaat    6360 acggggggaac agcaggctat ggatctgttc tacgcctcct ccctccaggc aaacggcggc   6420
cagatgttcc acactatcgc aggcgcactt gacctggtgc taacatcttt tggtctggcc    6480
gacggcggtt cgcgctgggg tgcggtatct actgcaatgg ccagcatcgc cgatttgtcc    6540
gccgcagcct gtcacacgac cgcagagcgc ctcagccagt ctgaggtcta ccgccgccgc    6600
cgccaggagt gggaaatcca gcgcaacgcc gcgcagtctg aaattgacca gattgacgct    6660
cagctggcct cactgacgat acgtcgcgag ggcgcggtac tgcagaaaac ctacctggaa    6720
acgcagcagg tcagatgca ggcgcagatg actttcctgc agaataagtt caccagcaag     6780
gcgctgtaca actggctgcg cggcaagctg gcggccattt actatcagtt ctacgacctg    6840
acggtatcgc gctgcctgat ggcagaagcc gcctatagct gggatattaa aggtaatcag    6900
gaaacaggta cctttatccg tcccggcgcc tggcagggca cctatgccgg cctgatggca    6960
ggggaaacgc tgatgctgaa tctggcacag atggaaaaca gctacctgac aaaagatgag    7020
cgcctgaaag aggtcacgcg cacggtctgc ctgtctgaag tttatgcagg gctctcttcg    7080
gattcgttcg cgctggctga taccgtcacc acactggtga gtaacgggaa aggcaacgcc    7140
ggcacggacg ataacggagt gaagatcgat gacaagcagc ttctggctac cctgaaactc    7200
tccgatctga gcattgataa cgattatccg gagtcactgg gcaaaacccg acgcattaag    7260
caaatcagcg tgacgctgcc gacgctggtc gggccgtatc aggacgtccg ggcggtactg    7320
agctatggcg gcagtgtggc tctgccacgc ggctgcacgg cggtcgccgt ttcgcacggc    7380
atgaatgaca gcggccagtt ccagctggac ttcaatgaca gccgctggtt gccgtttgaa    7440 ggtataccctg tcggggattc cggtacgctg acgctcagct cccggacat taccgataaa    7500 cagcaggaaa atctgctgct cagtctgagc gacatcatcc tgcacatccg ctataccatc    7560
gcaagctga                                                            7569
```

<210> SEQ ID NO 2
<211> LENGTH: 4266
<212> TYPE: DNA
<213> ORGANISM: Pantoea agglomerans

<400> SEQUENCE: 2

```
atgcaaaata cagatcagat gagcctgacg ccccccttcct taccctcagg tgggggtgcc     60
gtcaccggac tgaaaggcga tatgtcagga gccggccccg atggcgccgc cacgctgaac    120
cttcccttgc cgatcagccc cggacgtggc tatgcgccgt cgttgtctct gggttaccac    180
agtcgtaacg gcaacggtgt ttttggcgca ggctggagct gcggtcagat ggctattcgc    240
ctgcaaaccc gcaaaggcgt gccgttttat gacggcagcg acgtctttac cgctcctgac    300
```

-continued

| | |
|---|---|
| ggtgaggttc tggtgccggc gctggacgcc agcggcaaga ctgaggttcg cacgaccact | 360 |
| acgctgctcg gcgaaaacct cggcggcacc tttaccgtac agacctaccg ttcccgggtg | 420 |
| gaaaccgact tcagtcgcct ggagcgctgg gtttcgcagg ccgacgcagc ggctgatttc | 480 |
| tggttgattt atagtccgga cggccagatc cacctgctgg gtcgtaaccc gcaggcgcgg | 540 |
| gtgagcaacc ctgaggatac aacccagacc gccgcctggc tgatagagtc gtcggtctct | 600 |
| gccagcggcg agcagattta ctggcaatac cggcaggaag atgagctggg ctgtacgcag | 660 |
| gatgagaaaa cggctcatgc acacgcgctc gcccagcgct atctggtggc ggtatggtat | 720 |
| ggcaataaag cggccagccg gacgctgccg gggctgctgt ctgttcctgc ggctggcagc | 780 |
| tggctgttta cgctggtgct ggactacggt gagcggacga cagatcctgc aacgccaccg | 840 |
| gcctggcttt caccaggcag tggtacatgg ctctgccggc aggatgtgtt ttccagctgg | 900 |
| gaatatggct ttgagctgcg cacgcgtcgc ctgtgccgac aggtactgat gtatcatgac | 960 |
| gtcgcggcgc tggcaggtaa gcctggttca gatgccgtgc cacagctggt caccagactg | 1020 |
| ctgctggact ataacctgtc tccgtcgctg actaccctga aaaccgcaca gcaggccgcc | 1080 |
| tgggaagcgg atgggacgtt gcgcagtctg ccgccgctgg cgttcagctg gcagaccttc | 1140 |
| ccgtcaacac cagagaaaag tgtcagctgg cagcagcgga atgacatggg gaaactcaac | 1200 |
| ccacagcagc cttatcagat ggttgacctg cacggtgaag gactggcggg tatcctctac | 1260 |
| caggacagtg gtgcctggtg gtatcgggag ccggttcgtc agttgggcga tgatgataat | 1320 |
| gccgtgacct gggcggctgc ccgaccgctg ccggcgttcc ctgctctgcg caagggcgga | 1380 |
| atgctgctgg atctggacgg tgatggctac ctggaatggg tggtcaccgc gccaggcgtc | 1440 |
| gcgggctgct atgcgcaaac gcctgaacaa tgctggcagc gcttcacgcc gctgtctgca | 1500 |
| ctgcctgtgg aataccgcca ctcgcgaatg gagataaccg acgtcaccgg tgcgggtctt | 1560 |
| gcggatatgc tgctgatcgg cccgaaaagc gtacgcctgt acagcggcag cggcagaggc | 1620 |
| tggaaaaaag cacgaacggt catgcaggac agtggcatca ccctgccggt ccccggcaca | 1680 |
| aacgcccgtg tcatggtggc attcagcgat atggccggca gcggtcagca cacctgacg | 1740 |
| gaaatcaaag ccagcggcgt acgttactgg cccagcctgg ggcatggtcg ctttgcggcg | 1800 |
| ccggtgacac tccccggctt cagtcagccc gcagaaacct caacccggc acagctctat | 1860 |
| ctggccgacg ttgacggttc cggtaccacc gatctgatct atgctctgag cgatcatctg | 1920 |
| ctggtatggc taaaccagag cggaaaccgc tttgacgagc ctttccgcat cgaccttccg | 1980 |
| gaaggcgtgc gctatgacaa tacctgcagc ttgcaggtcg ccgatattca ggggctgggc | 2040 |
| atctccagcc tggtgctgtc ggtgccacat ccgacgccgc gccattgggt atgtcacctg | 2100 |
| acggcggaaa agccctggct gctcgacggc atgaacaaca atatgggtgc cgccatact | 2160 |
| ctctgttacc gtagttcggc gcagttctgg ctggatgaaa aggctgctgc tactgccgat | 2220 |
| cggcccgcgc cggcgtgtta tatgccgttt gcgttgcata cactgagccg tactgaagtc | 2280 |
| agtgatgaaa ttaccggaaa ccggctcacc aggacgatac gctaccggca cggcgtctgg | 2340 |
| gacaggcgcg agcgagagtt ccgcggcttt ggctttgttg aagtcagtga tgccgaagcg | 2400 |
| ctggcaaaaac aaactgaagg gatgagcgca ccggcagtta acgcagctg gtatgctacc | 2460 |
| ggactgacag ccgtggatgc acagctcccg gatgagttct ggaaaggcga tcatgcggcc | 2520 |
| tttgccggtt ttaccctcg ttttaccacc ggctatggtg aacaagaggc ggcactggat | 2580 |
| accatcagcg acgatacccg tttctggctg acccgggcga ttcgcggtac gctgctgcgt | 2640 |
| agcgaactgt atggcgcgga tggcagcagc caggccggga tcccttacag catcacggaa | 2700 |

-continued

```
tcgcggccac aagtgcggtt gattactgag gcgggtaatt cgccggtggt ctggccctcc    2760
gttatcgaga accgcgccag tcattatgag cgcgtcagca gcgatccgca gtgcggccag    2820
cagatcctgt taaccagtaa tgaatatggt cagccgcttc gacagatcgg cgtcagttat    2880
ccccggcgca ccaggcccga tgccagcccc tacccgacg atctgccgga cggactgttt     2940
gccgacagct ttgatgagca acagcaggcg ttacgcctga cgctgacaca aagcagctgg    3000
catacgctga aagatatcag cagcggcatc tggctgccgg ccgtggctga tgcaacccga    3060
agcgatctgt tcgttcacca ggccgcgcag gtgccgccag cgggtcttac gctggagaat    3120
ttactcaccg atagtgcgct gctgaccagc ccggttttg gtggacagtc gcaaacctgg     3180
tatcaggaca gcgcgggtca ggcgagcacc acctcacccg attttcccct ccgaccgtcc    3240
tttagcgaaa ccgcagcgct ggacgaggca caggtcagcg cgctgtcagc cgatattgat    3300
caaacgaagc tggagcaggc gggctatacc cgctcagcgt atctgtttgc acgcagcggt    3360
gaggagggta aaaccctgtg gacagtgcgc cagggatata tcaccttcag cagcgcagac    3420 cattttatc tgccgattgc cgcacagcag acgctgctga ccggtaaaac cacggtcacc     3480
tatgatccgt acgactgtgt tgtcttacag gcaaaggatg ccgcaggtgc agttacctcc    3540
gcgacatacg actggcgttt tctcgcgccg acgcagatta ctgatatcaa cgataatctg    3600
aaaagcgtca cgctggatgc gctgggtcgg gtaacgtcgc agcgtttcag cggcagtgaa    3660
aacggaaaac cggcgggcta cagcgatgat gcgtttccac tgccggccag cgccgatgca    3720
gcgctggcgc tcagtgcccc gctaccggtg gcacagtgca tcatctacgt accggacagc    3780
tggatgctga ccggtgagca gcagcagccg ccgcacgtgg taacgctgct caccgaccgt    3840
tacgacagcg acagtcagca gcagatccga cagcaggttg ttttcagcga tggttttggc    3900
cgggtgctgc aggctgcctc aaggcaggtg aacggcgaag cgtggcagcg ggcggcaaac    3960
ggctcgttcg ttgccgaccc gaacggttcg cccgtgctga cggagaccac gttccgctgg    4020
gctgtcaccg gacgcactga atatgacaat aagggacagg ccattcgtac ttatcagcca    4080
tattttctgg acagctggaa atacgtgcgt gacgacagcg cgcgacacga tctgtacgcc    4140
gacacccact attacgatcc ggtgggcgg gagcggcagg tcattaccgc aaaaggtttg     4200
ctgcggcgtg tcacttacac ccctggttc gtagtcagcg aagacgaaaa cgatacgcag      4260
gcgtag                                                               4266
```

<210> SEQ ID NO 3
<211> LENGTH: 3015
<212> TYPE: DNA
<213> ORGANISM: Pantoea agglomerans

<400> SEQUENCE: 3

```
atgtccgccg cgtatgtctt aagtaattta tcttatcaac gggagaatac tatgagcacc     60
tcgctttaca gcaggacccc ctcagtcacg gtcctgaca accgcggcct gaccgtacgc     120
gatatcgcgt accaccgcca tccggatacc ccggcggtga ccagtgaacg catcacccgc    180
catcagtacg atgcccgcgg ctttctgacg cagagcgccg accgcgcct gcacgacgcc     240 gggctggcga acttcagcta ccggaccgac ctgaccggca gcgttctccg cctacagggc    300
gtcgataacg gcatcaccgt ggcgctgaac gatgccgccg acggccgtt tctggcggtc     360 agcaacatcc gcacggccgg tgatggctcg gaggacagaa gccaggcact gacccgtacg    420
tgtcagtacg aggacgcaac cctgcccgga cgtccgttaa gtattacgga gcaggtaaag    480
```

```
ggtggagccg cccgcatcac ggagcgcttc atctatgccg gtaacgctgt tgaggagaaa    540
gccctgaacc tcgccgggca gcccgtcagc cactatgata ccgccggtct gacacagaca    600
gacagcatcg ccctgaccgg cgtgccgctc tccgtcaccc gccgcctgct gaaggacgca    660
gacaatcctg acgccgtggc tgactggcag ggaacagacg cctccgtctg gaacgacccg    720
ctcgacgtgg aaacatacac taccctgtcc acggcagacg ccaccggcgc ggtgctgacc    780
accaccgatg cgaagggaaa cctgcagcgg ctggcctacg acgtggcggg cctgttgtcg    840
ggcagctggc tgacgctgaa ggatggcacg gagcaggtta tcgtgacgtc cctgacctac    900
tccgccgccg gcagaagct gcgcgaggag cacggcaacg cgtggtgac cacctacacg    960 tatgaagccg agacgcagcg cctgaccggc attaaaacgg cgcggccggc cggacacacc   1020
tcaggtgcga aggtgctgca ggacctgcgc tacacctatg acccggtggg caacgtcctg   1080
aaaatcagca acgatgccga agagacccgc ttctggcgta accagaaagt ggtgccggag   1140
agcgcgtacg tttatgacag cctgtaccag ctggtcagcg ccaccggacg cgagatggcg   1200
aacgccggtc agcagggcag cagctcatcg tcagccaccg tcccccttcc cgccgacagt   1260
tccgcgttta caaactatac ccgcaactat acttacgatg aggccggcaa cctgacgcag   1320
gtccgtcata ccccggctac gggcagcggc tacaccacaa aaataaccgt ctctgataaa   1380
agcaaccggg gtgtgctgag cacgctgacg gaaaatccct ccgacgttga gcgcgtgttc   1440
acggcgggcg gccagcagaa acagctgcag ccggggcaga gtctcatctg gacgccgcgt   1500
aacgagctgc tgaaggtgac gccggtagca cgtgacggcg gtgcggatga cagcgaaagc   1560
taccgctacg acggggggcag cctgcggctg ctgaaggtca gcgtgcagaa accgggaac   1620 agcacgcaga cgcagcgggc gctgtacctg ccaggactgg agctgcgcaa cacaacatcc   1680
ggtgatacga aaacggagag cctgcaggtg gttaccgtgg gtgaagcggg gcgcgcgcag   1740
gtgcgggtgc tgcactggga gagcggaacg ccggacagtg tcagcaacga ccagctacgc   1800
tacagctacg ataacctgac cggcagcagc gggcttgagc tggacagcag cggcaatatt   1860
atcagcatgg aggaatacta tccgtacggc ggcacggcgg tctggacggc gcgcagcgcg   1920
gtggaggcga agtacaaaac cgtgcgctac tcggccaagg agcgtgacgc cacggggctg   1980
tactactacg ggtaccggta ctaccagccg tgggctggcc gctggctgag cgcggacccg   2040
gcgggcacgc cggacgggct gaacctgttc aggatggtaa gaaataatcc ggttacgctt   2100
aaggacacaa acgggttgat cagtacgggt caggatgccc ggaaattagt ggccgaagca   2160
tttgttcacc ctttgcatat gactgtcttt gaaagaattt cttcagaaga aaatcttgca   2220
atgagcgtga gagaggctgg catttatact atttcggcac tgggtgaagg tgctgcagca   2280
aaagggcata atattcttga gaagaccatt aaacctggtt cattaaaggc tgtttatggt   2340
gataacgccg aatccattct tgcgcaggca aaacgcagcg gttttgttgg ccgggtaggt   2400
cagtgggatg catccggtgt acggggaatt tatgcacaca acacaccagg tggcgaagac   2460
ctggcctatc cagtcaactt aaaaaatagt tctgctaatg aacttgttaa tgcatggata   2520
aaatttaaaa tcatcacgcc ttataccggt gattatgaca tgcacgatat tattaaaatc   2580
tcggatggaa aagggcatgt gccccctggcg gaaagtaatg aggaaaaagg tgtaaaggat   2640
atgattaatg aaggtgttgc gcaggtcgac cctgccagac cctttacgtc tacagcgatg   2700
aatgttgttc gccatggccc tcaggtaaac tttgttccct atatgtggga acatgagcac   2760
gaaaatgtct aagggataa tggttatctg ggagtggtag ctcgtcccggg tccattccct   2820 gttgcgatgg tacataaggg tgaatggact gttttcgaca ataaaaacga gctgtttgag   2880
```

-continued

| ttttataaat ctacaaacac tcctcttccc gaacactggt ctcaggattt tgttgagaga | 2940 |
| gggaaaggaa atgttgcaac gccccgacac gctgaaattc ttgatcgtaa ttcctcgcgt | 3000 |
| ctaagagcgg cctga | 3015 |

<210> SEQ ID NO 4
<211> LENGTH: 2913
<212> TYPE: DNA
<213> ORGANISM: Pantoea agglomerans

<400> SEQUENCE: 4

| atgtgtagcg ttgccgattt tgatcggctg cacaacataa aacaggagaa tatcatgagc | 60 |
| acctcgcttt acagcaggac cccctcggtc acggtcctcg acaaccgcgg cctgaccgta | 120 |
| cgcgatatcg cgtaccaccg ccatccggat accccggcgg tgaccagtga acgcatcacc | 180 |
| cgccatcagt acgatgcccg cggctttctg acgcagagcg ccgacccgcg cctgcacgac | 240 |
| gccgggctgg cgaacttcag ctaccggacc gacctgaccg cagcgttcct ccgcctacag | 300 |
| ggcgtcgata acggcatcac cgtggcgctg aacgatgccg ccggacggcc gtttctggcg | 360 |
| gtcagcaaca tccgcacggc cggtgatggc tcggaggaca gaagccaggc actgacccgt | 420 |
| acgtgtcagt acgaggacgc aaccctgccc ggacgtccgt taagtattac ggagcaggta | 480 |
| aagggtggag ccgcccgcat cacggagcgc ttcatctatg ccgtaacgc tgttgaggag | 540 |
| aaagccctga acctcgccgg gcagcccgtc agccactatg ataccgccgg cctgacacag | 600 |
| acagacagca tcgccctgac cggcgtgccg ctctccgtca cccgccgcct gctgaaggac | 660 |
| gcggacaatc ctgacgccgt ggctgactgg cagggaacag acgcctccgt ctggaacgac | 720 |
| ctgctcggcg cggaaacata caccaccctg tccacggcag acgtcaccgg cgcggtgctg | 780 |
| accaccaccg atgcgaaggg aaacctgcag cggctggcct acgacgtggc gggcctgctg | 840 |
| tcaggcagct ggctgacgct gaaggatggc acggagcagg ttatcgtgac gtccctgacc | 900 |
| tactccgccg ccgggcagaa gctgcgcgag agcacggca acggcgtggt gaccacctac | 960 |
| acgtatgaag ccgaaacgca gcgcctgacc ggcattaaaa cggagcggcc ggccggacac | 1020 |
| gcctcaggtg cgaaggtgct gcaggacctg cgctacacct atgacccggt gggcaacgtc | 1080 |
| ctgaaaatca gcaacgacgc cgaagagacc cgcttctggc gcaaccagaa agtggtgccg | 1140 |
| gagaacgcgt acgtttatga cagcctgtac cagctggtca gcgccaccgg acgcgagatg | 1200 |
| gcgaacgccg gtcagcaggg cagcagctca tcgtcagcca ccgtccccct tcctgccgac | 1260 |
| agttccgcgt ttacaaacta tacccgcaac tatacttacg atgaggccgg caacctgacg | 1320 |
| caggtccgcc ataccccggc tacgggcagc ggctacacca caaaaataac cgtctctgat | 1380 |
| aaaagcaacc ggggtgtgct gagcacgctg acggaaaatc cctccgacgt tgacgcgctg | 1440 |
| ttcacggcgg gcggccagca gaaacagctg cagccggggc agagtcttat ctggacgccg | 1500 |
| cgcaacgagc tgctgaaggt gatgccgata atgcgtgacg gcggtacgga tgacagcgaa | 1560 |
| agctaccgct acgacggggg cagccagcgg ctgctgaagg tcagcgtgca gaaaaccggc | 1620 |
| aacagcacgc agacgcagcg ggcgctgtac ctgccgggac tggagctgcg gacgacaaaa | 1680 |
| tctggcgata cgctaacaga aagcctgcag gtgattaccg cgggcgaagc gggccggggcg | 1740 |
| caggtgcggg tgctgcactg ggagagcgga acgccggaca gtgtcagcaa cgaccagcta | 1800 |
| cgctacagct acgataacct gaccggcagc agcgggcttg agctggacag cagcggcaat | 1860 |
| attatcagta tggaggaata ctatccgtac ggcggcacgg cggtctggac ggcgcgcagc | 1920 |

```
gcagtggagg cgaagtacaa aaccgtgcgc tactcgggca aggagcgtga cgccacggga    1980
ctgtattact acggataccg gtattatcag ccgtgggcgg gcagatggct gagtgcggac    2040
ccggcgggca cggtggacgg gctgaacctg ttcagaatgg tgcgcaataa tccgctcaca    2100
ttaaaagata acgatgggct aaaaccaata aatgaaaatt tcagagaaaa taaaggcgat    2160
ctggtttatg ggctggctgc cccccgagga gcttatatat caacggcaat agggcgcaaa    2220
ttcgctccag aagagaaaga tgcacctgct tcaattattg acttatataa caatacggtt    2280
tccggacaag cccttcttag cgttgatttc aaaatactgc aagacttcat gaagtcacca    2340
aaaaaaaatg aaaaaaaact agcccctcca tctaacatta aagagttggt aaaaaaatcc    2400
agggattatc ctctgtggga ggattatttt ctggcagggg aaaacaaccc caaatttaac    2460
attgcatcca tatataaaga ggtcagaaaa gatgcaggaa agacccagta tcatgagtgg    2520
catatagcgg gaggacaatc ggcacctaag ctactttgga aacgaggaag taagttgggt    2580
attgaaatgg cggccagcgg tgctggcaat aaaatccatt ttgttcttga tgaactggat    2640
atatcaaatg ttgtaaataa ggaagggccg gggggaaat ctataacggc cagtgagtta    2700
cgttatgcgt acagaaatcg tgaaagactg actggaaata tacattttta caaaaataat    2760
gctgaaactg cgcaccatg ggatacaaat gctgaactgt gggcatctta tcaccccaaa    2820
ccaaagcata aggaaatga atcgacacac ataatgtcgc aaaggagaaa tggtagtctg    2880
ttcaaatcca tgagaaaggt tttctcaaga aat                                 2913

<210> SEQ ID NO 5
<211> LENGTH: 7572
<212> TYPE: DNA
<213> ORGANISM: Pantoea agglomerans

<400> SEQUENCE: 5
atgtatctga ccgaagaaat acttgccaaa ctgaatgccg gaaacggcaa actacaatct      60
actgtagagc agataattac gctgccagat attatggtgc gctcttttc tcaggtaaaa     120 gagctggcag agacaagct aagttggggt gagaaaaact ttctttatca gcaggctcag     180
acacagctga agaaaataa aatggcggaa tcccgcattc tcagccgtgc caacccgcaa     240
ctggcaaatg ctgtccggct gggcatccgt cagtcttcga tgctgggtag ctatgacgac     300
ctgttcccgc agcgcgccag ccgctttgtt aagccaggtg cggtggcctc aatgttttca     360
ccggctggct atctgaccga gctgtaccgt gaggccagag gattacacaa ggctgaatcg     420
caatataatc tcgataaacg ccgtccggat ctggcctcgc tggcgctatc ccagtcaaac     480
atggatgacg agttgtccac tctgtcactg tcaaatgagc tgctgctgaa taatatccag     540
cagcatgatg gcctcagcta tgacgatgcg ctgaagaagc tcgccggata ccgacaaacc     600
gggacaacac cctatagcca gccgtatgaa acgatccgcg aggctattct tctgcaggat     660
cctgcgttta ttcgattcg caacaatcca gctgtggcga ctaaaatgaa taccagtggc     720
ctgctgggac tgacagcaaa cctgccacct gaactgcatg cgatcctgac tgaaacgatt     780
accgaagaga atgcggaaca actgattaag gacaatttcg gtgatgtcaa cgtcagcaga     840
tttcaagatt ttagttatct tgcccgctgg tatgggatga cccttatga actgaactcg     900 gtgctgggac tgatggaggt gggcagcaat cctgtcgacg tgttacgta ttaccaggat     960 gaccagctga tttccctggt ggataatggc ggtaatctgg atgctgtgct gatgcaacgt    1020
gcgggcggtg acaattatag ccagtttggt tatatcgaac tgctaccggt gtcagggat     1080 acctaccagc ttcggtttac cgtacaaagt ggttacgtgg gtcaggactc agaagtccgc    1140
```

```
attggaactt cagagaatgc cggaagcaag gatattctta gcgatggtcg catcgccgga    1200
cttaacatcc ctatggtcct gaacgttaaa cttgacagca ctaagttggc ccaggggatc    1260
actatcggcg taacccgata cgaccccagc ggtagttata taaattttgc gtccgttcgt    1320
ttccagagat acgactttc ttataatgtc ttcctgctca aattaaacaa aattattcgc     1380
ctctacaaag ccaccggcat ttcgccatcc gatatccaga ccctgattga aagtgctaat    1440
catgacctgg ctattaccga agatgtacta agccagctct tctggacgaa ctattatacg    1500
cagcgttacg gtattgattt ttctgctgcg ctggtgctgg cgggtgcgaa catcagtcag    1560
attgcccaca gcaataaaca gagcgcgttc acccgcttgt ttaacactcc gccgctgaac    1620 aatcagttt tttatgctga tgggaaaaag ctgaacctcg aacccggtaa gtcggatgac     1680
tcacacggtc ttggggtact caaacgggca ttacaggtta atgatagcgc cctgtatacc    1740 cttttaatc tgacctttgc ggataaagac gcccagggta atgctgttgt tttcaccaaa     1800
actcctgaaa atctttctgc gctgtaccgt accagattgc tggcgacggt taacaacctg    1860
accgttaacg aactgagcct gctgctttcc gtttcaccat acgtaaaggt gaagctggct    1920
acgctaaaag acgaggcgct cagccagctg tcgactaccc tggaaaggta tacgcaatgg    1980
ctggacaaga tgaactggac gatcggcgat ctgtacctga tgctgacccc tgtttacagc    2040
accgttctgt cgccggatat tgaaaatctg gtgacgacgc tgaaaaatgg cctggcgggt    2100
caggacttaa ccagcgatga aaaacgcatc gctgcgctgg ctccgtttgt tgctgccgcc    2160
actcagctgg actctgcgga gacgccaggg gcgcttttac gatggctgaa cgatcttaaa    2220
ccgggaaccc tgtcattagc ggattttatc gcgcaggtta caacaccac ccaaaccgaa     2280 aatctggtca cattcagcca ggtgatggcg cagctcgccc ttattacgcg caacgccagc    2340
ctgagtgcaa atgagctgtc atgggcggtt gcgcacccgg aaattttcca ggaaaaggcc    2400
actgttctta aaaacgacat cgccactctc aatgatctga cgcagctgca tgatctgctg    2460
gcgcgctgtg gcagccatgc ctcagagatc cttacctcgc tgagtgggaa tgccagcaag    2520
gctgaaaata accttgccgt cagcaccctg gcgacggcgt taaatctgga cgagcgggca    2580
ctgacccagg cgctggcgaa ggtttccacc tatgaatatt tttataattg ggcacactta    2640
aatgaagcgc tgcagtggct ggacgttgcc accacctttg gcatcacgcc cgataacctg    2700
gccgcgctga ttgggctgaa gttcgataat caggatgacg cctcgtttgc cagctggctt    2760
accgcaagcc ggtttatgca ggcagggctt aacacgcagc agacagctca gctgtccgcc    2820
actctggatg aatccctcag cgcagcggtc agcgcctacg cgatcaaaaa tatttctcc     2880 ggcgcggtaa gtaacaggga gcagctctac agctggctgc tgattgataa ccaggtgtcg    2940
gcgcaggtca aaaccacccg catcgccgaa gcgattgcca gcgtgcagct gtatgtaaac    3000
cgggcattaa gcggccttga gaatggccaa tcagccactg acgctgttga taatgccgtt    3060
aaatccgggg tatttttac ccgcgactgg gatacataca acaaacgcta cagcacctgg     3120
gccggcgtct ctgagctggt ttactatccg gaaaactatg ttgacccgac cctgcgcctt    3180
ggtcagaccg gcatgatgga tgagatgctg cagacgctca gccagagcca gctgacgtcc    3240
gatacggtgg aagacgcgtt caaaacctac atgacccgct ttgaagaaat cgctaacctg    3300
gatattgtca gcggctatca tgacaacctc agcgaccaga agggtgtaac atatctgatc    3360
ggtcgctccg ctgctggcga ctattattgg cgttcggcag atatcagtaa gctttctgac    3420
ggtaagctcc cggctaacgc ctgggccgag tggaaaaaaa ttaccaccgc gctgacgccc    3480
```

```
gtaaataacc tggtgcgccc ggtaatatt  cagtcacgat tgtatgtgac ctgggtggaa    3540
agccgcgagg tcggcatatc cgccgtcaaa aagcaaaaca gtgaaaccaa acctctggag    3600
tatgctctga agtatgcaca tattctgcat gacggtacct ggagcgcacc cgtgtctgtt    3660
aagcttgaga acggaacgct gcctcttgac agcgtggcta ttgatgttac aggcatgtat    3720
tgcgcaaagg atacacagca tgaccagctt tatattttat tttataagaa aaaggaaact    3780
tacaatgacg tcaatgacgt tctgaaagga ataatactgc acgatgacgg gactaccacc    3840
attacttccg gtaatagcgt atctggattg gttgtctata aacaactgga tactactaag    3900
gaagtcaggc tgaatacgcc ttacccggga ggaaaaacat actactctat taataatatg    3960
agggaatcga gtaaatgggg agatgataat atttcaatgc tgtcaggatg tagcgtgaaa    4020
gattttgtct ttaccgaagg cgatgggaaa ctgaatgttg cgttcaatgc caccgaacgc    4080
attatatacc gtggtaatcc ggatagtcag ggctatgtgg ccctggtcaa tatgattaaa    4140
gctatcggaa atattggaga cacctttaaa attccggttt tgaattcaaa tggagagggc    4200
ttagacagac cttttacatg tatattcaga cagcctgatg aaaagactga tgcgattgct    4260
tatttctccg atgtccaggg attaaatata gatcatttcg ctttcaacga tgaaagtcag    4320
aaaatgctgg gtcgtatctt aaggcctgaa gagaaagatt tttataaatt agagtgtgtc    4380
aatactaatc tccatatata caaagacagt agcaaaacaa tcaaaccgga taacttcgtg    4440
tattttggcc caggcatgga tcttatcgta gttaaaggaa tgatcgtgga aacccttttt    4500
ggattatttg gagagcttaa aaccggaata aagataaga  gtgtgaaact atccgtttct    4560
gccggagtca ttgacaattc accagccgct acgaagacta agtatacatt cgacgaatcg    4620
ctgtatgtta ttgaaggcca aaccgtttct attcaactta gtgaatttaa agaaaataat    4680
attgaccttg aattcacttt cttggcttct ggagacagtg ggaactcact aggccaaagt    4740
gtcatcagcg caacattgac ccgaacgagt gaaaacacta tacccgttat ttctctgaat    4800
aaaacctctg acaacgcgca gtatttgcag tatggcattc atcgcataag ggtgaatacg    4860
ctgtttgcaa aacagctggt tgcgcgcgcg aacgccggac tggacactgt actgtctatg    4920
gcaacccagc agctgacgga acctaaaatg ggcaaaggtg cgtacattga ccttgaactt    4980
aatgccagca gcgatggcag ttcggcggta tttgaagtat tgatgtgtga cgttttacc    5040
aacggtgacc gcattgcttt tgaccagcgg cacactcagcc ccacagcacg caccagctgc    5100
tcatttttcg tgccccgact ggatgagtct actgcatctg catataatat gtacttttgc    5160
gtaaaaactc agaatactga gagtaagcgg gtagaagtaa cggaggcga  ggggaaatgg    5220
gattaccagt acgtcgatga atctggtgct gccattaagc cgccctatac cgatccatat    5280
attgcaagca tatatgtacg gaacgataca acagagccga tggacttcaa cggtgccaat    5340
gcgctctatt tctgggaaat gttctattac gtgccgatga tggtatttaa gcgcctgcta    5400
agcgaaagta agttcgctga agcgacccag tggatcaaat atatctggaa tcccgatggc    5460
tatctggtga acaatcagcc cgcgacctat acctggaatg tgcgccctct ggaggaggat    5520
acctcctggc acgctgaccc gctagactcg gttaacccgg atgctgtcgc gcaggccgat    5580
ccgctgcact acaaggttgc tacctttatg gcgtaccttg atctgctgat tgcccgcggt    5640
gatgccgcct atcgccagct gcagcgcgac accctgaatg aagcaaaaat gtggtacgtg    5700
caggcgctga acatccttgg cgatgaaccc taccagtcat catccagcga ctggagctcg    5760
ccagttctct ccagcgcagc agatcagact acagagaaaa acgttcagca ggcgatgctg    5820
gcggtgcgtc agcagcctga cgcaggagaa ctgcgcaccg ccaattctct gaccagtctg    5880
```

```
ttcctgccgc agcagaatga aaagctggct ggttactggc agacgctggc gcagcgcctg    5940
tataacctgc gccacaacct gtcaattgac ggcagcccat tgtcactggc catctatgcc    6000
gcgccagccg atccggcagc gctgctcagc gcggcggtca acagcgcgtc cggcggcagc    6060
gaactgcctg ctgctgttat gccgctgtac cgcttcccga ttattctgga gagcgcccgg    6120
gggatggcag gtcaactgac ccagttcggc agcacgctgc tcagcattgc tgaacggcag    6180
gatgcggaag ccttgtcgga gctgatgcag actcagggta gtcaactgat tttgcagagc    6240
atcgccctgc aaaacagtac gatttctgaa attgatgcgg ataaaaccgt gctggaagcg    6300
agcctaagcg gtgcacgttc gcgcctcgac cgatacacca cgctgtatga cgaggatgta    6360
aatacggggg aacagcaggc tatggatctg ttctacgcct cctctatcca ggcaaacggc    6420
ggccaggcgt tccacactgt cgcaggcgga cttgacctgg cgcctaacat ctttggtctg    6480
gctgacggcg gttcgcgctg gggtgcagca tttactgcat tggccagcat cgccgatttg    6540
tccgccgcag cctctcacac ggccgcagag cgcctcagcc agtctgaggt ctaccgccgc    6600
cgccgccagg agtgggaaat ccagcgcaac gccgcgcagt ctgaaattga ccagattgac    6660
gctcagctgg cctcactgac gatacgtcgc aaaggcgcgg tactgcagaa aacctacctg    6720
gaaactcagc agggtcagat gcaggcgcag atgaccttcc tgcagaataa gttcaccagc    6780
aaggcgctgt acaactggct gcgcggcaag ctggcggcca tctactatca gttctacgac    6840
ctgacggtat cgcgctgcct gatggcagaa gccgcctata gctggcatat taaaggtaat    6900
caggaaacag gtacctttat ccgtcccggc gcctggcagg gaatctatgc cggcctgatg    6960 gcagggaag cgctgatgct gaatctggca cagatggaaa acagctacct gacaaaagat    7020
gagcgcctgc aagaggtcac gcgcacggtc tgcctgtctg aattttattc agggctctct    7080
tcgaataagt tcgcgctggc tgataccgtt accacactgg tgaatagcgg gaaaggcaac    7140
gccggcacga ccgataacgg agtgaagatc gatggcaagc agcttctggc tacccctgaaa   7200 ctctccgatc tgaacattaa gacggattat ccagagtcac tggacaaagc caaacgcatt    7260
aagcaaatca gcgtgacgct gccgatgctg gtcgggccgt atcaggacgt ccgggcggta    7320
ctgagctatg gcggcagcgt ggttctgcca ccgcgctgca cggcggtcgc cgtttcgcac    7380
ggcatgaacg acagcggcca gttccagctg gacttcaatg acagccgctg gctgcctttt    7440
gaaggtatac ctgttgatga ttccggtacg ctgacgctca gcttcccgga cattaccgat    7500
aagcaacagg aaaatctgct gctcagtctg agcgacatca tcctgcacat ccgctatacc    7560
atcgcaagct ga                                                        7572
```

<210> SEQ ID NO 6
<211> LENGTH: 4266
<212> TYPE: DNA
<213> ORGANISM: Pantoea agglomerans

<400> SEQUENCE: 6

```
atgcaaaata cagatcagat gagcctgacg ccccccttcct taccctcagg tgggggtgcc     60
gtcaccggac tgaaaggcga tatgtcagga gccggacccg atggcgccgc cacgctgagc    120
cttcccctgc cgatcagccc cggacgtggc tatgcccccgt cgctgtcact gggttaccac    180
agtcgtaacg gcaacggtgt ttttggcgca ggctggagct gcggtcagat ggctattcgc    240
ctccaaaccc gcaaaggcgt gccgttttat gacggcagcg acgtcttttac cgctcctgat    300 ggtgaggttc tggtgccggc gctggacgcc agcggcaagg ctgaggttcg cacgaccact    360
```

-continued

```
acgctgctcg gcgaaaacct cggcggcacc tttaccgtac agacctaccg ttcccgagtg    420
gaaaccgact tcagtcgcct ggagcgctgg gttccgcaga ccgacgcagc ggctgatttc    480
tggttgattt atagtccgga cggccagatc cacctgctgg gtcgtaaccc gcaggcgcgg    540
gtgaacaacc ctgaggatac aacccagacc gccgcctggc tgatagagtc gtcggtctcc    600
gccagcggcg agcagattta ctggcaatac cggcaggaag atgagctggg ctgtacgcag    660
gatgagaaaa cggctcacgc acacgcgctc gcccagcgct atctggtggc ggtatggtat    720
ggcaataaag cggccagccg gacgctgccg gggctgctgt ctgttcctgc ggctggcagc    780
tggctgttta cgctggtgct ggactacggt gagcgggcga cagatcctgc aacaccaccg    840
gcctggctgt caccgggcag tggcacatgg ctctgccggc aggatgtgtt ctccagctgg    900
gaatatggct ttgagctgcg cacgcgtcgc ctgtgccgac aggtactgat gtatcatgac    960
gtcgcggcgc tggcaggtca gtcaggttca gatgccgtgc cacagctggt caccagactg   1020
ctgctggact ataacacgtc tccgtcgctg actaccctga aaaccgcaca gcaggccgcc   1080
tgggaaccgg atgggacgtt gcgcagtctg ccgccgctgc gttcagctg gcagaccttc    1140 ccgtcaacac cagagaaaag tgtcagctgg cagcggcgga atgacatggg gaaactcaac   1200
ccacagcagc cttatcagat ggttgacctg cacggtgaag gactggcggg tatcctctat   1260
caggacagtg gtgcctggtg gtatcgggag ccggttcgtc agtcgggtga tgatgataat   1320
gccgtgacct gggcggctgc ccgaccgctg ccggcgttcc ctgctctgcg caagggcgga   1380
atgctgctgg atctggacgg tgatggttac ctggaatggg tggtcaccgc gccgggcgtc   1440
gcgggctgct atgcgcaagc gcctgaacaa tgctggcagc gcttcacgcc gctgtctgcg   1500
ctgccagtgg aataccgcca ctcgcgaatg gagataaccg acgtcaccgg tgcgggtctt   1560
gcggatatgc tgctgatcgg cccgaaaagc gtacgcctgt acagcggcag cggcagaggc   1620
tggaaaaaag cacgaacggt catgcaggac agtggcatca ccctgccggt tcccggtaca   1680
aatgcccgtg tcatggtggc attcagcgat atggccggca gcggtcagca cacctgacg   1740 gaaatcaaag ccagcggcgt acgttactgg cccagcctgg ggcatggtcg ctttgcggct   1800
ccggtgacac tccccggctt cagtcagccc gctgaaacct tcaacccggc acagctctat   1860
ctggccgacg ttgacggttc cggcaccacc gatctgatct atgctctgag cgatcatctg   1920
ctggtatggc taaccagag cggaaacagc tttgacgcgc cttccgtat cagtcttcca    1980 gaaggcgtgc gctatgacaa tacctgcagt ttgcaggtcg ccgatattca ggggctgggc   2040
atctccagcc tggtgctatc ggtgccacat ccgacgccgc gccattgggt atgtcacctg   2100
acgacggaaa agccctggct gctcgacggc atgaacaaca atatgggtgc ccgccatact   2160
ctctgttacc gtagttcggc gcagttctgg ctggatgaaa aggctgctgc taccgccgat   2220
cgacccgcgc cggcgtgtta tctgccgttt gcgctgcata cactgagccg tactgaagtc   2280
agtgatgaaa tcaccggaaa ccggctcacc aggacgatac gctaccggca cggggtctgg   2340
gacaggcgcg agcgagagtt ccgcggcttt ggctttgttg aagtcagcga tgccgaagcg   2400
ctggcaaaac aaactgaggg gatgagcgca ccagcagtta acgcagctg gtatgctacc    2460 ggactggcag ccgtggatgc acagctcccg gatgagttct ggaaagggga tcatgcagcc   2520
tttgccggtt ttaccccctcg ctttaccacc ggcgatggcg aacaagaggc ggcactggat   2580
accatcagcg acgatacccg tttctggctg accgggcga ttcgcggtac gctgctgcgt    2640
agcgaactgt atggcgcgga tggcagcagc caggccggga tcccttacag catcacggaa   2700
tcgcggccac aagtgcggtt gattactgag gcgggtaatt cgccggtggt ctggccctcc   2760
```

```
gttatcgaga accgcgccag tcattatgag cgcgtcagca gcgatccgca gtgcggccag    2820
cagatcctgt taaccagtaa tgaatacggc cagccgctcc gtcagatcgg catcagttat    2880
ccccggcgca ccaggcccga taccagcccc tacccggacg atctgccgga cggactgttt    2940
gccgacagct ttgatgagca acagcaggcg ctgcgcctga cgctgacaca aagcagctgg    3000
catacgctga aagatatcag cagcggcatc tggctgccgg ccgtggcgga tgcaacccga    3060
agcgatctgt tcgttcacca ggcagcgcag gtgccgccag cgggtcttac gctggagaat    3120
ttactcaccg atagcgcgct gctgaccagc ccggttttttg gcggacagtc gcaaatctgg    3180
tatcaggaca gggcgggtca ggcgagcatc acctcacccg attttccccc ccgaccgtcc    3240
tttagcgaaa ccgcagcgct ggacgaggca caggtcagcg cgctgtcagc cgatattgat    3300
caaacgaagc tggagcaggc gggctatacc cgctcagcgt atctgtttgc acgcagcggt    3360
gaggagagta aaacgctgtg ggcagtgcgc cagggatata tcaccttcag cggcgcagac    3420
catttctatc tgccgattgc cgcacagcag acgctgctgg ccgtaaaaac cacagtcacc    3480
tatgatccgt acgactgtgt tgtcttacag gcaaaggacg ccgcaggtgc ggttacctcc    3540
gcgacatacg actggcgttt tctcgcgccg acgcagatta ctgatattaa cgataatctg    3600
aaaagcgtca cgctggatgc gctgggtcgg gtaacgtcgc agcgtttcag cggcactgaa    3660
aacggaaagc cggcgggcta cagcgatgac gagtttccac tgccggccag cgccgatgca    3720
gcgctggcgc tcagtgcccc gctaccggtg gcacagtgca tcatctacgt accggacagc    3780
tggatgctga ccggggagca gcagcagccg ccgcacgtga taacgctgct caccgaccgt    3840
tacgacagcg acagtcagca gcagatccgt cagcaggttg ttttcagcga tggttttggc    3900
cgggtgctgc aggctgcctc aaggcaggtg aacggcgaag cgtggcagcg ggcggcaaac    3960
ggctcgttcg ttgccggcac gaacgattcg cccgtgctga ctgagacaac gttccgctgg    4020
gccgttaccg gacgcactga atatgacaat aagggacagg ccatccgtgc ttatcagcca    4080
tattttctgg acagctggaa atacgtgcgt gacgacagcg cgcgacagga tctgtacgcc    4140
gacacccact attacgatcc ggtggggcgg gagcggcagg tcattaccgc aaaaggctgg    4200
ctgcggcgcg tcactcacac cccctggttc gtagtcagcg aagacgaaaa cgatacccag    4260
gcgtag                                                              4266
```

<210> SEQ ID NO 7
<211> LENGTH: 3015
<212> TYPE: DNA
<213> ORGANISM: Pantoea agglomerans

<400> SEQUENCE: 7

```
atgtccgccg cgtatgtctt aagtaattta tcttataaac tggagaatcc tatgagcacc      60
tcgctttaca gcaggacccc ctcagtcacg atcctcgaca accggggcct gaccgtacgc     120
ggtatcgcgt accagcgcca tccggatacc ccggcggtga ccagtgaacg catcacccgc     180
catcagtacg acgcccgcgg ctttctgatg caaagcgccg accgcgcct gcacgacgcc     240 gggctggcga acgtcagcta ccggaccaac ctgaccggca gcgttctccg ctcacagggc     300
gtggataacg gcatcaccgt gacgctgaac gatgccgccg gacggccgtt tctggcggtc     360
agcaacatca gcactgccgg tgatggcacg gaggacagaa gccaggcagt gacccgtacg     420
tgtcagtacg aggacgccac cctgcccgga cgtccgttaa gtattacgga gcaggtgaat     480
ggtggagccg cccgcatcac ggagcgcttc gtctatgccg gtaacgctgt tgaggagaaa     540
```

```
gccctgaacc tcgccgggca gcccgtcagc cactatgata ccgccggtct gacacagaca    600
gacagcatcg ccctgaccgg cgtgccgctc tccgtcaccc gccgcctgct gaaggacgca    660
gacaatcctg acgccgtggc tgactggcag ggaacagacg cctccgtctg aacgacccg     720
ctcgacgtgg aaacatacac taccctgtcc acggcagacg ccaccggcgc ggtgctgacc    780
accaccgatg cgaagggaaa cctgcagcgg ctggcctacg acgtggcggg cctgttgtcg    840
ggcagctggc tgacgctgaa ggatggcacg gagcaggtta tcgtgacgtc cctgacctac    900
tccgccgccg ggcagaagct cgcgcgaggag cacggcaacg cgtggtgac cacctacacg     960
tatgaagccg agacgcagcg cctgaccggc attaaaacgg cgcggccggc cggacacacc   1020
tcaggtgcga aggtgctgca ggacctgcga tacacctatg acccggtggg caacgtcctg   1080
aaaatcagca cgatgccga agagacccgc ttctggcgta accagaaagt ggcgccggag   1140
agcgcgtacg tttatgacag cctgtaccag ctggtcagcg ccaccggacg cgagatggcg   1200
aacgccggtc agcagggcag cagctcatcg tcagccaccg tcccccttcc cgccgacagt   1260
tccgcgttta caactatac ccgcaactat acttacgatg aggccggcaa cctgacgcag   1320
gtccgtcata ccccggctac gggcagcggc tacaccacaa aaataaccgt ctctgataaa   1380
agcaaccggg gtgtgctgag cacgctgacg gaaaatccct ccgacgttga cgcgctgttc   1440
acggcgggcg ccagcagaa acagctgcag ccggggcaga gtctcatctg gacgccgcgt   1500
aacgagctgc tgaaggtgac gccggtagca cgtgacggcg gtgcggatga cagcgaaagc   1560
taccgctacg acggggggcag cctgcggctg ctgaaggtca gcgtgcagaa accgggaac   1620
agcacgcaga cgcagcgggc gctgtacctg ccaggactgg agctgcgcaa cacaacatcc   1680
ggtgatacgg aaacggagag cctgcaggtg gttaccgtgg gtgaagcggg gcgcgcgcag   1740
gtgcgggtgc tgcactggga gagcggaacg ccggacagtg tcagcaacga cccggtgcgt   1800
tacagctacg ataacctgac cggcagcagc gggcttgagc tggacagcag cggcaatatt   1860
atcagcatgg aggaatacta tccgtacggc ggcacggcgg tctggacggc gcgcagcgcg   1920
gtggaggcga agtacaaaac cgtgcgctac tcggccaagg agcgtgacgc cacggggctg   1980
tactactacg ggtaccggta ctaccagccg tgggctggcc gctggctgag cgcggaccccg   2040
gcgggcacgg cggacgggct gaacctgttc aggatggtaa gaaataatcc ggttacgctt   2100
aaggacacaa acgggttgat cagtacgggt caggatgccc ggaaattagt ggccgaagca   2160
tttgttcacc ctttgcatat gactgtcttt gaaagaattt cttcagaaga aaatcttgca   2220
atgagcgtga gagaggctgg catttatact atttcggcac tgggtgaagg tgctgcagca   2280
aaagggcata atattcttga aagaccatt aaacctggtt cattaaaggc tgtttatggt   2340
gataacgccg aatccattct tgcgcaggca aaacgcagcg gttttgttgg ccgggtaggt   2400
cagtgggatg catccggtgt acggggaatt tatgcacaca acacaccagg tggcgaagac   2460
ctggcctatc cagtcaactt aaaaaatagt tctgctaatg aacttgttaa tgcatggata   2520
aaatttaaaa tcatcacgcc ttataccggt gattatgaca tgcacgatat tattaaaatc   2580
tcggatggaa aagggcatgt gcccatggcg aaagtaatg aggaaaaagg tgtaaaggat   2640
atgattaatg aaggtgttgc gcaggtcgac cctgccagac cctttacgtc tacagcgatg   2700
aatgttgttc gccatggccc tcaggtaaac tttgttccct atatgtggga acatgagcac   2760
gaaaatgtcg taaggataa tggttatctg ggagtggtag ctcgtccggg tccattccct   2820
gttgcgatgg tacataaggg tgaatggact gttttcgaca ataaaaacga gctgtttgag   2880
ttttataaat ctacaaacac tcctcttccc gaacactggt ctcaggattt tgttgagaga   2940
```
gggaaaggaa atgttgcaac gccccgacac gctgaaattc ttgatcgtaa ttcctcgcgt    3000
ctaagagcgg cctga                                                     3015

<210> SEQ ID NO 8
<211> LENGTH: 2916
<212> TYPE: DNA
<213> ORGANISM: Pantoea agglomerans

<400> SEQUENCE: 8
atgtgtagcg ttgccgattt tgatcggctg cacaacataa acaggagaa tatcatgggc       60 acctcgcttt acagcaagac cccctcagtc acgatcctcg acaaccgcgg cctgtccgta     120
cgcgatatcg cgtaccagcg ccatccggat accccggcgg tgaccagtga atgcatcacc     180
cgccatcagt acgacgcccg cggctttctg atgcaaagcg ccgacccgcg cctgcacgac     240
gccggcctgg cgaacttcag ctaccggacc gacctgaccg gcagcgttct ccgctcacag     300
ggcgtggata cggcatcac cgtgacgctg aacgatgccg ccggacggcc gtttctggcg     360
gtcagcaaca tcagcactgc cggtgatggc acggaggaca aagccaggc agtgacccgt     420 acgtgtcagt acgaggacgc cacccctgccc ggacgtccgt taagtattac ggagcaggtg     480
aatggtggag ccgcccgcat cacggagcgc ttcatctatg ccggtaacgc tgttgaggag     540
aaagccctga acctcgccgg gcagcccgtc agccactatg ataccgccgg cctgacacag     600
acagacagca tcgccctgac cggtgcgccg ctctccgtca cccgccgcct gctgaaggac     660
gcggacaatc ctgacgccgt ggctgactgg cagggaacag acgcctccgt ctggaacgac     720
ccgctcgacg tggaaacata cactaccctg tccacggcag acgccaccgg cgcggtgctg     780
accaccaccg atgcgaaggg aaacctgcag cggctggcct acgacgtggc gggcctgttg     840
tcgggcagct ggctgacgct gaaggatggc acggagcagg ttatcgtgac gtccctgacc     900
tactccgccg ccgggcagaa gctgcgcgag gagcacggca acggcgtggt gaccacctac     960
acgtatgaag ccgagacgca cgcctgacc ggcattaaaa cggcgcggcc ggccggacac    1020
acctcaggtg cgaaggtgct gcaggacctg cgctacacct atgacccggt gggcaacgtc    1080
ctgaaaatca gcaacgatgc cgaagagacc cgcttctggc gtaaccagaa agtggtgccg    1140
gagagcgcgt acgtttatga cagcctgtac cagctggtca cgccaccgg acgcgagatg    1200 gcgaacgccg gtcagcaggg cagcagctca tcgtcagcca ccgtccccct tcccgccgac    1260
agttccgcgt ttacaaacta cccgcaac tatacttacg atgaggccgg caacctgacg    1320
caggtccgtc ataccccggc tacgggcagc ggctacacca aaaaataac cgtctctgat    1380 aaaagcaacc ggggtgtgct gagcacgctg acggaaaatc cctccgacgt tgacgcgctg    1440
ttcacggcgg cgggccagca gaaacagctg cagccggggc agagtcttat ctggacgccg    1500
cgcaatgagc tgctgaaggt gatgccgata atgcgtgacg gcggtacgga tgacagcgaa    1560
agctaccgct acgacggggg cagccagcgg ctgctgaagg tcagcgtgca gaaaaccggg    1620
aacagcacgc agacgcagcg ggcgctgtac ctgccggggc tggagctgcg caacacaaca    1680
tccggtgata cggaaacgga gagcctgcag gtggttaccg cgggtgaagc ggggcgcgcg    1740
caggtgcggg tgctgcactg ggagagcgga acgccggaca tgtcagcaa cgacccggtg    1800 cgttacagct acgataacct gaccggcagc agcgggcttg agctggacag cagcggcaat    1860
attatcagca tggaggaata ctatccgtac ggcggcacgg cggtctggac ggcgcgcagc    1920
gcggtggagg cgaagtacaa aaccgtgcgc tactcggcca aggagcgtga cgccacgggg    1980

| | |
|---|---|
| ctgtactact acgggtaccg gtactaccag ccgtgggctg gccgctggct gagcgcggac | 2040 |
| ccggcgggca cggtggacgg gctgaacctg ttcagaatgg tgcgcaataa tccgctcaca | 2100 |
| ttaaaggata acgatgggct aaaaccaata aatgaaaatt tcagagaaaa taaaggcgat | 2160 |
| ctggtttatg ggctggctgc cccccgagga gcttatatat caacggcaat agggcgcgaa | 2220 |
| ttcgctccag aagagaaaga tgcacctgct tcaattattg acttatataa caatacggtt | 2280 |
| tccggacaag cccttcttag cgttgatttc aaaatactgc aagacttcat gaagtcacca | 2340 |
| aaaaaacatg aaaaaaaact agcccctcca tctaacatta aagagttagt aaaaaaatcc | 2400 |
| agggtttatc ctctgtggga ggattatttt ctggcagggg aaaataaccc caaatttaac | 2460 |
| attgcatcca tatataaaga ggtcagaaaa gatgcaggaa agacccagta tcatgagtgg | 2520 |
| catatagcgg gaggacaatc ggcacctaag ctactttgga aacgaggaag taaattgggt | 2580 |
| attgaaatgg cggccagcgg tgctggtaat aaaatccatt ttgttcttga tgaactggat | 2640 |
| atatcaaatg ttgtaaataa ggaagggccg gggggaaaat ctataacggc cagtgagtta | 2700 |
| cgttatgcgt acagaaatcg tgaaagactg actgaaaata tacatttta caaaaataat | 2760 |
| gctgaaactg gcgcgccatg ggatacaaat gctgaactgt gggcatctta ccaccccaaa | 2820 |
| ccaaagcata aggaaatga atcgacacac atgatgtctc aaaggagaaa tggtagtctg | 2880 |
| ttcaaatcta tgagaaaggt tttctcgaga aattaa | 2916 |

<210> SEQ ID NO 9
<211> LENGTH: 7557
<212> TYPE: DNA
<213> ORGANISM: Pantoea agglomerans

<400> SEQUENCE: 9

| | |
|---|---|
| atgtatctga ccgaagaaat acttgccaaa ctgaatgccg aaacggcaa actacaatct | 60 |
| actgtagagc agataattac gctgccagat attatgctgc actcttttgc tcaggtaaaa | 120 |
| gaactggcag gagacaagtt aagttggggt gagaaaaact tcctttatca acaggctcag | 180 |
| aaacagctga agaaaataa atggcggaa tcccgcattc tcagccgtgc caacccgcaa | 240 |
| ctggcaaatg ctgtccggat gggcatccgt cagtctgcga tgctgggtag ctatgacgac | 300 |
| ctgttcccgc agcgcgccag ccgctttgtt aagccgggtg cggtggcctc aatgttttca | 360 |
| ccggctggtt atctgaccga gctgtatcgg gaagcccgag gcctgcacga cgacacgtca | 420 |
| gactatcatc tggatacccg ccgtccggac ctggcatcaa tggtgttgtc tcagtcaaat | 480 |
| atggacactg agttgtccac cctgtcgctc tccaatgaac tgttgctgaa gttaattcag | 540 |
| tcaaaggaaa gcctgaatta tgaccaggtt attgaaaagc tggcgactta cagactgacc | 600 |
| ggcaccacgc cttacaatca accctatgaa accatccgtc aggctatttt gctgcaggac | 660 |
| ccggagttta acgcattcag taataatccg gcagtggccg taaaaatcaa caccagcggg | 720 |
| ctattaggta ttacttccga tatcgccccg gagctgcatg cgatactgac tgaagagata | 780 |
| acagaaaaaa aaacggaagc actgattaaa agaacttcg gcgatgccaa tatcaaccag | 840 |
| ttccaaaatc ttgcgtggct ggcccactgg tacggcttgt cctatgagga gcttaataac | 900 |
| ctggtaggca tgatttggtc cagagatgat cttgaccccg ctgttgagca ctataaaaat | 960 |
| tccagcctgg tcactttggt ggctgaagac ggtggatcgc ttaacgcggt gttgattaag | 1020 |
| cgtactaaag gccatgattc cgatgatatg cattatgcgg aattaattcc tgtgggagga | 1080 |
| gacaaatttc agtacaactt cagccttatt gatgctgaaa gcagtagtgt ttattatcaa | 1140 |
| ttcggtacaa aaggaaagaa ctcccaagat ttagttcctg taatccatga gcctttgctg | 1200 |

```
ggtaatactc cctatgctgt tacattcaca cttacacaag agcagctaag taacccagtt    1260
gaaatatccc tgacgcatgg tagtggcggt ggtgatcgcc ttacctcaac aattttcact    1320
gttacgactt acccatttga taccttcctg ctgaagctga ataaactcat acgcctctat    1380
aaagccaccg gtatctcccc ggccagcatc aggaccgtga ttgaaagcga taacactgac    1440
cttatcatca cagaaagcgt attaaaccag ctattctgga ctaattacta tacacaaacg    1500
ttcgaaatgg aattttctgc cgcactggtg ctggcaggag cggacatcgg tcagatagca    1560
cacagtgaaa gccagccaag tgcgttcacc cgcctgttta acacaccgtt gctggataac    1620
cagcagtttt cggccagcga cgagtcactg gatctggagc cgggtaaggg agccgatgct    1680
ttccgtatcg ctgtactcaa gcgtgcattg caggtgaatg acgccggact gtataccctt    1740
tatggtctga gtttcaccga taagataaa acggtaagt tgattccgtt caccaccaat    1800
attgagaacc tttctgccct ctatcgcacc cgactgctgg ccgacatatt taatatttct    1860
gttactgagc tgagcatgct gctgtcggtt tcaccttatg ccagtcagaa ggtggacagc    1920
cttaaaggtc aggcactata tcagtttgtt gctaccctca gtgactatat gcaacggctg    1980
aaagcgatga actggagcgt cagcgatctc tacctgatgc tgaccaacag ctacagcacg    2040
gtactgtcgc cagaaattaa aaacctgatg actaccctga aaaatggact cagcgagcag    2100
gattttaata acacggatga aatcgctcag ctgaatgcga cggcaccttt aatcgccgca    2160
gcgatgcagc ttgacttcac agaaaccgca gcagcactgc tggaatggct taatcaattg    2220
caaccagcag gctgacagt ggcaggtttc ctgtctcttg tgaatcagac gacactcgaa    2280
gataaggatg ttgtaaaact ggtctctttc tgccaggtta tggggcagct tgcactgatc    2340
gtgcgcaagg cggctctggg ctccagcgaa atcacctttg cagttgcgca tccggctatt    2400
tttaaaaaag atgcgaactc actggctcag gatattggca cgctctttga cctgacccag    2460
ctgcatgcat ttctgacaga ctgtggtact tatgcctctg aaattctcac ctcactgaat    2520
gaagggaatc tcgacgttag cacggtggcg acggcgctga cgctggacaa aacttcactg    2580
gcgcaggcac ttgctcaggt ttcagaatct caggcctttt ctaactggca cgaactgcgt    2640
gatgcacttc agtggacaga tgccgccagc attttcaaca tcacaccagt ggctctgact    2700
gcgatggtga acctgaaatt cagcggtgac aactcttctc cgtatcagga gtgggtaacg    2760
gtcagcaaag ctatgcaggt cgggctgaat cagacgcaaa gcgctcagct gcaagcctcg    2820
ctggatgaat ccctcagcgc agcactcagc gcctacgtca ttaagaacat aacacccca    2880 tcagtaactg atcgcgacga actttacggc tggctgctga ttgacaatca ggtctctgca    2940
cagattaaaa ctacccgcat tgctgaagcg attgccagcg ttcagcttta cgtaaaccgg    3000
tcactgacgg gtcaggaaga tggcgtggat agcaaggtta aatccggcca gttctttacg    3060
gcagactggg atacttataa caaacgctac agtacatggg ccggtgtgtc ggagctggtc    3120
tattatccgg aaaactatgt tgatccgacg ctgcgtatcg ggcagaccgg gatgatggat    3180
gaaatgttgc agacgctcag ccagagccag attaatttag acaccgtcag tgatggtatg    3240
gggcgttacc ttactgattt tgaagaaata gcaaatctaa aattcctcag tggttatcat    3300
gataatgttt ctggccgtca ggggaaaacc tggtttatcg gtggcagtca gtctgaaccc    3360
caaaaatttt actggcgatc cctggattac agtaaaggcg atggggagga attcgctgcc    3420
aatgcatggt cagaatggaa ccatatctca tgtgcaataa cacccttacc tggttttgtt    3480
cgtgtggttt tatttaactc ccgactatat cttgcttgcg tggaaaaaaa agaaaattcgg    3540
```

-continued

| | |
|---|---|
| gatagtgaaa acaaaaataa agcatcgtat caattaaaga tagctcacat cctttacaat | 3600 |
| ggtgagtgga gcgctcccct ctcacacgat attactgatt tatatgaggc aggctttgat | 3660 |
| ccgagtacaa cagtaatgca cttatctgta catgatgaga gtgatgcaat agtttgtata | 3720 |
| tttaataaca gcgcgctaga aagtgacaaa aataaagggg tggcagtcaa tgctgatatg | 3780 |
| tcatttaaca acattgacag caaaagagta gatcagataa ttagtctttt agttcctgat | 3840 |
| cgttttatag atgaaggtaa tgttatagat aatttagttt ctgagttaaa gggatcggaa | 3900 |
| gtcacggaaa ataaaaaaac gctggagaat gattcgttca ctatagatgg atcaataaat | 3960 |
| ttgaataagc attctatcga tatcacaggg aaggccaatt tagatattca ggcatcaatt | 4020 |
| gctgtgcgta gtaaagcatc tcctactagc catgagcgcg agctaatagg ctggttagat | 4080 |
| gaatctcaat ttgattacat tcgattattc aggggtggct ataattttgg ccagaacgac | 4140 |
| ggcattttgg aatcatgcat gatttcggca gttaatagtg cctatacctg cttcctttta | 4200 |
| cgagctgacc acttcagtgg tttatttagt tatggatatg accttttgt attcaacggt | 4260 |
| gacgggtcaa aaacatatac acctcaagtg ttgtttgaag atgatattca agggactatg | 4320 |
| gtgctcaaga tcgtgctcct aaatgaggat aaaaattcaa aactggaaaa ctttgaatcc | 4380 |
| ctggggctta tgaaaacatc agcaggcgat catcaggag aaatagtttg cgaacttgct | 4440 |
| aaaagaagga cacctgagcc ttactgtgta gaattgagtc gctacttacc ctcgaatgtt | 4500 |
| actgttaccg ttcatcacc atcggggaac tttactgcca aagactatgt gttacctctt | 4560 |
| cccgcattca ataatggcga cgctgactat aaattcgcac cattccccct ctcgcttgaa | 4620 |
| agtatatggg gagatggaaa aagtaccagt cgggacatta agtttacaat aagcgtaaaa | 4680 |
| gatacttgcg gcaaggtggc cacctcagag ctaatcttta cactttataa aaacacctcg | 4740 |
| cctgaattaa ttcactgaa aacgagtgac gcgggagcgc agtatatgca gcagggagtg | 4800 |
| taccgcacaa ggcttaatac cctgtttgca cagaaattga tcaagcgtgt tagcgccgga | 4860 |
| attgatgcag tgctgtcgtg ggaaacccag cagttgcagg agcctaaact gggtactggc | 4920 |
| agttacattt cagtgcttat ccccgcctat atcaaacttg agcacggaga tagcagacag | 4980 |
| gctaacctgc agtttagtaa tgtcgatcaa acaggaccgg ataatgggaa ttatatatta | 5040 |
| tggtccggct cattaaatga cactccgcag caggtcacga ttttgtgcc cacgatgcaa | 5100 |
| actattggcg agctgcaatt cccttatgac cggactagtg gcctgaatct gagtttagca | 5160 |
| tgtgcagctg gagtttattt gcaggggaca ttcaagaata tatctgcgtc cgatttatct | 5220 |
| ttaactgagt ttgttgctgc aaagaacaat gactctaaac gggatgtcga agtgacagta | 5280 |
| ttaacttcaa tcaatacgga gccaatggac ttcaagggtg ccaacgccct ctatttctgg | 5340 |
| gagatgttct actacctccc tatgatggtg tttaaacgcc ttctcagcga aagtcggttt | 5400 |
| actgaagcca ctcagtggat aaggtacgtc tggaacccgg acggctacct ggtaaacgac | 5460 |
| acgcccgcca cctaccagtg gaacgtgcgc ccgctggagg atgaaacctc ctggcacgct | 5520 |
| aacccgctgg actccgtgga cccggatgcc atagcccagg ctgacccgct gcactacaag | 5580 |
| gtcgccacct ttatggcgta ccttgacctg ctgattgccc gcggcgacgc ggcctaccgt | 5640 |
| cagcttgagc gcgatgcgct cagcgaagca aaaatgtggt acgtgcaggc gctgacacc | 5700 |
| cttggcgatg agccgtacct gagccagaac acaggctggg cgtcccatg cctgacggat | 5760 |
| gctgccgatg agaccaccca taaaaacagg cagcaggcaa tgctgaccgt gcgccagaag | 5820 |
| gttgcctcca gcgaactgcg caccgccaac tccctaaccg ccctgttcct gccacagcag | 5880 |
| aacgcgaagc tggcaggcta ctggcagacg ctgaaccagc gcctgtataa cctgcgcaac | 5940 |

```
aacctctcca ttgacggtaa cccgctgtcg ctgtccattt atgccacccc gactgacccg    6000
gcggcgctgc tcagctcggc ggtgattagt tctcaggggg gcagtgacct gccagcggcc    6060
gttatgccgc tgtaccgctt cccggtgatt ctggaaagcg cacggagcat ggtgaatcag    6120
ctgacccagt tcggcagcac gctgctcggc atcaccgagc gtcaggatgc agaggcgctg    6180
tctgatctgc tgcagacaca gggggctgga ctggcgctgc aaagcattgc cctgcagaac    6240
agtaccatca gcgagattga tgcggatagg gccgcgctca gggagagcct cagtggcgca    6300
cagtcgcgcc tcaacagcta taccaccctg tatgatgaaa atgttaatgc tggtgaaacg    6360
cacgccatga acctgtttct ttcctccgcc atcctggcag atggcgggca ggcctatcat    6420
accgccgcgg gtgcgcttga cctggcgccg aatatctttg gcctggccga cggggggttcc   6480 cgctggggtg cggcatttac cgcaatggcc ggaatagctg atttggccgc tcggccacc     6540
```

```
tggttgattt atagtccgga cggccagatc cacctgctgg gtcgtaaccc gcaggcgcgg    540
gtgaacaacc ctgaggatac aacccagacc gccgcctggc tgatagagtc gtcggtctcc    600
gccagcggcg agcagattta ctggcaatac cggcaggaag atgagctggg ctgtacgcag    660
gatgagaaaa cggctcacgc acacgcgctc gcccagcgct atctggtggc ggtatggtat    720
ggcaataaag cggccagccg gacgctgccg gggctgctgt ctgttcctgc ggctggcagc    780
tggctgttta cgctggcgct ggactacggt gagcgggcga cagatcctgc aacaccaccg    840
gcctggctgt caccgggcag tggcacatgg ctctgccggc aggatgtgtt ctccagctgg    900
gaatatggct ttgagctgcg cacgcgtcgc ctgtgccgac aggtactgat gtatcatgac    960
gtcgcggcgc tggcaggtca gtcaggttca gatgccgtgc cacagctggt caccagactg   1020
ctgctggact ataacacgtc tccgtcgctg actaccctga aaaccgcaca gcaggccgcc   1080
tgggaaccgg atgggacgtt gcgcagtctg ccgccgctgg cgttcagctg gcagaccttc   1140
ccgtcaacac cagagaaaag tgtcagctgg cagcggcgga atgacatggg gaaactcaac   1200
ccacagcagc cttatcagat ggttgacctg cacggtgaag gactggcggg tatcctctat   1260
caggacagtg gtgcctggtg gtatcgggag ccggttcgtc agtcgggtga tgatgataat   1320
gccgtgacct gggcggctgc ccgaccgctg ccggcgttcc ctgctctgcg caagggcgga   1380
atgctgctgg atctggacgg tgatggttac ctggaatggg tggtcaccgc gccgggcgtc   1440
gcgggctgct atgcgcaagc gcctgaacaa tactggcagc gcttcacgcc gctgtctgcg   1500
ctgccagtgg aataccgcca ctcgcgaatg gagatagccg acgtcaccgg tgcgggtctt   1560
gcggatatgc tgctgatcgg cccgaaaagc gtacgcctgt acagcggcag cggcagaggc   1620
tggaaaaaag cacgaacggt catgcaggac agtggcatca ccctgccggt tcccggtaca   1680
aatgcccgtg tcatggtggc attcagcgat atggccggca gcgtcagca acacctgacg   1740 gaaatcaaag ccagcggcgt acgttactgg cccagccttg ggcatggtcg ctttgcggct   1800
ccggtgacac tccccggctt cagtcagccc gctgaaacct tcaacccggc acagctctat   1860
ctggccgacg ttgacggttc cggcaccacc gatctgatct atgctctgag cgatcatctg   1920
ctggtatggc taaaccagag cggaaacagc tttgacgcgc cttccgtat cagtcttcca   1980 gaaggcgtgc gctatgacaa tacctgcagt ttgcaggtcg ccgatattca ggggctgggc   2040
atctccagcc tggtgctatc ggtgccacat ccgacgccgc gccattgggt atgtcacctg   2100
acgacggaaa agccctggct gctcgacggc atgaacaaca atatgggtgc ccgccatact   2160
ctctgttacc gtagttcggc gcagttctgg ctggatgaaa aggctgctgc taccgccgat   2220
cgacccgcgc cggcgtgtta tctgccgttt gcgctgcata cactgagccg tactgaagtc   2280
agtgatgaaa tcaccggaaa ccggctcacc aggacgatac gctaccggca cggggtctgg   2340
gacaggcgcg agcgagagtt ccgcggcttt ggctttgttg aagtcagcga tgccgaagcg   2400
ctggcaaaac aaactgaggg gatgagcgca ccagcagtta aacgcagctg gtatgctacc   2460
ggactggcag ccgtggatgc acagctcccg gatgagttct ggaaagggga tcatgcagcc   2520
tttgccggtt ttaccctcg ctttaccacc ggcgatggcg aacaagaggc ggcactggat   2580
accatcagcg acgatacccg tttctggctg accccggcga ttcgcggtac gctgctgcgt   2640
agcgaactgt atggcgcgga tggcagcagc caggccggga tcccttacag catcacggaa   2700
tcgcggccac aagtgcggtt gattactgag gcgggtaatt cgccggtggt ctggccctcc   2760
gttatcgaga accgcgccag tcattatgag cgcgtcagca gcgatccgca gtgcggccag   2820
cagatcctgt taaccagtaa tgaatacggc cagccgctcc gtcagatcgg catcagttat   2880
```

```
ccccggcgca ccaggcccga tgccagcccc tacccggacg atctgccgga cggactgttt      2940
gccgacagct ttgatgagca acagcaggcg ctgcgcctga cgctgacaca aagcagctgg      3000
catacgctga aagatatcag cagcggcatc tggctgccgg ccgtggcgga tgcaacccga      3060
agcgatctgt tcgttcacca ggcagcgcag gtgccgccag cgggtcttac gctggagaat      3120
ttactcaccg atagcgcgct gctgaccagc ccggtttttg gcggacagtc gcaaatctgg      3180
tatcaggaca gggcgggtca ggcgagcatc acctcacccg attttccccc cgaccgtcc       3240
tttagcgaaa ccgcagcgct ggacgaggca caggtcagca cgctgtcagc cgatattgat      3300
caaacgaagc tggagcaggc gggctatacc cgctcagcgt atctgtttgc acgcagcggt      3360
gaggagagta aaacgctgtg ggcagtgcgc cagggatata tcaccttcag cggcgcagac      3420
catttctatc tgccgattgc cgcacagcag acgctgctgg ccgtaaaaac cacagtcacc      3480
tatgatccgt acgactgtgt tgtcttacag gcaaaggacg ccgcaggtgc ggttacctcc      3540
gcgacatacg actggcgttt tctcgcgccg acgcagatta ctgatattaa cgataatctg      3600
aaaagcgtca cgctggatgc gctgggtcgg gtaacgtcgc agcgtttcag cggcactgaa      3660
aacggaaaac cggcgggcta cagcgatcac gagtttccac tgccggccag cgccgatgca      3720
gcgctggcgc tcagtgcccc gctaccggtg gcacagtgca tcatctacgt accggacagc      3780
tggatgctga ccggggagca gcagcagccg ccgcacgtgg taacgctgct caccgaccgt      3840
tacgacagcg acagtcagca gcagatccgt cagcaggttg ttttcagcga tggttttggc      3900
cgggtgctgc aggctgcctc aaggcaggtg aacggcgaag cgtggcagcg ggcggcaaac      3960
ggctcgttcg ttgccggcac gaacgattcg cccgtgctga ctgagacaac gttccgctgg      4020
gccgttaccg gacgcactga atatgacaat aagggacagg ccatccgtgc ttatcagcca      4080
tattttctgg acagctggaa atacgtgcgt gacgacagcg cgcgacagga tctgtacgcc      4140
gacacccact attacgatcc ggtggggcgg gagcggcagg tcattaccgc aaaaggctgg      4200
ctgcggcgcg tcactcacac cccctggttc gtagtcagcg aagacgaaaa cgataccag       4260
gcgtag                                                                 4266
```

<210> SEQ ID NO 11
<211> LENGTH: 2856
<212> TYPE: DNA
<213> ORGANISM: Pantoea agglomerans

<400> SEQUENCE: 11

```
atgtccgccg cgtatgtctt aagtaattta tcttatcaac gggagaatac tatgagcacc       60
tcgctttaca gcaggacccc ctcagtcacg gtcctcgaca accgcggcct gaccgtacgc      120
gatatcgcgt accaccgcca tccggatacc ccggcggtga ccagtgaacg catcacccgc      180
catcagtacg atgcccgcgg ctttctgacg cagagcgccg acccgcgcct gcacgacgcc      240
gggctggcga acttcagcta ccggaccgac ctgaccggca cgttctccg cctacagggc       300
gtcgataacg gcatcaccgt ggcgctgaac gatgccgccg acggccgtt tctggcggtc       360
agcaacatcc gcacggccgg tgatggctcg gaggacagaa gccaggcagt gacccgtacg      420
tgtcagtacg aggacgccac cctgcccgga cgtccgttaa gtattacgga gcaggtaaag      480
ggtggagccg cccgcatcac ggagcgcttc atctatgccg gtaacgctgt tgaggagaaa      540
gccctgaacc tcgccgggca gcccgtcagc cactatgata ccgccggtct gacacagaca      600
gacagcatcg ccctgaccgg cgtgccgctc tccgtcaccc gccgcctgct gaaggacgca      660
```

```
gacaatcctg acgccgtggc tgactggcag ggaacagacg cctccgtctg gaacgacccg    720
ctcgacgtgg aaacatacac taccctgtcc acggcagacg ccaccggcgc ggtgctgacc    780
accaccgatg cgaagggaaa cctgcagcgg ctggcctacg acgtggcggg cctgttgtcg    840
ggcagctggc tgacgctgaa ggatggcacg gagcaggtta tcgtgacgtc cctgacctac    900
tccgccgccg ggcagaagct gcgcgaggag cacggcaacg gcgtggtgac cacctacacg    960
tatgaagccg agacgcagcg cctgaccggc attaaaacgg cgcggccggc cggacacacc   1020
tcaggtgcga aggtgctgca ggacctgcgc tacacctatg acccggtggg caacgtcctg   1080
aaaatcagca cgatgccga agagacccgc ttctggcgta accagaaagt ggcgccggag    1140
agcgcgtacg tttatgacag cctgtaccag ctggtcagcg ccaccggacg cgagatggcg   1200
aacgccggtc agcagggcag cagctcatcg tcagccaccg tccccttcc cgccgacagt    1260 tccgcgttta caaactatac ccgcaactat acttacgatg aggccggcaa cctgacgcag   1320
gtccgtcata ccccggctac gggcagcggc tacaccacaa aaataaccgt ctctgataaa   1380
agcaaccggg gtgtgctgag cacgctgacg gaaaatccct ccgacgttga cgcgctgttc   1440
acggcgggcg gccagcagaa acagctgcag ccggggcaga gtctcatctg gacgccgcgt   1500
aacgagctgc tgaaggtgac gccggtagca cgtgacggcg gtgcggatga cagcgaaagc   1560
taccgctacg acgggggcag cctgcggctg ctgaaggtca gcgtgcagaa aaccgggaac   1620
agcacgcaga cgcagcgggc gctgtacctg ccagggctgg agctgcgcaa cacaacatcc   1680
ggtgatacgg aaacggagag cctgcaggtg gttaccgtgg gtgaagcggg gcgcgcgcag   1740
gtgcgggtgc tgcactggga gagcggaacg ccggacagtg tcagcaacga cccggtgcgt   1800
tacagctacg ataacctgac cggcagcagc gggcttgagc tggacagcag cggcaatatt   1860
atcagcatgg aggaatacta tccgtacggc ggcacggcgg tctggacggc gcgcagcgcg   1920
gtggaggcgg agtacaaaac cgtgcgctac tcgggcaagg agcgtgacgc cacggggctg   1980
tactactacg ggtaccggta ctaccagccg tgggctggcc gctggctgag cgcggacccg   2040
gcgggcacgg tggacgggct gaatttgttc aggatggtaa ggaataaccc ggtaacattg   2100
gttgatgata atggtttatt cacgtcctcc cctttattgg ggatttatga aaaggagatg   2160 aaaaccttg atagtatcaa attgtcgatt ggttcttata aatacaaacc atctaaattt    2220
gatgaaaaga aggtaagta tgttagctca gataaataca aactgataat ggcagatgat   2280
aacgatctta atgggtattt atttgacgag cgcgagatga caagccatct aaaggactat   2340
gctgataagt tcagtaaaat aagcaggcta aatataggcg atgagcggat gaaaaccaat   2400
attaattttg ggactagaat atcaagatat ttgctatctt cagcacaagc atcatcacgc   2460
gaaaatcgtg aagtagatgt tttgtcattc gaaagaaaat tttttgctgt agtaaagaaa   2520
aaagataaaa gtcattattt tggacgaaaa atatatgcca taggagaagc tcatgtacta   2580
acagattttg aagagaaaaa agaaccatt gccattaaga ctctagttgc gcaccccctat   2640 acgcaaatta tgaaagcat taaaatagat attaatgatt ttgataaaga atataacgtt   2700
aaagggattg gaacttttgc aacgtttaaa gctacgaaca agctcatagg tggtattaag   2760
ggagctttaa aatataagac taaagtgttg actcaagcgg taaatgtacg ctcggcagct   2820
atagcaataa agtatggggc aaagcacgtt ccgtaa                             2856
```

<210> SEQ ID NO 12
<211> LENGTH: 7572
<212> TYPE: DNA
<213> ORGANISM: Pantoea agglomerans

<400> SEQUENCE: 12

```
atgtatctga ccgaagaaat acttgccaaa ctgaatgccg aaacggcaa  actacaatct    60
actgtagagc agataattac gctgccagat attatggtgc gctctttttc tcaggtaaaa   120
gagctggcag gagacaagct aagttggggt gagaaaaact ttctttatca gcaggctcag   180
acacagctga agaaaataa  aatggcggaa tcccgcattc tcagccgtgc caacccgcaa   240
ctggcaaatg ctgtccggct gggcatccgt cagtcttcga tgctgggtag ctatgacgac   300
ctgttcccgc agcgcgccag ccgctttgtt aagccaggtg cggtggcctc aatgttttca   360
ccggctggct atctgaccga gctgtaccgt gaggccagag gattacacaa ggctgaatcg   420
caatataatc tcgataaacg ccgtccggat ctggcctcgc tggcgctatc ccagtcaaac   480
atggatgacg agttgtccac tctgtcactg tcaaatgagc tgctgctgaa taatatccag   540
cagcatgatg gcctcagcta tgacgatgcg ctgaagaagc tcgccggata ccgacaaacc   600
gggacaacac cctatagcca gccgtatgaa acgatccgcg aggctattct tctgcaggat   660
cctgcgttta ttcgattcg  caacaatcca gctgtggcga ctaaaatgaa taccagtggc   720
ctgctgggac tgacagcaaa cctgccacct gaactgcatg cgatcctgac tgaaacgatt   780
accgaagaga atgcggaaca actgattaag gacaatttcg gtgatgtcaa cgtcagcaga   840
tttcaagatg ttagttatct tgcccgctgg tatgggatga ccccttatga actgaactcg   900
gtgctgggac tgatggaggt gggcagcaat cctgtcgacg gtgttacgta ttaccaggat   960
gaccagctga tttccctggt ggataatggc ggtaatctgg atgctgtgct gatgcaacgt  1020
gcgggcggtg acaattatag ccagtttggt tatatcgaac tgctaccggt gtcagggat   1080
acctaccagc ttcggtttac cgtacaaagt ggttacgtgg gtcaggactc agaagtccgc  1140
attggaactt cagagaatgc cggaagcaag gatattctta gcgatggtcg catcgccgga  1200
cttaacatcc ctatggtcct gaacgttaaa cttgacagca ctaagttggc ccaggggatc  1260
actatcggcg taacccgata cgacccccagc ggtagttata taaattttgc gtccgttcgt  1320
ttccagagat acgacttttc ttataatgtc ttcctgctca aattaaacaa aattattcgc  1380
ctctacaaag ccaccggcat ttcgccatcc gatatccaga ccctgattga aagtgctaat  1440
catgacctgg ctattaccga agatgtacta agccagctct tctggacgaa ctattatacg  1500
cagcgttacg gtattgattt ttctgctgcg ctggtgctgg cgggtgcgaa catcagtcag  1560
attgcccaca gcaataaaca gagcgcgttc acccgcttgt ttaacactcc gccgctgaac  1620
aatcagtttt tttatgctga tgggaaaaag ctgaacctcg aacccggtaa gtcggatgac  1680
tcacacggtc ttggggtact caaacgggca ttacaggtta atgatagcgc cctgtatacc  1740
cttttttaatc tgacctttgc ggataaagac gcccagggta atgctgttgt tttcaccaaa  1800
actcctgaaa atctttctgc gctgtaccgt accagattgc tggcgacggt taacaacctg  1860
accgttaacg aactgagcct gctgctttcc gtttcaccat acgtaaaggt gaagctggct  1920
acgctaaaag acgaggcgct cagccagctg tcgactaccc tggaaaggta tacgcaatgg  1980
ctggacaaga tgaactggac gatcggcgat ctgtacctga tgctgacccc tgtttacagc  2040
accgttctgt cgccggatat tgaaaatctg gtgacgacg  tgaaaatgg  cctggcgggt  2100
caggacttaa ccagcgatga aaaacgcatc gctgcgctgg ctccgtttgt tgctgccgcc  2160
actcagctgg actctgcgga gacgccaggg gcgcttttac gatggctgaa cgatcttaaa  2220
ccgggaaccc tgtcattagc ggattttatc gcgcaggtta acaacaccac ccaaaccgaa  2280
```

```
aatctggtca cattcagcca ggtgatggcg cagctcgccc ttattacgcg caacgccagc    2340
ctgagtgcaa atgagctgtc atgggcggtt gcgcacccgg aaattttcca ggaaaaggcc    2400
actgttctta aaaacgacat cgccactctc aatgatctga cgcagctgca tgatctgctg    2460
gcgcgctgtg gcagccatgc ctcagagatc cttacctcgc tgagtgggaa tgccagcaag    2520
gctgaaaata accttgccgt cagcaccctg gcgacggcgt taaatctgga cgagcgggca    2580
ctgacccagg cgctggcgaa ggtttccacc tatgaatatt tttataattg gcacactta    2640 aatgaagcgc tgcagtggct ggacgttgcc accacctttg gcatcacgcc cgataacctg    2700
gccgcgctga ttgggctgaa gttcgataat caggatgacg cctcgtttgc cagctggctt    2760
accgcaagcc ggtttatgca ggcagggctt aacacgcagc agacagctca gctgtccgcc    2820
actctggatg aatccctcag cgcagcggtc agcgcctacg cgatcaaaaa tattttctcc    2880
ggcgcggtaa gtaacaggga gcagctctac agctggctgc tgattgataa ccaggtgtcg    2940
gcgcaggtca aaaccacccg catcgccgaa gcgattgcca gcgtgcagct gtatgtaaac    3000
cgggcattaa gcggccttga gaatggccaa tcagccactg acgctgttga taatgccgtt    3060
aaatccgggg tattttttac ccgcgactgg gatacataca acaaacgcta cagcacctgg    3120
gccggcgtct ctgagctggt ttactatccg gaaaactatg ttgacccgac cctgcgcctt    3180
ggtcagaccg gcatgatgga tgagatgctg cagacgctca gccagagcca gctgacgtcc    3240
gatacggtgg aagacgcgtt caaaacctac atgacccgct tgaagaaat cgctaacctg    3300 gatattgtca gcggctatca tgacaacctc agcgaccaga agggtgtaac atatctgatc    3360
ggtcgctccg ctgctggcga ctattattgg cgttcggcag atatcagtaa gctttctgac    3420
ggtaagctcc cggctaacgc ctgggccgag tggaaaaaaa ttaccaccgc gctgacgccc    3480
gtaaataacc tggtgcgccc ggtaatattt cagtcacgat tgtatgtgac ctgggtggaa    3540
agccgcgagg tcggcatatc cgccgtcaaa agcaaaaca gtgaaaccaa acctctggag    3600
tatgctctga gtatgcaca tattctgcat gacggtacct ggagcgcacc cgtgtctgtt    3660
aagcttgaga acggaacgct gcctcttgac agcgtggcta ttgatgttac aggcatgtat    3720
tgcgcaaagg atacacagca tgaccagctt tatattttat tttataagaa aaaggaaact    3780
tacaatgacg tcaatgacgt tctgaaagga ataatactgc acgatgacgg gactaccacc    3840
attacttccg gtaatagcgt atctggattg gttgtctata aacaactgga tactactaag    3900
gaagtcaggc tgaatacgcc ttacccggga ggaaaaacat actactctat taataatatg    3960
agggaatcga gtaaatgggg agatgataat atttcaatgc tgtcaggatg tagcgtgaaa    4020
gattttgtct ttaccgaagg cgatgggaaa ctgaatgttg cgttcaatgc caccgaacgc    4080
attatatacc gtggtaatcc ggatagtcag ggctatgtgg ccctggtcaa tatgattaaa    4140
gctatcggaa atattggaga cactttaaaa attccggttt tgaattcaaa tggagagggc    4200
ttagacagac ctttttacatg tatattcaga cagcctgatg aaaagactga tgcgattgct    4260
tatttctccg atgtccaggg attaaatata gatcatttcg ctttcaacga tgaaagtcag    4320
aaaatgctgg gtcgtatctt aaggcctgaa gagaaagatt tttataaatt agagtgtgtc    4380
aatactaatc tccatatata caagacagt agcaaaacaa tcaaaccgga taacttcgtg    4440
tattttggcc caggcatgga tcttatcgta gttaaaggaa tgatcgtgga aaccctttt    4500 ggattatttg gagagcttaa aaccggaata aagataaga gtgtgaaact atccgtttct    4560 gccgagtca ttgacaattc accagccgct acgaagacta agtatacatt cgacgaatcg    4620
ctgtatgtta ttgaaggcca aaccgtttct attcaactta gtgaatttaa agaaaataat    4680
```

```
attgaccttg aattcacttt cttggcttct ggagacagtg ggaactcact aggccaaagt    4740
gtcatcagcg caacattgac ccgaacgagt gaaaacacta tacccgttat ttctctgaat    4800
aaaacctctg acaacgcgca gtatttgcag tatggcattc atcgcataag ggtgaatacg    4860
ctgtttgcaa aacagctggt tgcgcgcgcg aacgccggac tggacactgt actgtctatg    4920
gcaacccagc agctgacgga acctaaaatg ggcaaggtg cgtacattga ccttgaactt    4980
aatgccagca gcgatggcag ttcggcggta tttgaagtat tgatgtgtga cgttttacc    5040 aacggtgacc gcattgcttt gaccagcggc acactcagcc ccacagcacg caccagctgc    5100
tcatttttcg tgccccgact ggatgagtct actgcatctg catataatat gtacttttgc    5160
gtaaaaactc agaatactga gagtaagcgg gtagaagtaa cgggaggcga ggggaaatgg    5220
gattaccagt acgtcgatga atctggtgct gccattaagc cgccctatac cgatccatat    5280
attgcaagca tatatgtacg gaacgataca acagagccga tggacttcaa cggtgccaat    5340
gcgctctatt tctgggaaat gttctattac gtgccgatga tggtatttaa gcgcctgcta    5400
agcgaaagta agttcgctga agcgacccag tgatcaaat atatctggaa tcccgatggc    5460
tatctggtga acaatcagcc cgcgacctat acctggaatg tgcgccctct ggaggaggat    5520
acctcctggc acgctgaccc gctagactcg gttaacccgg atgctgtcgc gcaggccgat    5580
ccgctgcact acaaggttgc tacctttatg gcgtaccttg atctgctgat tgcccgcgt    5640 gatgccgcct atcgccagct gcagcgcgac accctgaatg aagcaaaaat gtggtacgtg    5700
caggcgctga acatccttgg cgatgaaccc taccagtcat catccagcga ctggagctcg    5760
ccagttctct ccagcgcagc agatcagact acagagaaaa acgttcagca ggcgatgctg    5820
gcggtgcgtc agcagcctga cgcaggagaa ctgcgcaccg ccaattctct gaccagtctg    5880
ttcctgccgc agcagaatga aaagctggct ggttactggc agacgctggc gcagcgcctg    5940
tataacctgc gccacaacct gtcaattgac ggcagcccat tgtcactggc catctatgcc    6000
gcgccagccg atccggcagc gctgctcagc gcggcggtca acagcgcgtc cggcggcagc    6060
gaactgcctg ctgctgttat gccgctgtac cgcttcccga ttattctgga gagcgcccgg    6120
gggatggcag gtcaactgac ccagttcggc agcacgctgc tcagcattgc tgaacggcag    6180
gatgcggaag ccttgtcgga gctgatgcag actcagggta gtcaactgat tttgcagagc    6240
atcgccctgc aaaacagtac gatttctgaa attgatgcgg ataaaccgt gctggaagcg    6300 agcctaagcg gtgcacgttc gcgcctcgac cgatacacca cgctgtatga cgaggatgta    6360
aatacggggg aacagcaggc tatggatctg ttctacgcct cctctatcca ggcaaacggc    6420
ggccaggcgt tccacactgt cgcaggcgga cttgacctgg cgcctaacat ctttggtctg    6480
gctgacggcg gttcgcgctg gggtgcagca tttactgcat tggccagcat cgccgatttg    6540
tccgccgcag cctctcacac ggccgcagag cgcctcagcc agtctgaggt ctaccgccgc    6600
cgccgccagg agtgggaaat ccagcgcaac gccgcgcagt ctgaaattga ccagattgac    6660
gctcagctgg cctcactgac gatacgtcgc aaaggcgcgg tactgcagaa aacctacctg    6720
gaaactcagc agggtcagat gcaggcgcag atgaccttcc tgcagaataa gttcaccagc    6780
aaggcgctgt acaactggct gcgcggcaag ctggcggcca tctactatca gttctacgac    6840
ctgacggtat cgcgctgcct gatggcagaa gccgcctata gctggcatat taaaggtaat    6900
caggaaacag gtacctttat ccgtcccggc gcctggcagg gaatctatgc cggcctgatg    6960
gcaggggaag cgctgatgct gaatctggca cagatggaaa acagctacct gacaaaagat    7020
```

```
gagcgcctgc aagaggtcac gcgcacggtc tgcctgtctg aattttattc agggctctct    7080
tcgaataagt tcgcgctggc tgataccgtt accacactgg tgaatagcgg gaaaggcaac    7140
gccggcacga ccgataacgg agtgaagatc gatggcaagc agcttctggc taccctgaaa    7200
ctctccgatc tgaacattaa gacggattat ccagagtcac tggacaaagc caaacgcatt    7260
aagcaaatca gcgtgacgct gccgatgctg gtcgggccgt atcaggacgt ccgggcggta    7320
ctgagctatg cggcagcgt ggttctgcca cgcggctgca cggcggtcgc cgtttcgcac    7380
ggcatgaacg acagcggcca gttccagctg gacttcaatg acagccgctg gctgccttt    7440 gaaggtatac ctgttgatga ttccggtacg ctgacgctca gcttcccgga cattaccgat    7500
aagcaacagg aaaatctgct gctcagtctg agcgacatca tcctgcacat ccgctatacc    7560
atcgcaagct ga                                                       7572

<210> SEQ ID NO 13
<211> LENGTH: 4266
<212> TYPE: DNA
<213> ORGANISM: Pantoea agglomerans

<400> SEQUENCE: 13
atgcaaaata cagatcagat gagcctgacg cccccttcct taccctcagg tggggtgcc      60 gtcaccggac tgaaaggcga tatgtcagga gccggacccg atggcgccgc cacgctgagc    120 cttccctgc cgatcagccc cggacgtggc tatgccccgt cgctgtcact gggttaccac    180
agtcgtaacg gcaacggtgt ttttggcgca ggctggagct gcggtcagat ggctattcgc    240
ctccaaaccc gcaaaggcgt gccgttttat gacggcagcg acgtctttac cgctcctgat    300
ggtgaggttc tggtgccggc gctggacgcc agcggcaagg ctgaggttcg cacgaccact    360
acgctgctcg gcgaaaacct cggcggcacc tttaccgtac agacctaccg ttcccgagtg    420
gaaaccgact tcagtcgcct ggagcgctgg gttccgcaga ccgacgcagc ggctgatttc    480
tggttgattt atagtccgga cggccagatc cacctgctgg gtcgtaaccc gcaggcgcgg    540
gtgaacaacc ctgaggatac aaccccagacc gccgcctggc tgatagagtc gtcggtctcc    600
gccagcggcg agcagattta ctggcaatac cggcaggaag atgagctggg ctgtacgcag    660
gatgagaaaa cggctcacgc acacgcgctc gcccagcgct atctggtggc ggtatggtat    720
ggcaataaag cggccagccg gacgctgccg gggctgctgt ctgttcctgc ggctggcagc    780
tggctgtttt cgctggtgct ggactacggt gagcggacga cagatcctgc aacgctaccg    840
gcctggctgt caccgggcag tggcacatgg ctctgccggc aggatgtgtt ctccagctgg    900
gaatatggct ttgagctgcg cacgcgtcgc ctgtgccgac aggtactgat gtatcatgac    960
gtcgcagcgc tggcaggtca gtcaggttca gatgccgtgc cacagctggt caccagactg    1020
ctgctggact ataacctatc tccgtcgctg actaccctga aaaccgcaca gcaggccgcc    1080
tgggaaccgg atgggacgtt gcgcagtctg ccgccgctgg cgttcagctg gcagaccttc    1140
ccgtcaacac cagagaaaag tgtcagctgg caacggcgga atgacatggg gaaactcaac    1200
ccacagcagc cttatcagat ggttgacctg cacggtgaag actggcgggg tatcctctat    1260
caggacagtg gtgcctggtg gtatcgggag ccggttcgtc agtcgggtga tgatgataat    1320
gccgtgacct gggcggctgc ccgaccgctg ccggcgttcc ctgctctgcg caagggcgga    1380
atgctgctgg atcgacggg tgatggttac ctggaatggg tggtcaccgc gccgggcgtc    1440
gcgggctgct atgcgcaagc gcctgaacaa tgctggcagc gcttcacgcc gctgtctgcg    1500
ctgccagtgg aataccgcca ctcgcgaatg gagatagccg acgtcaccgg tgcgggtctt    1560
```

```
gcggatatgc tgctgatcgg cccgaaaagc gtacgcctgt acagcggcag cggcagaggc   1620
tggaaaaaag cacgaacggt catgcaggac agtggcatca ccctgccggt tcccggtaca   1680
aatgcccgtg tcatggtggc attcagcgat atggccggca gcggtcagca cacctgacg    1740 gaaatcaaag ccagcggcgt acgttactgg cccagcctgg ggcatggtcg ctttgcggct   1800
ccggtgacac tccccggctt cagtcagccc gctgaaacct tcaacccggc acagctctat   1860
ctggccgacg ttgacggttc cggcaccacc gatctgatct atgctctgag cgatcatctg   1920
ctggtatggc taaaccagag cggaaacagc tttgacgcgc ctttccgtat cagtcttcca   1980
gaaggcgtgc gctatgacaa tacctgcagt ttgcaggtcg ccgatattca ggggctgggc   2040
atctccagcc tggtgctatc ggtgccacat ccgacgccgc gccattgggt atgtcacctg   2100
acgacggaaa agccctggct gctcgacggc atgaacaaca atatgggtgc cgccatact    2160 ctctgttacc gtagttcggc gcagttctgg ctggatgaaa aggctgctgc taccgccgat   2220
cggcccgcgc cggcgtgtta tctgccgttt gcgctgcata cactgagccg tactgaagtc   2280
agtgatgaaa tcaccggaaa ccggctcacc aggacgatac gctaccggca cggcgtctgg   2340
gacaggcgcg agcgagagtt ccgcggcttt ggctttgttg aagtcagcga tgccgaagcg   2400
ctggcaaaac aaactgaggg gatgagcgca ccagcagtta aacgcagctg gtatgctacc   2460
ggactggcag ccgtggatgc acagctcccg gatgagttct ggaaagggga tcatgcagcc   2520
tttgccggtt ttaccccctcg ctttaccacc ggcgatggcg aacaagaggc ggtactggat   2580
accatcagcg acgatacccg tttctggctg accggggcga ttcgcggtac gctgctgcgt   2640
agcgaactgt atggcgcgga tggcagcagc caggccggga tcccttacag catcacggaa   2700
tcgcggccac aagtgcggtt gattactgag gcgggtaatt cgccggtggt ctggccctcc   2760
gttatcgaga accgtaccag tcattatgag cgcgtcagca gcgatccgca gtgcggccag   2820
cagatcctgt taaccagtaa tgaatacggc cagccgctcc gtcagatcgg catcagttat   2880
ccccggcgca ccaggcccga tgccagcccc tacccggacg atctgccgga cggactgttt   2940
gccgacagct tgatgagca acagcaggcg ctgcgcctga cgctgacaca aagcagctgg   3000
catacgctga agatatcag cagcggcatc tggctgccgg ccgtggcgga tgcaacccga   3060
agcgatctgt tcgttcacca ggcagcgcag gtgccgccag cgggtcttac gctggagaat   3120
ttactcaccg atagcgcgct gctgaccagc ccggttttg cggacagtc gcaaatctgg     3180 tatcaggaca gggcgggtca ggcgagcatc acctcacccg attttccccc ccgaccgtcc   3240
tttagcgaaa ccgcagcgct ggacgaggca caggtcagcg cgctgtcagc cgatattgat   3300
caaacgaagc tggagcaggc gggctatacc cgctcagcgt atctgtttgc acgcagcggt   3360
gaggagagta aaacgctgtg ggcagtgcgc cagggatata tcaccttcag cggcgcagac   3420
catttctatc tgccgattgc cgcacagcag acgctgctgg ccggtaaaac cacagtcacc   3480
tatgatccgt acgactgtgt tgtcttacag gcaaaggacg ccgcaggtgc ggttacctcc   3540
gcgacatacg actggcgttt tctcgcgccg acgcagatta ctgatattaa cgataatctg   3600
aaaagcgtca cgctggatgc gctgggtcgg gtaacgtcgc agcgtttcag cggcactgaa   3660
aacgaaaagc cggcgggcta cagcgatgac gagtttccac tgccggccag cgccgatgca   3720
gcgctggcgc tcagtgcccc gctaccggtg gcacagtgca tcatctacgt accggacagc   3780
tggatgctga ccggggagca gcagcagccg ccgcacgtga taacgctgct caccgaccgt   3840
tacgacagcg acagtcagca gcagatccgt cagcaggttg ttttcagcga tggttttggc   3900
```

| | |
|---|---:|
| cgggtgctgc aggctgcctc aaggcaggtg aacggcgaag cgtggcagcg ggcggcaaac | 3960 |
| ggctcgttcg ttgccggcac gaacgattcg cccgtgctga ctgagacaac gttccgctgg | 4020 |
| gccgttaccg gacgcactga atatgacaat aagggacagg ccatccgtgc ttatcagcca | 4080 |
| tattttctgg acagctggaa atacgtgcgt gacgacagcg cgcgacagga tctgtacgcc | 4140 |
| gacacccact attacgatcc ggtggggcgg gagcggcagg tcattaccgc aaaaggctgg | 4200 |
| ctgcggcgcg tcattcacac cccctggttc gtagtcagcg aagacgaaaa cgatacccag | 4260 |
| gcgtag | 4266 |

<210> SEQ ID NO 14
<211> LENGTH: 3015
<212> TYPE: DNA
<213> ORGANISM: Pantoea agglomerans

<400> SEQUENCE: 14

| | |
|---|---:|
| atgtccgccg cgtatgtctt aagtaattta tcttataaac tggagaatcc tatgagcacc | 60 |
| tcgctttaca gcaggacccc ctcggtcacg atcctcgaca accggggcct gaccgtacgc | 120 |
| ggtatcgcgt accagcgcca tccggatacc ccggcggtga ccagtgaacg catcacccgc | 180 |
| catcagtacg atgcccgcgg ctttctgatg caaagcgccg accgcgcct gcacgacgcc | 240 |
| gggctggcga acgtcagcta ccggaccaac ctgaccggca cgttctccg ctcacagggc | 300 |
| gtggataacg catcaccgt gacgctgaac gatgccgccg acggccgtt tctggcggtc | 360 |
| agcaacatca gcactgccgg tgatggcacg gaggacagaa gccaggcagt gacccgtacg | 420 |
| tgtcagtacg aggacgccac cctgcccgga cgtccgttaa gtattacgga gcaggtgaat | 480 |
| ggtggagccg cccgcatcac ggagcgcttc gtctatgccg gtaacgctgt tgaggagaaa | 540 |
| gccctgaacc tcgccgggca gccgtcagc cactatgata ccgccggtct gacacagaca | 600 |
| gacagcatcg ccctgaccgg cgtgccgctc tccgtcaccc gccgctgct gaaggacgca | 660 |
| gacaatcctg acgccgtggc tgactggcag ggaacagacg cctccgtctg gaacgacccg | 720 |
| ctcgacgtgg aaacatacac taccctgtcc acggcagacg ccaccggcgc ggtgctgacc | 780 |
| accaccgatg cgaagggaaa cctgcagcgg ctggcctacg acgtggcggg cctgttgtcg | 840 |
| ggcagctggc tgacgctgaa ggatggcacg gagcaggtta tcgtgacgtc cctgacctac | 900 |
| tccgccgccg gcagaagct gcgcgaggag cacggcaacg cgtggtgac cacctacacg | 960 |
| tatgaagccg agacgcagcg cctgaccggc attaaaacgg cgcggccggc cggacacacc | 1020 |
| tcaggtgcga aggtgctgca ggacctgcgc tacacctatg acccggtggg caacgtcctg | 1080 |
| aaaatcagca acgatgccga agagacccgc ttctggcgta accagaaagt ggcgccggag | 1140 |
| agcgcgtacg tttatgacag cctgtaccag ctggtcagcg ccaccggacg cgagatggcg | 1200 |
| aacgccggtc agcagggcag cagctcatcg tcagccaccg tcccccttcc cgccgacagt | 1260 |
| tccgcgttta caaactatac ccgcacttat gcttacgatg aggccggcaa cctgacgcag | 1320 |
| gtccgtcata ccccggctac gggcagcggc tacaccacaa aaataaccgt ctctgataaa | 1380 |
| agcaaccggg ccgtgctgag cgtgctgacg aaaaatccct ctgatgtgga cgcgctgttc | 1440 |
| acggcgggcg ccagcagaa acagctgcag ccggggcaga gtcttatctg gacgccgcgc | 1500 |
| aatgagctgc tgaaggtgat gccgataatg cgtgacggcg gtacggatga cagcgaaagc | 1560 |
| taccgctacg acgggggcag ccagcggctg ctgaaggtca gcgtgcagaa aaccggcaac | 1620 |
| agcacgcaga cgcagcgggc gctgtacctg ccaggactgg agctgcgcaa cacaacatcc | 1680 |
| ggtgatacgg aaacggagag cctgcaggtg gttaccgcgg gtgaagcggg gcgcgcgcag | 1740 |

-continued

| | |
|---|---|
| gtgcgggtgc tgcactggga gagcggaacg ccggacagtg tcagcaacga ccagctacgc | 1800 |
| tacagctacg ataacctgac cggcagcagc gggcttgagc tggacagcag cggcaatatt | 1860 |
| atcagcatgg aggaatacta tccgtacggc ggcacggcgg tctggacggc gcgcagcgcg | 1920 |
| gtggaggcga agtacaaaac cgtgcgctac tcgggcaagg agcgtgacgc cacggggctg | 1980 |
| tactactacg ggtaccggta ctaccagccg tgggctggcc gctggctgag cgcggacccg | 2040 |
| gcgggcacgg cggacgggct gaacctgttc aggatggtaa gaataatcc ggttacgctt | 2100 |
| aaggacacaa acgggttgat cagtacgggt caggatgccc ggaaattagt ggccgaagca | 2160 |
| tttgttcacc ctttgcatat gactgtcttt gaaagaattt cttcagaaga aaatcttgca | 2220 |
| atgagcgtga gagaggctgg catttatact atttcggcac tgggtgaagg tgctgcagca | 2280 |
| aaagggcata atattcttga aagaccatt aaacctggtt cattaaaggc tgtttatggt | 2340 |
| gataacgccg aatccattct gcgcaggca aaacgcagcg gttttgttgg ccgggtaggt | 2400 |
| cagtgggatg catccggtgt acggggaatt tatgcacaca acaccagg tggcgaagac | 2460 |
| ctggcctatc cagtcaactt aaaaaatagt tctgctaatg aacttgttaa tgcatggata | 2520 |
| aaatttaaaa tcatcacgcc ttataccggt gattatgaca tgcacgatat tattaaaatc | 2580 |
| tcggatggaa aagggcatgt gcccatggcg gaaagtaatg aggaaaaagg tgtaaaggat | 2640 |
| atgattaatg aaggtgttgc gcaggtcgac cctgccagac cctttacgtc tacagcgatg | 2700 |
| aatgttgttc gccatggccc tcaggtaaac tttgttccct atatgtggga acatgagcac | 2760 |
| gaaaatgtcg taagggataa tggttatctg ggagtggtag ctcgtccggg tccattccct | 2820 |
| gttgcgatgg tacataaggg tgaatggact gttttcgaca ataaaaacga gctgtttgag | 2880 |
| tttataaaat ctacaaacac tcctcttccc gaacactggt ctcaggattt tgttgagaga | 2940 |
| gggaaaggaa atgttgcaac gccccgacac gctgaaattc ttgatcgtaa ttcctcgcgt | 3000 |
| ctaagagcgg cctga | 3015 |

<210> SEQ ID NO 15
<211> LENGTH: 2079
<212> TYPE: DNA
<213> ORGANISM: Pantoea agglomerans

<400> SEQUENCE: 15

| | |
|---|---|
| atgtgtagcg ttgccgattt tgatcggctg cacaacataa acaggagaa tatcatgggc | 60 |
| acctcgcttt acagcaagac cccctcggtc acgatcctcg acaaccgcgg cctgaccgta | 120 |
| cgcgatatcg cgtaccagcg ccatccggat accccggcgg tgaccagtga acgcatcacc | 180 |
| cgccatcagt acgatgcccg cggctttctg atgcaaagcg ccgacccgcg cctgcacgac | 240 |
| gccgggctgc cgaacgtcag ctaccggacc aacctgaccg gcagcgttct ccgctcacag | 300 |
| ggcgtggata acggcatcac cgtgacgctg aacgatgccg ccggacggcc gtttctggcg | 360 |
| gtcagcaaca tcagcactgc cggtgatggc acggaggaca gaagccaggc agtgaccccgt | 420 |
| acgtgtcagt acgaggacgc caccctgccc ggacgtccgt taagtattac ggagcaggtg | 480 |
| aatggtggag ccgcccgcat cacggagcgc ttcgtctatg ccggtaacgc tgttgaggag | 540 |
| aaagccctga acctcgccgg gcagcccgtc agccactatg ataccgccgg tctgacacag | 600 |
| acagacagca tcgccctgac cggcgtgccg ctctccgtca cccgccgcct gctgaaggac | 660 |
| gcagacaatc ctgacgccgt ggctgactgg cagggaacag acgcctccgt ctggaacgac | 720 |
| ccgctcgacg tggaaacata cactaccctg tccacggcag acgccaccgg cgcggtgctg | 780 |

```
accaccaccg atgcgaaggg aaacctgcag cggctggcct acgacgtggc gggcctgttg    840
tcgggcagct ggctgacgct gaaggatggc acggagcagg ttatcgtgac gtccctgacc    900
tactccgccg ccgggcagaa gctgcgcgag gagcacggca acggcgtggt gaccacctac    960
acgtatgaag ccgagacgca cgcctgacc ggcattaaaa cggcgcggcc ggccggacac   1020
acctcaggtg cgaaggtgct gcaggacctg cgctacacct atgacccggt gggcaacgtc   1080
ctgaaaatca gcaacgatgc cgaagagacc cgcttctggc gtaaccagaa agtggtgccg   1140
gagagcgcgt acgtttatga cagcctgtac cagctggtca gcgccaccgg acgcgagatg   1200
gcgaacgccg gtcagcaggg cagcagctca tcgtcagcca ccgtccccct tcccgccgac   1260
agttccgcgt ttacaaacta tacccgcaac tatacttacg atgaggccgg caacctgacg   1320
caggtccgtc ataccccggc tacgggcagc ggctacacca caaaaataac cgtctctgat   1380
aaaagcaacc ggggtgtgct gagcacgctg acggaaaatc cctccgacgt tgacgcgctg   1440
ttcacggcgg gcggccagca gaaacagctg cagccggggc agagtctcat ctggacgccg   1500
cgtaacgagc tgctgaaggt gacgccgta gcacgtgacg gcggtgcgga tgacagcgaa   1560
agctaccgct acgacggggg cagcctgcgg ctgctgaagg tcagcgtgca gaaaaccggg   1620
aacagcacgc agacgcagcg ggcgctgtac ctgccagggc tggagctgcg caacacaaca   1680
tccggtgata cggaaacgga gagcctgcag gtggttaccg tgggtgaagc ggggcgcgcg   1740
caggtgcggg tgctgcactg ggagagcgga acgccggaca gtgtcagcaa cgacccggtg   1800
cgttacagct acgataacct gaccggcagc agcgggcttg agctggacag cagcggcaat   1860
attatcagca tggaggaata ctatccgtac ggcggcacgg cggtctggac ggcgcgcagc   1920
gcggtggagg cgaagtacaa aaccgtgcgc tactcgggca aggagcgtga cgccacgggg   1980
ctgtactact acgggtaccg gtactaccag ccgtgggctg agcgcggacc cggcgggcac   2040
ggtggacggg ctgaacctgt tcagaatggt gcgcaataa                          2079

<210> SEQ ID NO 16
<211> LENGTH: 7557
<212> TYPE: DNA
<213> ORGANISM: Pantoea agglomerans

<400> SEQUENCE: 16
atgtatctga ccgaagaaat acttgccaaa ctgaatgccg aaacggcaa actacaatct      60 actgtagagc agataattac gctgccagat attatgctgc actcttttgc tcaggtaaaa    120
gaactggcag gagacaagtt aagttggggt gagaaaaact tcctttatca gcaggctcag    180
aaacagctga agaaaataa atggcggaa tcccgcattc agccgtgc caacccgcaa        240 ctggcaaatg ctgtccggat gggcatccgt cagtctgcga tgctgggtag ctatgacgac    300
ctgttcccgc agcgcgccag ccgctttgtt aagccgggtg cggtggcctc aatgttttca    360
ccggctggtt atctgaccga gctgtatcgg gaagcccgag gcctgcacga cgacacgtca    420
gactatcatc tggatacccg ccgtccggac ctggcatcaa tggtgttgtc tcagtcaaat    480
atggacactg agttgtccac cctgtcgctc tccaatgaac tgttgctgaa gttaattcag    540
tcaaaggaaa gcctgaatta tgaccaggtt attgaaaagc tggcgactta cagactgacc    600
ggcaccacgc cttacaatca accctatgaa accatccgtc aggctatttt gctgcaggac    660 ccggagtttta acgcattcag taataatccg gcagtggccg taaaaatcaa caccagcggg    720
ctattaggta ttacttccga tatcgccccg gagctgcatg cgatactgac tgaagagata    780
acagaaaaaa aaacggaagc actgattaaa aagaacttcg gcgatgccaa tatcaaccag    840
```

```
ttccaaaatc ttgcgtggct ggcccactgg tacggcttgt cctatgagga gcttaataac    900
ctggtaggca tgatttggtc cagagatgat cttgaccccg ctgttgagca ctataaaaat    960
tccagcctgg tcactttggt ggctgaagac ggtggatcgc ttaacgcggt gttgattaag   1020
cgtactaaag gccatgattc cgatgatatg cattatgcgg aattaattcc tgtgggagga   1080
gacaaatttc agtacaactt cagccttatt gatgctgaaa gcagtagtgt ttattatcaa   1140
ttcggtacaa aaggaaagaa ctcccaagat ttagttcctg taatccatga gcctttgctg   1200
ggtaatactc cctatgctgt tacattcaca cttacacaag agcagctaag taacccagtt   1260
gaaatatccc tgacgcatgg tagtggcggt ggtgatcgcc ttacctcaac aattttcact   1320
gttacgactt acccatttga taccttcctg ctgaagctga ataaactcat acgcctctat   1380
aaagccaccg gtatctcccc ggccagcatc aggaccgtga ttgaaagcga taacactgac   1440
cttatcatca cagaaagcgt attaaaccag ctattctgga ctaattacta tacacaaacg   1500
ttcgaaatgg aattttctgc cgcactggtg ctggcaggag cggacatcgg tcagatagca   1560
cacagtgaaa gccagccaag tgcgttcacc cgcctgttta acacaccgtt gctggataac   1620
cagcagtttt cggccagcga cgagtcactg gatctggagc cgggtaaggg agccgatgct   1680
ttccgtatcg ctgtactcaa gcgtgcattg caggtgaatg acgccggact gtataccctt   1740
tatggtctga gtttcaccga taaagataaa aacggtaagt tgattccgtt caccaccaat   1800
attgagaacc tttctgccct ctatcgcacc cgactgctgg ccgacatatt taatatttct   1860
gttactgagc tgagcatgct gctgtcggtt tcaccttatg ccagtcagaa ggtggacagc   1920
cttaaaggtc aggcactata tcagtttgtt gctaccctca gtgactatat gcaacggctg   1980
aaagcgatga actggagcgt cagcgatctc tacctgatgc tgaccaacag ctacagcacg   2040
gtactgtcgc cagaaattaa aaacctgatg actaccctga aaaatggact cagcgagcag   2100
gattttaata cacggatga  aatcgctcag ctgaatgcga cggcaccttt aatcgccgca   2160
gcgatgcagc ttgacttcac agaaaccgca gcagcactgc tggaatggct taatcaattg   2220
caaccagcag ggctgacagt ggcaggtttc ctgtctcttg tgaatcagac gacactcgaa   2280
gataaggatg ttgtaaaact ggtctctttc tgccaggtta tggggcagct tgcactgatc   2340
gtgcgcaagg cggctctggg ctccagcgaa atcacctttg cagttgcgca tccggctatt   2400
tttaaaaaag atgcgaactc actggctcag gatattggca cgctctttga cctgacccag   2460
ctgcatgcat ttctgacaga ctgtggtact tatgcctctg aaattctcac ctcactgaat   2520
gaagggaatc tcgacgttag cacggtggcg acggcgctga cgctggacaa aacttcactg   2580
gcgcaggcac ttgctcaggt ttcagaatct caggcctttt ctaactggca cgaactgcgt   2640
gatgcacttc agtggacaga tgccgccagc attttcaaca tcacaccagt ggctctgact   2700
gcgatggtga acctgaaatt cagcggtgac aactcttctc cgtatcagga gtgggtaacg   2760
gtcagcaaag ctatgcaggt cgggctgaat cagacgcaaa gcgctcagct gcaagcctcg   2820
ctggatgaat ccctcagcgc agcactcagc gcctacgtca ttaagaacat aacaccccca   2880
tcagtaactg atcgcgacga actttacggc tggctgctga ttgacaatca ggtctctgca   2940
cagattaaaa ctacccgcat tgctgaagcg attgccagcg ttcagcttta cgtaaaccgg   3000
tcactgacgg gtcaggaaga tggcgtggat agcaaggtta atccggcca  gttctttacg   3060
gcagactggg atacttataa caaacgctac agtacatggg ccgtgtgtc  ggagctggtc   3120
tattatccgg aaaactatgt tgatccgacg ctgcgtatcg ggcagaccgg gatgatggat   3180
```

```
gaaatgttgc agacgctcag ccagagccag attaatttag acaccgtcag tgatggtatg    3240
gggcgttacc ttactgattt tgaagaaata gcaaatctaa aattcctcag tggttatcat    3300
gataatgttt ctggccgtca ggggaaaacc tggtttatcg gtggcagtca gtctgaaccc    3360
caaaaatttt actggcgatc cctggattac agtaaaggcg atggggagga attcgctgcc    3420
aatgcatggt cagaatggaa ccatatctca tgtgcaataa cacccttacc tggttttgtt    3480
cgtgtggttt tatttaactc ccgactatat cttgcttgcg tggaaaaaaa agaaattcgg    3540
gatagtgaaa acaaaaataa agcatcgtat caattaaaga tagctcacat cctttacaat    3600
ggtgagtgga gcgctccctt ctcacacgat attactgatt tatatgaggc aggctttgat    3660
ccgagtacaa cagtaatgca cttatctgta catgatgaga gtgatgcaat agtttgtata    3720
tttaataaca gcgcgctaga aagtgacaaa aataaagggg tggcagtcaa tgctgatatg    3780
tcatttaaca acattgacag caaaagagta gatcagataa ttagtctttt agttcctgat    3840
cgttttatag atgaaggtaa tgttatagat aatttagttt ctgagttaaa gggatcggaa    3900
gtcacggaaa ataaaaaaac gctggagaat gattcgttca ctatagatgg atcaataaat    3960
ttgaataagc attctatcga tatcacaggg aaggccaatt tagatattca ggcatcaatt    4020
gctgtgcgta gtaaagcatc tcctactagc catgagcgcg agctaatagg ctggttagat    4080
gaatctcaat ttgattacat tcgattattc aggggtggct ataattttgg ccagaacgac    4140
ggcattttgg aatcatgcat gatttcggca gttaatagtg cctatacctg cttccttttα    4200 cgagctgacc acttcagtgg tttatttagt tatggatatg accttttgt attcaacggt    4260 gacgggtcaa aaacatatac acctcaagtg ttgtttgaag atgatattca agggactatg    4320
gtgctcaaga tcgtgctcct aaatgaggat aaaaattcaa aactggaaaa ctttgaatcc    4380
ctggggctta tgaaaacatc agcaggcgat catcagggag aaatagtttg cgaacttgct    4440
aaaagaagga cacctgagcc ttactgtgta gaattgagtc gctacttacc ctcgaatgtt    4500
actgttaccg ttacatcacc atcggggaac tttactgcca aagactatgt gttacctctt    4560
cccgcattca ataatggcga cgctgactat aaaattcgcac cattccccct ctcgcttgaa    4620
agtatatggg gagatggaaa aagtaccagt cgggacatta gtttacaat aagcgtaaaa    4680 gatacttgcg gcaaggtggc cacctcagag ctaatctta cactttataa aaacacctcg    4740
cctgaattaa ttacactgaa aacgagtgac gcgggagcgc agtatatgca gcagggagtg    4800
taccgcacaa ggcttaatac cctgtttgca cagaaattga tcaagcgtgt tagcgccgga    4860
attgatgcag tgctgtcgtg ggaaacccag cagttgcagg agcctaaaact gggtactggc    4920 agttacatttt cagtgcttat ccccgcctat atcaaacttg agcacggaga tagcagacag    4980
gctaacctgc agtttagtaa tgtcgatcaa acaggaccgg ataatgggaa ttatatatta    5040
tggtccggct cattaaatga cactccgcag caggtcacga ttttgtgcc cacgatgcaa    5100 actattggcg agctgcaatt cccttatgac cggactagtg gcctgaatct gagttagca    5160 tgtgcagctg gagtttattt gcagggggaca ttcaagaata tatctgcgtc cgatttatct    5220
ttaactgagt ttgttgctgc aaagaacaat gactctaaac gggatgtcga agtgacagta    5280
ttaacttcaa tcaatacgga gccaatggac ttcaagggtg ccaacgccct ctatttctgg    5340
gagatgttct actacctccc tatgatggtg tttaaacgcc ttctcagcga aagtcggttt    5400
actgaagcca ctcagtggat aaggtacgtc tggaacccgg acggctacct ggtaaacgac    5460
acgcccgcca cctaccagtg gaacgtgcgc ccgctggagg atgaaccctc ctggcacgct    5520
aacccgctgg actccgtgga cccggatgcc atagcccagg ctgacccgct gcactacaag    5580
```

```
gtcgccacct ttatggcgta ccttgacctg ctgattgccc gcggcgacgc ggcctaccgt    5640
cagcttgagc gcgatgcgct cagcgaagca aaaatgtggt acgtgcaggc gctggacacc    5700
cttggcgatg agccgtacct gagccagaac acaggctggg cgtccccatg cctgacggat    5760
gctgccgatg agaccaccca taaaaacagg cagcaggcaa tgctgaccgt gcgccagaag    5820
gttgcctcca gcgaactgcg caccgccaac tccctaaccg ccctgttcct gccacagcag    5880
aacgcgaagc tggcaggcta ctggcagacg ctgaaccagc gcctgtataa cctgcgcaac    5940
aacctctcca ttgacggtaa cccgctgtcg ctgtccattt atgccacccc gactgacccg    6000
gcggcgctgc tcagctcggc ggtgattagt tctcaggggg gcagtgacct gccagcggcc    6060
gttatgccgc tgtaccgctt cccggtgatt ctggaaagcg cacggagcat ggtgaatcag    6120
ctgacccagt tcggcagcac gctgctcggc atcaccgagc gtcaggatgc agaggcgctg    6180
tctgatctgc tgcagacaca gggggctgga ctggcgctgc aaagcattgc cctgcagaac    6240
agtaccatca gcgagattga tgcggatagg gccgcgctca gggagagcct cagtggcgca    6300
cagtcgcgcc tcaacagcta taccaccctg tatgatgaaa atgttaatgc tggtgaaacg    6360
cacgccatga acctgtttct ttcctccgcc atcctggcag atggcgggca ggcctatcat    6420
accgccgcgg gtgcgcttga cctggcgccg aatatctttg gcctggccga cggggggttcc    6480 cgctggggtg cggcatttac cgcaatggcc ggaatagctg attggccgc ctcggccacc    6540 catacggccg ccgaccgcat cagccagtct gaggcatacc gccgccgccg ccaggagtgg    6600
gaaatccagc gcaacgcggc gcagttcgag gtcagccaaa tcaatgccca gctggacgcg    6660
ctggcggtgc gtcgtgaaag cgccgtgctg cagaagacct atctggaaac acagcagggc    6720
cagatgcagg cgcagatgac cttcctgcag aacaagttca ccagcaaagc actgtataac    6780
tggttgcgcg gtaaactggc ggccatctac tatcagttct atgacctgac cgtttcacgc    6840
tgtctgatgg cagaagctgc ctacagctgg gagatgaaag gctctcagga tacgggcacc    6900
tttatccgtc ccggcgcctg gcagggaacc tatgccggcc tgatggcagg ggaaacgctg    6960
atgctgaatc tggcacagat ggaaaacagc tatctgacaa agaggagcg ccagaaagag    7020 gtcacgcgca cggtctgcct gtctgaagtt tatgcagggc tctcttcggg ttcgttcgcg    7080
ctggctgata ccgtcaccac actggtgggt agcgggaaag gcaccgccgg cacgaacgat    7140
aacggagtga agatcgatgg caagcagctt ctggctaccc tgaaactctc cgatctgaac    7200
attaagacgg attatccaga gtcactggac aaagccaaac gcattaagca aatcagcgtg    7260
acgctgccga tgctggtcgg gccgtatcag gacgtccggg cggtactgag ctatggcggc    7320
agcgtggttc tgccacgcgg ctgcacggcg gtcgccgttt cgcacggcat gaacgacagc    7380
ggccagttcc agctggactt caatgacagc cgctggctgc cttttgaagg tatacctgtt    7440
gatgattccg gtacgctgac gctcagcttc ccggacatta ccgataagca acaggaaaat    7500
ctgctgctca gtctgagcga catcatcctg cacatccgct ataccatcgc aagctga      7557
```

<210> SEQ ID NO 17  
<211> LENGTH: 4266  
<212> TYPE: DNA  
<213> ORGANISM: Pantoea agglomerans

<400> SEQUENCE: 17

```
atgcaaaata cagatcagat gagcctgacg ccccccttcct taccctcagg tgggggtgcc     60
gtcaccggac tgaaaggcga tatgtcagga gccggacccg atggcgccgc cacgctgagc    120
```

-continued

```
cttcccctgc cgatcagccc cggacgtggc tatgccccgt cgctgtcact gggttaccac      180
agtcgtaacg gcaacggtgt ttttggcgca ggctggagct gcggtcagat ggctattcgc      240
ctccaaaccc gcaaaggcgt gccgttttat gacggcagcg acgtctttac cgctcctgat      300
ggtgaggttc tggtgccggc gctggacgcc agcggcaagg ctgaggttcg cacgaccact      360
acgctgctcg gcgaaaacct cggcggcacc tttaccgtac agacctaccg ttcccgagtg      420
gaaaccgact tcagtcgcct ggagcgctgg gttccgcaga ccgacgcagc ggctgatttc      480
tggttgattt atagtccgga cggccagatc cacctgctgg gtcgtaaccc gcaggcgcgg      540
gtgaacaacc ctgaggatac aacccagacc gccgcctggc tgatagagtc gtcggtctcc      600
gccagcggcg agcagattta ctggcaatac cggcaggaag atgagctggg ctgtacgcag      660
gatgagaaaa cggctcacgc acacgcgctc gcccagcgct atctggtggc ggtatggtat      720
ggcaataaag cggccagccg gacgctgccg gggctgctgt ctgttcctgc ggctggcagc      780
tggctgttta cgctgcgct ggactacggt gagcgggcga cagatcctgc aacaccaccg      840
gcctggctgt caccgggcag tgcacatggc tctgccggc aggatgtgtt ctccagctgg      900
gaatatggct ttgagctgcg cacgcgtcgc ctgtgccgac aggtactgat gtatcatgac      960
gtcgcggcgc tggcaggtca gtcaggttca gatgccgtgc cacagctggt caccagactg     1020
ctgctggact ataacacgtc tccgtcgctg actaccctga aaaccgcaca gcaggccgcc     1080
tgggaaccgg atgggacgtt gcgcagtctg ccgccgctgg cgttcagctg gcagaccttc     1140
ccgtcaacac cagagaaaag tgtcagctgg cagcggcgga atgacatggg gaaactcaac     1200
ccacagcagc cttatcagat ggttgacctg cacggtgaag gactggcggg tatcctctat     1260
caggacagtg gtgcctggtg gtatcgggag ccggttcgtc agtcgggtga tgatgataat     1320
gccgtgacct gggcggctgc ccgaccgctg ccggcgttcc ctgctctgcg caagggcgga     1380
atgctgctgg atctggacgg tgatggttac ctggaatggg tggtcaccgc gccgggcgtc     1440
gcgggctgct atgcgcaagc gcctgaacaa tactggcagc gcttcacgcc gctgtctgcg     1500
ctgccagtgg aataccgcca ctcgcgaatg gagatagccg acgtcaccgg tgcgggtctt     1560
gcggatatgc tgctgatcgg cccgaaaagc gtacgcctgt acagcggcag cggcagaggc     1620
tggaaaaaag cacgaacggt catgcaggac agtggcatca ccctgccggt tcccggtaca     1680
aatgcccgtg tcatggtggc attcagcgat atggccggca gcggtcagca acacctgacg     1740
gaaatcaaag ccagcggcgt acgttactgg cccagccttg gcatggtcg ctttgcggct     1800 ccggtgacac tccccggctt cagtcagccc gctgaaacct tcaacccggc acagctctat     1860
ctggccgacg ttgacggttc cggcaccacc gatctgatct atgctctgag cgatcatctg     1920
ctggtatggc taaccagag cggaaacagc tttgacgcgc cttccgtat cagtcttcca      1980 gaaggcgtgc gctatgacaa tacctgcagt ttgcaggtcg ccgatattca ggggctgggc     2040
atctccagcc tggtgctatc ggtgccacat ccgacgccgc gccattgggt atgtcacctg     2100
acgacggaaa agccctggct gctcgacggc atgaacaaca tatgggtgc ccgccatact      2160 ctctgttacc gtagttcggc gcagttctgg ctggatgaaa aggctgctgc taccgccgat     2220
cgacccgcgc cggcgtgtta tctgccgttt gcgctgcata cactgagccg tactgaagtc     2280
agtgatgaaa tcaccggaaa ccggctcacc aggacgatac gctaccggca cggggtctgg     2340
gacaggcgcg agcgagagtt ccgcggcttt ggctttgttg aagtcagcga tgccgaagcg     2400
ctggcaaaac aaactgaggg gatgagcgca ccagcagtta aacgcagctg gtatgctacc     2460
ggactggcag ccgtggatgc acagctcccg gatgagttct ggaaagggga tcatgcagcc     2520
```

```
tttgccggtt ttacccctcg ctttaccacc ggcgatggcg aacaagaggc ggcactggat    2580
accatcagcg acgatacccg tttctggctg acccgggcga ttcgcggtac gctgctgcgt    2640
agcgaactgt atggcgcgga tggcagcagc caggccggga tcccttacag catcacggaa    2700
tcgcggccac aagtgcggtt gattactgag gcgggtaatt cgccggtggt ctggccctcc    2760
gttatcgaga accgcgccag tcattatgag cgcgtcagca gcgatccgca gtgcggccag    2820
cagatcctgt taaccagtaa tgaataccgg cagccgctcc gtcagatcgg catcagttat    2880
ccccggcgca ccaggcccga tgccagcccc tacccggacg atctgccgga cggactgttt    2940
gccgacagct tgatgagcac acagcaggcg ctgcgcctga cgctgacaca aagcagctgg    3000
catacgctga aagatatcag cagcggcatc tggctgccgg ccgtggcgga tgcaacccga    3060
agcgatctgt tcgttcacca ggcagcgcag gtgccgccag cgggtcttac gctggagaat    3120
ttactcaccg atagcgcgct gctgaccagc ccggttttg gcggacagtc gcaaatctgg    3180
tatcaggaca gggcgggtca ggcgagcatc acctcacccg attttccccc ccgaccgtcc    3240
tttagcgaaa ccgcagcgct ggacgaggca caggtcagca cgctgtcagc cgatattgat    3300
caaacgaagc tggagcaggc gggctatacc cgctcagcgt atctgtttgc acgcagcggt    3360
gaggagagta aaacgctgtg ggcagtgcgc cagggatata tcaccttcag cggcgcagac    3420
catttctatc tgccgattgc cgcacagcag acgctgctgg ccggtaaaac cacagtcacc    3480
tatgatccgt acgactgtgt tgtcttacag gcaaaggacg ccgcaggtgc ggttacctcc    3540
gcgacatacg actggcgttt tctcgcgccc acgcagatta ctgatattaa cgataatctg    3600
aaaagcgtca cgctggatgc gctgggtcgg gtaacgtcgc agcgtttcag cggcactgaa    3660
aacggaaaac cggcgggcta cagcgatcac gagtttccac tgccggccag cgccgatgca    3720
gcgctggcgc tcagtgcccc gctaccggtg gcacagtgca tcatctacgt accggacagc    3780
tggatgctga ccggggagca gcagcagccg ccgcacgtgg taacgctgct caccgaccgt    3840
tacgacagcg acagtcagca gcagatccgt cagcaggttg ttttcagcga tggttttggc    3900
cgggtgctgc aggctgcctc aaggcaggtg aacggcgaag cgtggcagcg ggcggcaaac    3960
ggctcgttcg ttgccggcac gaacgattcg cccgtgctga ctgagacaac gttccgctgg    4020
gccgttaccg gacgcactga atatgacaat aagggacagg ccatccgtgc ttatcagcca    4080
tattttctgg acagctggaa atacgtgcgt gacgacagcg cgcgacagga tctgtacgcc    4140
gacacccact attacgatcc ggtggggcgg gagcggcagg tcattaccgc aaaaggctgg    4200
ctgcggcgcg tcactcacac cccctggttc gtagtcagcg aagacgaaaa cgatacccag    4260
gcgtag                                                                4266
```

<210> SEQ ID NO 18
<211> LENGTH: 2856
<212> TYPE: DNA
<213> ORGANISM: Pantoea agglomerans

<400> SEQUENCE: 18

```
atgtccgccg cgtatgtctt aagtaattta tcttataaac tggagaatcc tatgagcacc      60
tcgctttaca gcaggacccc ctcggtcacg atcctcgaca accggggcct gtccgtacgc     120
gatatcgcgt accagcgcca tccggatacc ccggcggtga ccagtgaacg catcacccgc     180
catcagtacg atgcccgcgg ctttctgatg caaagcgccg acccgcgcct gcacgacgcc     240
gggctggcga acgtcagcta ccggaccaac ctgaccggca gcgttctccg ctcacagggc     300
```

```
gtggataacg gcatcaccgt gacgctgaac gatgccgccg gacggccgtt tctggcggtc    360
agcaacatca gcactgccgg tgatggcacg gaggacagaa gccaggcagt gacccgtacg    420
tgtcagtacg aggacgccac cctgcccgga cgtccgttaa gtattacgga gcaggtgaat    480
ggtggagccg cccgcatcac ggagcgcttc gtctatgccg gtaacgctgt tgaggagaaa    540
gccctgaacc tcgccgggca gcccgtcagc cactatgata ccgccggtct gacacagaca    600
gacagcatcg ccctgaccgg cgtgccgctc tccgtcaccc gccgcctgct gaaggacgca    660
gacaatcctg acgccgtggc tgactggcag ggaacagacg cctccgtctg gaacgacccg    720
ctcgacgtgg aaacatacac taccctgtcc acggcagacg ccaccggcgc ggtgctgacc    780
accaccgatg cgaagggaaa cctgcagcgg ctggcctacg acgtggcggg cctgttgtcg    840
ggcagctggc tgacgctgaa ggatggcacg gagcaggtta tcgtgacgtc cctgacctac    900
tccgccgccg ggcagaagct gcgcgaggag cacggcaacg cgtggtgac  cacctacacg    960 tatgaagccg aaacgcagcg cctgaccggc attaaacggc gcggccggc  cggacacgcc   1020 tcaggtgcga aggtgctgca ggacctgcgc tacacctatg acccgtggg  caacgtcctg   1080 aaaatcagca cgatgccgga agagacccgc ttctggcgta accagaaagt ggcgccggag   1140
agcgcgtacg tttatgacag cctgtaccag ctggtcagcg ccaccggacg cgagatggcg   1200
aacgccggtc agcagggcag cagctcatcg tcagccaccg tccccccttcc cgccgacagt   1260 tccgcgttta caaactatac ccgcaactat acttacgatg aggccggcaa cctgacgcag   1320
gtccgtcata ccccggctac gggcagcggc tacaccacaa aaataaccgt ctctgataaa   1380
agcaaccggg gtgtgctgag cacgctgacg gaaaatccct ccgacgttga cgcgctgttc   1440
acggcgggcg gccagcagaa acagctgcag ccggggcaga gtctcatctg gacgccgcgt   1500
aacgagctgc tgaaggtgac gccggtagca cgtgacggcg gtgcggatga cagcgaaagc   1560
taccgctacg acgggggcag cctgcggctg ctgaaggtca gcgtgcagaa accgggaac    1620 agcacgcaga cgcagcgggc gctgtacctg ccagggctgg agctgcgcaa cacaacatcc   1680
ggtgatacgg aaacggagag cctgcaggtg gttaccgtgg gtgaagcggg gcgcgcgcag   1740
gtgcgggtgc tgcactggga gagcggaacg ccggacagtg tcagcaacga cccggtgcgt   1800
tacagctacg ataacctgac cggcagcagc gggcttgagc tggacagcag cggcaatatt   1860
atcagcatga aggaatacta tccgtacggc ggcacggcgg tctggacggc gcgcagcgcg   1920
gtggaggcgg agtacaaaac cgtgcgctac tcgggcaagg agcgtgacgc cacggggctg   1980
tactactacg ggtaccggta ctaccagccg tgggctggcc gctggctgag cgcggacccg   2040
gcgggcacgg tggacgggct gaatttgttc aggatggtaa ggaataaccc ggtaacattg   2100
gttgatgata atggtttatt cacgtcctcc cctttattgg ggatttatga aaaggagatg   2160
aaaacctttg atagtatcaa attgtcgatt ggttcttata aatacaaacc atctaaattt   2220
gatgaaaaga aaggtaagta tgttagctca gataaataca aactgataat ggcagatgat   2280
aacgatctta atgggtattt atttgacgag cgcgagatga caagccatct aaaggactat   2340
gctgataagt tcagtaaaat aagcaggcta aatataggcg atgagcggat gaaaaccaat   2400
attaattttg ggactagaat atcaagatat ttgctatctt cagcacaagc atcatcacgc   2460
gaaaatcgtg aagtagatgt tttgtcattc gaaagaaaat ttttgctgt  agtaaagaaa   2520 aaagataaaa gtcattattt tggacgaaaa atatatgcca taggagaagc tcatgtacta   2580
acagattttg aagagaaaaa aagaaccatt gccattaaga ctctagttgc gcaccccat    2640 acgcaaatta atgaaagcat taaaaataga attaatgatt ttgataaaga ataaacgtt    2700
```

-continued

```
aaagggattg gaacttttgc aacgtttaaa gctacgaaca agctcatagg tggtattaag    2760
ggagctttaa aatataagac taaagtgttg actcaagcgg taaatgtacg ctcggcagct    2820
atagcaataa agtatggggc aaagcacgtt ccgtaa                              2856
```

<210> SEQ ID NO 19
<211> LENGTH: 2522
<212> TYPE: PRT
<213> ORGANISM: Pantoea agglomerans

<400> SEQUENCE: 19

```
Met Tyr Leu Thr Glu Glu Ile Leu Ala Lys Leu Asn Ala Gly Asn Gly
1               5                   10                  15

Lys Leu Gln Ser Thr Val Glu Gln Ile Thr Leu Pro Asp Ile Met
            20                  25                  30

Val Arg Ser Phe Ala Gln Val Lys Glu Leu Ala Gly Asp Arg Leu Ser
        35                  40                  45

Trp Gly Glu Lys Asn Phe Leu Tyr Gln Gln Ala Gln Thr Gln Leu Lys
    50                  55                  60

Glu Asn Lys Met Ala Glu Ser Arg Ile Leu Ser Arg Ala Asn Pro Gln
65                  70                  75                  80

Leu Ala Asn Ala Val Arg Leu Gly Ile Arg Gln Ser Ser Met Leu Gly
                85                  90                  95

Ser Tyr Asp Asp Leu Phe Pro Gln Arg Ala Ser Arg Phe Val Lys Pro
            100                 105                 110

Gly Ala Val Ala Ser Met Phe Ser Pro Ala Gly Tyr Leu Thr Glu Leu
        115                 120                 125

Tyr Arg Glu Ala Arg Gly Leu His Lys Ala Glu Ser Gln Tyr Asn Leu
    130                 135                 140

Asp Asn Arg Arg Pro Asp Leu Ala Ser Leu Thr Leu Ser Gln Ser Asn
145                 150                 155                 160

Met Asp Asp Glu Leu Ser Thr Leu Ser Leu Ser Asn Glu Leu Leu Leu
                165                 170                 175

Lys Leu Ile Gln Ser Lys Glu Ser Leu Thr Tyr Glu Gln Val Met Glu
            180                 185                 190

Lys Leu Ala Thr Tyr Arg Leu Thr Gly Thr Thr Pro Tyr Asn Gln Pro
        195                 200                 205

Tyr Glu Ala Ile Arg Gln Ala Ile Leu Leu Gln Asp Pro Glu Phe Asn
    210                 215                 220

Ala Phe Ser Asn Asn Pro Ala Val Ala Ala Lys Ile Asn Thr Ser Gly
225                 230                 235                 240

Leu Leu Gly Ile Thr Ser Asp Ile Ala Pro Glu Leu His Ala Ile Leu
                245                 250                 255

Thr Glu Glu Ile Thr Glu Glu Asn Ala Glu Ala Leu Val Lys Lys Asn
            260                 265                 270

Phe Gly Asp Val Asn Ile Lys Gln Phe Gln Asn Leu Ala Trp Leu Ala
        275                 280                 285

Asn Trp Tyr Gly Leu Ser Tyr Glu Lys Leu Asn Asn Leu Val Gly Met
    290                 295                 300

Ile Trp Ser Arg Asp Asp Leu Asp Pro Ala Ile Glu His Tyr Lys Asn
305                 310                 315                 320

Ser Ser Leu Val Thr Leu Val Ala Glu Asp Gly Gly Ser Leu Asn Ala
                325                 330                 335

Val Leu Ile Lys Arg Thr Lys Gly His Asp Ser Asp Asp Met His Tyr
```

```
                340             345             350
Ala Glu Leu Ile Pro Val Gly Gly Asp Lys Phe Gln Tyr Asn Phe Ser
            355                 360                 365

Leu Ile Asp Ala Glu Ala Ser Ser Tyr Tyr Gln Phe Gly Thr Lys
        370                 375                 380

Gly Lys Tyr Ser Gln Asp Leu Val Pro Ala Ile His Lys Pro Leu Leu
385                 390                 395                 400

Gly Asn Thr Pro Tyr Ala Val Thr Phe Thr Leu Thr Gln Glu Gln Leu
                405                 410                 415

Ser Asn Pro Val Glu Ile Ser Leu Thr His Gly Ser Gly Gly Gly Asp
            420                 425                 430

Arg Leu Thr Ser Thr Ile Phe Thr Val Thr Thr Ser Pro Phe Asp Ile
            435                 440                 445

Phe Leu Leu Lys Leu Asn Lys Leu Ile Arg Leu Tyr Lys Ala Thr Gly
        450                 455                 460

Ile Ser Pro Ala Ser Ile Arg Thr Val Ile Glu Ser Asp Asn Thr Asp
465                 470                 475                 480

Leu Ile Ile Thr Glu Ser Val Leu Ser Gln Leu Phe Trp Thr Asn Tyr
                485                 490                 495

Tyr Thr Gln Thr Phe Glu Met Glu Phe Ser Ala Ala Leu Val Leu Ala
            500                 505                 510

Gly Ala Asp Ile Gly Gln Ile Ala His Ser Glu Ser Gln Pro Ser Ala
            515                 520                 525

Phe Thr Arg Leu Phe Asn Thr Pro Leu Asp Asn Gln Gln Phe Ser
        530                 535                 540

Ala Ser Asp Glu Ser Leu Asp Leu Glu Pro Gly Lys Gly Ala Asp Ala
545                 550                 555                 560

Phe Arg Ile Ala Val Leu Lys Arg Ala Leu Gln Val Asn Asp Ala Gly
                565                 570                 575

Leu Tyr Thr Leu Tyr Gly Leu Ser Phe Thr Asp Lys Asp Lys Asn Gly
            580                 585                 590

Glu Leu Ile Pro Phe Thr Thr Lys Ile Glu Asn Leu Ser Ala Leu Tyr
        595                 600                 605

Arg Thr Arg Leu Leu Ala Asp Ile Phe Asn Ile Ser Val Thr Glu Leu
        610                 615                 620

Ser Met Leu Leu Ser Val Ser Pro Tyr Ala Ser Gln Lys Val Asp Ser
625                 630                 635                 640

Leu Lys Gly Gln Ala Leu His Gln Phe Val Thr Thr Leu Ser Asp Tyr
                645                 650                 655

Met Gln Arg Leu Lys Ala Met Asn Trp Ser Val Ser Asp Leu Tyr Leu
            660                 665                 670

Met Leu Thr Asn Ser Tyr Ser Thr Val Leu Ser Pro Glu Ile Lys Ser
            675                 680                 685

Leu Met Thr Thr Leu Lys Asn Gly Leu Ser Glu Gln Asp Phe Asn Asn
        690                 695                 700

Thr Asp Glu Ile Ala Gln Leu Asn Ala Thr Ala Pro Leu Ile Ala Ala
705                 710                 715                 720

Ala Met Gln Leu Asp Ser Thr Glu Thr Ala Ala Leu Leu Glu Trp
            725                 730                 735

Leu Asn Gln Leu Gln Pro Ala Gly Leu Thr Val Ala Gly Phe Leu Ser
            740                 745                 750

Leu Val Asn Gln Thr Thr Pro Glu Asp Lys Asp Val Val Lys Leu Val
        755                 760                 765
```

Ser Phe Cys Gln Val Met Gly Gln Leu Ala Leu Ile Val Arg Lys Ala
770                 775                 780

Ala Leu Gly Ser Ser Glu Ile Ile Phe Ala Val Ala His Pro Ala Ile
785                 790                 795                 800

Phe Asn Lys Asp Ala Asn Ser Leu Ala Gln Asp Ile Gly Thr Leu Phe
            805                 810                 815

Asp Leu Thr Gln Leu His Ala Phe Leu Thr Glu Cys Gly Thr Tyr Ala
            820                 825                 830

Ser Glu Ile Leu Thr Ser Leu Asn Glu Gly Asn Leu Asp Val Ser Thr
        835                 840                 845

Val Ala Thr Ala Leu Thr Leu Asp Lys Thr Thr Leu Ala Gln Ala Leu
850                 855                 860

Ala Gln Val Ser Glu Ser Lys Ala Phe Ser Asn Trp His Glu Leu Arg
865                 870                 875                 880

Asp Ala Leu Gln Trp Thr Asp Ala Ala Ser Ile Phe Asn Ile Thr Pro
            885                 890                 895

Val Ala Leu Thr Ala Met Val Asn Leu Lys Phe Ser Gly Asp Asn Ala
            900                 905                 910

Ser Pro Tyr Gln Glu Trp Val Thr Val Ser Lys Ala Met Gln Ala Gly
        915                 920                 925

Leu Asn Gln Thr Gln Ser Ala Gln Leu Gln Ala Ser Leu Asp Glu Ser
930                 935                 940

Leu Gly Ala Ala Val Ser Ala Tyr Val Ile Lys Asn Ser Ser Pro Ser
945                 950                 955                 960

Trp Val Thr Asp Arg Asp Lys Leu Tyr Ser Trp Leu Leu Ile Asp Asn
            965                 970                 975

Gln Val Ser Ala Gln Val Lys Thr Thr Arg Ile Ala Glu Ala Ile Ala
            980                 985                 990

Ser Val Gln Leu Tyr Val Asn Arg Ala Leu Ser Gly Leu Glu Asn Gly
        995                 1000                1005

Gln Ser Ile Thr Asp Ala Val Asp Asn Ala Val Lys Ser Gly Val
    1010                1015                1020

Phe Phe Thr Arg Asp Trp Asp Thr Tyr Asn Lys Arg Tyr Ser Thr
    1025                1030                1035

Trp Ala Gly Val Ser Glu Leu Val Tyr Tyr Pro Glu Asn Tyr Val
    1040                1045                1050

Asp Pro Thr Leu Arg Pro Gly Gln Thr Gly Met Met Asp Glu Met
    1055                1060                1065

Leu Gln Thr Leu Ser Gln Ser Gln Leu Thr Ser Asp Ser Val Glu
    1070                1075                1080

Asp Ala Phe Lys Thr Tyr Met Thr Arg Phe Glu Glu Ile Ala Asn
    1085                1090                1095

Leu Asp Ile Val Ser Gly Tyr His Asp Asn Leu Asn Asp Gln Lys
    1100                1105                1110

Gly Val Thr Tyr Leu Ile Gly Arg Ser Ala Ala Gly Asp Tyr Tyr
    1115                1120                1125

Trp Arg Ser Ala Asp Ile Ser Lys Leu Ser Asp Gly Lys Leu Pro
    1130                1135                1140

Ala Asn Ala Trp Ala Glu Trp Lys Lys Ile Thr Thr Ala Leu Thr
    1145                1150                1155

Pro Val Asn Asn Leu Val Arg Pro Val Ile Phe Gln Ser Arg Leu
    1160                1165                1170

```
Tyr Val Thr Trp Val Glu Ser Arg Glu Val Gly Ile Ser Ala Asp
1175                1180                1185

Lys Glu His Asn Ser Glu Thr Lys Ile Leu Glu Tyr Ala Leu Lys
1190                1195                1200

Tyr Ala His Ile Leu His Asp Gly Thr Trp Ser Ala Pro Val Ser
1205                1210                1215

Val Lys Leu Glu Asn Gly Thr Leu Pro Leu Asp Ser Val Ala Ile
1220                1225                1230

Asp Val Thr Gly Met Tyr Cys Ala Lys Asp Thr Gln His Asp Gln
1235                1240                1245

Leu Tyr Ile Leu Phe Tyr Lys Lys Glu Thr Tyr Asn Asp Val
1250                1255                1260

Asn Asp Val Leu Lys Gly Ile Ile Leu His Asp Asp Gly Thr Thr
1265                1270                1275

Thr Ile Thr Ser Gly Asn Ser Val Ser Gly Leu Val Val Tyr Lys
1280                1285                1290

Gln Leu Asp Thr Thr Lys Glu Val Arg Leu Asn Thr Pro Tyr Pro
1295                1300                1305

Gly Gly Lys Thr Tyr Tyr Ser Ile Asn Asn Met Arg Glu Ser Ser
1310                1315                1320

Lys Trp Gly Asp Asp Asn Ile Ser Met Leu Ser Gly Cys Ser Val
1325                1330                1335

Lys Asp Phe Val Phe Thr Glu Gly Asp Gly Lys Leu Asn Val Ala
1340                1345                1350

Phe Asn Ala Thr Glu Arg Ile Ile Tyr Arg Gly Asn Pro Asp Ser
1355                1360                1365

Gln Gly Tyr Val Ala Leu Val Asn Met Ile Lys Ala Ile Gly Asn
1370                1375                1380

Ile Gly Asp Thr Phe Lys Ile Pro Val Leu Asn Ser Asn Gly Glu
1385                1390                1395

Gly Leu Asp Lys Pro Phe Thr Cys Ile Phe Arg Gln Pro Asp Glu
1400                1405                1410

Lys Thr Asp Ala Ile Ala Tyr Phe Ser Asp Val Gln Gly Leu Asn
1415                1420                1425

Ile Asp His Phe Ala Phe Asn Asp Glu Ser Gln Lys Met Leu Gly
1430                1435                1440

Arg Ile Leu Arg Pro Glu Glu Lys Asp Phe Tyr Lys Leu Glu Cys
1445                1450                1455

Val Asn Thr Asn Leu His Ile Tyr Lys Asp Ser Ser Lys Thr Ile
1460                1465                1470

Lys Pro Asp Asn Phe Val Tyr Phe Gly Pro Gly Met Asp Leu Ile
1475                1480                1485

Val Val Lys Gly Met Ile Val Glu Thr Leu Phe Gly Leu Phe Gly
1490                1495                1500

Glu Leu Lys Thr Gly Ile Lys Asp Lys Ser Val Lys Leu Ser Val
1505                1510                1515

Ser Ala Gly Val Ile Asp Asn Ser Pro Ala Ala Thr Lys Thr Lys
1520                1525                1530

Tyr Thr Phe Asp Glu Ser Leu Tyr Val Ile Glu Gly Gln Thr Val
1535                1540                1545

Ser Ile Gln Leu Ser Glu Phe Lys Glu Asn Asn Ile Asp Leu Glu
1550                1555                1560

Phe Thr Phe Phe Ala Ser Gly Asp Ser Gly Asn Ser Leu Gly Lys
```

```
            1565                1570                1575

Ser Val Ile Ser Ala Thr Leu Thr Arg Thr Ser Glu Asn Thr Ile
    1580                1585                1590

Pro Val Ile Ser Leu Asn Lys Thr Ser Asp Asn Ala Gln Tyr Leu
    1595                1600                1605

Gln Tyr Gly Ile His Arg Ile Arg Val Asn Thr Leu Phe Ala Lys
    1610                1615                1620

Gln Leu Val Ala Arg Ala Asn Ala Gly Leu Asp Thr Val Leu Ser
    1625                1630                1635

Met Ala Thr Gln Gln Leu Thr Glu Pro Lys Met Gly Lys Gly Ala
    1640                1645                1650

Tyr Ile Asp Leu Glu Leu Asn Ala Ser Ser Asp Gly Ser Ser Ala
    1655                1660                1665

Val Phe Glu Val Leu Met Cys Asp Val Phe Thr Lys Gly Asp Arg
    1670                1675                1680

Ile Ala Leu Thr Ser Gly Thr Leu Ser Pro Thr Ala Arg Thr Ser
    1685                1690                1695

Cys Ser Phe Phe Ile Pro Arg Leu Gly Glu Ser Thr Glu Ser Pro
    1700                1705                1710

Trp Asn Met Tyr Phe Cys Val Lys Thr Gln Asn Asp Glu Ser Lys
    1715                1720                1725

Arg Val Glu Val Met Gly Gly Glu Gly Lys Trp Ser Tyr Gln Tyr
    1730                1735                1740

Val Asp Glu Ser Gly Thr Ala Ile Lys Pro Pro Tyr Thr Asp Pro
    1745                1750                1755

Tyr Ile Ala Ser Val Tyr Val Arg Asn Asp Thr Thr Glu Pro Met
    1760                1765                1770

Asp Phe Asn Gly Ala Asn Ala Leu Tyr Phe Trp Glu Met Phe Tyr
    1775                1780                1785

Tyr Val Pro Met Met Val Phe Lys Arg Leu Leu Ser Glu Ser Lys
    1790                1795                1800

Phe Ala Glu Ala Thr Gln Trp Ile Lys Tyr Ile Trp Asn Pro Asp
    1805                1810                1815

Gly Tyr Leu Val Asn Asn Gln Pro Ala Thr Tyr Ser Trp Asn Val
    1820                1825                1830

Arg Pro Leu Glu Glu Asp Thr Ser Trp His Ala Asp Pro Leu Asp
    1835                1840                1845

Ser Val Asn Pro Asp Ala Val Ala Gln Ala Asp Pro Leu His Tyr
    1850                1855                1860

Lys Val Ala Thr Phe Met Ala Tyr Leu Asp Leu Leu Ile Ala Arg
    1865                1870                1875

Gly Asp Ala Ala Tyr Arg Gln Leu Glu Arg Asp Thr Leu Asn Glu
    1880                1885                1890

Ala Lys Met Trp Tyr Val Gln Ala Leu Asn Ile Leu Gly Asp Glu
    1895                1900                1905

Pro Tyr Gln Ser Ser Ser Ser Gly Trp Ser Ser Pro Val Leu Ser
    1910                1915                1920

Ser Ala Ala Ala Gln Thr Thr Glu Lys Asn Val Gln Gln Ala Met
    1925                1930                1935

Leu Ala Val Arg Gln Gln Pro Asp Ala Gly Glu Leu Arg Thr Ala
    1940                1945                1950

Asn Ser Leu Thr Asp Leu Phe Leu Pro Gln Gln Asn Ala Lys Leu
    1955                1960                1965
```

Ala Gly Tyr Trp Gln Thr Leu Ala Gln Arg Leu Tyr Asn Leu Arg
1970             1975                 1980

His Asn Leu Ser Ile Asp Gly Ser Pro Leu Ser Leu Ala Ile Tyr
    1985             1990                 1995

Ala Ala Pro Ala Asp Pro Ala Ala Leu Leu Ser Ala Ala Val Asn
    2000             2005                 2010

Ser Ala Ser Gly Gly Ser Asp Leu Pro Ala Val Val Met Pro Leu
    2015             2020                 2025

Tyr Arg Phe Pro Val Ile Leu Glu Ser Ala Arg Gly Met Ala Gly
    2030             2035                 2040

Gln Leu Ile Gln Phe Gly Ser Thr Leu Leu Ser Ile Ala Glu Arg
    2045             2050                 2055

Gln Asp Ala Glu Ala Leu Ser Glu Leu Met Gln Thr Gln Gly Ser
    2060             2065                 2070

Gln Leu Ile Leu Gln Ser Ile Ala Leu Gln Asn Ser Thr Ile Ser
    2075             2080                 2085

Glu Ile Asp Ala Asp Lys Thr Val Leu Glu Ala Ser Leu Ser Gly
    2090             2095                 2100

Ala Arg Ser Arg Leu Asp Arg Tyr Thr Thr Leu Tyr Asp Glu Asp
    2105             2110                 2115

Val Asn Thr Gly Glu Gln Gln Ala Met Asp Leu Phe Tyr Ala Ser
    2120             2125                 2130

Ser Leu Gln Ala Asn Gly Gly Gln Met Phe His Thr Ile Ala Gly
    2135             2140                 2145

Ala Leu Asp Leu Val Pro Asn Ile Phe Gly Leu Ala Asp Gly Gly
    2150             2155                 2160

Ser Arg Trp Gly Ala Val Ser Thr Ala Met Ala Ser Ile Ala Asp
    2165             2170                 2175

Leu Ser Ala Ala Ala Cys His Thr Thr Ala Glu Arg Leu Ser Gln
    2180             2185                 2190

Ser Glu Val Tyr Arg Arg Arg Gln Glu Trp Glu Ile Gln Arg
    2195             2200                 2205

Asn Ala Ala Gln Ser Glu Ile Asp Gln Ile Asp Ala Gln Leu Ala
    2210             2215                 2220

Ser Leu Thr Ile Arg Arg Glu Gly Ala Val Leu Gln Lys Thr Tyr
    2225             2230                 2235

Leu Glu Thr Gln Gln Gly Gln Met Gln Ala Gln Met Thr Phe Leu
    2240             2245                 2250

Gln Asn Lys Phe Thr Ser Lys Ala Leu Tyr Asn Trp Leu Arg Gly
    2255             2260                 2265

Lys Leu Ala Ala Ile Tyr Tyr Gln Phe Tyr Asp Leu Thr Val Ser
    2270             2275                 2280

Arg Cys Leu Met Ala Glu Ala Ala Tyr Ser Trp Asp Ile Lys Gly
    2285             2290                 2295

Asn Gln Glu Thr Gly Thr Phe Ile Arg Pro Gly Ala Trp Gln Gly
    2300             2305                 2310

Thr Tyr Ala Gly Leu Met Ala Gly Glu Thr Leu Met Leu Asn Leu
    2315             2320                 2325

Ala Gln Met Glu Asn Ser Tyr Leu Thr Lys Asp Glu Arg Leu Lys
    2330             2335                 2340

Glu Val Thr Arg Thr Val Cys Leu Ser Glu Val Tyr Ala Gly Leu
    2345             2350                 2355

```
Ser Ser Asp Ser Phe Ala Leu Ala Asp Thr Val Thr Thr Leu Val
    2360            2365            2370

Ser Asn Gly Lys Gly Asn Ala Gly Thr Asp Asp Asn Gly Val Lys
    2375            2380            2385

Ile Asp Asp Lys Gln Leu Leu Ala Thr Leu Lys Leu Ser Asp Leu
    2390            2395            2400

Ser Ile Asp Asn Asp Tyr Pro Glu Ser Leu Gly Lys Thr Arg Arg
    2405            2410            2415

Ile Lys Gln Ile Ser Val Thr Leu Pro Thr Leu Val Gly Pro Tyr
    2420            2425            2430

Gln Asp Val Arg Ala Val Leu Ser Tyr Gly Gly Ser Val Ala Leu
    2435            2440            2445

Pro Arg Gly Cys Thr Ala Val Ala Val Ser His Gly Met Asn Asp
    2450            2455            2460

Ser Gly Gln Phe Gln Leu Asp Phe Asn Asp Ser Arg Trp Leu Pro
    2465            2470            2475

Phe Glu Gly Ile Pro Val Gly Asp Ser Gly Thr Leu Thr Leu Ser
    2480            2485            2490

Phe Pro Asp Ile Thr Asp Lys Gln Gln Glu Asn Leu Leu Leu Ser
    2495            2500            2505

Leu Ser Asp Ile Ile Leu His Ile Arg Tyr Thr Ile Ala Ser
    2510            2515            2520

<210> SEQ ID NO 20
<211> LENGTH: 1421
<212> TYPE: PRT
<213> ORGANISM: Pantoea agglomerans

<400> SEQUENCE: 20

Met Gln Asn Thr Asp Gln Met Ser Leu Thr Pro Pro Ser Leu Pro Ser
1               5                   10                  15

Gly Gly Gly Ala Val Thr Gly Leu Lys Gly Asp Met Ser Gly Ala Gly
            20                  25                  30

Pro Asp Gly Ala Ala Thr Leu Asn Leu Pro Leu Pro Ile Ser Pro Gly
        35                  40                  45

Arg Gly Tyr Ala Pro Ser Leu Ser Leu Gly Tyr His Ser Arg Asn Gly
    50                  55                  60

Asn Gly Val Phe Gly Ala Gly Trp Ser Cys Gly Gln Met Ala Ile Arg
65                  70                  75                  80

Leu Gln Thr Arg Lys Gly Val Pro Phe Tyr Asp Gly Ser Asp Val Phe
                85                  90                  95

Thr Ala Pro Asp Gly Glu Val Leu Val Pro Ala Leu Asp Ala Ser Gly
            100                 105                 110

Lys Thr Glu Val Arg Thr Thr Thr Leu Leu Gly Asn Leu Gly
        115                 120                 125

Gly Thr Phe Thr Val Gln Thr Tyr Arg Ser Arg Val Glu Thr Asp Phe
    130                 135                 140

Ser Arg Leu Glu Arg Trp Val Ser Gln Ala Asp Ala Ala Asp Phe
145                 150                 155                 160

Trp Leu Ile Tyr Ser Pro Asp Gly Gln Ile His Leu Leu Gly Arg Asn
                165                 170                 175

Pro Gln Ala Arg Val Ser Asn Pro Glu Asp Thr Thr Gln Thr Ala Ala
            180                 185                 190

Trp Leu Ile Glu Ser Ser Val Ser Ala Ser Gly Glu Gln Ile Tyr Trp
        195                 200                 205
```

-continued

```
Gln Tyr Arg Gln Glu Asp Glu Leu Gly Cys Thr Gln Asp Glu Lys Thr
    210                 215                 220

Ala His Ala His Ala Leu Ala Gln Arg Tyr Leu Val Ala Val Trp Tyr
225                 230                 235                 240

Gly Asn Lys Ala Ala Ser Arg Thr Leu Pro Gly Leu Leu Ser Val Pro
                245                 250                 255

Ala Ala Gly Ser Trp Leu Phe Thr Leu Val Leu Asp Tyr Gly Glu Arg
            260                 265                 270

Thr Thr Asp Pro Ala Thr Pro Pro Ala Trp Leu Ser Pro Gly Ser Gly
        275                 280                 285

Thr Trp Leu Cys Arg Gln Asp Val Phe Ser Ser Trp Glu Tyr Gly Phe
290                 295                 300

Glu Leu Arg Thr Arg Arg Leu Cys Arg Gln Val Leu Met Tyr His Asp
305                 310                 315                 320

Val Ala Ala Leu Ala Gly Lys Pro Gly Ser Asp Ala Val Pro Gln Leu
                325                 330                 335

Val Thr Arg Leu Leu Leu Asp Tyr Asn Leu Ser Pro Ser Leu Thr Thr
            340                 345                 350

Leu Lys Thr Ala Gln Gln Ala Ala Trp Glu Ala Asp Gly Thr Leu Arg
        355                 360                 365

Ser Leu Pro Pro Leu Ala Phe Ser Trp Gln Thr Phe Pro Ser Thr Pro
370                 375                 380

Glu Lys Ser Val Ser Trp Gln Gln Arg Asn Asp Met Gly Lys Leu Asn
385                 390                 395                 400

Pro Gln Gln Pro Tyr Gln Met Val Asp Leu His Gly Glu Gly Leu Ala
                405                 410                 415

Gly Ile Leu Tyr Gln Asp Ser Gly Ala Trp Trp Tyr Arg Glu Pro Val
            420                 425                 430

Arg Gln Leu Gly Asp Asp Asn Ala Val Thr Trp Ala Ala Ala Arg
        435                 440                 445

Pro Leu Pro Ala Phe Pro Ala Leu Arg Lys Gly Gly Met Leu Leu Asp
450                 455                 460

Leu Asp Gly Asp Gly Tyr Leu Glu Trp Val Val Thr Ala Pro Gly Val
465                 470                 475                 480

Ala Gly Cys Tyr Ala Gln Thr Pro Glu Gln Cys Trp Gln Arg Phe Thr
                485                 490                 495

Pro Leu Ser Ala Leu Pro Val Glu Tyr Arg His Ser Arg Met Glu Ile
            500                 505                 510

Thr Asp Val Thr Gly Ala Gly Leu Ala Asp Met Leu Leu Ile Gly Pro
        515                 520                 525

Lys Ser Val Arg Leu Tyr Ser Gly Ser Arg Gly Trp Lys Lys Ala
530                 535                 540

Arg Thr Val Met Gln Asp Ser Gly Ile Thr Leu Pro Val Pro Gly Thr
545                 550                 555                 560

Asn Ala Arg Val Met Val Ala Phe Ser Asp Met Ala Gly Ser Gly Gln
                565                 570                 575

Gln His Leu Thr Glu Ile Lys Ala Ser Gly Val Arg Tyr Trp Pro Ser
            580                 585                 590

Leu Gly His Gly Arg Phe Ala Ala Pro Val Thr Leu Pro Gly Phe Ser
        595                 600                 605

Gln Pro Ala Glu Thr Phe Asn Pro Ala Gln Leu Tyr Leu Ala Asp Val
610                 615                 620
```

```
Asp Gly Ser Gly Thr Thr Asp Leu Ile Tyr Ala Leu Ser Asp His Leu
625                 630                 635                 640

Leu Val Trp Leu Asn Gln Ser Gly Asn Arg Phe Asp Glu Pro Phe Arg
            645                 650                 655

Ile Asp Leu Pro Glu Gly Val Arg Tyr Asp Asn Thr Cys Ser Leu Gln
                660                 665                 670

Val Ala Asp Ile Gln Gly Leu Gly Ile Ser Ser Leu Val Leu Ser Val
            675                 680                 685

Pro His Pro Thr Pro Arg His Trp Val Cys His Leu Thr Ala Glu Lys
    690                 695                 700

Pro Trp Leu Leu Asp Gly Met Asn Asn Asn Met Gly Ala Arg His Thr
705                 710                 715                 720

Leu Cys Tyr Arg Ser Ser Ala Gln Phe Trp Leu Asp Glu Lys Ala Ala
                725                 730                 735

Ala Thr Ala Asp Arg Pro Ala Pro Ala Cys Tyr Met Pro Phe Ala Leu
            740                 745                 750

His Thr Leu Ser Arg Thr Glu Val Ser Asp Glu Ile Thr Gly Asn Arg
        755                 760                 765

Leu Thr Arg Thr Ile Arg Tyr Arg His Gly Val Trp Asp Arg Arg Glu
770                 775                 780

Arg Glu Phe Arg Gly Phe Gly Phe Val Glu Val Ser Asp Ala Glu Ala
785                 790                 795                 800

Leu Ala Lys Gln Thr Glu Gly Met Ser Ala Pro Ala Val Lys Arg Ser
                805                 810                 815

Trp Tyr Ala Thr Gly Leu Thr Ala Val Asp Ala Gln Leu Pro Asp Glu
            820                 825                 830

Phe Trp Lys Gly Asp His Ala Ala Phe Ala Gly Phe Thr Pro Arg Phe
        835                 840                 845

Thr Thr Gly Tyr Gly Glu Gln Glu Ala Ala Leu Asp Thr Ile Ser Asp
850                 855                 860

Asp Thr Arg Phe Trp Leu Thr Arg Ala Ile Arg Gly Thr Leu Leu Arg
865                 870                 875                 880

Ser Glu Leu Tyr Gly Ala Asp Gly Ser Ser Gln Ala Gly Ile Pro Tyr
                885                 890                 895

Ser Ile Thr Glu Ser Arg Pro Gln Val Arg Leu Ile Thr Glu Ala Gly
            900                 905                 910

Asn Ser Pro Val Val Trp Pro Ser Val Ile Glu Asn Arg Ala Ser His
        915                 920                 925

Tyr Glu Arg Val Ser Ser Asp Pro Gln Cys Gly Gln Gln Ile Leu Leu
930                 935                 940

Thr Ser Asn Glu Tyr Gly Gln Pro Leu Arg Gln Ile Gly Val Ser Tyr
945                 950                 955                 960

Pro Arg Arg Thr Arg Pro Asp Ala Ser Pro Tyr Asp Asp Leu Pro
                965                 970                 975

Asp Gly Leu Phe Ala Asp Ser Phe Asp Glu Gln Gln Ala Leu Arg
            980                 985                 990

Leu Thr Leu Thr Gln Ser Ser Trp His Thr Leu Lys Asp Ile Ser Ser
        995                 1000                1005

Gly Ile Trp Leu Pro Ala Val Ala Asp Ala Thr Arg Ser Asp Leu
    1010                1015                1020

Phe Val His Gln Ala Ala Gln Val Pro Pro Ala Gly Leu Thr Leu
    1025                1030                1035

Glu Asn Leu Leu Thr Asp Ser Ala Leu Leu Thr Ser Pro Val Phe
```

```
            1040                1045                1050

Gly Gly Gln Ser Gln Thr Trp Tyr Gln Asp Ser Ala Gly Gln Ala
        1055                1060                1065

Ser Thr Thr Ser Pro Asp Phe Pro Leu Arg Pro Ser Phe Ser Glu
        1070                1075                1080

Thr Ala Ala Leu Asp Glu Ala Gln Val Ser Ala Leu Ser Ala Asp
        1085                1090                1095

Ile Asp Gln Thr Lys Leu Glu Gln Ala Gly Tyr Thr Arg Ser Ala
        1100                1105                1110

Tyr Leu Phe Ala Arg Ser Gly Glu Gly Lys Thr Leu Trp Thr
        1115                1120                1125

Val Arg Gln Gly Tyr Ile Thr Phe Ser Ser Ala Asp His Phe Tyr
        1130                1135                1140

Leu Pro Ile Ala Ala Gln Gln Thr Leu Leu Thr Gly Lys Thr Thr
        1145                1150                1155

Val Thr Tyr Asp Pro Tyr Asp Cys Val Val Leu Gln Ala Lys Asp
        1160                1165                1170

Ala Ala Gly Ala Val Thr Ser Ala Thr Tyr Asp Trp Arg Phe Leu
        1175                1180                1185

Ala Pro Thr Gln Ile Thr Asp Ile Asn Asp Asn Leu Lys Ser Val
        1190                1195                1200

Thr Leu Asp Ala Leu Gly Arg Val Thr Ser Gln Arg Phe Ser Gly
        1205                1210                1215

Ser Glu Asn Gly Lys Pro Ala Gly Tyr Ser Asp Ala Phe Pro
        1220                1225                1230

Leu Pro Ala Ser Ala Asp Ala Ala Leu Ala Leu Ser Ala Pro Leu
        1235                1240                1245

Pro Val Ala Gln Cys Ile Ile Tyr Val Pro Asp Ser Trp Met Leu
        1250                1255                1260

Thr Gly Glu Gln Gln Gln Pro Pro His Val Val Thr Leu Leu Thr
        1265                1270                1275

Asp Arg Tyr Asp Ser Asp Ser Gln Gln Gln Ile Arg Gln Gln Val
        1280                1285                1290

Val Phe Ser Asp Gly Phe Gly Arg Val Leu Gln Ala Ala Ser Arg
        1295                1300                1305

Gln Val Asn Gly Glu Ala Trp Gln Arg Ala Ala Asn Gly Ser Phe
        1310                1315                1320

Val Ala Asp Pro Asn Gly Ser Pro Val Leu Thr Glu Thr Thr Phe
        1325                1330                1335

Arg Trp Ala Val Thr Gly Arg Thr Glu Tyr Asp Asn Lys Gly Gln
        1340                1345                1350

Ala Ile Arg Thr Tyr Gln Pro Tyr Phe Leu Asp Ser Trp Lys Tyr
        1355                1360                1365

Val Arg Asp Asp Ser Ala Arg His Asp Leu Tyr Ala Asp Thr His
        1370                1375                1380

Tyr Tyr Asp Pro Val Gly Glu Arg Gln Val Ile Thr Ala Lys
        1385                1390                1395

Gly Leu Leu Arg Arg Val Thr Tyr Thr Pro Trp Phe Val Val Ser
        1400                1405                1410

Glu Asp Glu Asn Asp Thr Gln Ala
        1415                1420

<210> SEQ ID NO 21
```

-continued

```
<211> LENGTH: 1004
<212> TYPE: PRT
<213> ORGANISM: Pantoea agglomerans

<400> SEQUENCE: 21
```

| | | | | | | | | | | | | | | |
|---|---|---|---|---|---|---|---|---|---|---|---|---|---|---|
| Met | Ser | Ala | Ala | Tyr | Val | Leu | Ser | Asn | Leu | Ser | Tyr | Gln | Arg | Glu | Asn |
| 1 | | | | 5 | | | | | 10 | | | | | 15 | |
| Thr | Met | Ser | Thr | Ser | Leu | Tyr | Ser | Arg | Thr | Pro | Ser | Val | Thr | Val | Leu |
| | | | 20 | | | | | 25 | | | | | 30 | | |
| Asp | Asn | Arg | Gly | Leu | Thr | Val | Arg | Asp | Ile | Ala | Tyr | His | Arg | His | Pro |
| | | | 35 | | | | | 40 | | | | | 45 | | |
| Asp | Thr | Pro | Ala | Val | Thr | Ser | Glu | Arg | Ile | Thr | Arg | His | Gln | Tyr | Asp |
| | 50 | | | | | 55 | | | | | 60 | | | | |
| Ala | Arg | Gly | Phe | Leu | Thr | Gln | Ser | Ala | Asp | Pro | Arg | Leu | His | Asp | Ala |
| 65 | | | | | 70 | | | | | 75 | | | | | 80 |
| Gly | Leu | Ala | Asn | Phe | Ser | Tyr | Arg | Thr | Asp | Leu | Thr | Gly | Ser | Val | Leu |
| | | | | 85 | | | | | 90 | | | | | 95 | |
| Arg | Leu | Gln | Gly | Val | Asp | Asn | Gly | Ile | Thr | Val | Ala | Leu | Asn | Asp | Ala |
| | | | 100 | | | | | 105 | | | | | 110 | | |
| Ala | Gly | Arg | Pro | Phe | Leu | Ala | Val | Ser | Asn | Ile | Arg | Thr | Ala | Gly | Asp |
| | | | 115 | | | | | 120 | | | | | 125 | | |
| Gly | Ser | Glu | Asp | Arg | Ser | Gln | Ala | Leu | Thr | Arg | Thr | Cys | Gln | Tyr | Glu |
| | 130 | | | | | 135 | | | | | 140 | | | | |
| Asp | Ala | Thr | Leu | Pro | Gly | Arg | Pro | Leu | Ser | Ile | Thr | Glu | Gln | Val | Lys |
| 145 | | | | | 150 | | | | | 155 | | | | | 160 |
| Gly | Gly | Ala | Ala | Arg | Ile | Thr | Glu | Arg | Phe | Ile | Tyr | Ala | Gly | Asn | Ala |
| | | | | 165 | | | | | 170 | | | | | 175 | |
| Val | Glu | Glu | Lys | Ala | Leu | Asn | Leu | Ala | Gly | Gln | Pro | Val | Ser | His | Tyr |
| | | | 180 | | | | | 185 | | | | | 190 | | |
| Asp | Thr | Ala | Gly | Leu | Thr | Gln | Thr | Asp | Ser | Ile | Ala | Leu | Thr | Gly | Val |
| | | | 195 | | | | | 200 | | | | | 205 | | |
| Pro | Leu | Ser | Val | Thr | Arg | Arg | Leu | Leu | Lys | Asp | Ala | Asp | Asn | Pro | Asp |
| | 210 | | | | | 215 | | | | | 220 | | | | |
| Ala | Val | Ala | Asp | Trp | Gln | Gly | Thr | Asp | Ala | Ser | Val | Trp | Asn | Asp | Pro |
| 225 | | | | | 230 | | | | | 235 | | | | | 240 |
| Leu | Asp | Val | Glu | Thr | Tyr | Thr | Thr | Leu | Ser | Thr | Ala | Asp | Ala | Thr | Gly |
| | | | | 245 | | | | | 250 | | | | | 255 | |
| Ala | Val | Leu | Thr | Thr | Thr | Asp | Ala | Lys | Gly | Asn | Leu | Gln | Arg | Leu | Ala |
| | | | 260 | | | | | 265 | | | | | 270 | | |
| Tyr | Asp | Val | Ala | Gly | Leu | Leu | Ser | Gly | Ser | Trp | Leu | Thr | Leu | Lys | Asp |
| | | | 275 | | | | | 280 | | | | | 285 | | |
| Gly | Thr | Glu | Gln | Val | Ile | Val | Thr | Ser | Leu | Thr | Tyr | Ser | Ala | Ala | Gly |
| | 290 | | | | | 295 | | | | | 300 | | | | |
| Gln | Lys | Leu | Arg | Glu | Glu | His | Gly | Asn | Gly | Val | Val | Thr | Thr | Tyr | Thr |
| 305 | | | | | 310 | | | | | 315 | | | | | 320 |
| Tyr | Glu | Ala | Glu | Thr | Gln | Arg | Leu | Thr | Gly | Ile | Lys | Thr | Ala | Arg | Pro |
| | | | | 325 | | | | | 330 | | | | | 335 | |
| Ala | Gly | His | Thr | Ser | Gly | Ala | Lys | Val | Leu | Gln | Asp | Leu | Arg | Tyr | Thr |
| | | | 340 | | | | | 345 | | | | | 350 | | |
| Tyr | Asp | Pro | Val | Gly | Asn | Val | Leu | Lys | Ile | Ser | Asn | Asp | Ala | Glu | Glu |
| | | | 355 | | | | | 360 | | | | | 365 | | |
| Thr | Arg | Phe | Trp | Arg | Asn | Gln | Lys | Val | Val | Pro | Glu | Ser | Ala | Tyr | Val |
| | 370 | | | | | 375 | | | | | 380 | | | | |
| Tyr | Asp | Ser | Leu | Tyr | Gln | Leu | Val | Ser | Ala | Thr | Gly | Arg | Glu | Met | Ala |

```
             385                 390                 395                 400
Asn Ala Gly Gln Gln Gly Ser Ser Ser Ser Ala Thr Val Pro Leu
                405                 410                 415
Pro Ala Asp Ser Ser Ala Phe Thr Asn Tyr Thr Arg Asn Tyr Thr Tyr
                420                 425                 430
Asp Glu Ala Gly Asn Leu Thr Gln Val Arg His Thr Pro Ala Thr Gly
                435                 440                 445
Ser Gly Tyr Thr Thr Lys Ile Thr Val Ser Asp Lys Ser Asn Arg Gly
    450                 455                 460
Val Leu Ser Thr Leu Thr Glu Asn Pro Ser Asp Val Asp Ala Leu Phe
465                 470                 475                 480
Thr Ala Gly Gly Gln Gln Lys Gln Leu Gln Pro Gly Gln Ser Leu Ile
                485                 490                 495
Trp Thr Pro Arg Asn Glu Leu Leu Lys Val Thr Pro Val Ala Arg Asp
                500                 505                 510
Gly Gly Ala Asp Asp Ser Glu Ser Tyr Arg Tyr Asp Gly Gly Ser Leu
            515                 520                 525
Arg Leu Leu Lys Val Ser Val Gln Lys Thr Gly Asn Ser Thr Gln Thr
    530                 535                 540
Gln Arg Ala Leu Tyr Leu Pro Gly Leu Glu Leu Arg Asn Thr Thr Ser
545                 550                 555                 560
Gly Asp Thr Glu Thr Glu Ser Leu Gln Val Val Thr Val Gly Glu Ala
                565                 570                 575
Gly Arg Ala Gln Val Arg Val Leu His Trp Glu Ser Gly Thr Pro Asp
                580                 585                 590
Ser Val Ser Asn Asp Gln Leu Arg Tyr Ser Tyr Asp Asn Leu Thr Gly
            595                 600                 605
Ser Ser Gly Leu Glu Leu Asp Ser Ser Gly Asn Ile Ile Ser Met Glu
    610                 615                 620
Glu Tyr Pro Tyr Gly Gly Thr Ala Val Trp Thr Ala Arg Ser Ala
625                 630                 635                 640
Val Glu Ala Lys Tyr Lys Thr Val Arg Tyr Ser Ala Lys Glu Arg Asp
                645                 650                 655
Ala Thr Gly Leu Tyr Tyr Gly Tyr Arg Tyr Tyr Gln Pro Trp Ala
                660                 665                 670
Gly Arg Trp Leu Ser Ala Asp Pro Ala Gly Thr Ala Asp Gly Leu Asn
    675                 680                 685
Leu Phe Arg Met Val Arg Asn Asn Pro Val Thr Leu Lys Asp Thr Asn
    690                 695                 700
Gly Leu Ile Ser Thr Gly Gln Asp Ala Arg Lys Leu Val Ala Glu Ala
705                 710                 715                 720
Phe Val His Pro Leu His Met Thr Val Phe Glu Arg Ile Ser Ser Glu
                725                 730                 735
Glu Asn Leu Ala Met Ser Val Arg Glu Ala Gly Ile Tyr Thr Ile Ser
                740                 745                 750
Ala Leu Gly Glu Gly Ala Ala Ala Lys Gly His Asn Ile Leu Glu Lys
            755                 760                 765
Thr Ile Lys Pro Gly Ser Leu Lys Ala Val Tyr Gly Asp Asn Ala Glu
            770                 775                 780
Ser Ile Leu Ala Gln Ala Lys Arg Ser Gly Phe Val Gly Arg Val Gly
785                 790                 795                 800
Gln Trp Asp Ala Ser Gly Val Arg Gly Ile Tyr Ala His Asn Thr Pro
                805                 810                 815
```

```
Gly Gly Glu Asp Leu Ala Tyr Pro Val Asn Leu Lys Asn Ser Ser Ala
            820                 825                 830

Asn Glu Leu Val Asn Ala Trp Ile Lys Phe Lys Ile Ile Thr Pro Tyr
            835                 840                 845

Thr Gly Asp Tyr Asp Met His Asp Ile Ile Lys Ile Ser Asp Gly Lys
    850                 855                 860

Gly His Val Pro Leu Ala Glu Ser Asn Glu Glu Lys Gly Val Lys Asp
865                 870                 875                 880

Met Ile Asn Glu Gly Val Ala Gln Val Asp Pro Ala Arg Pro Phe Thr
                885                 890                 895

Ser Thr Ala Met Asn Val Val Arg His Gly Pro Gln Val Asn Phe Val
            900                 905                 910

Pro Tyr Met Trp Glu His Glu His Glu Asn Val Val Arg Asp Asn Gly
            915                 920                 925

Tyr Leu Gly Val Val Ala Arg Pro Gly Pro Phe Pro Val Ala Met Val
    930                 935                 940

His Lys Gly Glu Trp Thr Val Phe Asp Asn Lys Asn Glu Leu Phe Glu
945                 950                 955                 960

Phe Tyr Lys Ser Thr Asn Thr Pro Leu Pro Glu His Trp Ser Gln Asp
                965                 970                 975

Phe Val Glu Arg Gly Lys Gly Asn Val Ala Thr Pro Arg His Ala Glu
            980                 985                 990

Ile Leu Asp Arg Asn Ser Ser Arg  Leu Arg Ala Ala
            995                 1000

<210> SEQ ID NO 22
<211> LENGTH: 971
<212> TYPE: PRT
<213> ORGANISM: Pantoea agglomerans

<400> SEQUENCE: 22

Met Cys Ser Val Ala Asp Phe Asp Arg Leu His Asn Ile Lys Gln Glu
1               5                   10                  15

Asn Ile Met Ser Thr Ser Leu Tyr Ser Arg Thr Pro Ser Val Thr Val
            20                  25                  30

Leu Asp Asn Arg Gly Leu Thr Val Arg Asp Ile Ala Tyr His Arg His
            35                  40                  45

Pro Asp Thr Pro Ala Val Thr Ser Glu Arg Ile Thr Arg His Gln Tyr
    50                  55                  60

Asp Ala Arg Gly Phe Leu Thr Gln Ser Ala Asp Pro Arg Leu His Asp
65                  70                  75                  80

Ala Gly Leu Ala Asn Phe Ser Tyr Arg Thr Asp Leu Thr Gly Ser Val
                85                  90                  95

Leu Arg Leu Gln Gly Val Asp Asn Gly Ile Thr Val Ala Leu Asn Asp
            100                 105                 110

Ala Ala Gly Arg Pro Phe Leu Ala Val Ser Asn Ile Arg Thr Ala Gly
            115                 120                 125

Asp Gly Ser Glu Asp Arg Ser Gln Ala Leu Thr Arg Thr Cys Gln Tyr
    130                 135                 140

Glu Asp Ala Thr Leu Pro Gly Arg Pro Leu Ser Ile Thr Glu Gln Val
145                 150                 155                 160

Lys Gly Gly Ala Ala Arg Ile Thr Glu Arg Phe Ile Tyr Ala Gly Asn
                165                 170                 175

Ala Val Glu Glu Lys Ala Leu Asn Leu Ala Gly Gln Pro Val Ser His
```

-continued

```
              180                 185                 190
Tyr Asp Thr Ala Gly Leu Thr Gln Thr Asp Ser Ile Ala Leu Thr Gly
            195                 200                 205
Val Pro Leu Ser Val Thr Arg Arg Leu Leu Lys Asp Ala Asp Asn Pro
        210                 215                 220
Asp Ala Val Ala Asp Trp Gln Gly Thr Asp Ala Ser Val Trp Asn Asp
225                 230                 235                 240
Leu Leu Gly Ala Glu Thr Tyr Thr Thr Leu Ser Thr Ala Asp Val Thr
                245                 250                 255
Gly Ala Val Leu Thr Thr Thr Asp Ala Lys Gly Asn Leu Gln Arg Leu
            260                 265                 270
Ala Tyr Asp Val Ala Gly Leu Leu Ser Gly Ser Trp Leu Thr Leu Lys
        275                 280                 285
Asp Gly Thr Glu Gln Val Ile Val Thr Ser Leu Thr Tyr Ser Ala Ala
        290                 295                 300
Gly Gln Lys Leu Arg Glu Glu His Gly Asn Gly Val Val Thr Thr Tyr
305                 310                 315                 320
Thr Tyr Glu Ala Glu Thr Gln Arg Leu Thr Gly Ile Lys Thr Glu Arg
                325                 330                 335
Pro Ala Gly His Ala Ser Gly Ala Lys Val Leu Gln Asp Leu Arg Tyr
            340                 345                 350
Thr Tyr Asp Pro Val Gly Asn Val Leu Lys Ile Ser Asn Asp Ala Glu
        355                 360                 365
Glu Thr Arg Phe Trp Arg Asn Gln Lys Val Val Pro Glu Asn Ala Tyr
        370                 375                 380
Val Tyr Asp Ser Leu Tyr Gln Leu Val Ser Ala Thr Gly Arg Glu Met
385                 390                 395                 400
Ala Asn Ala Gly Gln Gln Gly Ser Ser Ser Ser Ala Thr Val Pro
                405                 410                 415
Leu Pro Ala Asp Ser Ser Ala Phe Thr Asn Tyr Thr Arg Asn Tyr Thr
            420                 425                 430
Tyr Asp Glu Ala Gly Asn Leu Thr Gln Val Arg His Thr Pro Ala Thr
        435                 440                 445
Gly Ser Gly Tyr Thr Thr Lys Ile Thr Val Ser Asp Lys Ser Asn Arg
        450                 455                 460
Gly Val Leu Ser Thr Leu Thr Glu Asn Pro Ser Asp Val Asp Ala Leu
465                 470                 475                 480
Phe Thr Ala Gly Gly Gln Gln Lys Gln Leu Gln Pro Gly Gln Ser Leu
                485                 490                 495
Ile Trp Thr Pro Arg Asn Glu Leu Leu Lys Val Met Pro Ile Met Arg
            500                 505                 510
Asp Gly Gly Thr Asp Asp Ser Glu Ser Tyr Arg Tyr Asp Gly Gly Ser
        515                 520                 525
Gln Arg Leu Leu Lys Val Ser Val Gln Lys Thr Gly Asn Ser Thr Gln
        530                 535                 540
Thr Gln Arg Ala Leu Tyr Leu Pro Gly Leu Glu Leu Arg Thr Thr Lys
545                 550                 555                 560
Ser Gly Asp Thr Leu Thr Glu Ser Leu Gln Val Ile Thr Ala Gly Glu
                565                 570                 575
Ala Gly Arg Ala Gln Val Arg Val Leu His Trp Glu Ser Gly Thr Pro
            580                 585                 590
Asp Ser Val Ser Asn Asp Gln Leu Arg Tyr Ser Tyr Asp Asn Leu Thr
        595                 600                 605
```

Gly Ser Ser Gly Leu Glu Leu Asp Ser Ser Gly Asn Ile Ile Ser Met
610                 615                 620

Glu Glu Tyr Tyr Pro Tyr Gly Gly Thr Ala Val Trp Thr Ala Arg Ser
625                 630                 635                 640

Ala Val Glu Ala Lys Tyr Lys Thr Val Arg Tyr Ser Gly Lys Glu Arg
            645                 650                 655

Asp Ala Thr Gly Leu Tyr Tyr Tyr Gly Tyr Arg Tyr Tyr Gln Pro Trp
            660                 665                 670

Ala Gly Arg Trp Leu Ser Ala Asp Pro Ala Gly Thr Val Asp Gly Leu
        675                 680                 685

Asn Leu Phe Arg Met Val Arg Asn Asn Pro Leu Thr Leu Lys Asp Asn
        690                 695                 700

Asp Gly Leu Lys Pro Ile Asn Glu Asn Phe Arg Glu Asn Lys Gly Asp
705                 710                 715                 720

Leu Val Tyr Gly Leu Ala Ala Pro Arg Gly Ala Tyr Ile Ser Thr Ala
                725                 730                 735

Ile Gly Arg Lys Phe Ala Pro Glu Glu Lys Asp Ala Pro Ala Ser Ile
            740                 745                 750

Ile Asp Leu Tyr Asn Asn Thr Val Ser Gly Gln Ala Leu Leu Ser Val
        755                 760                 765

Asp Phe Lys Ile Leu Gln Asp Phe Met Lys Ser Pro Lys Lys Asn Glu
770                 775                 780

Lys Lys Leu Ala Pro Pro Ser Asn Ile Lys Glu Leu Val Lys Lys Ser
785                 790                 795                 800

Arg Asp Tyr Pro Leu Trp Glu Asp Tyr Phe Leu Ala Gly Glu Asn Asn
                805                 810                 815

Pro Lys Phe Asn Ile Ala Ser Ile Tyr Lys Glu Val Arg Lys Asp Ala
            820                 825                 830

Gly Lys Thr Gln Tyr His Glu Trp His Ile Ala Gly Gln Ser Ala
        835                 840                 845

Pro Lys Leu Leu Trp Lys Arg Gly Ser Lys Leu Gly Ile Glu Met Ala
850                 855                 860

Ala Ser Gly Ala Gly Asn Lys Ile His Phe Val Leu Asp Glu Leu Asp
865                 870                 875                 880

Ile Ser Asn Val Val Asn Lys Glu Gly Pro Gly Gly Lys Ser Ile Thr
                885                 890                 895

Ala Ser Glu Leu Arg Tyr Ala Tyr Arg Asn Arg Glu Arg Leu Thr Gly
            900                 905                 910

Asn Ile His Phe Tyr Lys Asn Asn Ala Glu Thr Gly Ala Pro Trp Asp
        915                 920                 925

Thr Asn Ala Glu Leu Trp Ala Ser Tyr His Pro Lys Pro Lys His Lys
930                 935                 940

Gly Asn Glu Ser Thr His Ile Met Ser Gln Arg Arg Asn Gly Ser Leu
945                 950                 955                 960

Phe Lys Ser Met Arg Lys Val Phe Ser Arg Asn
                965                 970

<210> SEQ ID NO 23
<211> LENGTH: 2523
<212> TYPE: PRT
<213> ORGANISM: Pantoea agglomerans

<400> SEQUENCE: 23

Met Tyr Leu Thr Glu Glu Ile Leu Ala Lys Leu Asn Ala Gly Asn Gly

```
1               5                   10                  15
Lys Leu Gln Ser Thr Val Glu Gln Ile Ile Thr Leu Pro Asp Ile Met
                20                  25                  30

Val Arg Ser Phe Ser Gln Val Lys Glu Leu Ala Gly Asp Lys Leu Ser
                35                  40                  45

Trp Gly Glu Lys Asn Phe Leu Tyr Gln Gln Ala Gln Thr Gln Leu Lys
    50                  55                  60

Glu Asn Lys Met Ala Glu Ser Arg Ile Leu Ser Arg Ala Asn Pro Gln
65                  70                  75                  80

Leu Ala Asn Ala Val Arg Leu Gly Ile Arg Gln Ser Ser Met Leu Gly
                85                  90                  95

Ser Tyr Asp Asp Leu Phe Pro Gln Arg Ala Ser Arg Phe Val Lys Pro
                100                 105                 110

Gly Ala Val Ala Ser Met Phe Ser Pro Ala Gly Tyr Leu Thr Glu Leu
                115                 120                 125

Tyr Arg Glu Ala Arg Gly Leu His Lys Ala Glu Ser Gln Tyr Asn Leu
                130                 135                 140

Asp Lys Arg Arg Pro Asp Leu Ala Ser Leu Ala Leu Ser Gln Ser Asn
145                 150                 155                 160

Met Asp Asp Glu Leu Ser Thr Leu Ser Leu Ser Asn Glu Leu Leu Leu
                165                 170                 175

Asn Asn Ile Gln Gln His Asp Gly Leu Ser Tyr Asp Asp Ala Leu Lys
                180                 185                 190

Lys Leu Ala Gly Tyr Arg Gln Thr Gly Thr Thr Pro Tyr Ser Gln Pro
                195                 200                 205

Tyr Glu Thr Ile Arg Glu Ala Ile Leu Leu Gln Asp Pro Ala Phe Asn
                210                 215                 220

Ser Ile Arg Asn Asn Pro Ala Val Ala Thr Lys Met Asn Thr Ser Gly
225                 230                 235                 240

Leu Leu Gly Leu Thr Ala Asn Leu Pro Pro Glu Leu His Ala Ile Leu
                245                 250                 255

Thr Glu Thr Ile Thr Glu Glu Asn Ala Glu Gln Leu Ile Lys Asp Asn
                260                 265                 270

Phe Gly Asp Val Asn Val Ser Arg Phe Gln Asp Val Ser Tyr Leu Ala
                275                 280                 285

Arg Trp Tyr Gly Met Thr Pro Tyr Glu Leu Asn Ser Val Leu Gly Leu
                290                 295                 300

Met Glu Val Gly Ser Asn Pro Val Asp Gly Val Thr Tyr Tyr Gln Asp
305                 310                 315                 320

Asp Gln Leu Ile Ser Leu Val Asp Asn Gly Asn Leu Asp Ala Val
                325                 330                 335

Leu Met Gln Arg Ala Gly Gly Asp Asn Tyr Ser Gln Phe Gly Tyr Ile
                340                 345                 350

Glu Leu Leu Pro Val Ser Gly Asp Thr Tyr Gln Leu Arg Phe Thr Val
                355                 360                 365

Gln Ser Gly Tyr Val Gly Gln Asp Ser Glu Val Arg Ile Gly Thr Ser
                370                 375                 380

Glu Asn Ala Gly Ser Lys Asp Ile Leu Ser Asp Gly Arg Ile Ala Gly
385                 390                 395                 400

Leu Asn Ile Pro Met Val Leu Asn Val Lys Leu Asp Ser Thr Lys Leu
                405                 410                 415

Ala Gln Gly Ile Thr Ile Gly Val Thr Arg Tyr Asp Pro Ser Gly Ser
                420                 425                 430
```

```
Tyr Ile Asn Phe Ala Ser Val Arg Phe Gln Arg Tyr Asp Phe Ser Tyr
        435                 440                 445

Asn Val Phe Leu Leu Lys Leu Asn Lys Ile Ile Arg Leu Tyr Lys Ala
    450                 455                 460

Thr Gly Ile Ser Pro Ser Asp Ile Gln Thr Leu Ile Glu Ser Ala Asn
465                 470                 475                 480

His Asp Leu Ala Ile Thr Glu Asp Val Leu Ser Gln Leu Phe Trp Thr
                485                 490                 495

Asn Tyr Tyr Thr Gln Arg Tyr Gly Ile Asp Phe Ser Ala Ala Leu Val
            500                 505                 510

Leu Ala Gly Ala Asn Ile Ser Gln Ile Ala His Ser Asn Lys Gln Ser
        515                 520                 525

Ala Phe Thr Arg Leu Phe Asn Thr Pro Pro Leu Asn Asn Gln Phe Phe
    530                 535                 540

Tyr Ala Asp Gly Lys Lys Leu Asn Leu Glu Pro Gly Lys Ser Asp Asp
545                 550                 555                 560

Ser His Gly Leu Gly Val Leu Lys Arg Ala Leu Gln Val Asn Asp Ser
                565                 570                 575

Ala Leu Tyr Thr Leu Phe Asn Leu Thr Phe Ala Asp Lys Asp Ala Gln
            580                 585                 590

Gly Asn Ala Val Val Phe Thr Lys Thr Pro Glu Asn Leu Ser Ala Leu
        595                 600                 605

Tyr Arg Thr Arg Leu Leu Ala Thr Val Asn Asn Leu Thr Val Asn Glu
    610                 615                 620

Leu Ser Leu Leu Leu Ser Val Ser Pro Tyr Val Lys Val Lys Leu Ala
625                 630                 635                 640

Thr Leu Lys Asp Glu Ala Leu Ser Gln Leu Ser Thr Thr Leu Glu Arg
                645                 650                 655

Tyr Thr Gln Trp Leu Asp Lys Met Asn Trp Thr Ile Gly Asp Leu Tyr
            660                 665                 670

Leu Met Leu Thr Pro Val Tyr Ser Thr Val Leu Ser Pro Asp Ile Glu
        675                 680                 685

Asn Leu Val Thr Thr Leu Lys Asn Gly Leu Ala Gly Gln Asp Leu Thr
    690                 695                 700

Ser Asp Glu Lys Arg Ile Ala Ala Leu Ala Pro Phe Val Ala Ala Ala
705                 710                 715                 720

Thr Gln Leu Asp Ser Ala Glu Thr Ala Arg Ala Leu Leu Arg Trp Leu
                725                 730                 735

Asn Asp Leu Lys Pro Gly Thr Leu Ser Leu Ala Asp Phe Ile Ala Gln
            740                 745                 750

Val Asn Asn Thr Thr Gln Thr Glu Asn Leu Val Thr Phe Ser Gln Val
        755                 760                 765

Met Ala Gln Leu Ala Leu Ile Thr Arg Asn Ala Ser Leu Ser Ala Asn
    770                 775                 780

Glu Leu Ser Trp Ala Val Ala His Pro Glu Ile Phe Gln Glu Lys Ala
785                 790                 795                 800

Thr Val Leu Lys Asn Asp Ile Ala Thr Leu Asn Asp Leu Thr Gln Leu
                805                 810                 815

His Asp Leu Leu Ala Arg Cys Gly Ser His Ala Ser Glu Ile Leu Thr
            820                 825                 830

Ser Leu Ser Gly Asn Ala Ser Lys Ala Glu Asn Asn Leu Ala Val Ser
        835                 840                 845
```

```
Thr Leu Ala Thr Ala Leu Asn Leu Asp Glu Arg Ala Leu Thr Gln Ala
850                 855                 860

Leu Ala Lys Val Ser Thr Tyr Glu Tyr Phe Tyr Asn Trp Ala His Leu
865                 870                 875                 880

Asn Glu Ala Leu Gln Trp Leu Asp Val Ala Thr Thr Phe Gly Ile Thr
            885                 890                 895

Pro Asp Asn Leu Ala Ala Leu Ile Gly Leu Lys Phe Asp Asn Gln Asp
            900                 905                 910

Asp Ala Ser Phe Ala Ser Trp Leu Thr Ala Ser Arg Phe Met Gln Ala
            915                 920                 925

Gly Leu Asn Thr Gln Gln Thr Ala Gln Leu Ser Ala Thr Leu Asp Glu
930                 935                 940

Ser Leu Ser Ala Ala Val Ser Ala Tyr Ala Ile Lys Asn Ile Phe Ser
945                 950                 955                 960

Gly Ala Val Ser Asn Arg Glu Gln Leu Tyr Ser Trp Leu Leu Ile Asp
                965                 970                 975

Asn Gln Val Ser Ala Gln Val Lys Thr Thr Arg Ile Ala Glu Ala Ile
            980                 985                 990

Ala Ser Val Gln Leu Tyr Val Asn Arg Ala Leu Ser Gly Leu Glu Asn
            995                 1000                1005

Gly Gln Ser Ala Thr Asp Ala Val Asp Asn Ala Val Lys Ser Gly
        1010                1015                1020

Val Phe Phe Thr Arg Asp Trp Asp Thr Tyr Asn Lys Arg Tyr Ser
        1025                1030                1035

Thr Trp Ala Gly Val Ser Glu Leu Val Tyr Tyr Pro Glu Asn Tyr
        1040                1045                1050

Val Asp Pro Thr Leu Arg Leu Gly Gln Thr Gly Met Met Asp Glu
        1055                1060                1065

Met Leu Gln Thr Leu Ser Gln Ser Gln Leu Thr Ser Asp Thr Val
        1070                1075                1080

Glu Asp Ala Phe Lys Thr Tyr Met Thr Arg Phe Glu Glu Ile Ala
        1085                1090                1095

Asn Leu Asp Ile Val Ser Gly Tyr His Asp Asn Leu Ser Asp Gln
        1100                1105                1110

Lys Gly Val Thr Tyr Leu Ile Gly Arg Ser Ala Ala Gly Asp Tyr
        1115                1120                1125

Tyr Trp Arg Ser Ala Asp Ile Ser Lys Leu Ser Asp Gly Lys Leu
        1130                1135                1140

Pro Ala Asn Ala Trp Ala Glu Trp Lys Lys Ile Thr Thr Ala Leu
        1145                1150                1155

Thr Pro Val Asn Asn Leu Val Arg Pro Val Ile Phe Gln Ser Arg
        1160                1165                1170

Leu Tyr Val Thr Trp Val Glu Ser Arg Glu Val Gly Ile Ser Ala
        1175                1180                1185

Val Lys Lys Gln Asn Ser Glu Thr Lys Pro Leu Glu Tyr Ala Leu
        1190                1195                1200

Lys Tyr Ala His Ile Leu His Asp Gly Thr Trp Ser Ala Pro Val
        1205                1210                1215

Ser Val Lys Leu Glu Asn Gly Thr Leu Pro Leu Asp Ser Val Ala
        1220                1225                1230

Ile Asp Val Thr Gly Met Tyr Cys Ala Lys Asp Thr Gln His Asp
        1235                1240                1245

Gln Leu Tyr Ile Leu Phe Tyr Lys Lys Lys Glu Thr Tyr Asn Asp
```

-continued

```
               1250                1255                1260
Val Asn Asp Val Leu Lys Gly Ile Ile Leu His Asp Asp Gly Thr
               1265                1270                1275
Thr Thr Ile Thr Ser Gly Asn Ser Val Ser Gly Leu Val Val Tyr
               1280                1285                1290
Lys Gln Leu Asp Thr Thr Lys Glu Val Arg Leu Asn Thr Pro Tyr
               1295                1300                1305
Pro Gly Gly Lys Thr Tyr Tyr Ser Ile Asn Asn Met Arg Glu Ser
               1310                1315                1320
Ser Lys Trp Gly Asp Asp Asn Ile Ser Met Leu Ser Gly Cys Ser
               1325                1330                1335
Val Lys Asp Phe Val Phe Thr Glu Gly Asp Gly Lys Leu Asn Val
               1340                1345                1350
Ala Phe Asn Ala Thr Glu Arg Ile Ile Tyr Arg Gly Asn Pro Asp
               1355                1360                1365
Ser Gln Gly Tyr Val Ala Leu Val Asn Met Ile Lys Ala Ile Gly
               1370                1375                1380
Asn Ile Gly Asp Thr Phe Lys Ile Pro Val Leu Asn Ser Asn Gly
               1385                1390                1395
Glu Gly Leu Asp Arg Pro Phe Thr Cys Ile Phe Arg Gln Pro Asp
               1400                1405                1410
Glu Lys Thr Asp Ala Ile Ala Tyr Phe Ser Asp Val Gln Gly Leu
               1415                1420                1425
Asn Ile Asp His Phe Ala Phe Asn Asp Glu Ser Gln Lys Met Leu
               1430                1435                1440
Gly Arg Ile Leu Arg Pro Glu Glu Lys Asp Phe Tyr Lys Leu Glu
               1445                1450                1455
Cys Val Asn Thr Asn Leu His Ile Tyr Lys Asp Ser Ser Lys Thr
               1460                1465                1470
Ile Lys Pro Asp Asn Phe Val Tyr Phe Gly Pro Gly Met Asp Leu
               1475                1480                1485
Ile Val Val Lys Gly Met Ile Val Glu Thr Leu Phe Gly Leu Phe
               1490                1495                1500
Gly Glu Leu Lys Thr Gly Ile Lys Asp Lys Ser Val Lys Leu Ser
               1505                1510                1515
Val Ser Ala Gly Val Ile Asp Asn Ser Pro Ala Ala Thr Lys Thr
               1520                1525                1530
Lys Tyr Thr Phe Asp Glu Ser Leu Tyr Val Ile Glu Gly Gln Thr
               1535                1540                1545
Val Ser Ile Gln Leu Ser Glu Phe Lys Glu Asn Asn Ile Asp Leu
               1550                1555                1560
Glu Phe Thr Phe Leu Ala Ser Gly Asp Ser Gly Asn Ser Leu Gly
               1565                1570                1575
Gln Ser Val Ile Ser Ala Thr Leu Thr Arg Thr Ser Glu Asn Thr
               1580                1585                1590
Ile Pro Val Ile Ser Leu Asn Lys Thr Ser Asp Asn Ala Gln Tyr
               1595                1600                1605
Leu Gln Tyr Gly Ile His Arg Ile Arg Val Asn Thr Leu Phe Ala
               1610                1615                1620
Lys Gln Leu Val Ala Arg Ala Asn Ala Gly Leu Asp Thr Val Leu
               1625                1630                1635
Ser Met Ala Thr Gln Gln Leu Thr Glu Pro Lys Met Gly Lys Gly
               1640                1645                1650
```

```
Ala Tyr Ile Asp Leu Glu Leu Asn Ala Ser Ser Asp Gly Ser Ser
1655                1660                1665

Ala Val Phe Glu Val Leu Met Cys Asp Val Phe Thr Asn Gly Asp
1670                1675                1680

Arg Ile Ala Leu Thr Ser Gly Thr Leu Ser Pro Thr Ala Arg Thr
1685                1690                1695

Ser Cys Ser Phe Phe Val Pro Arg Leu Asp Glu Ser Thr Ala Ser
1700                1705                1710

Ala Tyr Asn Met Tyr Phe Cys Val Lys Thr Gln Asn Thr Glu Ser
1715                1720                1725

Lys Arg Val Glu Val Thr Gly Gly Glu Gly Lys Trp Asp Tyr Gln
1730                1735                1740

Tyr Val Asp Glu Ser Gly Ala Ala Ile Lys Pro Pro Tyr Thr Asp
1745                1750                1755

Pro Tyr Ile Ala Ser Ile Tyr Val Arg Asn Asp Thr Thr Glu Pro
1760                1765                1770

Met Asp Phe Asn Gly Ala Asn Ala Leu Tyr Phe Trp Glu Met Phe
1775                1780                1785

Tyr Tyr Val Pro Met Met Val Phe Lys Arg Leu Leu Ser Glu Ser
1790                1795                1800

Lys Phe Ala Glu Ala Thr Gln Trp Ile Lys Tyr Ile Trp Asn Pro
1805                1810                1815

Asp Gly Tyr Leu Val Asn Asn Gln Pro Ala Thr Tyr Thr Trp Asn
1820                1825                1830

Val Arg Pro Leu Glu Glu Asp Thr Ser Trp His Ala Asp Pro Leu
1835                1840                1845

Asp Ser Val Asn Pro Asp Ala Val Ala Gln Ala Asp Pro Leu His
1850                1855                1860

Tyr Lys Val Ala Thr Phe Met Ala Tyr Leu Asp Leu Leu Ile Ala
1865                1870                1875

Arg Gly Asp Ala Ala Tyr Arg Gln Leu Gln Arg Asp Thr Leu Asn
1880                1885                1890

Glu Ala Lys Met Trp Tyr Val Gln Ala Leu Asn Ile Leu Gly Asp
1895                1900                1905

Glu Pro Tyr Gln Ser Ser Ser Ser Asp Trp Ser Ser Pro Val Leu
1910                1915                1920

Ser Ser Ala Ala Asp Gln Thr Thr Glu Lys Asn Val Gln Gln Ala
1925                1930                1935

Met Leu Ala Val Arg Gln Gln Pro Asp Ala Gly Glu Leu Arg Thr
1940                1945                1950

Ala Asn Ser Leu Thr Ser Leu Phe Leu Pro Gln Gln Asn Glu Lys
1955                1960                1965

Leu Ala Gly Tyr Trp Gln Thr Leu Ala Gln Arg Leu Tyr Asn Leu
1970                1975                1980

Arg His Asn Leu Ser Ile Asp Gly Ser Pro Leu Ser Leu Ala Ile
1985                1990                1995

Tyr Ala Ala Pro Ala Asp Pro Ala Ala Leu Leu Ser Ala Ala Val
2000                2005                2010

Asn Ser Ala Ser Gly Gly Ser Glu Leu Pro Ala Ala Val Met Pro
2015                2020                2025

Leu Tyr Arg Phe Pro Ile Ile Leu Glu Ser Ala Arg Gly Met Ala
2030                2035                2040
```

```
Gly Gln Leu Thr Gln Phe Gly Ser Thr Leu Leu Ser Ile Ala Glu
    2045                2050                2055

Arg Gln Asp Ala Glu Ala Leu Ser Glu Leu Met Gln Thr Gln Gly
    2060                2065                2070

Ser Gln Leu Ile Leu Gln Ser Ile Ala Leu Gln Asn Ser Thr Ile
    2075                2080                2085

Ser Glu Ile Asp Ala Asp Lys Thr Val Leu Glu Ala Ser Leu Ser
    2090                2095                2100

Gly Ala Arg Ser Arg Leu Asp Arg Tyr Thr Thr Leu Tyr Asp Glu
    2105                2110                2115

Asp Val Asn Thr Gly Glu Gln Gln Ala Met Asp Leu Phe Tyr Ala
    2120                2125                2130

Ser Ser Ile Gln Ala Asn Gly Gly Gln Ala Phe His Thr Val Ala
    2135                2140                2145

Gly Gly Leu Asp Leu Ala Pro Asn Ile Phe Gly Leu Ala Asp Gly
    2150                2155                2160

Gly Ser Arg Trp Gly Ala Ala Phe Thr Ala Leu Ala Ser Ile Ala
    2165                2170                2175

Asp Leu Ser Ala Ala Ala Ser His Thr Ala Ala Glu Arg Leu Ser
    2180                2185                2190

Gln Ser Glu Val Tyr Arg Arg Arg Arg Gln Glu Trp Glu Ile Gln
    2195                2200                2205

Arg Asn Ala Ala Gln Ser Glu Ile Asp Gln Ile Asp Ala Gln Leu
    2210                2215                2220

Ala Ser Leu Thr Ile Arg Arg Lys Gly Ala Val Leu Gln Lys Thr
    2225                2230                2235

Tyr Leu Glu Thr Gln Gln Gly Gln Met Gln Ala Gln Met Thr Phe
    2240                2245                2250

Leu Gln Asn Lys Phe Thr Ser Lys Ala Leu Tyr Asn Trp Leu Arg
    2255                2260                2265

Gly Lys Leu Ala Ala Ile Tyr Tyr Gln Phe Tyr Asp Leu Thr Val
    2270                2275                2280

Ser Arg Cys Leu Met Ala Glu Ala Ala Tyr Ser Trp His Ile Lys
    2285                2290                2295

Gly Asn Gln Glu Thr Gly Thr Phe Ile Arg Pro Gly Ala Trp Gln
    2300                2305                2310

Gly Ile Tyr Ala Gly Leu Met Ala Gly Glu Ala Leu Met Leu Asn
    2315                2320                2325

Leu Ala Gln Met Glu Asn Ser Tyr Leu Thr Lys Asp Glu Arg Leu
    2330                2335                2340

Gln Glu Val Thr Arg Thr Val Cys Leu Ser Glu Phe Tyr Ser Gly
    2345                2350                2355

Leu Ser Ser Asn Lys Phe Ala Leu Ala Asp Thr Val Thr Thr Leu
    2360                2365                2370

Val Asn Ser Gly Lys Gly Asn Ala Gly Thr Thr Asp Asn Gly Val
    2375                2380                2385

Lys Ile Asp Gly Lys Gln Leu Leu Ala Thr Leu Lys Leu Ser Asp
    2390                2395                2400

Leu Asn Ile Lys Thr Asp Tyr Pro Glu Ser Leu Asp Lys Ala Lys
    2405                2410                2415

Arg Ile Lys Gln Ile Ser Val Thr Leu Pro Met Leu Val Gly Pro
    2420                2425                2430

Tyr Gln Asp Val Arg Ala Val Leu Ser Tyr Gly Gly Ser Val Val
```

```
                    2435                2440                2445
Leu Pro Arg Gly Cys Thr Ala Val Ala Val Ser His Gly Met Asn
        2450                2455                2460

Asp Ser Gly Gln Phe Gln Leu Asp Phe Asn Asp Ser Arg Trp Leu
        2465                2470                2475

Pro Phe Glu Gly Ile Pro Val Asp Asp Ser Gly Thr Leu Thr Leu
        2480                2485                2490

Ser Phe Pro Asp Ile Thr Asp Lys Gln Gln Glu Asn Leu Leu Leu
        2495                2500                2505

Ser Leu Ser Asp Ile Ile Leu His Ile Arg Tyr Thr Ile Ala Ser
        2510                2515                2520

<210> SEQ ID NO 24
<211> LENGTH: 1421
<212> TYPE: PRT
<213> ORGANISM: Pantoea agglomerans

<400> SEQUENCE: 24

Met Gln Asn Thr Asp Gln Met Ser Leu Thr Pro Ser Leu Pro Ser
1               5                   10                  15

Gly Gly Gly Ala Val Thr Gly Leu Lys Gly Asp Met Ser Gly Ala Gly
            20                  25                  30

Pro Asp Gly Ala Ala Thr Leu Ser Leu Pro Leu Pro Ile Ser Pro Gly
        35                  40                  45

Arg Gly Tyr Ala Pro Ser Leu Ser Leu Gly Tyr His Ser Arg Asn Gly
    50                  55                  60

Asn Gly Val Phe Gly Ala Gly Trp Ser Cys Gly Gln Met Ala Ile Arg
65                  70                  75                  80

Leu Gln Thr Arg Lys Gly Val Pro Phe Tyr Asp Gly Ser Asp Val Phe
                85                  90                  95

Thr Ala Pro Asp Gly Glu Val Leu Val Pro Ala Leu Asp Ala Ser Gly
            100                 105                 110

Lys Ala Glu Val Arg Thr Thr Thr Leu Leu Gly Glu Asn Leu Gly
        115                 120                 125

Gly Thr Phe Thr Val Gln Thr Tyr Arg Ser Arg Val Glu Thr Asp Phe
    130                 135                 140

Ser Arg Leu Glu Arg Trp Val Pro Gln Thr Asp Ala Ala Ala Asp Phe
145                 150                 155                 160

Trp Leu Ile Tyr Ser Pro Asp Gly Gln Ile His Leu Leu Gly Arg Asn
                165                 170                 175

Pro Gln Ala Arg Val Asn Asn Pro Glu Asp Thr Thr Gln Thr Ala Ala
            180                 185                 190

Trp Leu Ile Glu Ser Ser Val Ser Ala Ser Gly Glu Gln Ile Tyr Trp
        195                 200                 205

Gln Tyr Arg Gln Glu Asp Glu Leu Gly Cys Thr Gln Asp Glu Lys Thr
    210                 215                 220

Ala His Ala His Ala Leu Ala Gln Arg Tyr Leu Val Ala Val Trp Tyr
225                 230                 235                 240

Gly Asn Lys Ala Ala Ser Arg Thr Leu Pro Gly Leu Leu Ser Val Pro
                245                 250                 255

Ala Ala Gly Ser Trp Leu Phe Thr Leu Val Leu Asp Tyr Gly Glu Arg
            260                 265                 270

Ala Thr Asp Pro Ala Thr Pro Pro Ala Trp Leu Ser Pro Gly Ser Gly
        275                 280                 285
```

```
Thr Trp Leu Cys Arg Gln Asp Val Phe Ser Ser Trp Glu Tyr Gly Phe
    290                 295                 300

Glu Leu Arg Thr Arg Arg Leu Cys Arg Gln Val Leu Met Tyr His Asp
305                 310                 315                 320

Val Ala Ala Leu Ala Gly Gln Ser Gly Ser Asp Ala Val Pro Gln Leu
                325                 330                 335

Val Thr Arg Leu Leu Leu Asp Tyr Asn Thr Ser Pro Ser Leu Thr Thr
            340                 345                 350

Leu Lys Thr Ala Gln Gln Ala Ala Trp Glu Pro Asp Gly Thr Leu Arg
        355                 360                 365

Ser Leu Pro Pro Leu Ala Phe Ser Trp Gln Thr Phe Pro Ser Thr Pro
    370                 375                 380

Glu Lys Ser Val Ser Trp Gln Arg Arg Asn Asp Met Gly Lys Leu Asn
385                 390                 395                 400

Pro Gln Gln Pro Tyr Gln Met Val Asp Leu His Gly Glu Gly Leu Ala
                405                 410                 415

Gly Ile Leu Tyr Gln Asp Ser Gly Ala Trp Trp Tyr Arg Glu Pro Val
            420                 425                 430

Arg Gln Ser Gly Asp Asp Asn Ala Val Thr Trp Ala Ala Ala Arg
        435                 440                 445

Pro Leu Pro Ala Phe Pro Ala Leu Arg Lys Gly Gly Met Leu Leu Asp
    450                 455                 460

Leu Asp Gly Asp Gly Tyr Leu Glu Trp Val Val Thr Ala Pro Gly Val
465                 470                 475                 480

Ala Gly Cys Tyr Ala Gln Ala Pro Glu Gln Cys Trp Gln Arg Phe Thr
                485                 490                 495

Pro Leu Ser Ala Leu Pro Val Glu Tyr Arg His Ser Arg Met Glu Ile
            500                 505                 510

Thr Asp Val Thr Gly Ala Gly Leu Ala Asp Met Leu Leu Ile Gly Pro
        515                 520                 525

Lys Ser Val Arg Leu Tyr Ser Gly Ser Gly Arg Gly Trp Lys Lys Ala
    530                 535                 540

Arg Thr Val Met Gln Asp Ser Gly Ile Thr Leu Pro Val Pro Gly Thr
545                 550                 555                 560

Asn Ala Arg Val Met Val Ala Phe Ser Asp Met Ala Gly Ser Gly Gln
                565                 570                 575

Gln His Leu Thr Glu Ile Lys Ala Ser Gly Val Arg Tyr Trp Pro Ser
            580                 585                 590

Leu Gly His Gly Arg Phe Ala Ala Pro Val Thr Leu Pro Gly Phe Ser
        595                 600                 605

Gln Pro Ala Glu Thr Phe Asn Pro Ala Gln Leu Tyr Leu Ala Asp Val
    610                 615                 620

Asp Gly Ser Gly Thr Thr Asp Leu Ile Tyr Ala Leu Ser Asp His Leu
625                 630                 635                 640

Leu Val Trp Leu Asn Gln Ser Gly Asn Ser Phe Asp Ala Pro Phe Arg
                645                 650                 655

Ile Ser Leu Pro Glu Gly Val Arg Tyr Asp Asn Thr Cys Ser Leu Gln
            660                 665                 670

Val Ala Asp Ile Gln Gly Leu Gly Ile Ser Ser Leu Val Leu Ser Val
        675                 680                 685

Pro His Pro Thr Pro Arg His Trp Val Cys His Leu Thr Thr Glu Lys
    690                 695                 700

Pro Trp Leu Leu Asp Gly Met Asn Asn Asn Met Gly Ala Arg His Thr
```

-continued

```
            705                 710                 715                 720
Leu Cys Tyr Arg Ser Ser Ala Gln Phe Trp Leu Asp Glu Lys Ala Ala
                    725                 730                 735

Ala Thr Ala Asp Arg Pro Ala Pro Ala Cys Tyr Leu Pro Phe Ala Leu
                740                 745                 750

His Thr Leu Ser Arg Thr Glu Val Ser Asp Glu Ile Thr Gly Asn Arg
                755                 760                 765

Leu Thr Arg Thr Ile Arg Tyr Arg His Gly Val Trp Asp Arg Arg Glu
        770                 775                 780

Arg Glu Phe Arg Gly Phe Gly Phe Val Glu Val Ser Asp Ala Glu Ala
785                 790                 795                 800

Leu Ala Lys Gln Thr Glu Gly Met Ser Ala Pro Ala Val Lys Arg Ser
                    805                 810                 815

Trp Tyr Ala Thr Gly Leu Ala Ala Val Asp Ala Gln Leu Pro Asp Glu
                820                 825                 830

Phe Trp Lys Gly Asp His Ala Ala Phe Ala Gly Phe Thr Pro Arg Phe
            835                 840                 845

Thr Thr Gly Asp Gly Glu Gln Glu Ala Ala Leu Asp Thr Ile Ser Asp
        850                 855                 860

Asp Thr Arg Phe Trp Leu Thr Arg Ala Ile Arg Gly Thr Leu Leu Arg
865                 870                 875                 880

Ser Glu Leu Tyr Gly Ala Asp Gly Ser Ser Gln Ala Gly Ile Pro Tyr
                    885                 890                 895

Ser Ile Thr Glu Ser Arg Pro Gln Val Arg Leu Ile Thr Glu Ala Gly
                900                 905                 910

Asn Ser Pro Val Val Trp Pro Ser Val Ile Glu Asn Arg Ala Ser His
            915                 920                 925

Tyr Glu Arg Val Ser Ser Asp Pro Gln Cys Gly Gln Gln Ile Leu Leu
        930                 935                 940

Thr Ser Asn Glu Tyr Gly Gln Pro Leu Arg Gln Ile Gly Ile Ser Tyr
945                 950                 955                 960

Pro Arg Arg Thr Arg Pro Asp Thr Ser Pro Tyr Pro Asp Asp Leu Pro
                    965                 970                 975

Asp Gly Leu Phe Ala Asp Ser Phe Asp Glu Gln Gln Ala Leu Arg
                980                 985                 990

Leu Thr Leu Thr Gln Ser Ser Trp His Thr Leu Lys Asp Ile Ser Ser
            995                1000                1005

Gly Ile Trp Leu Pro Ala Val Ala Asp Ala Thr Arg Ser Asp Leu
        1010                1015                1020

Phe Val His Gln Ala Ala Gln Val Pro Pro Ala Gly Leu Thr Leu
    1025                1030                1035

Glu Asn Leu Leu Thr Asp Ser Ala Leu Leu Thr Ser Pro Val Phe
    1040                1045                1050

Gly Gly Gln Ser Gln Ile Trp Tyr Gln Asp Arg Ala Gly Gln Ala
    1055                1060                1065

Ser Ile Thr Ser Pro Asp Phe Pro Pro Arg Pro Ser Phe Ser Glu
    1070                1075                1080

Thr Ala Ala Leu Asp Glu Ala Gln Val Ser Ala Leu Ser Ala Asp
    1085                1090                1095

Ile Asp Gln Thr Lys Leu Glu Gln Ala Gly Tyr Thr Arg Ser Ala
    1100                1105                1110

Tyr Leu Phe Ala Arg Ser Gly Glu Glu Ser Lys Thr Leu Trp Ala
    1115                1120                1125
```

-continued

```
Val Arg Gln Gly Tyr Ile Thr Phe Ser Gly Ala Asp His Phe Tyr
    1130            1135            1140

Leu Pro Ile Ala Ala Gln Thr Leu Leu Ala Gly Lys Thr Thr
    1145            1150            1155

Val Thr Tyr Asp Pro Tyr Asp Cys Val Val Leu Gln Ala Lys Asp
    1160            1165            1170

Ala Ala Gly Ala Val Thr Ser Ala Thr Tyr Asp Trp Arg Phe Leu
    1175            1180            1185

Ala Pro Thr Gln Ile Thr Asp Ile Asn Asp Asn Leu Lys Ser Val
    1190            1195            1200

Thr Leu Asp Ala Leu Gly Arg Val Thr Ser Gln Arg Phe Ser Gly
    1205            1210            1215

Thr Glu Asn Gly Lys Pro Ala Gly Tyr Ser Asp Asp Glu Phe Pro
    1220            1225            1230

Leu Pro Ala Ser Ala Asp Ala Ala Leu Ala Leu Ser Ala Pro Leu
    1235            1240            1245

Pro Val Ala Gln Cys Ile Ile Tyr Val Pro Asp Ser Trp Met Leu
    1250            1255            1260

Thr Gly Glu Gln Gln Gln Pro Pro His Val Ile Thr Leu Leu Thr
    1265            1270            1275

Asp Arg Tyr Asp Ser Asp Ser Gln Gln Gln Ile Arg Gln Gln Val
    1280            1285            1290

Val Phe Ser Asp Gly Phe Gly Arg Val Leu Gln Ala Ala Ser Arg
    1295            1300            1305

Gln Val Asn Gly Glu Ala Trp Gln Arg Ala Ala Asn Gly Ser Phe
    1310            1315            1320

Val Ala Gly Thr Asn Asp Ser Pro Val Leu Thr Glu Thr Thr Phe
    1325            1330            1335

Arg Trp Ala Val Thr Gly Arg Thr Glu Tyr Asp Asn Lys Gly Gln
    1340            1345            1350

Ala Ile Arg Ala Tyr Gln Pro Tyr Phe Leu Asp Ser Trp Lys Tyr
    1355            1360            1365

Val Arg Asp Asp Ser Ala Arg Gln Asp Leu Tyr Ala Asp Thr His
    1370            1375            1380

Tyr Tyr Asp Pro Val Gly Arg Glu Arg Gln Val Ile Thr Ala Lys
    1385            1390            1395

Gly Trp Leu Arg Arg Val Thr His Thr Pro Trp Phe Val Val Ser
    1400            1405            1410

Glu Asp Glu Asn Asp Thr Gln Ala
    1415            1420

<210> SEQ ID NO 25
<211> LENGTH: 1004
<212> TYPE: PRT
<213> ORGANISM: Pantoea agglomerans

<400> SEQUENCE: 25

Met Ser Ala Ala Tyr Val Leu Ser Asn Leu Ser Tyr Lys Leu Glu Asn
1               5                   10                  15

Pro Met Ser Thr Ser Leu Tyr Ser Arg Thr Pro Ser Val Thr Ile Leu
                20                  25                  30

Asp Asn Arg Gly Leu Thr Val Arg Gly Ile Ala Tyr Gln Arg His Pro
            35                  40                  45

Asp Thr Pro Ala Val Thr Ser Glu Arg Ile Thr Arg His Gln Tyr Asp
```

```
                50                  55                  60
Ala Arg Gly Phe Leu Met Gln Ser Ala Asp Pro Arg Leu His Asp Ala
 65                  70                  75                  80
Gly Leu Ala Asn Val Ser Tyr Arg Thr Asn Leu Thr Gly Ser Val Leu
                     85                  90                  95
Arg Ser Gln Gly Val Asp Asn Gly Ile Thr Val Thr Leu Asn Asp Ala
                100                 105                 110
Ala Gly Arg Pro Phe Leu Ala Val Ser Asn Ile Ser Thr Ala Gly Asp
                115                 120                 125
Gly Thr Glu Asp Arg Ser Gln Ala Val Thr Arg Thr Cys Gln Tyr Glu
            130                 135                 140
Asp Ala Thr Leu Pro Gly Arg Pro Leu Ser Ile Thr Glu Gln Val Asn
145                 150                 155                 160
Gly Gly Ala Ala Arg Ile Thr Glu Arg Phe Val Tyr Ala Gly Asn Ala
                165                 170                 175
Val Glu Glu Lys Ala Leu Asn Leu Ala Gly Gln Pro Val Ser His Tyr
            180                 185                 190
Asp Thr Ala Gly Leu Thr Gln Thr Asp Ser Ile Ala Leu Thr Gly Val
            195                 200                 205
Pro Leu Ser Val Thr Arg Arg Leu Leu Lys Asp Ala Asp Asn Pro Asp
210                 215                 220
Ala Val Ala Asp Trp Gln Gly Thr Asp Ala Ser Val Trp Asn Asp Pro
225                 230                 235                 240
Leu Asp Val Glu Thr Tyr Thr Thr Leu Ser Thr Ala Asp Ala Thr Gly
                245                 250                 255
Ala Val Leu Thr Thr Thr Asp Ala Lys Gly Asn Leu Gln Arg Leu Ala
                260                 265                 270
Tyr Asp Val Ala Gly Leu Leu Ser Gly Ser Trp Leu Thr Leu Lys Asp
                275                 280                 285
Gly Thr Glu Gln Val Ile Val Thr Ser Leu Thr Tyr Ser Ala Ala Gly
305             290                 295                 300
Gln Lys Leu Arg Glu Glu His Gly Asn Gly Val Val Thr Thr Tyr Thr
305                 310                 315                 320
Tyr Glu Ala Glu Thr Gln Arg Leu Thr Gly Ile Lys Thr Ala Arg Pro
                325                 330                 335
Ala Gly His Thr Ser Gly Ala Lys Val Leu Gln Asp Leu Arg Tyr Thr
                340                 345                 350
Tyr Asp Pro Val Gly Asn Val Leu Lys Ile Ser Asn Asp Ala Glu Glu
                355                 360                 365
Thr Arg Phe Trp Arg Asn Gln Lys Val Ala Pro Glu Ser Ala Tyr Val
370                 375                 380
Tyr Asp Ser Leu Tyr Gln Leu Val Ser Ala Thr Gly Arg Glu Met Ala
385                 390                 395                 400
Asn Ala Gly Gln Gln Gly Ser Ser Ser Ser Ala Thr Val Pro Leu
                405                 410                 415
Pro Ala Asp Ser Ser Ala Phe Thr Asn Tyr Thr Arg Asn Tyr Thr Tyr
                420                 425                 430
Asp Glu Ala Gly Asn Leu Thr Gln Val Arg His Thr Pro Ala Thr Gly
                435                 440                 445
Ser Gly Tyr Thr Thr Lys Ile Thr Val Ser Asp Lys Ser Asn Arg Gly
                450                 455                 460
Val Leu Ser Thr Leu Thr Glu Asn Pro Ser Asp Val Asp Ala Leu Phe
465                 470                 475                 480
```

```
Thr Ala Gly Gly Gln Gln Lys Gln Leu Gln Pro Gly Gln Ser Leu Ile
                485                 490                 495

Trp Thr Pro Arg Asn Glu Leu Leu Lys Val Thr Pro Val Ala Arg Asp
            500                 505                 510

Gly Gly Ala Asp Asp Ser Glu Ser Tyr Arg Tyr Asp Gly Gly Ser Leu
            515                 520                 525

Arg Leu Leu Lys Val Ser Val Gln Lys Thr Gly Asn Ser Thr Gln Thr
        530                 535                 540

Gln Arg Ala Leu Tyr Leu Pro Gly Leu Glu Leu Arg Asn Thr Thr Ser
545                 550                 555                 560

Gly Asp Thr Glu Thr Glu Ser Leu Gln Val Val Thr Val Gly Glu Ala
                565                 570                 575

Gly Arg Ala Gln Val Arg Val Leu His Trp Glu Ser Gly Thr Pro Asp
                580                 585                 590

Ser Val Ser Asn Asp Pro Val Arg Tyr Ser Tyr Asp Asn Leu Thr Gly
                595                 600                 605

Ser Ser Gly Leu Glu Leu Asp Ser Ser Gly Asn Ile Ile Ser Met Glu
        610                 615                 620

Glu Tyr Tyr Pro Tyr Gly Gly Thr Ala Val Trp Thr Ala Arg Ser Ala
625                 630                 635                 640

Val Glu Ala Lys Tyr Lys Thr Val Arg Tyr Ser Ala Lys Glu Arg Asp
                645                 650                 655

Ala Thr Gly Leu Tyr Tyr Tyr Gly Tyr Arg Tyr Tyr Gln Pro Trp Ala
                660                 665                 670

Gly Arg Trp Leu Ser Ala Asp Pro Ala Gly Thr Ala Asp Gly Leu Asn
                675                 680                 685

Leu Phe Arg Met Val Arg Asn Asn Pro Val Thr Leu Lys Asp Thr Asn
        690                 695                 700

Gly Leu Ile Ser Thr Gly Gln Asp Ala Arg Lys Leu Val Ala Glu Ala
705                 710                 715                 720

Phe Val His Pro Leu His Met Thr Val Phe Glu Arg Ile Ser Ser Glu
                725                 730                 735

Glu Asn Leu Ala Met Ser Val Arg Glu Ala Gly Ile Tyr Thr Ile Ser
                740                 745                 750

Ala Leu Gly Glu Gly Ala Ala Ala Lys Gly His Asn Ile Leu Glu Lys
                755                 760                 765

Thr Ile Lys Pro Gly Ser Leu Lys Ala Val Tyr Gly Asp Asn Ala Glu
        770                 775                 780

Ser Ile Leu Ala Gln Ala Lys Arg Ser Gly Phe Val Gly Arg Val Gly
785                 790                 795                 800

Gln Trp Asp Ala Ser Gly Val Arg Gly Ile Tyr Ala His Asn Thr Pro
                805                 810                 815

Gly Gly Glu Asp Leu Ala Tyr Pro Val Asn Leu Lys Asn Ser Ser Ala
                820                 825                 830

Asn Glu Leu Val Asn Ala Trp Ile Lys Phe Lys Ile Thr Pro Tyr
        835                 840                 845

Thr Gly Asp Tyr Asp Met His Asp Ile Ile Lys Ile Ser Asp Gly Lys
        850                 855                 860

Gly His Val Pro Met Ala Glu Ser Asn Glu Glu Lys Gly Val Lys Asp
865                 870                 875                 880

Met Ile Asn Glu Gly Val Ala Gln Val Asp Pro Ala Arg Pro Phe Thr
                885                 890                 895
```

```
Ser Thr Ala Met Asn Val Val Arg His Gly Pro Gln Val Asn Phe Val
            900                 905                 910

Pro Tyr Met Trp Glu His Glu His Glu Asn Val Val Arg Asp Asn Gly
        915                 920                 925

Tyr Leu Gly Val Val Ala Arg Pro Gly Pro Phe Pro Val Ala Met Val
        930                 935                 940

His Lys Gly Glu Trp Thr Val Phe Asp Asn Lys Asn Glu Leu Phe Glu
945                 950                 955                 960

Phe Tyr Lys Ser Thr Asn Thr Pro Leu Pro Glu His Trp Ser Gln Asp
                965                 970                 975

Phe Val Glu Arg Gly Lys Gly Asn Val Ala Thr Pro Arg His Ala Glu
            980                 985                 990

Ile Leu Asp Arg Asn Ser Ser Arg  Leu Arg Ala Ala
            995                 1000

<210> SEQ ID NO 26
<211> LENGTH: 971
<212> TYPE: PRT
<213> ORGANISM: Pantoea agglomerans

<400> SEQUENCE: 26

Met Cys Ser Val Ala Asp Phe Asp Arg Leu His Asn Ile Lys Gln Glu
1               5                   10                  15

Asn Ile Met Gly Thr Ser Leu Tyr Ser Lys Thr Pro Ser Val Thr Ile
            20                  25                  30

Leu Asp Asn Arg Gly Leu Ser Val Arg Asp Ile Ala Tyr Gln Arg His
        35                  40                  45

Pro Asp Thr Pro Ala Val Thr Ser Glu Cys Ile Thr Arg His Gln Tyr
    50                  55                  60

Asp Ala Arg Gly Phe Leu Met Gln Ser Ala Asp Pro Arg Leu His Asp
65                  70                  75                  80

Ala Gly Leu Ala Asn Phe Ser Tyr Arg Thr Asp Leu Thr Gly Ser Val
                85                  90                  95

Leu Arg Ser Gln Gly Val Asp Asn Gly Ile Thr Val Thr Leu Asn Asp
            100                 105                 110

Ala Ala Gly Arg Pro Phe Leu Ala Val Ser Asn Ile Ser Thr Ala Gly
        115                 120                 125

Asp Gly Thr Glu Asp Arg Ser Gln Ala Val Thr Arg Thr Cys Gln Tyr
    130                 135                 140

Glu Asp Ala Thr Leu Pro Gly Arg Pro Leu Ser Ile Thr Glu Gln Val
145                 150                 155                 160

Asn Gly Gly Ala Ala Arg Ile Thr Glu Arg Phe Ile Tyr Ala Gly Asn
                165                 170                 175

Ala Val Glu Glu Lys Ala Leu Asn Leu Ala Gly Gln Pro Val Ser His
            180                 185                 190

Tyr Asp Thr Ala Gly Leu Thr Gln Thr Asp Ser Ile Ala Leu Thr Gly
        195                 200                 205

Ala Pro Leu Ser Val Thr Arg Arg Leu Leu Lys Asp Ala Asp Asn Pro
    210                 215                 220

Asp Ala Val Ala Asp Trp Gln Gly Thr Asp Ala Ser Val Trp Asn Asp
225                 230                 235                 240

Pro Leu Asp Val Glu Thr Tyr Thr Thr Leu Ser Thr Ala Asp Ala Thr
                245                 250                 255

Gly Ala Val Leu Thr Thr Thr Asp Ala Lys Gly Asn Leu Gln Arg Leu
            260                 265                 270
```

```
Ala Tyr Asp Val Ala Gly Leu Leu Ser Gly Ser Trp Leu Thr Leu Lys
    275                 280                 285

Asp Gly Thr Glu Gln Val Ile Val Thr Ser Leu Thr Tyr Ser Ala Ala
    290                 295                 300

Gly Gln Lys Leu Arg Glu Glu His Gly Asn Gly Val Val Thr Thr Tyr
305                 310                 315                 320

Thr Tyr Glu Ala Glu Thr Gln Arg Leu Thr Gly Ile Lys Thr Ala Arg
                325                 330                 335

Pro Ala Gly His Thr Ser Gly Ala Lys Val Leu Gln Asp Leu Arg Tyr
                340                 345                 350

Thr Tyr Asp Pro Val Gly Asn Val Leu Lys Ile Ser Asn Asp Ala Glu
            355                 360                 365

Glu Thr Arg Phe Trp Arg Asn Gln Lys Val Val Pro Glu Ser Ala Tyr
        370                 375                 380

Val Tyr Asp Ser Leu Tyr Gln Leu Val Ser Ala Thr Gly Arg Glu Met
385                 390                 395                 400

Ala Asn Ala Gly Gln Gln Gly Ser Ser Ser Ser Ala Thr Val Pro
                405                 410                 415

Leu Pro Ala Asp Ser Ser Ala Phe Thr Asn Tyr Thr Arg Asn Tyr Thr
            420                 425                 430

Tyr Asp Glu Ala Gly Asn Leu Thr Gln Val Arg His Thr Pro Ala Thr
        435                 440                 445

Gly Ser Gly Tyr Thr Thr Lys Ile Thr Val Ser Asp Lys Ser Asn Arg
    450                 455                 460

Gly Val Leu Ser Thr Leu Thr Glu Asn Pro Ser Asp Val Asp Ala Leu
465                 470                 475                 480

Phe Thr Ala Gly Gly Gln Gln Lys Gln Leu Gln Pro Gly Gln Ser Leu
                485                 490                 495

Ile Trp Thr Pro Arg Asn Glu Leu Leu Lys Val Met Pro Ile Met Arg
            500                 505                 510

Asp Gly Gly Thr Asp Asp Ser Glu Ser Tyr Arg Tyr Asp Gly Gly Ser
        515                 520                 525

Gln Arg Leu Leu Lys Val Ser Val Gln Lys Thr Gly Asn Ser Thr Gln
    530                 535                 540

Thr Gln Arg Ala Leu Tyr Leu Pro Gly Leu Glu Leu Arg Asn Thr Thr
545                 550                 555                 560

Ser Gly Asp Thr Glu Thr Glu Ser Leu Gln Val Val Thr Ala Gly Glu
                565                 570                 575

Ala Gly Arg Ala Gln Val Arg Val Leu His Trp Glu Ser Gly Thr Pro
            580                 585                 590

Asp Ser Val Ser Asn Asp Pro Val Arg Tyr Ser Tyr Asp Asn Leu Thr
        595                 600                 605

Gly Ser Ser Gly Leu Glu Leu Asp Ser Ser Gly Asn Ile Ile Ser Met
    610                 615                 620

Glu Glu Tyr Tyr Pro Tyr Gly Gly Thr Ala Val Trp Thr Ala Arg Ser
625                 630                 635                 640

Ala Val Glu Ala Lys Tyr Lys Thr Val Arg Tyr Ser Ala Lys Glu Arg
                645                 650                 655

Asp Ala Thr Gly Leu Tyr Tyr Tyr Gly Tyr Arg Tyr Tyr Gln Pro Trp
            660                 665                 670

Ala Gly Arg Trp Leu Ser Ala Asp Pro Ala Gly Thr Val Asp Gly Leu
        675                 680                 685
```

-continued

```
Asn Leu Phe Arg Met Val Arg Asn Asn Pro Leu Thr Leu Lys Asp Asn
            690                 695                 700
Asp Gly Leu Lys Pro Ile Asn Glu Asn Phe Arg Glu Asn Lys Gly Asp
705                 710                 715                 720
Leu Val Tyr Gly Leu Ala Ala Pro Arg Gly Ala Tyr Ile Ser Thr Ala
                725                 730                 735
Ile Gly Arg Glu Phe Ala Pro Glu Glu Lys Asp Ala Pro Ala Ser Ile
            740                 745                 750
Ile Asp Leu Tyr Asn Asn Thr Val Ser Gly Gln Ala Leu Leu Ser Val
                755                 760                 765
Asp Phe Lys Ile Leu Gln Asp Phe Met Lys Ser Pro Lys Lys His Glu
770                 775                 780
Lys Lys Leu Ala Pro Pro Ser Asn Ile Lys Glu Leu Val Lys Lys Ser
785                 790                 795                 800
Arg Val Tyr Pro Leu Trp Glu Asp Tyr Phe Leu Ala Gly Glu Asn Asn
                805                 810                 815
Pro Lys Phe Asn Ile Ala Ser Ile Tyr Lys Glu Val Arg Lys Asp Ala
            820                 825                 830
Gly Lys Thr Gln Tyr His Glu Trp His Ile Ala Gly Gly Gln Ser Ala
            835                 840                 845
Pro Lys Leu Leu Trp Lys Arg Gly Ser Lys Leu Gly Ile Glu Met Ala
850                 855                 860
Ala Ser Gly Ala Gly Asn Lys Ile His Phe Val Leu Asp Glu Leu Asp
865                 870                 875                 880
Ile Ser Asn Val Val Asn Lys Glu Gly Pro Gly Gly Lys Ser Ile Thr
                885                 890                 895
Ala Ser Glu Leu Arg Tyr Ala Tyr Arg Asn Arg Glu Arg Leu Thr Gly
            900                 905                 910
Asn Ile His Phe Tyr Lys Asn Asn Ala Glu Thr Gly Ala Pro Trp Asp
            915                 920                 925
Thr Asn Ala Glu Leu Trp Ala Ser Tyr His Pro Lys Pro Lys His Lys
            930                 935                 940
Gly Asn Glu Ser Thr His Met Met Ser Gln Arg Arg Asn Gly Ser Leu
945                 950                 955                 960
Phe Lys Ser Met Arg Lys Val Phe Ser Arg Asn
                965                 970

<210> SEQ ID NO 27
<211> LENGTH: 2518
<212> TYPE: PRT
<213> ORGANISM: Pantoea agglomerans

<400> SEQUENCE: 27

Met Tyr Leu Thr Glu Glu Ile Leu Ala Lys Leu Asn Ala Gly Asn Gly
1               5                   10                  15
Lys Leu Gln Ser Thr Val Glu Gln Ile Thr Leu Pro Asp Ile Met
            20                  25                  30
Leu His Ser Phe Ala Gln Val Lys Glu Leu Ala Gly Asp Lys Leu Ser
            35                  40                  45
Trp Gly Glu Lys Asn Phe Leu Tyr Gln Gln Ala Gln Lys Gln Leu Lys
        50                  55                  60
Glu Asn Lys Met Ala Glu Ser Arg Ile Leu Ser Arg Ala Asn Pro Gln
65                  70                  75                  80
Leu Ala Asn Ala Val Arg Met Gly Ile Arg Gln Ser Ala Met Leu Gly
                85                  90                  95
```

```
Ser Tyr Asp Asp Leu Phe Pro Gln Arg Ala Ser Arg Phe Val Lys Pro
                100                 105                 110

Gly Ala Val Ala Ser Met Phe Ser Pro Ala Gly Tyr Leu Thr Glu Leu
            115                 120                 125

Tyr Arg Glu Ala Arg Gly Leu His Asp Thr Ser Asp Tyr His Leu
        130                 135                 140

Asp Thr Arg Arg Pro Asp Leu Ala Ser Met Val Leu Ser Gln Ser Asn
145                 150                 155                 160

Met Asp Thr Glu Leu Ser Thr Leu Ser Leu Ser Asn Glu Leu Leu Leu
                165                 170                 175

Lys Leu Ile Gln Ser Lys Glu Ser Leu Asn Tyr Asp Gln Val Ile Glu
                180                 185                 190

Lys Leu Ala Thr Tyr Arg Leu Thr Gly Thr Thr Pro Tyr Asn Gln Pro
            195                 200                 205

Tyr Glu Thr Ile Arg Gln Ala Ile Leu Leu Gln Asp Pro Glu Phe Asn
        210                 215                 220

Ala Phe Ser Asn Asn Pro Ala Val Ala Val Lys Ile Asn Thr Ser Gly
225                 230                 235                 240

Leu Leu Gly Ile Thr Ser Asp Ile Ala Pro Glu Leu His Ala Ile Leu
                245                 250                 255

Thr Glu Glu Ile Thr Glu Lys Lys Thr Glu Ala Leu Ile Lys Lys Asn
                260                 265                 270

Phe Gly Asp Ala Asn Ile Asn Gln Phe Gln Asn Leu Ala Trp Leu Ala
            275                 280                 285

His Trp Tyr Gly Leu Ser Tyr Glu Glu Leu Asn Asn Leu Val Gly Met
        290                 295                 300

Ile Trp Ser Arg Asp Asp Leu Asp Pro Ala Val Glu His Tyr Lys Asn
305                 310                 315                 320

Ser Ser Leu Val Thr Leu Val Ala Glu Asp Gly Gly Ser Leu Asn Ala
                325                 330                 335

Val Leu Ile Lys Arg Thr Lys Gly His Asp Ser Asp Asp Met His Tyr
                340                 345                 350

Ala Glu Leu Ile Pro Val Gly Gly Asp Lys Phe Gln Tyr Asn Phe Ser
            355                 360                 365

Leu Ile Asp Ala Glu Ser Ser Ser Val Tyr Tyr Gln Phe Gly Thr Lys
        370                 375                 380

Gly Lys Asn Ser Gln Asp Leu Val Pro Val Ile His Glu Pro Leu Leu
385                 390                 395                 400

Gly Asn Thr Pro Tyr Ala Val Thr Phe Thr Leu Thr Gln Glu Gln Leu
                405                 410                 415

Ser Asn Pro Val Glu Ile Ser Leu Thr His Gly Ser Gly Gly Gly Asp
                420                 425                 430

Arg Leu Thr Ser Thr Ile Phe Thr Val Thr Thr Tyr Pro Phe Asp Thr
            435                 440                 445

Phe Leu Leu Lys Leu Asn Lys Leu Ile Arg Leu Tyr Lys Ala Thr Gly
        450                 455                 460

Ile Ser Pro Ala Ser Ile Arg Thr Val Ile Glu Ser Asp Asn Thr Asp
465                 470                 475                 480

Leu Ile Ile Thr Glu Ser Val Leu Asn Gln Leu Phe Trp Thr Asn Tyr
                485                 490                 495

Tyr Thr Gln Thr Phe Glu Met Glu Phe Ser Ala Ala Leu Val Leu Ala
                500                 505                 510
```

```
Gly Ala Asp Ile Gly Gln Ile Ala His Ser Glu Ser Gln Pro Ser Ala
            515                 520                 525

Phe Thr Arg Leu Phe Asn Thr Pro Leu Leu Asp Asn Gln Gln Phe Ser
            530                 535                 540

Ala Ser Asp Glu Ser Leu Asp Leu Glu Pro Gly Lys Gly Ala Asp Ala
545                 550                 555                 560

Phe Arg Ile Ala Val Leu Lys Arg Ala Leu Gln Val Asn Asp Ala Gly
            565                 570                 575

Leu Tyr Thr Leu Tyr Gly Leu Ser Phe Thr Asp Lys Asp Lys Asn Gly
            580                 585                 590

Lys Leu Ile Pro Phe Thr Thr Asn Ile Glu Asn Leu Ser Ala Leu Tyr
            595                 600                 605

Arg Thr Arg Leu Leu Ala Asp Ile Phe Asn Ile Ser Val Thr Glu Leu
            610                 615                 620

Ser Met Leu Leu Ser Val Ser Pro Tyr Ala Ser Gln Lys Val Asp Ser
625                 630                 635                 640

Leu Lys Gly Gln Ala Leu Tyr Gln Phe Val Ala Thr Leu Ser Asp Tyr
            645                 650                 655

Met Gln Arg Leu Lys Ala Met Asn Trp Ser Val Ser Asp Leu Tyr Leu
            660                 665                 670

Met Leu Thr Asn Ser Tyr Ser Thr Val Leu Ser Pro Glu Ile Lys Asn
            675                 680                 685

Leu Met Thr Thr Leu Lys Asn Gly Leu Ser Glu Gln Asp Phe Asn Asn
            690                 695                 700

Thr Asp Glu Ile Ala Gln Leu Asn Ala Thr Ala Pro Leu Ile Ala Ala
705                 710                 715                 720

Ala Met Gln Leu Asp Phe Thr Glu Thr Ala Ala Leu Leu Glu Trp
            725                 730                 735

Leu Asn Gln Leu Gln Pro Ala Gly Leu Thr Val Ala Gly Phe Leu Ser
            740                 745                 750

Leu Val Asn Gln Thr Thr Leu Glu Asp Lys Asp Val Val Lys Leu Val
            755                 760                 765

Ser Phe Cys Gln Val Met Gly Gln Leu Ala Leu Ile Val Arg Lys Ala
            770                 775                 780

Ala Leu Gly Ser Ser Glu Ile Thr Phe Ala Val Ala His Pro Ala Ile
785                 790                 795                 800

Phe Lys Lys Asp Ala Asn Ser Leu Ala Gln Asp Ile Gly Thr Leu Phe
            805                 810                 815

Asp Leu Thr Gln Leu His Ala Phe Leu Thr Asp Cys Gly Thr Tyr Ala
            820                 825                 830

Ser Glu Ile Leu Thr Ser Leu Asn Glu Gly Asn Leu Asp Val Ser Thr
            835                 840                 845

Val Ala Thr Ala Leu Thr Leu Asp Lys Thr Ser Leu Ala Gln Ala Leu
850                 855                 860

Ala Gln Val Ser Glu Ser Gln Ala Phe Ser Asn Trp His Glu Leu Arg
865                 870                 875                 880

Asp Ala Leu Gln Trp Thr Asp Ala Ala Ser Ile Phe Asn Ile Thr Pro
            885                 890                 895

Val Ala Leu Thr Ala Met Val Asn Leu Lys Phe Ser Gly Asp Asn Ser
            900                 905                 910

Ser Pro Tyr Gln Glu Trp Val Thr Val Ser Lys Ala Met Gln Val Gly
            915                 920                 925

Leu Asn Gln Thr Gln Ser Ala Gln Leu Gln Ala Ser Leu Asp Glu Ser
```

```
                    930                 935                 940
Leu Ser Ala Ala Leu Ser Ala Tyr Val Ile Lys Asn Ile Thr Pro Pro
945                 950                 955                 960

Ser Val Thr Asp Arg Asp Glu Leu Tyr Gly Trp Leu Leu Ile Asp Asn
                    965                 970                 975

Gln Val Ser Ala Gln Ile Lys Thr Thr Arg Ile Ala Glu Ala Ile Ala
                980                 985                 990

Ser Val Gln Leu Tyr Val Asn Arg Ser Leu Thr Gly Gln Glu Asp Gly
            995                 1000                1005

Val Asp Ser Lys Val Lys Ser Gly Gln Phe Phe Thr Ala Asp Trp
    1010                1015                1020

Asp Thr Tyr Asn Lys Arg Tyr Ser Thr Trp Ala Gly Val Ser Glu
    1025                1030                1035

Leu Val Tyr Tyr Pro Glu Asn Tyr Val Asp Pro Thr Leu Arg Ile
    1040                1045                1050

Gly Gln Thr Gly Met Met Asp Glu Met Leu Gln Thr Leu Ser Gln
    1055                1060                1065

Ser Gln Ile Asn Leu Asp Thr Val Ser Asp Gly Met Gly Arg Tyr
    1070                1075                1080

Leu Thr Asp Phe Glu Glu Ile Ala Asn Leu Lys Phe Leu Ser Gly
    1085                1090                1095

Tyr His Asp Asn Val Ser Gly Arg Gln Gly Lys Thr Trp Phe Ile
    1100                1105                1110

Gly Gly Ser Gln Ser Glu Pro Gln Lys Phe Tyr Trp Arg Ser Leu
    1115                1120                1125

Asp Tyr Ser Lys Gly Asp Gly Glu Glu Phe Ala Ala Asn Ala Trp
    1130                1135                1140

Ser Glu Trp Asn His Ile Ser Cys Ala Ile Thr Pro Leu Pro Gly
    1145                1150                1155

Phe Val Arg Val Val Leu Phe Asn Ser Arg Leu Tyr Leu Ala Cys
    1160                1165                1170

Val Glu Lys Lys Glu Ile Arg Asp Ser Glu Asn Lys Asn Lys Ala
    1175                1180                1185

Ser Tyr Gln Leu Lys Ile Ala His Ile Leu Tyr Asn Gly Glu Trp
    1190                1195                1200

Ser Ala Pro Phe Ser His Asp Ile Thr Asp Leu Tyr Glu Ala Gly
    1205                1210                1215

Phe Asp Pro Ser Thr Thr Val Met His Leu Ser Val His Asp Glu
    1220                1225                1230

Ser Asp Ala Ile Val Cys Ile Phe Asn Asn Ser Ala Leu Glu Ser
    1235                1240                1245

Asp Lys Asn Lys Gly Val Ala Val Asn Ala Asp Met Ser Phe Asn
    1250                1255                1260

Asn Ile Asp Ser Lys Arg Val Asp Gln Ile Ile Ser Leu Leu Val
    1265                1270                1275

Pro Asp Arg Phe Ile Asp Glu Gly Asn Val Ile Asp Asn Leu Val
    1280                1285                1290

Ser Glu Leu Lys Gly Ser Glu Val Thr Glu Asn Lys Lys Thr Leu
    1295                1300                1305

Glu Asn Asp Ser Phe Thr Ile Asp Gly Ser Ile Asn Leu Asn Lys
    1310                1315                1320

His Ser Ile Asp Ile Thr Gly Lys Ala Asn Leu Asp Ile Gln Ala
    1325                1330                1335
```

```
Ser Ile Ala Val Arg Ser Lys Ala Ser Pro Thr Ser His Glu Arg
    1340            1345                1350

Glu Leu Ile Gly Trp Leu Asp Glu Ser Gln Phe Asp Tyr Ile Arg
    1355            1360                1365

Leu Phe Arg Gly Gly Tyr Asn Phe Gly Gln Asn Asp Gly Ile Leu
    1370            1375                1380

Glu Ser Cys Met Ile Ser Ala Val Asn Ser Ala Tyr Thr Cys Phe
    1385            1390                1395

Leu Leu Arg Ala Asp His Phe Ser Gly Leu Phe Ser Tyr Gly Tyr
    1400            1405                1410

Asp Leu Phe Val Phe Asn Gly Asp Gly Ser Lys Thr Tyr Thr Pro
    1415            1420                1425

Gln Val Leu Phe Glu Asp Asp Ile Gln Gly Thr Met Val Leu Lys
    1430            1435                1440

Ile Val Leu Leu Asn Glu Asp Lys Asn Ser Lys Leu Glu Asn Phe
    1445            1450                1455

Glu Ser Leu Gly Leu Met Lys Thr Ser Ala Gly Asp His Gln Gly
    1460            1465                1470

Glu Ile Val Cys Glu Leu Ala Lys Arg Arg Thr Pro Glu Pro Tyr
    1475            1480                1485

Cys Val Glu Leu Ser Arg Tyr Leu Pro Ser Asn Val Thr Val Thr
    1490            1495                1500

Val Thr Ser Pro Ser Gly Asn Phe Thr Ala Lys Asp Tyr Val Leu
    1505            1510                1515

Pro Leu Pro Ala Phe Asn Asn Gly Asp Ala Asp Tyr Lys Phe Ala
    1520            1525                1530

Pro Phe Pro Leu Ser Leu Glu Ser Ile Trp Gly Asp Gly Lys Ser
    1535            1540                1545

Thr Ser Arg Asp Ile Lys Phe Thr Ile Ser Val Lys Asp Thr Cys
    1550            1555                1560

Gly Lys Val Ala Thr Ser Glu Leu Ile Phe Thr Leu Tyr Lys Asn
    1565            1570                1575

Thr Ser Pro Glu Leu Ile Thr Leu Lys Thr Ser Asp Ala Gly Ala
    1580            1585                1590

Gln Tyr Met Gln Gln Gly Val Tyr Arg Thr Arg Leu Asn Thr Leu
    1595            1600                1605

Phe Ala Gln Lys Leu Ile Lys Arg Val Ser Ala Gly Ile Asp Ala
    1610            1615                1620

Val Leu Ser Trp Glu Thr Gln Gln Leu Gln Glu Pro Lys Leu Gly
    1625            1630                1635

Thr Gly Ser Tyr Ile Ser Val Leu Ile Pro Ala Tyr Ile Lys Leu
    1640            1645                1650

Glu His Gly Asp Ser Arg Gln Ala Asn Leu Gln Phe Ser Asn Val
    1655            1660                1665

Asp Gln Thr Gly Pro Asp Asn Gly Asn Tyr Ile Leu Trp Ser Gly
    1670            1675                1680

Ser Leu Asn Asp Thr Pro Gln Val Thr Ile Phe Val Pro Thr
    1685            1690                1695

Met Gln Thr Ile Gly Glu Leu Gln Phe Pro Tyr Asp Arg Thr Ser
    1700            1705                1710

Gly Leu Asn Leu Ser Leu Ala Cys Ala Ala Gly Val Tyr Leu Gln
    1715            1720                1725
```

```
Gly Thr Phe Lys Asn Ile Ser Ala Ser Asp Leu Ser Leu Thr Glu
    1730                1735                1740

Phe Val Ala Ala Lys Asn Asn Asp Ser Lys Arg Asp Val Glu Val
1745                1750                1755

Thr Val Leu Thr Ser Ile Asn Thr Glu Pro Met Asp Phe Lys Gly
    1760                1765                1770

Ala Asn Ala Leu Tyr Phe Trp Glu Met Phe Tyr Leu Pro Met
1775                1780                1785

Met Val Phe Lys Arg Leu Leu Ser Glu Ser Arg Phe Thr Glu Ala
    1790                1795                1800

Thr Gln Trp Ile Arg Tyr Val Trp Asn Pro Asp Gly Tyr Leu Val
1805                1810                1815

Asn Asp Thr Pro Ala Thr Tyr Gln Trp Asn Val Arg Pro Leu Glu
    1820                1825                1830

Asp Glu Thr Ser Trp His Ala Asn Pro Leu Asp Ser Val Asp Pro
1835                1840                1845

Asp Ala Ile Ala Gln Ala Asp Pro Leu His Tyr Lys Val Ala Thr
    1850                1855                1860

Phe Met Ala Tyr Leu Asp Leu Leu Ile Ala Arg Gly Asp Ala Ala
1865                1870                1875

Tyr Arg Gln Leu Glu Arg Asp Ala Leu Ser Glu Ala Lys Met Trp
    1880                1885                1890

Tyr Val Gln Ala Leu Asp Thr Leu Gly Asp Glu Pro Tyr Leu Ser
1895                1900                1905

Gln Asn Thr Gly Trp Ala Ser Pro Cys Leu Thr Asp Ala Ala Asp
    1910                1915                1920

Glu Thr Thr His Lys Asn Arg Gln Gln Ala Met Leu Thr Val Arg
1925                1930                1935

Gln Lys Val Ala Ser Ser Glu Leu Arg Thr Ala Asn Ser Leu Thr
    1940                1945                1950

Ala Leu Phe Leu Pro Gln Gln Asn Ala Lys Leu Ala Gly Tyr Trp
1955                1960                1965

Gln Thr Leu Asn Gln Arg Leu Tyr Asn Leu Arg Asn Asn Leu Ser
    1970                1975                1980

Ile Asp Gly Asn Pro Leu Ser Leu Ser Ile Tyr Ala Thr Pro Thr
1985                1990                1995

Asp Pro Ala Ala Leu Leu Ser Ser Ala Val Ile Ser Ser Gln Gly
    2000                2005                2010

Gly Ser Asp Leu Pro Ala Ala Val Met Pro Leu Tyr Arg Phe Pro
2015                2020                2025

Val Ile Leu Glu Ser Ala Arg Ser Met Val Asn Gln Leu Thr Gln
    2030                2035                2040

Phe Gly Ser Thr Leu Leu Gly Ile Thr Glu Arg Gln Asp Ala Glu
2045                2050                2055

Ala Leu Ser Asp Leu Leu Gln Thr Gln Gly Ala Gly Leu Ala Leu
    2060                2065                2070

Gln Ser Ile Ala Leu Gln Asn Ser Thr Ile Ser Glu Ile Asp Ala
2075                2080                2085

Asp Arg Ala Ala Leu Arg Glu Ser Leu Ser Gly Ala Gln Ser Arg
    2090                2095                2100

Leu Asn Ser Tyr Thr Thr Leu Tyr Asp Glu Asn Val Asn Ala Gly
2105                2110                2115

Glu Thr His Ala Met Asn Leu Phe Leu Ser Ser Ala Ile Leu Ala
```

-continued

```
                2120                2125                2130

Asp Gly Gly Gln Ala Tyr His Thr Ala Ala Gly Ala Leu Asp Leu
    2135                2140                2145

Ala Pro Asn Ile Phe Gly Leu Ala Asp Gly Ser Arg Trp Gly
    2150                2155                2160

Ala Ala Phe Thr Ala Met Ala Gly Ile Ala Asp Leu Ala Ala Ser
    2165                2170                2175

Ala Thr His Thr Ala Ala Asp Arg Ile Ser Gln Ser Glu Ala Tyr
    2180                2185                2190

Arg Arg Arg Arg Gln Glu Trp Glu Ile Gln Arg Asn Ala Ala Gln
    2195                2200                2205

Phe Glu Val Ser Gln Ile Asn Ala Gln Leu Asp Ala Leu Ala Val
    2210                2215                2220

Arg Arg Glu Ser Ala Val Leu Gln Lys Thr Tyr Leu Glu Thr Gln
    2225                2230                2235

Gln Gly Gln Met Gln Ala Gln Met Thr Phe Leu Gln Asn Lys Phe
    2240                2245                2250

Thr Ser Lys Ala Leu Tyr Asn Trp Leu Arg Gly Lys Leu Ala Ala
    2255                2260                2265

Ile Tyr Tyr Gln Phe Tyr Asp Leu Thr Val Ser Arg Cys Leu Met
    2270                2275                2280

Ala Glu Ala Ala Tyr Ser Trp Glu Met Lys Gly Ser Gln Asp Thr
    2285                2290                2295

Gly Thr Phe Ile Arg Pro Gly Ala Trp Gln Gly Thr Tyr Ala Gly
    2300                2305                2310

Leu Met Ala Gly Glu Thr Leu Met Leu Asn Leu Ala Gln Met Glu
    2315                2320                2325

Asn Ser Tyr Leu Thr Lys Glu Arg Gln Lys Glu Val Thr Arg
    2330                2335                2340

Thr Val Cys Leu Ser Glu Val Tyr Ala Gly Leu Ser Ser Gly Ser
    2345                2350                2355

Phe Ala Leu Ala Asp Thr Val Thr Thr Leu Val Gly Ser Gly Lys
    2360                2365                2370

Gly Thr Ala Gly Thr Asn Asp Asn Gly Val Lys Ile Asp Gly Lys
    2375                2380                2385

Gln Leu Leu Ala Thr Leu Lys Leu Ser Asp Leu Asn Ile Lys Thr
    2390                2395                2400

Asp Tyr Pro Glu Ser Leu Asp Lys Ala Lys Arg Ile Lys Gln Ile
    2405                2410                2415

Ser Val Thr Leu Pro Thr Leu Val Gly Pro Tyr Gln Asp Val Arg
    2420                2425                2430

Ala Val Leu Ser Tyr Gly Gly Ser Val Val Leu Pro Arg Gly Cys
    2435                2440                2445

Thr Ala Val Ala Val Ser His Gly Met Asn Asp Ser Gly Gln Phe
    2450                2455                2460

Gln Leu Asp Phe Asn Asp Ser Arg Trp Leu Pro Phe Glu Gly Ile
    2465                2470                2475

Pro Val Asp Asp Ser Gly Thr Leu Thr Leu Ser Phe Pro Asp Ile
    2480                2485                2490

Thr Asp Lys Gln Gln Glu Asn Leu Leu Leu Ser Leu Ser Asp Ile
    2495                2500                2505

Ile Leu His Ile Arg Tyr Thr Ile Ala Ser
    2510                2515
```

<210> SEQ ID NO 28
<211> LENGTH: 1421
<212> TYPE: PRT
<213> ORGANISM: Pantoea agglomerans

<400> SEQUENCE: 28

```
Met Gln Asn Thr Asp Gln Met Ser Leu Thr Pro Pro Ser Leu Pro Ser
1               5                   10                  15

Gly Gly Gly Ala Val Thr Gly Leu Lys Gly Asp Met Ser Gly Ala Gly
            20                  25                  30

Pro Asp Gly Ala Ala Thr Leu Ser Leu Pro Leu Pro Ile Ser Pro Gly
        35                  40                  45

Arg Gly Tyr Ala Pro Ser Leu Ser Leu Gly Tyr His Ser Arg Asn Gly
    50                  55                  60

Asn Gly Val Phe Gly Ala Gly Trp Ser Cys Gly Gln Met Ala Ile Arg
65                  70                  75                  80

Leu Gln Thr Arg Lys Gly Val Pro Phe Tyr Asp Gly Ser Asp Val Phe
                85                  90                  95

Thr Ala Pro Asp Gly Glu Val Leu Val Pro Ala Leu Asp Ala Ser Gly
            100                 105                 110

Lys Ala Glu Val Arg Thr Thr Thr Leu Leu Gly Glu Asn Leu Gly
        115                 120                 125

Gly Thr Phe Thr Val Gln Thr Tyr Arg Ser Arg Val Glu Thr Asp Phe
    130                 135                 140

Ser Arg Leu Glu Arg Trp Val Pro Gln Thr Asp Ala Ala Ala Asp Phe
145                 150                 155                 160

Trp Leu Ile Tyr Ser Pro Asp Gly Gln Ile His Leu Leu Gly Arg Asn
                165                 170                 175

Pro Gln Ala Arg Val Asn Asn Pro Glu Asp Thr Thr Gln Thr Ala Ala
            180                 185                 190

Trp Leu Ile Glu Ser Ser Val Ser Ala Ser Gly Glu Gln Ile Tyr Trp
        195                 200                 205

Gln Tyr Arg Gln Glu Asp Glu Leu Gly Cys Thr Gln Asp Glu Lys Thr
    210                 215                 220

Ala His Ala His Ala Leu Ala Gln Arg Tyr Leu Val Ala Val Trp Tyr
225                 230                 235                 240

Gly Asn Lys Ala Ala Ser Arg Thr Leu Pro Gly Leu Leu Ser Val Pro
                245                 250                 255

Ala Ala Gly Ser Trp Leu Phe Thr Leu Ala Leu Asp Tyr Gly Glu Arg
            260                 265                 270

Ala Thr Asp Pro Ala Thr Pro Pro Ala Trp Leu Ser Pro Gly Ser Gly
        275                 280                 285

Thr Trp Leu Cys Arg Gln Asp Val Phe Ser Ser Trp Glu Tyr Gly Phe
    290                 295                 300

Glu Leu Arg Thr Arg Arg Leu Cys Arg Gln Val Leu Met Tyr His Asp
305                 310                 315                 320

Val Ala Ala Leu Ala Gly Gln Ser Gly Ser Asp Ala Val Pro Gln Leu
                325                 330                 335

Val Thr Arg Leu Leu Asp Tyr Asn Thr Ser Pro Ser Leu Thr Thr
            340                 345                 350

Leu Lys Thr Ala Gln Gln Ala Ala Trp Glu Pro Asp Gly Thr Leu Arg
        355                 360                 365

Ser Leu Pro Pro Leu Ala Phe Ser Trp Gln Thr Phe Pro Ser Thr Pro
```

```
                370                 375                 380
Glu Lys Ser Val Ser Trp Gln Arg Arg Asn Asp Met Gly Lys Leu Asn
385                 390                 395                 400

Pro Gln Gln Pro Tyr Gln Met Val Asp Leu His Gly Glu Gly Leu Ala
            405                 410                 415

Gly Ile Leu Tyr Gln Asp Ser Gly Ala Trp Trp Tyr Arg Glu Pro Val
            420                 425                 430

Arg Gln Ser Gly Asp Asp Asn Ala Val Thr Trp Ala Ala Ala Arg
            435                 440                 445

Pro Leu Pro Ala Phe Pro Ala Leu Arg Lys Gly Gly Met Leu Leu Asp
450                 455                 460

Leu Asp Gly Asp Gly Tyr Leu Glu Trp Val Val Thr Ala Pro Gly Val
465                 470                 475                 480

Ala Gly Cys Tyr Ala Gln Ala Pro Glu Gln Tyr Trp Gln Arg Phe Thr
            485                 490                 495

Pro Leu Ser Ala Leu Pro Val Glu Tyr Arg His Ser Arg Met Glu Ile
            500                 505                 510

Ala Asp Val Thr Gly Ala Gly Leu Ala Asp Met Leu Leu Ile Gly Pro
            515                 520                 525

Lys Ser Val Arg Leu Tyr Ser Gly Ser Gly Arg Gly Trp Lys Lys Ala
530                 535                 540

Arg Thr Val Met Gln Asp Ser Gly Ile Thr Leu Pro Val Pro Gly Thr
545                 550                 555                 560

Asn Ala Arg Val Met Val Ala Phe Ser Asp Met Ala Gly Ser Gly Gln
            565                 570                 575

Gln His Leu Thr Glu Ile Lys Ala Ser Gly Val Arg Tyr Trp Pro Ser
            580                 585                 590

Leu Gly His Gly Arg Phe Ala Ala Pro Val Thr Leu Pro Gly Phe Ser
            595                 600                 605

Gln Pro Ala Glu Thr Phe Asn Pro Ala Gln Leu Tyr Leu Ala Asp Val
            610                 615                 620

Asp Gly Ser Gly Thr Thr Asp Leu Ile Tyr Ala Leu Ser Asp His Leu
625                 630                 635                 640

Leu Val Trp Leu Asn Gln Ser Gly Asn Ser Phe Asp Ala Pro Phe Arg
            645                 650                 655

Ile Ser Leu Pro Glu Gly Val Arg Tyr Asp Asn Thr Cys Ser Leu Gln
            660                 665                 670

Val Ala Asp Ile Gln Gly Leu Gly Ile Ser Ser Leu Val Leu Ser Val
            675                 680                 685

Pro His Pro Thr Pro Arg His Trp Val Cys His Leu Thr Thr Glu Lys
            690                 695                 700

Pro Trp Leu Leu Asp Gly Met Asn Asn Asn Met Gly Ala Arg His Thr
705                 710                 715                 720

Leu Cys Tyr Arg Ser Ser Ala Gln Phe Trp Leu Asp Glu Lys Ala Ala
            725                 730                 735

Ala Thr Ala Asp Arg Pro Ala Pro Ala Cys Tyr Leu Pro Phe Ala Leu
            740                 745                 750

His Thr Leu Ser Arg Thr Glu Val Ser Asp Glu Ile Thr Gly Asn Arg
            755                 760                 765

Leu Thr Arg Thr Ile Arg Tyr Arg His Gly Val Trp Asp Arg Arg Glu
            770                 775                 780

Arg Glu Phe Arg Gly Phe Gly Phe Val Glu Val Ser Asp Ala Glu Ala
785                 790                 795                 800
```

-continued

Leu Ala Lys Gln Thr Glu Gly Met Ser Ala Pro Ala Val Lys Arg Ser
              805                 810                 815

Trp Tyr Ala Thr Gly Leu Ala Ala Val Asp Ala Gln Leu Pro Asp Glu
              820                 825                 830

Phe Trp Lys Gly Asp His Ala Ala Phe Ala Gly Phe Thr Pro Arg Phe
              835                 840                 845

Thr Thr Gly Asp Gly Glu Gln Glu Ala Ala Leu Asp Thr Ile Ser Asp
              850                 855                 860

Asp Thr Arg Phe Trp Leu Thr Arg Ala Ile Arg Gly Thr Leu Leu Arg
865                 870                 875                 880

Ser Glu Leu Tyr Gly Ala Asp Gly Ser Ser Gln Ala Gly Ile Pro Tyr
              885                 890                 895

Ser Ile Thr Glu Ser Arg Pro Gln Val Arg Leu Ile Thr Glu Ala Gly
              900                 905                 910

Asn Ser Pro Val Val Trp Pro Ser Val Ile Glu Asn Arg Ala Ser His
              915                 920                 925

Tyr Glu Arg Val Ser Ser Asp Pro Gln Cys Gly Gln Gln Ile Leu Leu
              930                 935                 940

Thr Ser Asn Glu Tyr Gly Gln Pro Leu Arg Gln Ile Gly Ile Ser Tyr
945                 950                 955                 960

Pro Arg Arg Thr Arg Pro Asp Ala Ser Pro Tyr Pro Asp Asp Leu Pro
              965                 970                 975

Asp Gly Leu Phe Ala Asp Ser Phe Asp Glu Gln Gln Ala Leu Arg
              980                 985                 990

Leu Thr Leu Thr Gln Ser Ser Trp His Thr Leu Lys Asp Ile Ser Ser
              995                1000                1005

Gly Ile Trp Leu Pro Ala Val Ala Asp Ala Thr Arg Ser Asp Leu
              1010                1015                1020

Phe Val His Gln Ala Ala Gln Val Pro Pro Ala Gly Leu Thr Leu
              1025                1030                1035

Glu Asn Leu Leu Thr Asp Ser Ala Leu Leu Thr Ser Pro Val Phe
              1040                1045                1050

Gly Gly Gln Ser Gln Ile Trp Tyr Gln Asp Arg Ala Gly Gln Ala
              1055                1060                1065

Ser Ile Thr Ser Pro Asp Phe Pro Pro Arg Pro Ser Phe Ser Glu
              1070                1075                1080

Thr Ala Ala Leu Asp Glu Ala Gln Val Ser Thr Leu Ser Ala Asp
              1085                1090                1095

Ile Asp Gln Thr Lys Leu Glu Gln Ala Gly Tyr Thr Arg Ser Ala
              1100                1105                1110

Tyr Leu Phe Ala Arg Ser Gly Glu Glu Ser Lys Thr Leu Trp Ala
              1115                1120                1125

Val Arg Gln Gly Tyr Ile Thr Phe Ser Gly Ala Asp His Phe Tyr
              1130                1135                1140

Leu Pro Ile Ala Ala Gln Gln Thr Leu Leu Ala Gly Lys Thr Thr
              1145                1150                1155

Val Thr Tyr Asp Pro Tyr Asp Cys Val Val Leu Gln Ala Lys Asp
              1160                1165                1170

Ala Ala Gly Ala Val Thr Ser Ala Thr Tyr Asp Trp Arg Phe Leu
              1175                1180                1185

Ala Pro Thr Gln Ile Thr Asp Ile Asn Asp Asn Leu Lys Ser Val
              1190                1195                1200

```
Thr Leu Asp Ala Leu Gly Arg Val Thr Ser Gln Arg Phe Ser Gly
    1205                1210                1215

Thr Glu Asn Gly Lys Pro Ala Gly Tyr Ser Asp His Glu Phe Pro
    1220                1225                1230

Leu Pro Ala Ser Ala Asp Ala Ala Leu Ala Leu Ser Ala Pro Leu
    1235                1240                1245

Pro Val Ala Gln Cys Ile Ile Tyr Val Pro Asp Ser Trp Met Leu
    1250                1255                1260

Thr Gly Glu Gln Gln Gln Pro Pro His Val Val Thr Leu Leu Thr
    1265                1270                1275

Asp Arg Tyr Asp Ser Asp Ser Gln Gln Gln Ile Arg Gln Gln Val
    1280                1285                1290

Val Phe Ser Asp Gly Phe Gly Arg Val Leu Gln Ala Ala Ser Arg
    1295                1300                1305

Gln Val Asn Gly Glu Ala Trp Gln Arg Ala Ala Asn Gly Ser Phe
    1310                1315                1320

Val Ala Gly Thr Asn Asp Ser Pro Val Leu Thr Glu Thr Thr Phe
    1325                1330                1335

Arg Trp Ala Val Thr Gly Arg Thr Glu Tyr Asp Asn Lys Gly Gln
    1340                1345                1350

Ala Ile Arg Ala Tyr Gln Pro Tyr Phe Leu Asp Ser Trp Lys Tyr
    1355                1360                1365

Val Arg Asp Asp Ser Ala Arg Gln Asp Leu Tyr Ala Asp Thr His
    1370                1375                1380

Tyr Tyr Asp Pro Val Gly Arg Glu Arg Gln Val Ile Thr Ala Lys
    1385                1390                1395

Gly Trp Leu Arg Arg Val Thr His Thr Pro Trp Phe Val Val Ser
    1400                1405                1410

Glu Asp Glu Asn Asp Thr Gln Ala
    1415                1420

<210> SEQ ID NO 29
<211> LENGTH: 951
<212> TYPE: PRT
<213> ORGANISM: Pantoea agglomerans

<400> SEQUENCE: 29

Met Ser Ala Ala Tyr Val Leu Ser Asn Leu Ser Tyr Gln Arg Glu Asn
1               5                   10                  15

Thr Met Ser Thr Ser Leu Tyr Ser Arg Thr Pro Ser Val Thr Val Leu
                20                  25                  30

Asp Asn Arg Gly Leu Thr Val Arg Asp Ile Ala Tyr His Arg His Pro
            35                  40                  45

Asp Thr Pro Ala Val Thr Ser Glu Arg Ile Thr Arg His Gln Tyr Asp
        50                  55                  60

Ala Arg Gly Phe Leu Thr Gln Ser Ala Asp Pro Arg Leu His Asp Ala
    65                  70                  75                  80

Gly Leu Ala Asn Phe Ser Tyr Arg Thr Asp Leu Thr Gly Ser Val Leu
                85                  90                  95

Arg Leu Gln Gly Val Asp Asn Gly Ile Thr Val Ala Leu Asn Asp Ala
            100                 105                 110

Ala Gly Arg Pro Phe Leu Ala Val Ser Asn Ile Arg Thr Ala Gly Asp
        115                 120                 125

Gly Ser Glu Asp Arg Ser Gln Ala Val Thr Arg Thr Cys Gln Tyr Glu
    130                 135                 140
```

```
Asp Ala Thr Leu Pro Gly Arg Pro Leu Ser Ile Thr Glu Gln Val Lys
145                 150                 155                 160

Gly Gly Ala Ala Arg Ile Thr Glu Arg Phe Ile Tyr Ala Gly Asn Ala
            165                 170                 175

Val Glu Glu Lys Ala Leu Asn Leu Ala Gly Gln Pro Val Ser His Tyr
            180                 185                 190

Asp Thr Ala Gly Leu Thr Gln Thr Asp Ser Ile Ala Leu Thr Gly Val
            195                 200                 205

Pro Leu Ser Val Thr Arg Arg Leu Leu Lys Asp Ala Asp Asn Pro Asp
210                 215                 220

Ala Val Ala Asp Trp Gln Gly Thr Asp Ala Ser Val Trp Asn Asp Pro
225                 230                 235                 240

Leu Asp Val Glu Thr Tyr Thr Thr Leu Ser Thr Ala Asp Ala Thr Gly
            245                 250                 255

Ala Val Leu Thr Thr Thr Asp Ala Lys Gly Asn Leu Gln Arg Leu Ala
            260                 265                 270

Tyr Asp Val Ala Gly Leu Leu Ser Gly Ser Trp Leu Thr Leu Lys Asp
            275                 280                 285

Gly Thr Glu Gln Val Ile Val Thr Ser Leu Thr Tyr Ser Ala Ala Gly
290                 295                 300

Gln Lys Leu Arg Glu Glu His Gly Asn Gly Val Val Thr Thr Tyr Thr
305                 310                 315                 320

Tyr Glu Ala Glu Thr Gln Arg Leu Thr Gly Ile Lys Thr Ala Arg Pro
            325                 330                 335

Ala Gly His Thr Ser Gly Ala Lys Val Leu Gln Asp Leu Arg Tyr Thr
            340                 345                 350

Tyr Asp Pro Val Gly Asn Val Leu Lys Ile Ser Asn Asp Ala Glu Glu
            355                 360                 365

Thr Arg Phe Trp Arg Asn Gln Lys Val Ala Pro Glu Ser Ala Tyr Val
370                 375                 380

Tyr Asp Ser Leu Tyr Gln Leu Val Ser Ala Thr Gly Arg Glu Met Ala
385                 390                 395                 400

Asn Ala Gly Gln Gln Gly Ser Ser Ser Ser Ala Thr Val Pro Leu
            405                 410                 415

Pro Ala Asp Ser Ser Ala Phe Thr Asn Tyr Thr Arg Asn Tyr Thr Tyr
            420                 425                 430

Asp Glu Ala Gly Asn Leu Thr Gln Val Arg His Thr Pro Ala Thr Gly
            435                 440                 445

Ser Gly Tyr Thr Thr Lys Ile Thr Val Ser Asp Lys Ser Asn Arg Gly
            450                 455                 460

Val Leu Ser Thr Leu Thr Glu Asn Pro Ser Asp Val Asp Ala Leu Phe
465                 470                 475                 480

Thr Ala Gly Gly Gln Gln Lys Gln Leu Gln Pro Gly Gln Ser Leu Ile
            485                 490                 495

Trp Thr Pro Arg Asn Glu Leu Leu Lys Val Thr Pro Val Ala Arg Asp
            500                 505                 510

Gly Gly Ala Asp Asp Ser Glu Ser Tyr Arg Tyr Asp Gly Gly Ser Leu
            515                 520                 525

Arg Leu Leu Lys Val Ser Val Gln Lys Thr Gly Asn Ser Thr Gln Thr
            530                 535                 540

Gln Arg Ala Leu Tyr Leu Pro Gly Leu Glu Leu Arg Asn Thr Thr Ser
545                 550                 555                 560
```

Gly Asp Thr Glu Thr Glu Ser Leu Gln Val Thr Val Gly Glu Ala
            565                 570                 575

Gly Arg Ala Gln Val Arg Val Leu His Trp Glu Ser Gly Thr Pro Asp
        580                 585                 590

Ser Val Ser Asn Asp Pro Val Arg Tyr Ser Tyr Asp Asn Leu Thr Gly
        595                 600                 605

Ser Ser Gly Leu Glu Leu Asp Ser Ser Gly Asn Ile Ile Ser Met Glu
    610                 615                 620

Glu Tyr Tyr Pro Tyr Gly Gly Thr Ala Val Trp Thr Ala Arg Ser Ala
625                 630                 635                 640

Val Glu Ala Glu Tyr Lys Thr Val Arg Tyr Ser Gly Lys Glu Arg Asp
                645                 650                 655

Ala Thr Gly Leu Tyr Tyr Tyr Gly Tyr Arg Tyr Tyr Gln Pro Trp Ala
            660                 665                 670

Gly Arg Trp Leu Ser Ala Asp Pro Ala Gly Thr Val Asp Gly Leu Asn
        675                 680                 685

Leu Phe Arg Met Val Arg Asn Asn Pro Val Thr Leu Val Asp Asp Asn
    690                 695                 700

Gly Leu Phe Thr Ser Ser Pro Leu Leu Gly Ile Tyr Glu Lys Glu Met
705                 710                 715                 720

Lys Thr Phe Asp Ser Ile Lys Leu Ser Ile Gly Ser Tyr Lys Tyr Lys
                725                 730                 735

Pro Ser Lys Phe Asp Glu Lys Lys Gly Lys Tyr Val Ser Ser Asp Lys
            740                 745                 750

Tyr Lys Leu Ile Met Ala Asp Asp Asn Asp Leu Asn Gly Tyr Leu Phe
        755                 760                 765

Asp Glu Arg Glu Met Thr Ser His Leu Lys Asp Tyr Ala Asp Lys Phe
    770                 775                 780

Ser Lys Ile Ser Arg Leu Asn Ile Gly Asp Glu Arg Met Lys Thr Asn
785                 790                 795                 800

Ile Asn Phe Gly Thr Arg Ile Ser Arg Tyr Leu Leu Ser Ser Ala Gln
                805                 810                 815

Ala Ser Ser Arg Glu Asn Arg Glu Val Asp Val Leu Ser Phe Glu Arg
            820                 825                 830

Lys Phe Phe Ala Val Val Lys Lys Lys Asp Lys Ser His Tyr Phe Gly
        835                 840                 845

Arg Lys Ile Tyr Ala Ile Gly Glu Ala His Val Leu Thr Asp Phe Glu
    850                 855                 860

Glu Lys Lys Arg Thr Ile Ala Ile Lys Thr Leu Val Ala His Pro Tyr
865                 870                 875                 880

Thr Gln Ile Asn Glu Ser Ile Lys Asn Arg Ile Asn Asp Phe Asp Lys
                885                 890                 895

Glu Tyr Asn Val Lys Gly Ile Gly Thr Phe Ala Thr Phe Lys Ala Thr
            900                 905                 910

Asn Lys Leu Ile Gly Gly Ile Lys Gly Ala Leu Lys Tyr Lys Thr Lys
        915                 920                 925

Val Leu Thr Gln Ala Val Asn Val Arg Ser Ala Ala Ile Ala Ile Lys
    930                 935                 940

Tyr Gly Ala Lys His Val Pro
945                 950

<210> SEQ ID NO 30
<211> LENGTH: 2523
<212> TYPE: PRT

<213> ORGANISM: Pantoea agglomerans

<400> SEQUENCE: 30

```
Met Tyr Leu Thr Glu Ile Leu Ala Lys Leu Asn Ala Gly Asn Gly
1               5                   10                  15

Lys Leu Gln Ser Thr Val Glu Gln Ile Ile Thr Leu Pro Asp Ile Met
            20                  25                  30

Val Arg Ser Phe Ser Gln Val Lys Glu Leu Ala Gly Asp Lys Leu Ser
            35                  40                  45

Trp Gly Glu Lys Asn Phe Leu Tyr Gln Gln Ala Gln Thr Gln Leu Lys
    50                  55                  60

Glu Asn Lys Met Ala Glu Ser Arg Ile Leu Ser Arg Ala Asn Pro Gln
65                  70                  75                  80

Leu Ala Asn Ala Val Arg Leu Gly Ile Arg Gln Ser Ser Met Leu Gly
                85                  90                  95

Ser Tyr Asp Asp Leu Phe Pro Gln Arg Ala Ser Arg Phe Val Lys Pro
            100                 105                 110

Gly Ala Val Ala Ser Met Phe Ser Pro Ala Gly Tyr Leu Thr Glu Leu
            115                 120                 125

Tyr Arg Glu Ala Arg Gly Leu His Lys Ala Glu Ser Gln Tyr Asn Leu
    130                 135                 140

Asp Lys Arg Arg Pro Asp Leu Ala Ser Leu Ala Leu Ser Gln Ser Asn
145                 150                 155                 160

Met Asp Asp Glu Leu Ser Thr Leu Ser Leu Ser Asn Glu Leu Leu Leu
                165                 170                 175

Asn Asn Ile Gln Gln His Asp Gly Leu Ser Tyr Asp Asp Ala Leu Lys
            180                 185                 190

Lys Leu Ala Gly Tyr Arg Gln Thr Gly Thr Thr Pro Tyr Ser Gln Pro
            195                 200                 205

Tyr Glu Thr Ile Arg Glu Ala Ile Leu Leu Gln Asp Pro Ala Phe Asn
    210                 215                 220

Ser Ile Arg Asn Asn Pro Ala Val Ala Thr Lys Met Asn Thr Ser Gly
225                 230                 235                 240

Leu Leu Gly Leu Thr Ala Asn Leu Pro Pro Glu Leu His Ala Ile Leu
                245                 250                 255

Thr Glu Thr Ile Thr Glu Glu Asn Ala Glu Gln Leu Ile Lys Asp Asn
            260                 265                 270

Phe Gly Asp Val Asn Val Ser Arg Phe Gln Asp Val Ser Tyr Leu Ala
            275                 280                 285

Arg Trp Tyr Gly Met Thr Pro Tyr Glu Leu Asn Ser Val Leu Gly Leu
    290                 295                 300

Met Glu Val Gly Ser Asn Pro Val Asp Gly Val Thr Tyr Tyr Gln Asp
305                 310                 315                 320

Asp Gln Leu Ile Ser Leu Val Asp Asn Gly Asn Leu Asp Ala Val
                325                 330                 335

Leu Met Gln Arg Ala Gly Gly Asp Asn Tyr Ser Gln Phe Gly Tyr Ile
            340                 345                 350

Glu Leu Leu Pro Val Ser Gly Asp Thr Tyr Gln Leu Arg Phe Thr Val
            355                 360                 365

Gln Ser Gly Tyr Val Gly Gln Asp Ser Glu Val Arg Ile Gly Thr Ser
    370                 375                 380

Glu Asn Ala Gly Ser Lys Asp Ile Leu Ser Asp Gly Arg Ile Ala Gly
385                 390                 395                 400
```

Leu Asn Ile Pro Met Val Leu Asn Val Lys Leu Asp Ser Thr Lys Leu
                405                 410                 415

Ala Gln Gly Ile Thr Ile Gly Val Thr Arg Tyr Asp Pro Ser Gly Ser
            420                 425                 430

Tyr Ile Asn Phe Ala Ser Val Arg Phe Gln Arg Tyr Asp Phe Ser Tyr
            435                 440                 445

Asn Val Phe Leu Leu Lys Leu Asn Lys Ile Ile Arg Leu Tyr Lys Ala
        450                 455                 460

Thr Gly Ile Ser Pro Ser Asp Ile Gln Thr Leu Ile Glu Ser Ala Asn
465                 470                 475                 480

His Asp Leu Ala Ile Thr Glu Asp Val Leu Ser Gln Leu Phe Trp Thr
                485                 490                 495

Asn Tyr Tyr Thr Gln Arg Tyr Gly Ile Asp Phe Ser Ala Ala Leu Val
            500                 505                 510

Leu Ala Gly Ala Asn Ile Ser Gln Ile Ala His Ser Asn Lys Gln Ser
        515                 520                 525

Ala Phe Thr Arg Leu Phe Asn Thr Pro Pro Leu Asn Asn Gln Phe Phe
530                 535                 540

Tyr Ala Asp Gly Lys Lys Leu Asn Leu Glu Pro Gly Lys Ser Asp Asp
545                 550                 555                 560

Ser His Gly Leu Gly Val Leu Lys Arg Ala Leu Gln Val Asn Asp Ser
                565                 570                 575

Ala Leu Tyr Thr Leu Phe Asn Leu Thr Phe Ala Asp Lys Asp Ala Gln
            580                 585                 590

Gly Asn Ala Val Val Phe Thr Lys Thr Pro Glu Asn Leu Ser Ala Leu
        595                 600                 605

Tyr Arg Thr Arg Leu Leu Ala Thr Val Asn Asn Leu Thr Val Asn Glu
610                 615                 620

Leu Ser Leu Leu Leu Ser Val Ser Pro Tyr Val Lys Val Lys Leu Ala
625                 630                 635                 640

Thr Leu Lys Asp Glu Ala Leu Ser Gln Leu Ser Thr Thr Leu Glu Arg
                645                 650                 655

Tyr Thr Gln Trp Leu Asp Lys Met Asn Trp Thr Ile Gly Asp Leu Tyr
            660                 665                 670

Leu Met Leu Thr Pro Val Tyr Ser Thr Val Leu Ser Pro Asp Ile Glu
        675                 680                 685

Asn Leu Val Thr Thr Leu Lys Asn Gly Leu Ala Gly Gln Asp Leu Thr
            690                 695                 700

Ser Asp Glu Lys Arg Ile Ala Ala Leu Ala Pro Phe Val Ala Ala Ala
705                 710                 715                 720

Thr Gln Leu Asp Ser Ala Glu Thr Ala Arg Ala Leu Leu Arg Trp Leu
                725                 730                 735

Asn Asp Leu Lys Pro Gly Thr Leu Ser Leu Ala Asp Phe Ile Ala Gln
            740                 745                 750

Val Asn Asn Thr Thr Gln Thr Glu Asn Leu Val Thr Phe Ser Gln Val
        755                 760                 765

Met Ala Gln Leu Ala Leu Ile Thr Arg Asn Ala Ser Leu Ser Ala Asn
770                 775                 780

Glu Leu Ser Trp Ala Val Ala His Pro Glu Ile Phe Gln Glu Lys Ala
785                 790                 795                 800

Thr Val Leu Lys Asn Asp Ile Ala Thr Leu Asn Asp Leu Thr Gln Leu
                805                 810                 815

His Asp Leu Leu Ala Arg Cys Gly Ser His Ala Ser Glu Ile Leu Thr

```
                    820                 825                 830
        Ser Leu Ser Gly Asn Ala Ser Lys Ala Glu Asn Asn Leu Ala Val Ser
                    835                 840                 845

Thr Leu Ala Thr Ala Leu Asn Leu Asp Glu Arg Ala Leu Thr Gln Ala
        850                 855                 860

Leu Ala Lys Val Ser Thr Tyr Glu Tyr Phe Tyr Asn Trp Ala His Leu
        865                 870                 875                 880

Asn Glu Ala Leu Gln Trp Leu Asp Val Ala Thr Thr Phe Gly Ile Thr
                        885                 890                 895

Pro Asp Asn Leu Ala Ala Leu Ile Gly Leu Lys Phe Asp Asn Gln Asp
                    900                 905                 910

Asp Ala Ser Phe Ala Ser Trp Leu Thr Ala Ser Arg Phe Met Gln Ala
                    915                 920                 925

Gly Leu Asn Thr Gln Gln Thr Ala Gln Leu Ser Ala Thr Leu Asp Glu
                    930                 935                 940

Ser Leu Ser Ala Ala Val Ser Ala Tyr Ala Ile Lys Asn Ile Phe Ser
        945                 950                 955                 960

Gly Ala Val Ser Asn Arg Glu Gln Leu Tyr Ser Trp Leu Leu Ile Asp
                        965                 970                 975

Asn Gln Val Ser Ala Gln Val Lys Thr Thr Arg Ile Ala Glu Ala Ile
                    980                 985                 990

Ala Ser Val Gln Leu Tyr Val Asn Arg Ala Leu Ser Gly Leu Glu Asn
                    995                 1000                1005

Gly Gln Ser Ala Thr Asp Ala Val Asp Asn Ala Val Lys Ser Gly
                    1010                1015                1020

Val Phe Phe Thr Arg Asp Trp Asp Thr Tyr Asn Lys Arg Tyr Ser
                    1025                1030                1035

Thr Trp Ala Gly Val Ser Glu Leu Val Tyr Tyr Pro Glu Asn Tyr
                    1040                1045                1050

Val Asp Pro Thr Leu Arg Leu Gly Gln Thr Gly Met Met Asp Glu
                    1055                1060                1065

Met Leu Gln Thr Leu Ser Gln Ser Gln Leu Thr Ser Asp Thr Val
                    1070                1075                1080

Glu Asp Ala Phe Lys Thr Tyr Met Thr Arg Phe Glu Glu Ile Ala
                    1085                1090                1095

Asn Leu Asp Ile Val Ser Gly Tyr His Asp Asn Leu Ser Asp Gln
                    1100                1105                1110

Lys Gly Val Thr Tyr Leu Ile Gly Arg Ser Ala Ala Gly Asp Tyr
                    1115                1120                1125

Tyr Trp Arg Ser Ala Asp Ile Ser Lys Leu Ser Asp Gly Lys Leu
                    1130                1135                1140

Pro Ala Asn Ala Trp Ala Glu Trp Lys Lys Ile Thr Thr Ala Leu
                    1145                1150                1155

Thr Pro Val Asn Asn Leu Val Arg Pro Val Ile Phe Gln Ser Arg
                    1160                1165                1170

Leu Tyr Val Thr Trp Val Glu Ser Arg Glu Val Gly Ile Ser Ala
                    1175                1180                1185

Val Lys Lys Gln Asn Ser Glu Thr Lys Pro Leu Glu Tyr Ala Leu
                    1190                1195                1200

Lys Tyr Ala His Ile Leu His Asp Gly Thr Trp Ser Ala Pro Val
                    1205                1210                1215

Ser Val Lys Leu Glu Asn Gly Thr Leu Pro Leu Asp Ser Val Ala
                    1220                1225                1230
```

```
Ile Asp Val Thr Gly Met Tyr Cys Ala Lys Asp Thr Gln His Asp
1235                1240                1245

Gln Leu Tyr Ile Leu Phe Tyr Lys Lys Glu Thr Tyr Asn Asp
1250                1255                1260

Val Asn Asp Val Leu Lys Gly Ile Ile Leu His Asp Asp Gly Thr
1265                1270                1275

Thr Thr Ile Thr Ser Gly Asn Ser Val Ser Gly Leu Val Val Tyr
1280                1285                1290

Lys Gln Leu Asp Thr Thr Lys Glu Val Arg Leu Asn Thr Pro Tyr
1295                1300                1305

Pro Gly Gly Lys Thr Tyr Tyr Ser Ile Asn Asn Met Arg Glu Ser
1310                1315                1320

Ser Lys Trp Gly Asp Asp Asn Ile Ser Met Leu Ser Gly Cys Ser
1325                1330                1335

Val Lys Asp Phe Val Phe Thr Glu Gly Asp Gly Lys Leu Asn Val
1340                1345                1350

Ala Phe Asn Ala Thr Glu Arg Ile Ile Tyr Arg Gly Asn Pro Asp
1355                1360                1365

Ser Gln Gly Tyr Val Ala Leu Val Asn Met Ile Lys Ala Ile Gly
1370                1375                1380

Asn Ile Gly Asp Thr Phe Lys Ile Pro Val Leu Asn Ser Asn Gly
1385                1390                1395

Glu Gly Leu Asp Arg Pro Phe Thr Cys Ile Phe Arg Gln Pro Asp
1400                1405                1410

Glu Lys Thr Asp Ala Ile Ala Tyr Phe Ser Asp Val Gln Gly Leu
1415                1420                1425

Asn Ile Asp His Phe Ala Phe Asn Asp Glu Ser Gln Lys Met Leu
1430                1435                1440

Gly Arg Ile Leu Arg Pro Glu Glu Lys Asp Phe Tyr Lys Leu Glu
1445                1450                1455

Cys Val Asn Thr Asn Leu His Ile Tyr Lys Asp Ser Ser Lys Thr
1460                1465                1470

Ile Lys Pro Asp Asn Phe Val Tyr Phe Gly Pro Gly Met Asp Leu
1475                1480                1485

Ile Val Val Lys Gly Met Ile Val Glu Thr Leu Phe Gly Leu Phe
1490                1495                1500

Gly Glu Leu Lys Thr Gly Ile Lys Asp Lys Ser Val Lys Leu Ser
1505                1510                1515

Val Ser Ala Gly Val Ile Asp Asn Ser Pro Ala Ala Thr Lys Thr
1520                1525                1530

Lys Tyr Thr Phe Asp Glu Ser Leu Tyr Val Ile Glu Gly Gln Thr
1535                1540                1545

Val Ser Ile Gln Leu Ser Glu Phe Lys Glu Asn Asn Ile Asp Leu
1550                1555                1560

Glu Phe Thr Phe Leu Ala Ser Gly Asp Ser Gly Asn Ser Leu Gly
1565                1570                1575

Gln Ser Val Ile Ser Ala Thr Leu Thr Arg Thr Ser Glu Asn Thr
1580                1585                1590

Ile Pro Val Ile Ser Leu Asn Lys Thr Ser Asp Asn Ala Gln Tyr
1595                1600                1605

Leu Gln Tyr Gly Ile His Arg Ile Arg Val Asn Thr Leu Phe Ala
1610                1615                1620
```

```
Lys Gln Leu Val Ala Arg Ala Asn Ala Gly Leu Asp Thr Val Leu
    1625                1630                1635

Ser Met Ala Thr Gln Gln Leu Thr Glu Pro Lys Met Gly Lys Gly
    1640                1645                1650

Ala Tyr Ile Asp Leu Glu Leu Asn Ala Ser Ser Asp Gly Ser Ser
    1655                1660                1665

Ala Val Phe Glu Val Leu Met Cys Asp Val Phe Thr Asn Gly Asp
    1670                1675                1680

Arg Ile Ala Leu Thr Ser Gly Thr Leu Ser Pro Thr Ala Arg Thr
    1685                1690                1695

Ser Cys Ser Phe Phe Val Pro Arg Leu Asp Glu Ser Thr Ala Ser
    1700                1705                1710

Ala Tyr Asn Met Tyr Phe Cys Val Lys Thr Gln Asn Thr Glu Ser
    1715                1720                1725

Lys Arg Val Glu Val Thr Gly Gly Glu Gly Lys Trp Asp Tyr Gln
    1730                1735                1740

Tyr Val Asp Glu Ser Gly Ala Ala Ile Lys Pro Pro Tyr Thr Asp
    1745                1750                1755

Pro Tyr Ile Ala Ser Ile Tyr Val Arg Asn Asp Thr Thr Glu Pro
    1760                1765                1770

Met Asp Phe Asn Gly Ala Asn Ala Leu Tyr Phe Trp Glu Met Phe
    1775                1780                1785

Tyr Tyr Val Pro Met Met Val Phe Lys Arg Leu Leu Ser Glu Ser
    1790                1795                1800

Lys Phe Ala Glu Ala Thr Gln Trp Ile Lys Tyr Ile Trp Asn Pro
    1805                1810                1815

Asp Gly Tyr Leu Val Asn Asn Gln Pro Ala Thr Tyr Thr Trp Asn
    1820                1825                1830

Val Arg Pro Leu Glu Glu Asp Thr Ser Trp His Ala Asp Pro Leu
    1835                1840                1845

Asp Ser Val Asn Pro Asp Ala Val Ala Gln Ala Asp Pro Leu His
    1850                1855                1860

Tyr Lys Val Ala Thr Phe Met Ala Tyr Leu Asp Leu Leu Ile Ala
    1865                1870                1875

Arg Gly Asp Ala Ala Tyr Arg Gln Leu Gln Arg Asp Thr Leu Asn
    1880                1885                1890

Glu Ala Lys Met Trp Tyr Val Gln Ala Leu Asn Ile Leu Gly Asp
    1895                1900                1905

Glu Pro Tyr Gln Ser Ser Ser Ser Asp Trp Ser Ser Pro Val Leu
    1910                1915                1920

Ser Ser Ala Ala Asp Gln Thr Thr Glu Lys Asn Val Gln Gln Ala
    1925                1930                1935

Met Leu Ala Val Arg Gln Gln Pro Asp Ala Gly Glu Leu Arg Thr
    1940                1945                1950

Ala Asn Ser Leu Thr Ser Leu Phe Leu Pro Gln Gln Asn Glu Lys
    1955                1960                1965

Leu Ala Gly Tyr Trp Gln Thr Leu Ala Gln Arg Leu Tyr Asn Leu
    1970                1975                1980

Arg His Asn Leu Ser Ile Asp Gly Ser Pro Leu Ser Leu Ala Ile
    1985                1990                1995

Tyr Ala Ala Pro Ala Asp Pro Ala Ala Leu Leu Ser Ala Ala Val
    2000                2005                2010

Asn Ser Ala Ser Gly Gly Ser Glu Leu Pro Ala Ala Val Met Pro
```

```
                2015                2020                2025

Leu Tyr Arg Phe Pro Ile Ile Leu Glu Ser Ala Arg Gly Met Ala
        2030                2035                2040

Gly Gln Leu Thr Gln Phe Gly Ser Thr Leu Leu Ser Ile Ala Glu
        2045                2050                2055

Arg Gln Asp Ala Glu Ala Leu Ser Glu Leu Met Gln Thr Gln Gly
        2060                2065                2070

Ser Gln Leu Ile Leu Gln Ser Ile Ala Leu Gln Asn Ser Thr Ile
        2075                2080                2085

Ser Glu Ile Asp Ala Asp Lys Thr Val Leu Glu Ala Ser Leu Ser
        2090                2095                2100

Gly Ala Arg Ser Arg Leu Asp Arg Tyr Thr Thr Leu Tyr Asp Glu
        2105                2110                2115

Asp Val Asn Thr Gly Glu Gln Ala Met Asp Leu Phe Tyr Ala
        2120                2125                2130

Ser Ser Ile Gln Ala Asn Gly Gly Gln Ala Phe His Thr Val Ala
        2135                2140                2145

Gly Gly Leu Asp Leu Ala Pro Asn Ile Phe Gly Leu Ala Asp Gly
        2150                2155                2160

Gly Ser Arg Trp Gly Ala Ala Phe Thr Ala Leu Ala Ser Ile Ala
        2165                2170                2175

Asp Leu Ser Ala Ala Ala Ser His Thr Ala Ala Glu Arg Leu Ser
        2180                2185                2190

Gln Ser Glu Val Tyr Arg Arg Arg Gln Glu Trp Glu Ile Gln
        2195                2200                2205

Arg Asn Ala Ala Gln Ser Glu Ile Asp Gln Ile Asp Ala Gln Leu
        2210                2215                2220

Ala Ser Leu Thr Ile Arg Arg Lys Gly Ala Val Leu Gln Lys Thr
        2225                2230                2235

Tyr Leu Glu Thr Gln Gln Gly Gln Met Gln Ala Gln Met Thr Phe
        2240                2245                2250

Leu Gln Asn Lys Phe Thr Ser Lys Ala Leu Tyr Asn Trp Leu Arg
        2255                2260                2265

Gly Lys Leu Ala Ala Ile Tyr Tyr Gln Phe Tyr Asp Leu Thr Val
        2270                2275                2280

Ser Arg Cys Leu Met Ala Glu Ala Ala Tyr Ser Trp His Ile Lys
        2285                2290                2295

Gly Asn Gln Glu Thr Gly Thr Phe Ile Arg Pro Gly Ala Trp Gln
        2300                2305                2310

Gly Ile Tyr Ala Gly Leu Met Ala Gly Glu Ala Leu Met Leu Asn
        2315                2320                2325

Leu Ala Gln Met Glu Asn Ser Tyr Leu Thr Lys Asp Glu Arg Leu
        2330                2335                2340

Gln Glu Val Thr Arg Thr Val Cys Leu Ser Glu Phe Tyr Ser Gly
        2345                2350                2355

Leu Ser Ser Asn Lys Phe Ala Leu Ala Asp Thr Val Thr Thr Leu
        2360                2365                2370

Val Asn Ser Gly Lys Gly Asn Ala Gly Thr Thr Asp Asn Gly Val
        2375                2380                2385

Lys Ile Asp Gly Lys Gln Leu Leu Ala Thr Leu Lys Leu Ser Asp
        2390                2395                2400

Leu Asn Ile Lys Thr Asp Tyr Pro Glu Ser Leu Asp Lys Ala Lys
        2405                2410                2415
```

```
Arg Ile Lys Gln Ile Ser Val Thr Leu Pro Met Leu Val Gly Pro
            2420                2425                2430

Tyr Gln Asp Val Arg Ala Val Leu Ser Tyr Gly Gly Ser Val Val
    2435                2440                2445

Leu Pro Arg Gly Cys Thr Ala Val Ala Val Ser His Gly Met Asn
    2450                2455                2460

Asp Ser Gly Gln Phe Gln Leu Asp Phe Asn Asp Ser Arg Trp Leu
    2465                2470                2475

Pro Phe Glu Gly Ile Pro Val Asp Asp Ser Gly Thr Leu Thr Leu
    2480                2485                2490

Ser Phe Pro Asp Ile Thr Asp Lys Gln Gln Glu Asn Leu Leu Leu
    2495                2500                2505

Ser Leu Ser Asp Ile Ile Leu His Ile Arg Tyr Thr Ile Ala Ser
    2510                2515                2520

<210> SEQ ID NO 31
<211> LENGTH: 1421
<212> TYPE: PRT
<213> ORGANISM: Pantoea agglomerans

<400> SEQUENCE: 31

Met Gln Asn Thr Asp Gln Met Ser Leu Thr Pro Pro Ser Leu Pro Ser
1               5                   10                  15

Gly Gly Gly Ala Val Thr Gly Leu Lys Gly Asp Met Ser Gly Ala Gly
            20                  25                  30

Pro Asp Gly Ala Ala Thr Leu Ser Leu Pro Leu Pro Ile Ser Pro Gly
        35                  40                  45

Arg Gly Tyr Ala Pro Ser Leu Ser Leu Gly Tyr His Ser Arg Asn Gly
    50                  55                  60

Asn Gly Val Phe Gly Ala Gly Trp Ser Cys Gly Gln Met Ala Ile Arg
65                  70                  75                  80

Leu Gln Thr Arg Lys Gly Val Pro Phe Tyr Asp Gly Ser Asp Val Phe
                85                  90                  95

Thr Ala Pro Asp Gly Glu Val Leu Val Pro Ala Leu Asp Ala Ser Gly
            100                 105                 110

Lys Ala Glu Val Arg Thr Thr Thr Leu Leu Gly Glu Asn Leu Gly
        115                 120                 125

Gly Thr Phe Thr Val Gln Thr Tyr Arg Ser Arg Val Glu Thr Asp Phe
    130                 135                 140

Ser Arg Leu Glu Arg Trp Val Pro Gln Thr Asp Ala Ala Ala Asp Phe
145                 150                 155                 160

Trp Leu Ile Tyr Ser Pro Asp Gly Gln Ile His Leu Leu Gly Arg Asn
                165                 170                 175

Pro Gln Ala Arg Val Asn Asn Pro Glu Asp Thr Thr Gln Thr Ala Ala
            180                 185                 190

Trp Leu Ile Glu Ser Ser Val Ser Ala Ser Gly Glu Gln Ile Tyr Trp
        195                 200                 205

Gln Tyr Arg Gln Glu Asp Glu Leu Gly Cys Thr Gln Asp Glu Lys Thr
    210                 215                 220

Ala His Ala His Ala Leu Ala Gln Arg Tyr Leu Val Ala Val Trp Tyr
225                 230                 235                 240

Gly Asn Lys Ala Ala Ser Arg Thr Leu Pro Gly Leu Leu Ser Val Pro
                245                 250                 255

Ala Ala Gly Ser Trp Leu Phe Ser Leu Val Leu Asp Tyr Gly Glu Arg
```

```
              260                 265                 270
Thr Thr Asp Pro Ala Thr Leu Pro Ala Trp Leu Ser Pro Gly Ser Gly
            275                 280                 285

Thr Trp Leu Cys Arg Gln Asp Val Phe Ser Ser Trp Glu Tyr Gly Phe
            290                 295                 300

Glu Leu Arg Thr Arg Arg Leu Cys Arg Gln Val Leu Met Tyr His Asp
305                 310                 315                 320

Val Ala Ala Leu Ala Gly Gln Ser Gly Ser Asp Ala Val Pro Gln Leu
                        325                 330                 335

Val Thr Arg Leu Leu Leu Asp Tyr Asn Leu Ser Pro Ser Leu Thr Thr
                        340                 345                 350

Leu Lys Thr Ala Gln Gln Ala Ala Trp Glu Pro Asp Gly Thr Leu Arg
                        355                 360                 365

Ser Leu Pro Pro Leu Ala Phe Ser Trp Gln Thr Phe Pro Ser Thr Pro
                        370                 375                 380

Glu Lys Ser Val Ser Trp Gln Arg Arg Asn Asp Met Gly Lys Leu Asn
385                 390                 395                 400

Pro Gln Gln Pro Tyr Gln Met Val Asp Leu His Gly Glu Gly Leu Ala
                        405                 410                 415

Gly Ile Leu Tyr Gln Asp Ser Gly Ala Trp Trp Tyr Arg Glu Pro Val
                        420                 425                 430

Arg Gln Ser Gly Asp Asp Asn Ala Val Thr Trp Ala Ala Ala Arg
                        435                 440                 445

Pro Leu Pro Ala Phe Pro Ala Leu Arg Lys Gly Gly Met Leu Leu Asp
                        450                 455                 460

Leu Asp Gly Asp Gly Tyr Leu Glu Trp Val Val Thr Ala Pro Gly Val
465                 470                 475                 480

Ala Gly Cys Tyr Ala Gln Ala Pro Glu Gln Cys Trp Gln Arg Phe Thr
                        485                 490                 495

Pro Leu Ser Ala Leu Pro Val Glu Tyr Arg His Ser Arg Met Glu Ile
                        500                 505                 510

Ala Asp Val Thr Gly Ala Gly Leu Ala Asp Met Leu Leu Ile Gly Pro
                        515                 520                 525

Lys Ser Val Arg Leu Tyr Ser Gly Ser Gly Arg Gly Trp Lys Lys Ala
                        530                 535                 540

Arg Thr Val Met Gln Asp Ser Gly Ile Thr Leu Pro Val Pro Gly Thr
545                 550                 555                 560

Asn Ala Arg Val Met Val Ala Phe Ser Asp Met Ala Gly Ser Gly Gln
                        565                 570                 575

Gln His Leu Thr Glu Ile Lys Ala Ser Gly Val Arg Tyr Trp Pro Ser
                        580                 585                 590

Leu Gly His Gly Arg Phe Ala Ala Pro Val Thr Leu Pro Gly Phe Ser
                        595                 600                 605

Gln Pro Ala Glu Thr Phe Asn Pro Ala Gln Leu Tyr Leu Ala Asp Val
                        610                 615                 620

Asp Gly Ser Gly Thr Thr Asp Leu Ile Tyr Ala Leu Ser Asp His Leu
625                 630                 635                 640

Leu Val Trp Leu Asn Gln Ser Gly Asn Ser Phe Asp Ala Pro Phe Arg
                        645                 650                 655

Ile Ser Leu Pro Glu Gly Val Arg Tyr Asp Asn Thr Cys Ser Leu Gln
                        660                 665                 670

Val Ala Asp Ile Gln Gly Leu Gly Ile Ser Ser Leu Val Leu Ser Val
                        675                 680                 685
```

```
Pro His Pro Thr Pro Arg His Trp Val Cys His Leu Thr Glu Lys
    690                 695                 700

Pro Trp Leu Leu Asp Gly Met Asn Asn Met Gly Ala Arg His Thr
705                 710                 715                 720

Leu Cys Tyr Arg Ser Ser Ala Gln Phe Trp Leu Asp Glu Lys Ala Ala
                    725                 730                 735

Ala Thr Ala Asp Arg Pro Ala Pro Ala Cys Tyr Leu Pro Phe Ala Leu
            740                 745                 750

His Thr Leu Ser Arg Thr Glu Val Ser Asp Glu Ile Thr Gly Asn Arg
                755                 760                 765

Leu Thr Arg Thr Ile Arg Tyr Arg His Gly Val Trp Asp Arg Arg Glu
    770                 775                 780

Arg Glu Phe Arg Gly Phe Gly Phe Val Glu Val Ser Asp Ala Glu Ala
785                 790                 795                 800

Leu Ala Lys Gln Thr Glu Gly Met Ser Ala Pro Ala Val Lys Arg Ser
                805                 810                 815

Trp Tyr Ala Thr Gly Leu Ala Ala Val Asp Ala Gln Leu Pro Asp Glu
            820                 825                 830

Phe Trp Lys Gly Asp His Ala Ala Phe Ala Gly Phe Thr Pro Arg Phe
            835                 840                 845

Thr Thr Gly Asp Gly Glu Gln Glu Ala Val Leu Asp Thr Ile Ser Asp
850                 855                 860

Asp Thr Arg Phe Trp Leu Thr Arg Ala Ile Arg Gly Thr Leu Leu Arg
865                 870                 875                 880

Ser Glu Leu Tyr Gly Ala Asp Gly Ser Ser Gln Ala Gly Ile Pro Tyr
                885                 890                 895

Ser Ile Thr Glu Ser Arg Pro Gln Val Arg Leu Ile Thr Glu Ala Gly
            900                 905                 910

Asn Ser Pro Val Val Trp Pro Ser Val Ile Glu Asn Arg Thr Ser His
            915                 920                 925

Tyr Glu Arg Val Ser Ser Asp Pro Gln Cys Gly Gln Gln Ile Leu Leu
    930                 935                 940

Thr Ser Asn Glu Tyr Gly Gln Pro Leu Arg Gln Ile Gly Ile Ser Tyr
945                 950                 955                 960

Pro Arg Arg Thr Arg Pro Asp Ala Ser Pro Tyr Pro Asp Asp Leu Pro
                965                 970                 975

Asp Gly Leu Phe Ala Asp Ser Phe Asp Glu Gln Gln Ala Leu Arg
            980                 985                 990

Leu Thr Leu Thr Gln Ser Ser Trp His Thr Leu Lys Asp Ile Ser Ser
                995                 1000                1005

Gly Ile Trp Leu Pro Ala Val Ala Asp Ala Thr Arg Ser Asp Leu
    1010                1015                1020

Phe Val His Gln Ala Ala Gln Val Pro Pro Ala Gly Leu Thr Leu
    1025                1030                1035

Glu Asn Leu Leu Thr Asp Ser Ala Leu Leu Thr Ser Pro Val Phe
    1040                1045                1050

Gly Gly Gln Ser Gln Ile Trp Tyr Gln Asp Arg Ala Gly Gln Ala
    1055                1060                1065

Ser Ile Thr Ser Pro Asp Phe Pro Pro Arg Pro Ser Phe Ser Glu
    1070                1075                1080

Thr Ala Ala Leu Asp Glu Ala Gln Val Ser Ala Leu Ser Ala Asp
    1085                1090                1095
```

```
Ile Asp Gln Thr Lys Leu Glu Gln Ala Gly Tyr Thr Arg Ser Ala
1100               1105                1110

Tyr Leu Phe Ala Arg Ser Gly Glu Glu Ser Lys Thr Leu Trp Ala
    1115                1120                1125

Val Arg Gln Gly Tyr Ile Thr Phe Ser Gly Ala Asp His Phe Tyr
1130                1135                1140

Leu Pro Ile Ala Ala Gln Gln Thr Leu Leu Ala Gly Lys Thr Thr
    1145                1150                1155

Val Thr Tyr Asp Pro Tyr Asp Cys Val Val Leu Gln Ala Lys Asp
1160                1165                1170

Ala Ala Gly Ala Val Thr Ser Ala Thr Tyr Asp Trp Arg Phe Leu
    1175                1180                1185

Ala Pro Thr Gln Ile Thr Asp Ile Asn Asp Asn Leu Lys Ser Val
1190                1195                1200

Thr Leu Asp Ala Leu Gly Arg Val Thr Ser Gln Arg Phe Ser Gly
    1205                1210                1215

Thr Glu Asn Gly Lys Pro Ala Gly Tyr Ser Asp Asp Glu Phe Pro
1220                1225                1230

Leu Pro Ala Ser Ala Asp Ala Ala Leu Ala Leu Ser Ala Pro Leu
    1235                1240                1245

Pro Val Ala Gln Cys Ile Ile Tyr Val Pro Asp Ser Trp Met Leu
1250                1255                1260

Thr Gly Glu Gln Gln Gln Pro Pro His Val Ile Thr Leu Leu Thr
    1265                1270                1275

Asp Arg Tyr Asp Ser Asp Ser Gln Gln Gln Ile Arg Gln Gln Val
1280                1285                1290

Val Phe Ser Asp Gly Phe Gly Arg Val Leu Gln Ala Ala Ser Arg
    1295                1300                1305

Gln Val Asn Gly Glu Ala Trp Gln Arg Ala Ala Asn Gly Ser Phe
1310                1315                1320

Val Ala Gly Thr Asn Asp Ser Pro Val Leu Thr Glu Thr Thr Phe
    1325                1330                1335

Arg Trp Ala Val Thr Gly Arg Thr Glu Tyr Asp Asn Lys Gly Gln
1340                1345                1350

Ala Ile Arg Ala Tyr Gln Pro Tyr Phe Leu Asp Ser Trp Lys Tyr
    1355                1360                1365

Val Arg Asp Asp Ser Ala Arg Gln Asp Leu Tyr Ala Asp Thr His
1370                1375                1380

Tyr Tyr Asp Pro Val Gly Arg Glu Arg Gln Val Ile Thr Ala Lys
    1385                1390                1395

Gly Trp Leu Arg Arg Val Ile His Thr Pro Trp Phe Val Val Ser
1400                1405                1410

Glu Asp Glu Asn Asp Thr Gln Ala
    1415                1420

<210> SEQ ID NO 32
<211> LENGTH: 1004
<212> TYPE: PRT
<213> ORGANISM: Pantoea agglomerans

<400> SEQUENCE: 32

Met Ser Ala Ala Tyr Val Leu Ser Asn Leu Ser Tyr Lys Leu Glu Asn
1               5                   10                  15

Pro Met Ser Thr Ser Leu Tyr Ser Arg Thr Pro Ser Val Thr Ile Leu
            20                  25                  30
```

Asp Asn Arg Gly Leu Thr Val Arg Gly Ile Ala Tyr Gln Arg His Pro
        35                  40                  45

Asp Thr Pro Ala Val Thr Ser Glu Arg Ile Thr Arg His Gln Tyr Asp
 50                  55                  60

Ala Arg Gly Phe Leu Met Gln Ser Ala Asp Pro Arg Leu His Asp Ala
 65                  70                  75                  80

Gly Leu Ala Asn Val Ser Tyr Arg Thr Asn Leu Thr Gly Ser Val Leu
                 85                  90                  95

Arg Ser Gln Gly Val Asp Asn Gly Ile Thr Val Thr Leu Asn Asp Ala
            100                 105                 110

Ala Gly Arg Pro Phe Leu Ala Val Ser Asn Ile Ser Thr Ala Gly Asp
        115                 120                 125

Gly Thr Glu Asp Arg Ser Gln Ala Val Thr Arg Thr Cys Gln Tyr Glu
    130                 135                 140

Asp Ala Thr Leu Pro Gly Arg Pro Leu Ser Ile Thr Glu Gln Val Asn
145                 150                 155                 160

Gly Gly Ala Ala Arg Ile Thr Glu Arg Phe Val Tyr Ala Gly Asn Ala
                165                 170                 175

Val Glu Glu Lys Ala Leu Asn Leu Ala Gly Gln Pro Val Ser His Tyr
            180                 185                 190

Asp Thr Ala Gly Leu Thr Gln Thr Asp Ser Ile Ala Leu Thr Gly Val
        195                 200                 205

Pro Leu Ser Val Thr Arg Arg Leu Leu Lys Asp Ala Asp Asn Pro Asp
    210                 215                 220

Ala Val Ala Asp Trp Gln Gly Thr Asp Ala Ser Val Trp Asn Asp Pro
225                 230                 235                 240

Leu Asp Val Glu Thr Tyr Thr Thr Leu Ser Thr Ala Asp Ala Thr Gly
                245                 250                 255

Ala Val Leu Thr Thr Thr Asp Ala Lys Gly Asn Leu Gln Arg Leu Ala
            260                 265                 270

Tyr Asp Val Ala Gly Leu Leu Ser Gly Ser Trp Leu Thr Leu Lys Asp
        275                 280                 285

Gly Thr Glu Gln Val Ile Val Thr Ser Leu Thr Tyr Ser Ala Ala Gly
    290                 295                 300

Gln Lys Leu Arg Glu Glu His Gly Asn Gly Val Val Thr Thr Tyr Thr
305                 310                 315                 320

Tyr Glu Ala Glu Thr Gln Arg Leu Thr Gly Ile Lys Thr Ala Arg Pro
                325                 330                 335

Ala Gly His Thr Ser Gly Ala Lys Val Leu Gln Asp Leu Arg Tyr Thr
            340                 345                 350

Tyr Asp Pro Val Gly Asn Val Leu Lys Ile Ser Asn Asp Ala Glu Glu
        355                 360                 365

Thr Arg Phe Trp Arg Asn Gln Lys Val Ala Pro Glu Ser Ala Tyr Val
    370                 375                 380

Tyr Asp Ser Leu Tyr Gln Leu Val Ser Ala Thr Gly Arg Glu Met Ala
385                 390                 395                 400

Asn Ala Gly Gln Gln Gly Ser Ser Ser Ser Ala Thr Val Pro Leu
                405                 410                 415

Pro Ala Asp Ser Ser Ala Phe Thr Asn Tyr Thr Arg Thr Tyr Ala Tyr
            420                 425                 430

Asp Glu Ala Gly Asn Leu Thr Gln Val Arg His Thr Pro Ala Thr Gly
        435                 440                 445

```
Ser Gly Tyr Thr Thr Lys Ile Thr Val Ser Asp Lys Ser Asn Arg Ala
    450                 455                 460

Val Leu Ser Val Leu Thr Lys Asn Pro Ser Asp Val Asp Ala Leu Phe
465                 470                 475                 480

Thr Ala Gly Gly Gln Gln Lys Gln Leu Gln Pro Gly Gln Ser Leu Ile
                    485                 490                 495

Trp Thr Pro Arg Asn Glu Leu Leu Lys Val Met Pro Ile Met Arg Asp
            500                 505                 510

Gly Gly Thr Asp Asp Ser Glu Ser Tyr Arg Tyr Asp Gly Gly Ser Gln
            515                 520                 525

Arg Leu Leu Lys Val Ser Val Gln Lys Thr Gly Asn Ser Thr Gln Thr
    530                 535                 540

Gln Arg Ala Leu Tyr Leu Pro Gly Leu Glu Leu Arg Asn Thr Thr Ser
545                 550                 555                 560

Gly Asp Thr Glu Thr Glu Ser Leu Gln Val Val Thr Ala Gly Glu Ala
                    565                 570                 575

Gly Arg Ala Gln Val Arg Val Leu His Trp Glu Ser Gly Thr Pro Asp
                580                 585                 590

Ser Val Ser Asn Asp Gln Leu Arg Tyr Ser Tyr Asp Asn Leu Thr Gly
            595                 600                 605

Ser Ser Gly Leu Glu Leu Asp Ser Ser Gly Asn Ile Ile Ser Met Glu
    610                 615                 620

Glu Tyr Tyr Pro Tyr Gly Gly Thr Ala Val Trp Thr Ala Arg Ser Ala
625                 630                 635                 640

Val Glu Ala Lys Tyr Lys Thr Val Arg Tyr Ser Gly Lys Glu Arg Asp
                    645                 650                 655

Ala Thr Gly Leu Tyr Tyr Tyr Gly Tyr Arg Tyr Tyr Gln Pro Trp Ala
                660                 665                 670

Gly Arg Trp Leu Ser Ala Asp Pro Ala Gly Thr Ala Asp Gly Leu Asn
            675                 680                 685

Leu Phe Arg Met Val Arg Asn Asn Pro Val Thr Leu Lys Asp Thr Asn
    690                 695                 700

Gly Leu Ile Ser Thr Gly Gln Asp Ala Arg Lys Leu Val Ala Glu Ala
705                 710                 715                 720

Phe Val His Pro Leu His Met Thr Val Phe Glu Arg Ile Ser Ser Glu
                    725                 730                 735

Glu Asn Leu Ala Met Ser Val Arg Glu Ala Gly Ile Tyr Thr Ile Ser
                740                 745                 750

Ala Leu Gly Glu Gly Ala Ala Lys Gly His Asn Ile Leu Glu Lys
            755                 760                 765

Thr Ile Lys Pro Gly Ser Leu Lys Ala Val Tyr Gly Asp Asn Ala Glu
    770                 775                 780

Ser Ile Leu Ala Gln Ala Lys Arg Ser Gly Phe Val Gly Arg Val Gly
785                 790                 795                 800

Gln Trp Asp Ala Ser Gly Val Arg Gly Ile Tyr Ala His Asn Thr Pro
                    805                 810                 815

Gly Gly Glu Asp Leu Ala Tyr Pro Val Asn Leu Lys Asn Ser Ser Ala
                820                 825                 830

Asn Glu Leu Val Asn Ala Trp Ile Lys Phe Lys Ile Thr Pro Tyr
            835                 840                 845

Thr Gly Asp Tyr Asp Met His Asp Ile Ile Lys Ile Ser Asp Gly Lys
    850                 855                 860

Gly His Val Pro Met Ala Glu Ser Asn Glu Glu Lys Gly Val Lys Asp
```

```
             865                 870                 875                 880
    Met Ile Asn Glu Gly Val Ala Gln Val Asp Pro Ala Arg Pro Phe Thr
                        885                 890                 895

Ser Thr Ala Met Asn Val Val Arg His Gly Pro Gln Val Asn Phe Val
                        900                 905                 910

Pro Tyr Met Trp Glu His Glu His Glu Asn Val Val Arg Asp Asn Gly
                        915                 920                 925

Tyr Leu Gly Val Val Ala Arg Pro Gly Phe Pro Val Ala Met Val
                930                 935                 940

His Lys Gly Glu Trp Thr Val Phe Asp Asn Lys Asn Glu Leu Phe Glu
    945                 950                 955                 960

Phe Tyr Lys Ser Thr Asn Thr Pro Leu Pro Glu His Trp Ser Gln Asp
                        965                 970                 975

Phe Val Glu Arg Gly Lys Gly Asn Val Ala Thr Pro Arg His Ala Glu
                        980                 985                 990

Ile Leu Asp Arg Asn Ser Ser Arg  Leu Arg Ala Ala
                        995                 1000

<210> SEQ ID NO 33
<211> LENGTH: 692
<212> TYPE: PRT
<213> ORGANISM: Pantoea agglomerans

<400> SEQUENCE: 33

Met Cys Ser Val Ala Asp Phe Asp Arg Leu His Asn Ile Lys Gln Glu
    1               5                   10                  15

Asn Ile Met Gly Thr Ser Leu Tyr Ser Lys Thr Pro Ser Val Thr Ile
                    20                  25                  30

Leu Asp Asn Arg Gly Leu Thr Val Arg Asp Ile Ala Tyr Gln Arg His
                    35                  40                  45

Pro Asp Thr Pro Ala Val Thr Ser Glu Arg Ile Thr Arg His Gln Tyr
                50                  55                  60

Asp Ala Arg Gly Phe Leu Met Gln Ser Ala Asp Pro Arg Leu His Asp
    65                  70                  75                  80

Ala Gly Leu Ala Asn Val Ser Tyr Arg Thr Asn Leu Thr Gly Ser Val
                    85                  90                  95

Leu Arg Ser Gln Gly Val Asp Asn Gly Ile Thr Val Thr Leu Asn Asp
                    100                 105                 110

Ala Ala Gly Arg Pro Phe Leu Ala Val Ser Asn Ile Ser Thr Ala Gly
                    115                 120                 125

Asp Gly Thr Glu Asp Arg Ser Gln Ala Val Thr Arg Thr Cys Gln Tyr
                    130                 135                 140

Glu Asp Ala Thr Leu Pro Gly Arg Pro Leu Ser Ile Thr Glu Gln Val
    145                 150                 155                 160

Asn Gly Gly Ala Ala Arg Ile Thr Glu Arg Phe Val Tyr Ala Gly Asn
                    165                 170                 175

Ala Val Glu Glu Lys Ala Leu Asn Leu Ala Gly Gln Pro Val Ser His
                    180                 185                 190

Tyr Asp Thr Ala Gly Leu Thr Gln Thr Asp Ser Ile Ala Leu Thr Gly
                    195                 200                 205

Val Pro Leu Ser Val Thr Arg Arg Leu Leu Lys Asp Ala Asp Asn Pro
                210                 215                 220

Asp Ala Val Ala Asp Trp Gln Gly Thr Asp Ala Ser Val Trp Asn Asp
    225                 230                 235                 240
```

```
Pro Leu Asp Val Glu Thr Tyr Thr Thr Leu Ser Thr Ala Asp Ala Thr
                245                 250                 255
Gly Ala Val Leu Thr Thr Thr Asp Ala Lys Gly Asn Leu Gln Arg Leu
            260                 265                 270
Ala Tyr Asp Val Ala Gly Leu Leu Ser Gly Ser Trp Leu Thr Leu Lys
        275                 280                 285
Asp Gly Thr Glu Gln Val Ile Val Thr Ser Leu Thr Tyr Ser Ala Ala
    290                 295                 300
Gly Gln Lys Leu Arg Glu His Gly Asn Gly Val Val Thr Thr Tyr
305                 310                 315                 320
Thr Tyr Glu Ala Glu Thr Gln Arg Leu Thr Gly Ile Lys Thr Ala Arg
                325                 330                 335
Pro Ala Gly His Thr Ser Gly Ala Lys Val Leu Gln Asp Leu Arg Tyr
            340                 345                 350
Thr Tyr Asp Pro Val Gly Asn Val Leu Lys Ile Ser Asn Asp Ala Glu
        355                 360                 365
Glu Thr Arg Phe Trp Arg Asn Gln Lys Val Val Pro Glu Ser Ala Tyr
    370                 375                 380
Val Tyr Asp Ser Leu Tyr Gln Leu Val Ser Ala Thr Gly Arg Glu Met
385                 390                 395                 400
Ala Asn Ala Gly Gln Gln Gly Ser Ser Ser Ser Ala Thr Val Pro
                405                 410                 415
Leu Pro Ala Asp Ser Ser Ala Phe Thr Asn Tyr Thr Arg Asn Tyr Thr
            420                 425                 430
Tyr Asp Glu Ala Gly Asn Leu Thr Gln Val Arg His Thr Pro Ala Thr
        435                 440                 445
Gly Ser Gly Tyr Thr Thr Lys Ile Thr Val Ser Asp Lys Ser Asn Arg
    450                 455                 460
Gly Val Leu Ser Thr Leu Thr Glu Asn Pro Ser Asp Val Asp Ala Leu
465                 470                 475                 480
Phe Thr Ala Gly Gly Gln Gln Lys Gln Leu Gln Pro Gly Gln Ser Leu
                485                 490                 495
Ile Trp Thr Pro Arg Asn Glu Leu Leu Lys Val Thr Pro Val Ala Arg
            500                 505                 510
Asp Gly Gly Ala Asp Asp Ser Glu Ser Tyr Arg Tyr Asp Gly Gly Ser
        515                 520                 525
Leu Arg Leu Leu Lys Val Ser Val Gln Lys Thr Gly Asn Ser Thr Gln
    530                 535                 540
Thr Gln Arg Ala Leu Tyr Leu Pro Gly Leu Glu Leu Arg Asn Thr Thr
545                 550                 555                 560
Ser Gly Asp Thr Glu Thr Glu Ser Leu Gln Val Val Thr Val Gly Glu
                565                 570                 575
Ala Gly Arg Ala Gln Val Arg Val Leu His Trp Glu Ser Gly Thr Pro
            580                 585                 590
Asp Ser Val Ser Asn Asp Pro Val Arg Tyr Ser Tyr Asp Asn Leu Thr
        595                 600                 605
Gly Ser Ser Gly Leu Glu Leu Asp Ser Ser Gly Asn Ile Ile Ser Met
    610                 615                 620
Glu Glu Tyr Tyr Pro Tyr Gly Gly Thr Ala Val Trp Thr Ala Arg Ser
625                 630                 635                 640
Ala Val Glu Ala Lys Tyr Lys Thr Val Arg Tyr Ser Gly Lys Glu Arg
                645                 650                 655
Asp Ala Thr Gly Leu Tyr Tyr Tyr Gly Tyr Arg Tyr Tyr Gln Pro Trp
```

```
                    660                 665                 670
Ala Glu Arg Gly Pro Gly Gly His Gly Gly Arg Ala Glu Pro Val Gln
                675                 680                 685

Asn Gly Ala Gln
    690

<210> SEQ ID NO 34
<211> LENGTH: 2518
<212> TYPE: PRT
<213> ORGANISM: Pantoea agglomerans

<400> SEQUENCE: 34

Met Tyr Leu Thr Glu Glu Ile Leu Ala Lys Leu Asn Ala Gly Asn Gly
1               5                   10                  15

Lys Leu Gln Ser Thr Val Glu Gln Ile Ile Thr Leu Pro Asp Ile Met
                20                  25                  30

Leu His Ser Phe Ala Gln Val Lys Glu Leu Ala Gly Asp Lys Leu Ser
            35                  40                  45

Trp Gly Glu Lys Asn Phe Leu Tyr Gln Gln Ala Gln Lys Gln Leu Lys
        50                  55                  60

Glu Asn Lys Met Ala Glu Ser Arg Ile Leu Ser Arg Ala Asn Pro Gln
65                  70                  75                  80

Leu Ala Asn Ala Val Arg Met Gly Ile Arg Gln Ser Ala Met Leu Gly
                85                  90                  95

Ser Tyr Asp Asp Leu Phe Pro Gln Arg Ala Ser Arg Phe Val Lys Pro
                100                 105                 110

Gly Ala Val Ala Ser Met Phe Ser Pro Ala Gly Tyr Leu Thr Glu Leu
            115                 120                 125

Tyr Arg Glu Ala Arg Gly Leu His Asp Asp Thr Ser Asp Tyr His Leu
        130                 135                 140

Asp Thr Arg Arg Pro Asp Leu Ala Ser Met Val Leu Ser Gln Ser Asn
145                 150                 155                 160

Met Asp Thr Glu Leu Ser Thr Leu Ser Leu Ser Asn Glu Leu Leu Leu
                165                 170                 175

Lys Leu Ile Gln Ser Lys Glu Ser Leu Asn Tyr Asp Gln Val Ile Glu
            180                 185                 190

Lys Leu Ala Thr Tyr Arg Leu Thr Gly Thr Thr Pro Tyr Asn Gln Pro
        195                 200                 205

Tyr Glu Thr Ile Arg Gln Ala Ile Leu Leu Gln Asp Pro Glu Phe Asn
    210                 215                 220

Ala Phe Ser Asn Asn Pro Ala Val Ala Val Lys Ile Asn Thr Ser Gly
225                 230                 235                 240

Leu Leu Gly Ile Thr Ser Asp Ile Ala Pro Glu Leu His Ala Ile Leu
                245                 250                 255

Thr Glu Glu Ile Thr Glu Lys Lys Thr Glu Ala Leu Ile Lys Lys Asn
            260                 265                 270

Phe Gly Asp Ala Asn Ile Asn Gln Phe Gln Asn Leu Ala Trp Leu Ala
        275                 280                 285

His Trp Tyr Gly Leu Ser Tyr Glu Glu Leu Asn Asn Leu Val Gly Met
    290                 295                 300

Ile Trp Ser Arg Asp Asp Leu Asp Pro Ala Val Glu His Tyr Lys Asn
305                 310                 315                 320

Ser Ser Leu Val Thr Leu Val Ala Glu Asp Gly Gly Leu Asn Ala
                325                 330                 335
```

```
Val Leu Ile Lys Arg Thr Lys Gly His Asp Ser Asp Asp Met His Tyr
            340                 345                 350

Ala Glu Leu Ile Pro Val Gly Gly Asp Lys Phe Gln Tyr Asn Phe Ser
            355                 360                 365

Leu Ile Asp Ala Glu Ser Ser Ser Val Tyr Tyr Gln Phe Gly Thr Lys
            370                 375                 380

Gly Lys Asn Ser Gln Asp Leu Val Pro Val Ile His Glu Pro Leu Leu
385                 390                 395                 400

Gly Asn Thr Pro Tyr Ala Val Thr Phe Thr Leu Thr Gln Glu Gln Leu
            405                 410                 415

Ser Asn Pro Val Glu Ile Ser Leu Thr His Gly Ser Gly Gly Gly Asp
            420                 425                 430

Arg Leu Thr Ser Thr Ile Phe Thr Val Thr Thr Tyr Pro Phe Asp Thr
            435                 440                 445

Phe Leu Leu Lys Leu Asn Lys Leu Ile Arg Leu Tyr Lys Ala Thr Gly
            450                 455                 460

Ile Ser Pro Ala Ser Ile Arg Thr Val Ile Glu Ser Asp Asn Thr Asp
465                 470                 475                 480

Leu Ile Ile Thr Glu Ser Val Leu Asn Gln Leu Phe Trp Thr Asn Tyr
            485                 490                 495

Tyr Thr Gln Thr Phe Glu Met Glu Phe Ser Ala Ala Leu Val Leu Ala
            500                 505                 510

Gly Ala Asp Ile Gly Gln Ile Ala His Ser Glu Ser Gln Pro Ser Ala
            515                 520                 525

Phe Thr Arg Leu Phe Asn Thr Pro Leu Leu Asp Asn Gln Gln Phe Ser
            530                 535                 540

Ala Ser Asp Glu Ser Leu Asp Leu Glu Pro Gly Lys Gly Ala Asp Ala
545                 550                 555                 560

Phe Arg Ile Ala Val Leu Lys Arg Ala Leu Gln Val Asn Asp Ala Gly
            565                 570                 575

Leu Tyr Thr Leu Tyr Gly Leu Ser Phe Thr Asp Lys Asp Lys Asn Gly
            580                 585                 590

Lys Leu Ile Pro Phe Thr Thr Asn Ile Glu Asn Leu Ser Ala Leu Tyr
            595                 600                 605

Arg Thr Arg Leu Leu Ala Asp Ile Phe Asn Ile Ser Val Thr Glu Leu
            610                 615                 620

Ser Met Leu Leu Ser Val Ser Pro Tyr Ala Ser Gln Lys Val Asp Ser
625                 630                 635                 640

Leu Lys Gly Gln Ala Leu Tyr Gln Phe Val Ala Thr Leu Ser Asp Tyr
            645                 650                 655

Met Gln Arg Leu Lys Ala Met Asn Trp Ser Val Ser Asp Leu Tyr Leu
            660                 665                 670

Met Leu Thr Asn Ser Tyr Ser Thr Val Leu Ser Pro Glu Ile Lys Asn
            675                 680                 685

Leu Met Thr Thr Leu Lys Asn Gly Leu Ser Gln Asp Phe Asn Asn
            690                 695                 700

Thr Asp Glu Ile Ala Gln Leu Asn Ala Thr Ala Pro Leu Ile Ala Ala
705                 710                 715                 720

Ala Met Gln Leu Asp Phe Thr Glu Thr Ala Ala Leu Leu Glu Trp
            725                 730                 735

Leu Asn Gln Leu Gln Pro Ala Gly Leu Thr Val Ala Gly Phe Leu Ser
            740                 745                 750

Leu Val Asn Gln Thr Thr Leu Glu Asp Lys Asp Val Val Lys Leu Val
```

```
              755                 760                 765
Ser Phe Cys Gln Val Met Gly Gln Leu Ala Leu Ile Val Arg Lys Ala
    770                 775                 780

Ala Leu Gly Ser Ser Glu Ile Thr Phe Ala Val Ala His Pro Ala Ile
785                 790                 795                 800

Phe Lys Lys Asp Ala Asn Ser Leu Ala Gln Asp Ile Gly Thr Leu Phe
                805                 810                 815

Asp Leu Thr Gln Leu His Ala Phe Leu Thr Asp Cys Gly Thr Tyr Ala
            820                 825                 830

Ser Glu Ile Leu Thr Ser Leu Asn Glu Gly Asn Leu Asp Val Ser Thr
        835                 840                 845

Val Ala Thr Ala Leu Thr Leu Asp Lys Thr Ser Leu Ala Gln Ala Leu
850                 855                 860

Ala Gln Val Ser Glu Ser Gln Ala Phe Ser Asn Trp His Glu Leu Arg
865                 870                 875                 880

Asp Ala Leu Gln Trp Thr Asp Ala Ala Ser Ile Phe Asn Ile Thr Pro
                885                 890                 895

Val Ala Leu Thr Ala Met Val Asn Leu Lys Phe Ser Gly Asp Asn Ser
            900                 905                 910

Ser Pro Tyr Gln Glu Trp Val Thr Val Ser Lys Ala Met Gln Val Gly
        915                 920                 925

Leu Asn Gln Thr Gln Ser Ala Gln Leu Gln Ala Ser Leu Asp Glu Ser
    930                 935                 940

Leu Ser Ala Ala Leu Ser Ala Tyr Val Ile Lys Asn Ile Thr Pro Pro
945                 950                 955                 960

Ser Val Thr Asp Arg Asp Glu Leu Tyr Gly Trp Leu Leu Ile Asp Asn
                965                 970                 975

Gln Val Ser Ala Gln Ile Lys Thr Thr Arg Ile Ala Glu Ala Ile Ala
            980                 985                 990

Ser Val Gln Leu Tyr Val Asn Arg Ser Leu Thr Gly Gln Glu Asp Gly
        995                1000                1005

Val Asp Ser Lys Val Lys Ser Gly Gln Phe Phe Thr Ala Asp Trp
    1010                1015                1020

Asp Thr Tyr Asn Lys Arg Tyr Ser Thr Trp Ala Gly Val Ser Glu
    1025                1030                1035

Leu Val Tyr Tyr Pro Glu Asn Tyr Val Asp Pro Thr Leu Arg Ile
    1040                1045                1050

Gly Gln Thr Gly Met Met Asp Glu Met Leu Gln Thr Leu Ser Gln
    1055                1060                1065

Ser Gln Ile Asn Leu Asp Thr Val Ser Asp Gly Met Gly Arg Tyr
    1070                1075                1080

Leu Thr Asp Phe Glu Glu Ile Ala Asn Leu Lys Phe Leu Ser Gly
    1085                1090                1095

Tyr His Asp Asn Val Ser Gly Arg Gln Gly Lys Thr Trp Phe Ile
    1100                1105                1110

Gly Gly Ser Gln Ser Glu Pro Gln Lys Phe Tyr Trp Arg Ser Leu
    1115                1120                1125

Asp Tyr Ser Lys Gly Asp Gly Glu Glu Phe Ala Ala Asn Ala Trp
    1130                1135                1140

Ser Glu Trp Asn His Ile Ser Cys Ala Ile Thr Pro Leu Pro Gly
    1145                1150                1155

Phe Val Arg Val Val Leu Phe Asn Ser Arg Leu Tyr Leu Ala Cys
    1160                1165                1170
```

```
Val Glu Lys Lys Glu Ile Arg Asp Ser Glu Asn Lys  Asn Lys Ala
1175             1180                1185

Ser Tyr Gln Leu Lys Ile Ala His Ile Leu Tyr Asn  Gly Glu Trp
1190             1195                1200

Ser Ala Pro Phe Ser His Asp Ile Thr Asp Leu Tyr  Glu Ala Gly
1205             1210                1215

Phe Asp Pro Ser Thr Thr Val Met His Leu Ser Val  His Asp Glu
1220             1225                1230

Ser Asp Ala Ile Val Cys Ile Phe Asn Asn Ser Ala  Leu Glu Ser
1235             1240                1245

Asp Lys Asn Lys Gly Val Ala Val Asn Ala Asp Met  Ser Phe Asn
1250             1255                1260

Asn Ile Asp Ser Lys Arg Val Asp Gln Ile Ile Ser  Leu Leu Val
1265             1270                1275

Pro Asp Arg Phe Ile Asp Glu Gly Asn Val Ile Asp  Asn Leu Val
1280             1285                1290

Ser Glu Leu Lys Gly Ser Glu Val Thr Glu Asn Lys  Lys Thr Leu
1295             1300                1305

Glu Asn Asp Ser Phe Thr Ile Asp Gly Ser Ile Asn  Leu Asn Lys
1310             1315                1320

His Ser Ile Asp Ile Thr Gly Lys Ala Asn Leu Asp  Ile Gln Ala
1325             1330                1335

Ser Ile Ala Val Arg Ser Lys Ala Ser Pro Thr Ser  His Glu Arg
1340             1345                1350

Glu Leu Ile Gly Trp Leu Asp Glu Ser Gln Phe Asp  Tyr Ile Arg
1355             1360                1365

Leu Phe Arg Gly Gly Tyr Asn Phe Gly Gln Asn Asp  Gly Ile Leu
1370             1375                1380

Glu Ser Cys Met Ile Ser Ala Val Asn Ser Ala Tyr  Thr Cys Phe
1385             1390                1395

Leu Leu Arg Ala Asp His Phe Ser Gly Leu Phe Ser  Tyr Gly Tyr
1400             1405                1410

Asp Leu Phe Val Phe Asn Gly Asp Gly Ser Lys Thr  Tyr Thr Pro
1415             1420                1425

Gln Val Leu Phe Glu Asp Asp Ile Gln Gly Thr Met  Val Leu Lys
1430             1435                1440

Ile Val Leu Leu Asn Glu Asp Lys Asn Ser Lys Leu  Glu Asn Phe
1445             1450                1455

Glu Ser Leu Gly Leu Met Lys Thr Ser Ala Gly Asp  His Gln Gly
1460             1465                1470

Glu Ile Val Cys Glu Leu Ala Lys Arg Arg Thr Pro  Glu Pro Tyr
1475             1480                1485

Cys Val Glu Leu Ser Arg Tyr Leu Pro Ser Asn Val  Thr Val Thr
1490             1495                1500

Val Thr Ser Pro Ser Gly Asn Phe Thr Ala Lys Asp  Tyr Val Leu
1505             1510                1515

Pro Leu Pro Ala Phe Asn Asn Gly Asp Ala Asp Tyr  Lys Phe Ala
1520             1525                1530

Pro Phe Pro Leu Ser Leu Glu Ser Ile Trp Gly Asp  Gly Lys Ser
1535             1540                1545

Thr Ser Arg Asp Ile Lys Phe Thr Ile Ser Val Lys  Asp Thr Cys
1550             1555                1560
```

Gly Lys Val Ala Thr Ser Glu Leu Ile Phe Thr Leu Tyr Lys Asn
1565                1570                1575

Thr Ser Pro Glu Leu Ile Thr Leu Lys Thr Ser Asp Ala Gly Ala
1580                1585                1590

Gln Tyr Met Gln Gln Gly Val Tyr Arg Thr Arg Leu Asn Thr Leu
1595                1600                1605

Phe Ala Gln Lys Leu Ile Lys Arg Val Ser Ala Gly Ile Asp Ala
1610                1615                1620

Val Leu Ser Trp Glu Thr Gln Gln Leu Gln Glu Pro Lys Leu Gly
1625                1630                1635

Thr Gly Ser Tyr Ile Ser Val Leu Ile Pro Ala Tyr Ile Lys Leu
1640                1645                1650

Glu His Gly Asp Ser Arg Gln Ala Asn Leu Gln Phe Ser Asn Val
1655                1660                1665

Asp Gln Thr Gly Pro Asp Asn Gly Asn Tyr Ile Leu Trp Ser Gly
1670                1675                1680

Ser Leu Asn Asp Thr Pro Gln Gln Val Thr Ile Phe Val Pro Thr
1685                1690                1695

Met Gln Thr Ile Gly Glu Leu Gln Phe Pro Tyr Asp Arg Thr Ser
1700                1705                1710

Gly Leu Asn Leu Ser Leu Ala Cys Ala Ala Gly Val Tyr Leu Gln
1715                1720                1725

Gly Thr Phe Lys Asn Ile Ser Ala Ser Asp Leu Ser Leu Thr Glu
1730                1735                1740

Phe Val Ala Ala Lys Asn Asn Asp Ser Lys Arg Asp Val Glu Val
1745                1750                1755

Thr Val Leu Thr Ser Ile Asn Thr Glu Pro Met Asp Phe Lys Gly
1760                1765                1770

Ala Asn Ala Leu Tyr Phe Trp Glu Met Phe Tyr Tyr Leu Pro Met
1775                1780                1785

Met Val Phe Lys Arg Leu Leu Ser Glu Ser Arg Phe Thr Glu Ala
1790                1795                1800

Thr Gln Trp Ile Arg Tyr Val Trp Asn Pro Asp Gly Tyr Leu Val
1805                1810                1815

Asn Asp Thr Pro Ala Thr Tyr Gln Trp Asn Val Arg Pro Leu Glu
1820                1825                1830

Asp Glu Thr Ser Trp His Ala Asn Pro Leu Asp Ser Val Asp Pro
1835                1840                1845

Asp Ala Ile Ala Gln Ala Asp Pro Leu His Tyr Lys Val Ala Thr
1850                1855                1860

Phe Met Ala Tyr Leu Asp Leu Leu Ile Ala Arg Gly Asp Ala Ala
1865                1870                1875

Tyr Arg Gln Leu Glu Arg Asp Ala Leu Ser Glu Ala Lys Met Trp
1880                1885                1890

Tyr Val Gln Ala Leu Asp Thr Leu Gly Asp Glu Pro Tyr Leu Ser
1895                1900                1905

Gln Asn Thr Gly Trp Ala Ser Pro Cys Leu Thr Asp Ala Ala Asp
1910                1915                1920

Glu Thr Thr His Lys Asn Arg Gln Gln Ala Met Leu Thr Val Arg
1925                1930                1935

Gln Lys Val Ala Ser Ser Glu Leu Arg Thr Ala Asn Ser Leu Thr
1940                1945                1950

Ala Leu Phe Leu Pro Gln Gln Asn Ala Lys Leu Ala Gly Tyr Trp

-continued

```
            1955                1960                1965
Gln Thr Leu Asn Gln Arg Leu Tyr Asn Leu Arg Asn Asn Leu Ser
            1970                1975                1980

Ile Asp Gly Asn Pro Leu Ser Leu Ser Ile Tyr Ala Thr Pro Thr
            1985                1990                1995

Asp Pro Ala Ala Leu Leu Ser Ser Ala Val Ile Ser Ser Gln Gly
            2000                2005                2010

Gly Ser Asp Leu Pro Ala Ala Val Met Pro Leu Tyr Arg Phe Pro
            2015                2020                2025

Val Ile Leu Glu Ser Ala Arg Ser Met Val Asn Gln Leu Thr Gln
            2030                2035                2040

Phe Gly Ser Thr Leu Leu Gly Ile Thr Glu Arg Gln Asp Ala Glu
            2045                2050                2055

Ala Leu Ser Asp Leu Leu Gln Thr Gln Gly Ala Gly Leu Ala Leu
            2060                2065                2070

Gln Ser Ile Ala Leu Gln Asn Ser Thr Ile Ser Glu Ile Asp Ala
            2075                2080                2085

Asp Arg Ala Ala Leu Arg Glu Ser Leu Ser Gly Ala Gln Ser Arg
            2090                2095                2100

Leu Asn Ser Tyr Thr Thr Leu Tyr Asp Glu Asn Val Asn Ala Gly
            2105                2110                2115

Glu Thr His Ala Met Asn Leu Phe Leu Ser Ser Ala Ile Leu Ala
            2120                2125                2130

Asp Gly Gly Gln Ala Tyr His Thr Ala Ala Gly Ala Leu Asp Leu
            2135                2140                2145

Ala Pro Asn Ile Phe Gly Leu Ala Asp Gly Gly Ser Arg Trp Gly
            2150                2155                2160

Ala Ala Phe Thr Ala Met Ala Gly Ile Ala Asp Leu Ala Ala Ser
            2165                2170                2175

Ala Thr His Thr Ala Ala Asp Arg Ile Ser Gln Ser Glu Ala Tyr
            2180                2185                2190

Arg Arg Arg Arg Gln Glu Trp Glu Ile Gln Arg Asn Ala Ala Gln
            2195                2200                2205

Phe Glu Val Ser Gln Ile Asn Ala Gln Leu Asp Ala Leu Ala Val
            2210                2215                2220

Arg Arg Glu Ser Ala Val Leu Gln Lys Thr Tyr Leu Glu Thr Gln
            2225                2230                2235

Gln Gly Gln Met Gln Ala Gln Met Thr Phe Leu Gln Asn Lys Phe
            2240                2245                2250

Thr Ser Lys Ala Leu Tyr Asn Trp Leu Arg Gly Lys Leu Ala Ala
            2255                2260                2265

Ile Tyr Tyr Gln Phe Tyr Asp Leu Thr Val Ser Arg Cys Leu Met
            2270                2275                2280

Ala Glu Ala Ala Tyr Ser Trp Glu Met Lys Gly Ser Gln Asp Thr
            2285                2290                2295

Gly Thr Phe Ile Arg Pro Gly Ala Trp Gln Gly Thr Tyr Ala Gly
            2300                2305                2310

Leu Met Ala Gly Glu Thr Leu Met Leu Asn Leu Ala Gln Met Glu
            2315                2320                2325

Asn Ser Tyr Leu Thr Lys Glu Glu Arg Gln Lys Glu Val Thr Arg
            2330                2335                2340

Thr Val Cys Leu Ser Glu Val Tyr Ala Gly Leu Ser Ser Gly Ser
            2345                2350                2355
```

```
Phe Ala Leu Ala Asp Thr Val Thr Thr Leu Val Gly Ser Gly Lys
    2360            2365            2370

Gly Thr Ala Gly Thr Asn Asp Asn Gly Val Lys Ile Asp Gly Lys
    2375            2380            2385

Gln Leu Leu Ala Thr Leu Lys Leu Ser Asp Leu Asn Ile Lys Thr
    2390            2395            2400

Asp Tyr Pro Glu Ser Leu Asp Lys Ala Lys Arg Ile Lys Gln Ile
    2405            2410            2415

Ser Val Thr Leu Pro Met Leu Val Gly Pro Tyr Gln Asp Val Arg
    2420            2425            2430

Ala Val Leu Ser Tyr Gly Gly Ser Val Val Leu Pro Arg Gly Cys
    2435            2440            2445

Thr Ala Val Ala Val Ser His Gly Met Asn Asp Ser Gly Gln Phe
    2450            2455            2460

Gln Leu Asp Phe Asn Asp Ser Arg Trp Leu Pro Phe Glu Gly Ile
    2465            2470            2475

Pro Val Asp Asp Ser Gly Thr Leu Thr Leu Ser Phe Pro Asp Ile
    2480            2485            2490

Thr Asp Lys Gln Gln Glu Asn Leu Leu Leu Ser Leu Ser Asp Ile
    2495            2500            2505

Ile Leu His Ile Arg Tyr Thr Ile Ala Ser
    2510            2515

<210> SEQ ID NO 35
<211> LENGTH: 1421
<212> TYPE: PRT
<213> ORGANISM: Pantoea agglomerans

<400> SEQUENCE: 35

Met Gln Asn Thr Asp Gln Met Ser Leu Thr Pro Pro Ser Leu Pro Ser
1               5                   10                  15

Gly Gly Gly Ala Val Thr Gly Leu Lys Gly Asp Met Ser Gly Ala Gly
                20                  25                  30

Pro Asp Gly Ala Ala Thr Leu Ser Leu Pro Leu Pro Ile Ser Pro Gly
            35                  40                  45

Arg Gly Tyr Ala Pro Ser Leu Ser Leu Gly Tyr His Ser Arg Asn Gly
        50                  55                  60

Asn Gly Val Phe Gly Ala Gly Trp Ser Cys Gly Gln Met Ala Ile Arg
65                  70                  75                  80

Leu Gln Thr Arg Lys Gly Val Pro Phe Tyr Asp Gly Ser Asp Val Phe
                85                  90                  95

Thr Ala Pro Asp Gly Glu Val Leu Val Pro Ala Leu Asp Ala Ser Gly
            100                 105                 110

Lys Ala Glu Val Arg Thr Thr Thr Leu Leu Gly Glu Asn Leu Gly
        115                 120                 125

Gly Thr Phe Thr Val Gln Thr Tyr Arg Ser Arg Val Glu Thr Asp Phe
    130                 135                 140

Ser Arg Leu Glu Arg Trp Val Pro Gln Thr Asp Ala Ala Asp Phe
145                 150                 155                 160

Trp Leu Ile Tyr Ser Pro Asp Gly Gln Ile His Leu Leu Gly Arg Asn
                165                 170                 175

Pro Gln Ala Arg Val Asn Asn Pro Glu Asp Thr Thr Gln Thr Ala Ala
            180                 185                 190

Trp Leu Ile Glu Ser Ser Val Ser Ala Ser Gly Glu Gln Ile Tyr Trp
```

```
            195                 200                 205
Gln Tyr Arg Gln Glu Asp Glu Leu Gly Cys Thr Gln Asp Glu Lys Thr
210                 215                 220

Ala His Ala His Ala Leu Ala Gln Arg Tyr Leu Val Ala Val Trp Tyr
225                 230                 235                 240

Gly Asn Lys Ala Ala Ser Arg Thr Leu Pro Gly Leu Leu Ser Val Pro
                245                 250                 255

Ala Ala Gly Ser Trp Leu Phe Thr Leu Ala Leu Asp Tyr Gly Glu Arg
                260                 265                 270

Ala Thr Asp Pro Ala Thr Pro Ala Trp Leu Ser Pro Gly Ser Gly
            275                 280                 285

Thr Trp Leu Cys Arg Gln Asp Val Phe Ser Ser Trp Glu Tyr Gly Phe
290                 295                 300

Glu Leu Arg Thr Arg Arg Leu Cys Arg Gln Val Leu Met Tyr His Asp
305                 310                 315                 320

Val Ala Ala Leu Ala Gly Gln Ser Gly Ser Asp Ala Val Pro Gln Leu
                325                 330                 335

Val Thr Arg Leu Leu Leu Asp Tyr Asn Thr Ser Pro Ser Leu Thr Thr
                340                 345                 350

Leu Lys Thr Ala Gln Gln Ala Ala Trp Glu Pro Asp Gly Thr Leu Arg
                355                 360                 365

Ser Leu Pro Pro Leu Ala Phe Ser Trp Gln Thr Phe Pro Ser Thr Pro
370                 375                 380

Glu Lys Ser Val Ser Trp Gln Arg Arg Asn Asp Met Gly Lys Leu Asn
385                 390                 395                 400

Pro Gln Gln Pro Tyr Gln Met Val Asp Leu His Gly Glu Gly Leu Ala
                405                 410                 415

Gly Ile Leu Tyr Gln Asp Ser Gly Ala Trp Trp Tyr Arg Glu Pro Val
                420                 425                 430

Arg Gln Ser Gly Asp Asp Asn Ala Val Thr Trp Ala Ala Arg
                435                 440                 445

Pro Leu Pro Ala Phe Pro Ala Leu Arg Lys Gly Gly Met Leu Leu Asp
450                 455                 460

Leu Asp Gly Asp Gly Tyr Leu Glu Trp Val Val Thr Ala Pro Gly Val
465                 470                 475                 480

Ala Gly Cys Tyr Ala Gln Ala Pro Glu Gln Tyr Trp Gln Arg Phe Thr
                485                 490                 495

Pro Leu Ser Ala Leu Pro Val Glu Tyr Arg His Ser Arg Met Glu Ile
                500                 505                 510

Ala Asp Val Thr Gly Ala Gly Leu Ala Asp Met Leu Leu Ile Gly Pro
                515                 520                 525

Lys Ser Val Arg Leu Tyr Ser Gly Ser Gly Arg Gly Trp Lys Lys Ala
530                 535                 540

Arg Thr Val Met Gln Asp Ser Gly Ile Thr Leu Pro Val Pro Gly Thr
545                 550                 555                 560

Asn Ala Arg Val Met Val Ala Phe Ser Asp Met Ala Gly Ser Gly Gln
                565                 570                 575

Gln His Leu Thr Glu Ile Lys Ala Ser Gly Val Arg Tyr Trp Pro Ser
                580                 585                 590

Leu Gly His Gly Arg Phe Ala Ala Pro Val Thr Leu Pro Gly Phe Ser
                595                 600                 605

Gln Pro Ala Glu Thr Phe Asn Pro Ala Gln Leu Tyr Leu Ala Asp Val
610                 615                 620
```

```
Asp Gly Ser Gly Thr Thr Asp Leu Ile Tyr Ala Leu Ser Asp His Leu
625                 630                 635                 640

Leu Val Trp Leu Asn Gln Ser Gly Asn Ser Phe Asp Ala Pro Phe Arg
            645                 650                 655

Ile Ser Leu Pro Glu Gly Val Arg Tyr Asp Asn Thr Cys Ser Leu Gln
            660                 665                 670

Val Ala Asp Ile Gln Gly Leu Gly Ile Ser Ser Leu Val Leu Ser Val
            675                 680                 685

Pro His Pro Thr Pro Arg His Trp Val Cys His Leu Thr Thr Glu Lys
690                 695                 700

Pro Trp Leu Leu Asp Gly Met Asn Asn Asn Met Gly Ala Arg His Thr
705                 710                 715                 720

Leu Cys Tyr Arg Ser Ser Ala Gln Phe Trp Leu Asp Glu Lys Ala Ala
            725                 730                 735

Ala Thr Ala Asp Arg Pro Ala Pro Ala Cys Tyr Leu Pro Phe Ala Leu
            740                 745                 750

His Thr Leu Ser Arg Thr Glu Val Ser Asp Glu Ile Thr Gly Asn Arg
            755                 760                 765

Leu Thr Arg Thr Ile Arg Tyr Arg His Gly Val Trp Asp Arg Arg Glu
770                 775                 780

Arg Glu Phe Arg Gly Phe Gly Phe Val Glu Val Ser Asp Ala Glu Ala
785                 790                 795                 800

Leu Ala Lys Gln Thr Glu Gly Met Ser Ala Pro Ala Val Lys Arg Ser
            805                 810                 815

Trp Tyr Ala Thr Gly Leu Ala Ala Val Asp Ala Gln Leu Pro Asp Glu
            820                 825                 830

Phe Trp Lys Gly Asp His Ala Ala Phe Ala Gly Phe Thr Pro Arg Phe
            835                 840                 845

Thr Thr Gly Asp Gly Glu Gln Glu Ala Ala Leu Asp Thr Ile Ser Asp
850                 855                 860

Asp Thr Arg Phe Trp Leu Thr Arg Ala Ile Arg Gly Thr Leu Leu Arg
865                 870                 875                 880

Ser Glu Leu Tyr Gly Ala Asp Gly Ser Ser Gln Ala Gly Ile Pro Tyr
            885                 890                 895

Ser Ile Thr Glu Ser Arg Pro Gln Val Arg Leu Ile Thr Glu Ala Gly
            900                 905                 910

Asn Ser Pro Val Val Trp Pro Ser Val Ile Glu Asn Arg Ala Ser His
            915                 920                 925

Tyr Glu Arg Val Ser Ser Asp Pro Gln Cys Gly Gln Gln Ile Leu Leu
            930                 935                 940

Thr Ser Asn Glu Tyr Gly Gln Pro Leu Arg Gln Ile Gly Ile Ser Tyr
945                 950                 955                 960

Pro Arg Arg Thr Arg Pro Asp Ala Ser Pro Tyr Pro Asp Leu Pro
            965                 970                 975

Asp Gly Leu Phe Ala Asp Ser Phe Asp Glu Gln Gln Ala Leu Arg
            980                 985                 990

Leu Thr Leu Thr Gln Ser Ser Trp His Thr Leu Lys Asp Ile Ser Ser
            995                 1000                1005

Gly Ile Trp Leu Pro Ala Val Ala Asp Ala Thr Arg Ser Asp Leu
            1010                1015                1020

Phe Val His Gln Ala Ala Gln Val Pro Pro Ala Gly Leu Thr Leu
            1025                1030                1035
```

```
Glu  Asn  Leu  Leu  Thr  Asp  Ser  Ala  Leu  Leu  Thr  Ser  Pro  Val  Phe
     1040                1045                1050

Gly  Gly  Gln  Ser  Gln  Ile  Trp  Tyr  Gln  Asp  Arg  Ala  Gly  Gln  Ala
     1055                1060                1065

Ser  Ile  Thr  Ser  Pro  Asp  Phe  Pro  Pro  Arg  Pro  Ser  Phe  Ser  Glu
     1070                1075                1080

Thr  Ala  Ala  Leu  Asp  Glu  Ala  Gln  Val  Ser  Thr  Leu  Ser  Ala  Asp
     1085                1090                1095

Ile  Asp  Gln  Thr  Lys  Leu  Glu  Gln  Ala  Gly  Tyr  Thr  Arg  Ser  Ala
     1100                1105                1110

Tyr  Leu  Phe  Ala  Arg  Ser  Gly  Glu  Glu  Ser  Lys  Thr  Leu  Trp  Ala
     1115                1120                1125

Val  Arg  Gln  Gly  Tyr  Ile  Thr  Phe  Ser  Gly  Ala  Asp  His  Phe  Tyr
     1130                1135                1140

Leu  Pro  Ile  Ala  Ala  Gln  Gln  Thr  Leu  Leu  Ala  Gly  Lys  Thr  Thr
     1145                1150                1155

Val  Thr  Tyr  Asp  Pro  Tyr  Asp  Cys  Val  Val  Leu  Gln  Ala  Lys  Asp
     1160                1165                1170

Ala  Ala  Gly  Ala  Val  Thr  Ser  Ala  Thr  Tyr  Asp  Trp  Arg  Phe  Leu
     1175                1180                1185

Ala  Pro  Thr  Gln  Ile  Thr  Asp  Ile  Asn  Asp  Asn  Leu  Lys  Ser  Val
     1190                1195                1200

Thr  Leu  Asp  Ala  Leu  Gly  Arg  Val  Thr  Ser  Gln  Arg  Phe  Ser  Gly
     1205                1210                1215

Thr  Glu  Asn  Gly  Lys  Pro  Ala  Gly  Tyr  Ser  Asp  His  Glu  Phe  Pro
     1220                1225                1230

Leu  Pro  Ala  Ser  Ala  Asp  Ala  Ala  Leu  Ala  Leu  Ser  Ala  Pro  Leu
     1235                1240                1245

Pro  Val  Ala  Gln  Cys  Ile  Ile  Tyr  Val  Pro  Asp  Ser  Trp  Met  Leu
     1250                1255                1260

Thr  Gly  Glu  Gln  Gln  Gln  Pro  Pro  His  Val  Val  Thr  Leu  Leu  Thr
     1265                1270                1275

Asp  Arg  Tyr  Asp  Ser  Asp  Ser  Gln  Gln  Gln  Ile  Arg  Gln  Gln  Val
     1280                1285                1290

Val  Phe  Ser  Asp  Gly  Phe  Gly  Arg  Val  Leu  Gln  Ala  Ala  Ser  Arg
     1295                1300                1305

Gln  Val  Asn  Gly  Glu  Ala  Trp  Gln  Arg  Ala  Ala  Asn  Gly  Ser  Phe
     1310                1315                1320

Val  Ala  Gly  Thr  Asn  Asp  Ser  Pro  Val  Leu  Thr  Glu  Thr  Thr  Phe
     1325                1330                1335

Arg  Trp  Ala  Val  Thr  Gly  Arg  Thr  Glu  Tyr  Asp  Asn  Lys  Gly  Gln
     1340                1345                1350

Ala  Ile  Arg  Ala  Tyr  Gln  Pro  Tyr  Phe  Leu  Asp  Ser  Trp  Lys  Tyr
     1355                1360                1365

Val  Arg  Asp  Asp  Ser  Ala  Arg  Gln  Asp  Leu  Tyr  Ala  Asp  Thr  His
     1370                1375                1380

Tyr  Tyr  Asp  Pro  Val  Gly  Arg  Glu  Arg  Gln  Val  Ile  Thr  Ala  Lys
     1385                1390                1395

Gly  Trp  Leu  Arg  Arg  Val  Thr  His  Thr  Pro  Trp  Phe  Val  Val  Ser
     1400                1405                1410

Glu  Asp  Glu  Asn  Asp  Thr  Gln  Ala
     1415                1420
```

```
<210> SEQ ID NO 36
<211> LENGTH: 950
<212> TYPE: PRT
<213> ORGANISM: Pantoea agglomerans

<400> SEQUENCE: 36

Ser Ala Ala Tyr Val Leu Ser Asn Leu Ser Tyr Lys Leu Glu Asn Pro
1               5                   10                  15

Met Ser Thr Ser Leu Tyr Ser Arg Thr Pro Ser Val Thr Ile Leu Asp
            20                  25                  30

Asn Arg Gly Leu Ser Val Arg Asp Ile Ala Tyr Gln Arg His Pro Asp
        35                  40                  45

Thr Pro Ala Val Thr Ser Glu Arg Ile Thr Arg His Gln Tyr Asp Ala
    50                  55                  60

Arg Gly Phe Leu Met Gln Ser Ala Asp Pro Arg Leu His Asp Ala Gly
65                  70                  75                  80

Leu Ala Asn Val Ser Tyr Arg Thr Asn Leu Thr Gly Ser Val Leu Arg
                85                  90                  95

Ser Gln Gly Val Asp Asn Gly Ile Thr Val Thr Leu Asn Asp Ala Ala
            100                 105                 110

Gly Arg Pro Phe Leu Ala Val Ser Asn Ile Ser Thr Ala Gly Asp Gly
        115                 120                 125

Thr Glu Asp Arg Ser Gln Ala Val Thr Arg Thr Cys Gln Tyr Glu Asp
    130                 135                 140

Ala Thr Leu Pro Gly Arg Pro Leu Ser Ile Thr Glu Gln Val Asn Gly
145                 150                 155                 160

Gly Ala Ala Arg Ile Thr Glu Arg Phe Val Tyr Ala Gly Asn Ala Val
                165                 170                 175

Glu Glu Lys Ala Leu Asn Leu Ala Gly Gln Pro Val Ser His Tyr Asp
            180                 185                 190

Thr Ala Gly Leu Thr Gln Thr Asp Ser Ile Ala Leu Thr Gly Val Pro
        195                 200                 205

Leu Ser Val Thr Arg Arg Leu Leu Lys Asp Ala Asp Asn Pro Asp Ala
    210                 215                 220

Val Ala Asp Trp Gln Gly Thr Asp Ala Ser Val Trp Asn Asp Pro Leu
225                 230                 235                 240

Asp Val Glu Thr Tyr Thr Thr Leu Ser Thr Ala Asp Ala Thr Gly Ala
                245                 250                 255

Val Leu Thr Thr Thr Asp Ala Lys Gly Asn Leu Gln Arg Leu Ala Tyr
            260                 265                 270

Asp Val Ala Gly Leu Leu Ser Gly Ser Trp Leu Thr Leu Lys Asp Gly
        275                 280                 285

Thr Glu Gln Val Ile Val Thr Ser Leu Thr Tyr Ser Ala Ala Gly Gln
    290                 295                 300

Lys Leu Arg Glu Glu His Gly Asn Gly Val Val Thr Thr Tyr Thr Tyr
305                 310                 315                 320

Glu Ala Glu Thr Gln Arg Leu Thr Gly Ile Lys Thr Ala Arg Pro Ala
                325                 330                 335

Gly His Ala Ser Gly Ala Lys Val Leu Gln Asp Leu Arg Tyr Thr Tyr
            340                 345                 350

Asp Pro Val Gly Asn Val Leu Lys Ile Ser Asn Asp Ala Glu Glu Thr
        355                 360                 365

Arg Phe Trp Arg Asn Gln Lys Val Ala Pro Glu Ser Ala Tyr Val Tyr
    370                 375                 380
```

```
Asp Ser Leu Tyr Gln Leu Val Ser Ala Thr Gly Arg Glu Met Ala Asn
385                 390                 395                 400

Ala Gly Gln Gln Gly Ser Ser Ser Ser Ala Thr Val Pro Leu Pro
            405                 410                 415

Ala Asp Ser Ser Ala Phe Thr Asn Tyr Thr Arg Asn Tyr Thr Tyr Asp
                420                 425                 430

Glu Ala Gly Asn Leu Thr Gln Val Arg His Thr Pro Ala Thr Gly Ser
        435                 440                 445

Gly Tyr Thr Thr Lys Ile Thr Val Ser Asp Lys Ser Asn Arg Gly Val
        450                 455                 460

Leu Ser Thr Leu Thr Glu Asn Pro Ser Asp Val Asp Ala Leu Phe Thr
465                 470                 475                 480

Ala Gly Gly Gln Gln Lys Gln Leu Gln Pro Gly Gln Ser Leu Ile Trp
                485                 490                 495

Thr Pro Arg Asn Glu Leu Leu Lys Val Thr Pro Val Ala Arg Asp Gly
            500                 505                 510

Gly Ala Asp Asp Ser Glu Ser Tyr Arg Tyr Asp Gly Gly Ser Leu Arg
                515                 520                 525

Leu Leu Lys Val Ser Val Gln Lys Thr Gly Asn Ser Thr Gln Thr Gln
530                 535                 540

Arg Ala Leu Tyr Leu Pro Gly Leu Glu Leu Arg Asn Thr Thr Ser Gly
545                 550                 555                 560

Asp Thr Glu Thr Glu Ser Leu Gln Val Val Thr Val Gly Glu Ala Gly
                565                 570                 575

Arg Ala Gln Val Arg Val Leu His Trp Glu Ser Gly Thr Pro Asp Ser
            580                 585                 590

Val Ser Asn Asp Pro Val Arg Tyr Ser Tyr Asp Asn Leu Thr Gly Ser
            595                 600                 605

Ser Gly Leu Glu Leu Asp Ser Ser Gly Asn Ile Ile Ser Met Glu Glu
        610                 615                 620

Tyr Tyr Pro Tyr Gly Gly Thr Ala Val Trp Thr Ala Arg Ser Ala Val
625                 630                 635                 640

Glu Ala Glu Tyr Lys Thr Val Arg Tyr Ser Gly Lys Glu Arg Asp Ala
                645                 650                 655

Thr Gly Leu Tyr Tyr Tyr Gly Tyr Arg Tyr Gln Pro Trp Ala Gly
            660                 665                 670

Arg Trp Leu Ser Ala Asp Pro Ala Gly Thr Val Asp Gly Leu Asn Leu
            675                 680                 685

Phe Arg Met Val Arg Asn Asn Pro Val Thr Leu Val Asp Asp Asn Gly
690                 695                 700

Leu Phe Thr Ser Ser Pro Leu Leu Gly Ile Tyr Glu Lys Glu Met Lys
705                 710                 715                 720

Thr Phe Asp Ser Ile Lys Leu Ser Ile Gly Ser Tyr Lys Tyr Lys Pro
                725                 730                 735

Ser Lys Phe Asp Glu Lys Gly Lys Tyr Val Ser Ser Asp Lys Tyr
            740                 745                 750

Lys Leu Ile Met Ala Asp Asp Asn Asp Leu Asn Gly Tyr Leu Phe Asp
                755                 760                 765

Glu Arg Glu Met Thr Ser His Leu Lys Asp Tyr Ala Asp Lys Phe Ser
        770                 775                 780

Lys Ile Ser Arg Leu Asn Ile Gly Asp Glu Arg Met Lys Thr Asn Ile
785                 790                 795                 800

Asn Phe Gly Thr Arg Ile Ser Arg Tyr Leu Leu Ser Ser Ala Gln Ala
```

```
              805                 810                 815
Ser Ser Arg Glu Asn Arg Glu Val Asp Val Leu Ser Phe Glu Arg Lys
        820                 825                 830

Phe Phe Ala Val Val Lys Lys Lys Asp Lys Ser His Tyr Phe Gly Arg
        835                 840                 845

Lys Ile Tyr Ala Ile Gly Glu Ala His Val Leu Thr Asp Phe Glu Glu
        850                 855                 860

Lys Lys Arg Thr Ile Ala Ile Lys Thr Leu Val Ala His Pro Tyr Thr
865                 870                 875                 880

Gln Ile Asn Glu Ser Ile Lys Asn Arg Ile Asn Asp Phe Asp Lys Glu
                885                 890                 895

Tyr Asn Val Lys Gly Ile Gly Thr Phe Ala Thr Phe Lys Ala Thr Asn
                900                 905                 910

Lys Leu Ile Gly Gly Ile Lys Gly Ala Leu Lys Tyr Lys Thr Lys Val
            915                 920                 925

Leu Thr Gln Ala Val Asn Val Arg Ser Ala Ala Ile Ala Ile Lys Tyr
        930                 935                 940

Gly Ala Lys His Val Pro
945                 950
```

<210> SEQ ID NO 37
<211> LENGTH: 1537
<212> TYPE: DNA
<213> ORGANISM: Pantoea agglomerans

<400> SEQUENCE: 37

```
attgaagagt ttgatcatgg ctcagattga acgctggcgg caggcctaac acatgcaagt    60
cggacggtag cacagagagc ttgctcttgg gtgacgagtg gcggacgggt gagtaatgtc   120
tgggaaactg cccgatggag ggggataact actggaaacg gtagctaata ccgcataacg   180
tcgcaagacc aaagtggggg accttcgggc ctcacaccat cggatgtgcc cagatgggat   240
tagctagtag gcgggtaat ggcccaccta ggcgacgatc cctagctggt ctgagaggat   300
gaccagccac actggaactg agacacggtc cagactccta cgggaggcag cagtggggaa   360
tattgcacaa tgggcgcaag cctgatgcag ccatgccgcg tgtatgaaga aggccttagg   420
gttgtaaagt actttcagcg gggaggaagg cggtgcggtt aataaccgtg ccgattgacg   480
ttacccgcag aagaagcacc ggctaactcc gtgccagcag ccgcggtaat acggagggtg   540
caagcgttaa tcggaattac tgggcgtaaa gcgcacgcag gcggtctgtt aagtcagatg   600
tgaaatcccc gggcttaacc tgggaactgc atttgaaact ggcaggcttg agtcttgtag   660
aggggggtag aattccaggt gtagcggtga atgcgtaga gatctggagg ataccggtg    720
gcgaaggcgg cccctggac aaagactgac gctcaggtgc gaaagcgtgg ggagcaaaca   780
ggattagata ccctggtagt ccacgccgta acgatgtcg acttggaggt tgttcccttg   840
aggagtggct tccggagcta acgcgttaag tcgaccgcct ggggagtacg gccgcaaggt   900
taaaactcaa atgaattgac gggggcccgc acaagcggtg gagcatgtgg tttaattcga   960
tgcaacgcga agaaccttac ctactcttga catccagcga actttccaga gatggattgg  1020
tgccttcggg aacgctgaga caggtgctgc atggctgtcg tcagctcgtg ttgtgaaatg  1080
ttgggttaag tcccgcaacg agcgcaaccc ttatcctttg ttgccagcga ttcggtcggg  1140
aactcaaagg agactgccgg tgataaaccg gaggaaggtg gggatgacgt caagtcatca  1200
tggcccttac gagtagggct acacacgtgc tacaatggcg catacaaaga gaagcgacct  1260
```

```
cgcgagagca agcggacctc acaaagtgcg tcgtagtccg atcggagtc tgcaactcga   1320 ctccgtgaag tcggaatcgc tagtaatcgt ggatcagaat gccacggtga atacgttccc   1380
gggccttgta cacaccgccc gtcacaccat gggagtgggt tgcaaaagaa gtaggtagct   1440
taaccttcgg gagggcgctt accactttgt gattcatgac tggggtgaag tcgtaacaag   1500
gtaaccgtag gggaacctgc ggttggatca cctcctt                            1537
```

<210> SEQ ID NO 38
<211> LENGTH: 1537
<212> TYPE: DNA
<213> ORGANISM: Pantoea agglomerans

<400> SEQUENCE: 38

```
attgaagagt ttgatcatgg ctcagattga acgctggcgg caggcctaac acatgcaagt    60
cggacggtag cacagagagc ttgctcttgg gtgacgagtg gcggacgggt gagtaatgtc   120
tgggaaactg cccgatggag ggggataact actggaaacg gtagctaata ccgcataacg   180
tcgcaagacc aaagtggggg accttcgggc ctcacaccat cggatgtgcc cagatgggat   240
tagctagtag gcggggtaat ggcccaccta ggcgacgatc cctagctggt ctgagaggat   300
gaccagccac actggaactg agacacggtc cagactccta cggaggcag cagtggggaa    360 tattgcacaa tgggcgcaag cctgatgcag ccatgccgcg tgtatgaaga aggccttagg   420
gttgtaaagt actttcagcg gggaggaagg cggtgcggtt aataaccgtg ccgattgacg   480
ttacccgcag aagaagcacc ggctaactcc gtgccagcag ccgcggtaat acggagggtg   540
caagcgttaa tcggaattac tgggcgtaaa gcgcacgcag gcggtctgtt aagtcagatg   600
tgaaatcccc gggcttaacc tgggaactgc atttgaaact ggcaggcttg agtcttgtag   660
aggggggtag aattccaggt gtagcggtga atgcgtaga gatctggagg aataccggtg    720
gcgaaggcgg cccctggac aaagactgac gctcaggtgc gaaagcgtgg ggagcaaaca    780
ggattagata ccctggtagt ccacgccgta aacgatgtcg acttggaggt tgttcccttg   840
aggagtggct tccggagcta acgcgttaag tcgaccgcct ggggagtacg gccgcaaggt   900
taaaactcaa atgaattgac ggggcccgc acaagcggtg gagcatgtgg tttaattcga   960
tgcaacgcga agaaccttac ctactcttga catccagcga actttccaga gatggattgg  1020
tgccttcggg aacgctgaga caggtgctgc atggctgtcg tcagctcgtg ttgtgaaatg  1080
ttgggttaag tcccgcaacg agcgcaaccc ttatcctttg ttgccagcga ttcggtcggg  1140
aactcaaagg agactgccgg tgataaaccg gaggaaggtg gggatgacgt caagtcatca  1200
tggcccttac gagtagggct acacacgtgc tacaatggcg catacaaaga gaagcgacct  1260
cgcgagagca agcggacctc acaaagtgcg tcgtagtccg atcggagtc tgcaactcga   1320 ctccgtgaag tcggaatcgc tagtaatcgt ggatcagaat gccacggtga atacgttccc   1380
gggccttgta cacaccgccc gtcacaccat gggagtgggt tgcaaaagaa gtaggtagct   1440
taaccttcgg gagggcgctt accactttgt gattcatgac tggggtgaag tcgtaacaag   1500
gtaaccgtag gggaacctgc ggttggatca cctcctt                            1537
```

<210> SEQ ID NO 39
<211> LENGTH: 1063
<212> TYPE: DNA
<213> ORGANISM: Pantoea agglomerans

<400> SEQUENCE: 39

```
ttgacgttac ccgcagaaga agcaccggct aactccgtgc cagcagccgc ggtaatacgg    60
```

```
agggtgcaag cgttaatcgg aattactggg cgtaaagcgc acgcaggcgg tctgttaagt      120
cagatgtgaa atccccgggc ttaacctggg aactgcattt gaaactggca ggcttgagtc      180
ttgtagaggg gggtagaatt ccaggtgtag cggtgaaatg cgtagagatc tggaggaata      240
ccggtggcga aggcggcccc ctggacaaag actgacgctc aggtgcgaaa gcgtggggag      300
caaacaggat tagataccct ggtagtccac gccgtaaacg atgtcgactt ggaggttgtt      360
cccttgagga gtggcttccg gagctaacgc gttaagtcga ccgcctgggg agtacgccg       420 caaggttaaa actcaaatga attgacgggg gcccgcacaa gcggtggagc atgtggttta      480
attcgatgca acgcgaagaa ccttacctac tcttgacatc cagcgaactt tccagagatg      540
gattggtgcc ttcgggaacg ctgagacagg tgctgcatgg ctgtcgtcag ctcgtgttgt      600
gaaatgttgg gttaagtccc gcaacgagcg caacccttat cctttgttgc cagcgattcg      660
gtcgggaact caaaggagac tgccggtgat aaaccggagg aaggtgggga tgacgtcaag      720
tcatcatggc ccttacgagt agggctacac acgtgctaca atggcgcata caaagagaag      780
cgacctcgcg agagcaagcg gacctcacaa agtgcgtcgt agtccggatc ggagtctgca      840
actcgactcc gtgaagtcgg aatcgctagt aatcgtggat cagaatgcca cggtgaatac      900
gttcccgggc cttgtacaca ccgcccgtca caccatggga gtgggttgca aaagaagtag      960
gtagcttaac cttcgggagg gcgcttacca ctttgtgatt catgactggg gtgaagtcgt     1020
aacaaggtaa ccgtagggga acctgcggtt ggatcacctc ctt                       1063
```